(12) United States Patent
Genieser et al.

(10) Patent No.: US 12,384,813 B2
(45) Date of Patent: Aug. 12, 2025

(54) POLYMER LINKED MULTIMERS OF GUANOSINE-3', 5'-CYCLIC MONOPHOSPHATES

(71) Applicant: MIRECA MEDICINES GMBH, Teubingen (DE)

(72) Inventors: Hans-Gottfried Genieser, Lemwerder (DE); Frank Schwede, Bremen (DE); Andreas Rentsch, Bremen (DE); Valeria Marigo, Modena (IT)

(73) Assignee: MIRECA MEDICINES GMBH, Tübingen (DE)

( * ) Notice: Subject to any disclaimer, the term of this patent is extended or adjusted under 35 U.S.C. 154(b) by 73 days.

(21) Appl. No.: 17/901,771

(22) Filed: Sep. 1, 2022

(65) Prior Publication Data
US 2023/0242568 A1 Aug. 3, 2023

Related U.S. Application Data

(63) Continuation of application No. 16/329,031, filed as application No. PCT/EP2017/071859 on Aug. 31, 2017, now abandoned.

(30) Foreign Application Priority Data

Aug. 31, 2016 (EP) ..................... 16186700

(51) Int. Cl.
*C07H 19/213* (2006.01)
(52) U.S. Cl.
CPC .................. *C07H 19/213* (2013.01)
(58) Field of Classification Search
None
See application file for complete search history.

(56) References Cited

U.S. PATENT DOCUMENTS

| 11,407,781 B2* | 8/2022 | Genieser .............. C07H 19/213 |
| 2010/0184989 A1 | 7/2010 | Riggs-Sauthier |
| 2016/0213774 A1 | 7/2016 | Ott |
| 2017/0095569 A1 | 4/2017 | Alargova |

FOREIGN PATENT DOCUMENTS

WO  WO-9925384 A2 * 5/1999 ....... A61K 47/48215

OTHER PUBLICATIONS

Kramer, R.H., et al., "Spanning binding sites on allosteric proteins with polymer-linked ligand dimers", Nature, Oct. 1998, 395(6703):710-3. doi: 10.1038/27227.

* cited by examiner

*Primary Examiner* — Traviss C McIntosh, III
(74) *Attorney, Agent, or Firm* — DUANE MORRIS LLP; Gregory M. Lefkowitz; Brandon A. Chan

(57) ABSTRACT

Embodiments of the invention are directed to new polymer linked multimeric guanosine-3',5'-cyclic monophosphate (cGMP) analogues that modulate the cGMP-signaling system, preferably having activating properties, and more preferably being activators of cGMP dependent protein kinase (PKG), and related monomeric precursors thereof. The invention is also directed to related monomeric compounds, which may also show modulating activity and/or may serve as monomeric precursors of the multimers. The invention further relates to the use of such compounds as reagents for signal transduction research and as modulators of cyclic nucleotide-regulated binding proteins and isoenzymes thereof, and as ligands for affinity chromatography, for antibody production or for diagnostic applications e.g. on chip surfaces.

10 Claims, 4 Drawing Sheets

Figure 1:
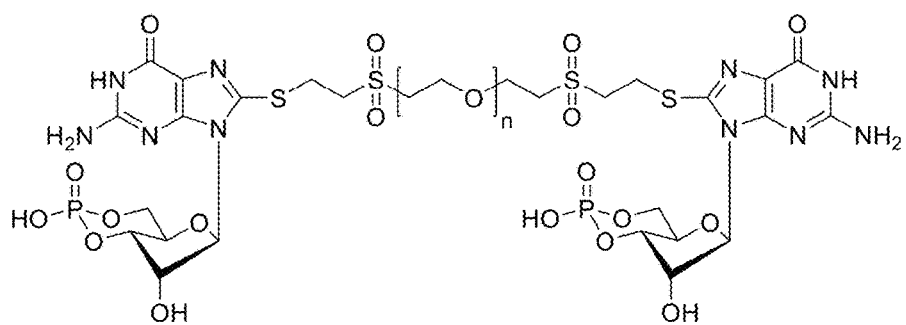

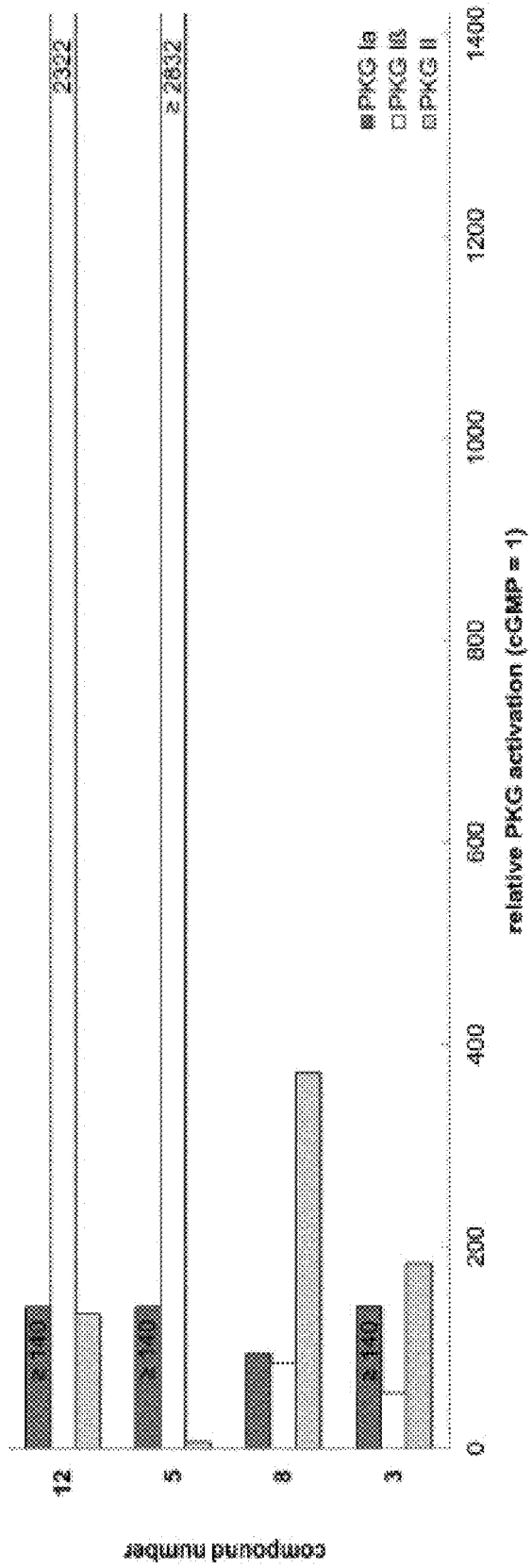
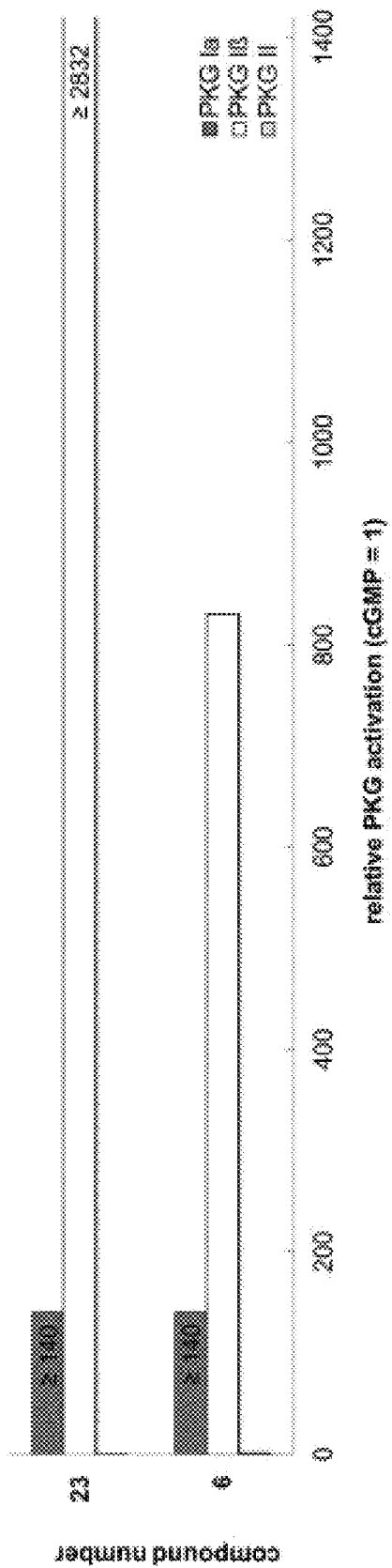

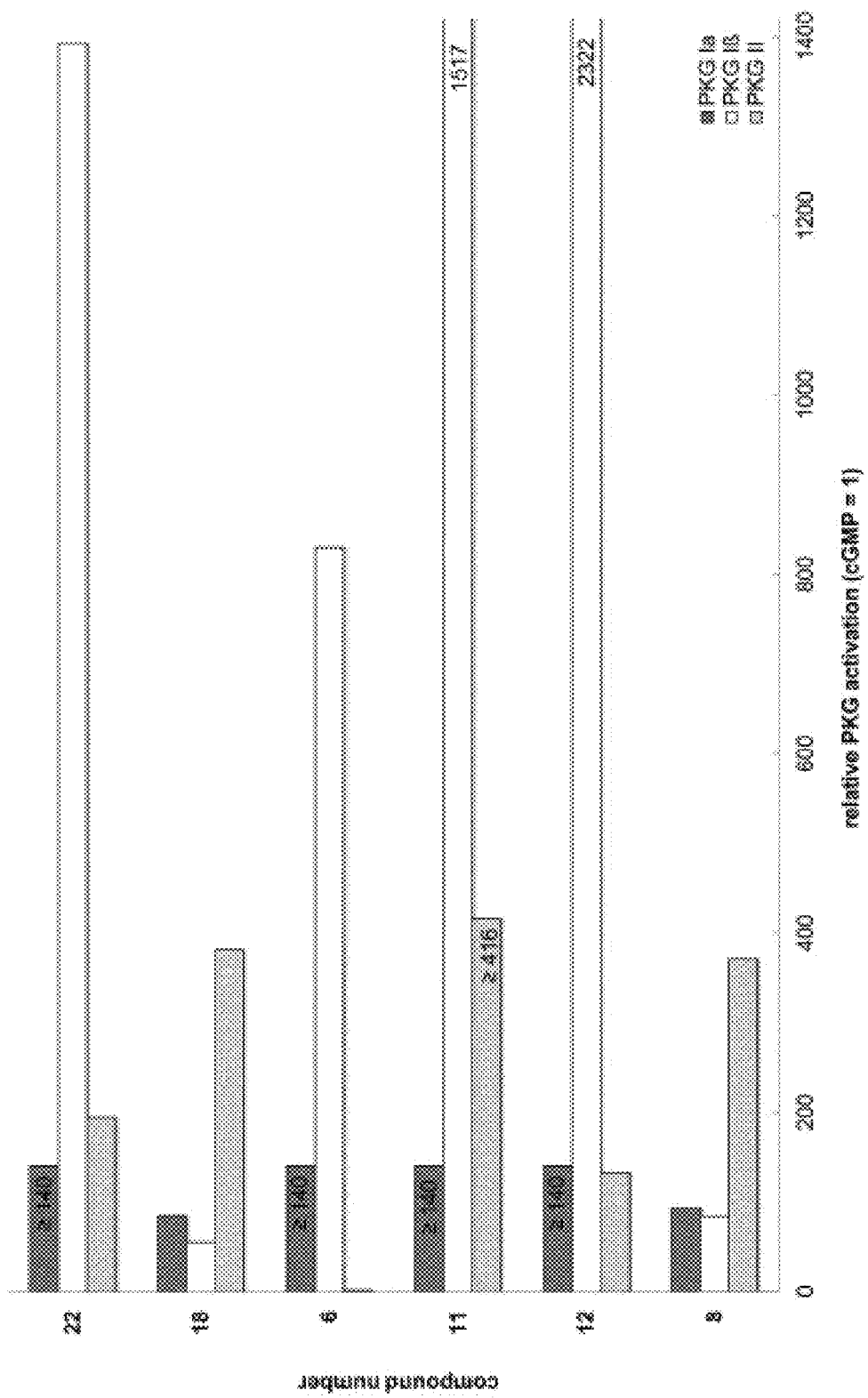

POLYMER LINKED MULTIMERS OF GUANOSINE-3', 5'-CYCLIC MONOPHOSPHATES

CROSS-REFERENCE TO RELATED APPLICATIONS

This application is a continuation of U.S. patent application Ser. No. 16/329,031, filed Feb. 27, 2019, which is a § 371 National Phase of International Patent Application No. PCT/EP2017/071859, filed Aug. 31, 2017, which claims the benefit of European Patent Application No. 16186700.7, filed Aug. 31, 2016. The entirety of each of these applications are hereby incorporated by reference for all purposes.

FIELD OF THE INVENTION

The present invention relates to novel polymer linked multimers of guanosine-3',5'-cyclic nucleotide monophosphates, including tethered di-, tri- and tetramers and their application in the fields of medicine and pharmacy. The invention also relates to specific monomers as precursors. The invention further relates to the use of such compounds as reagents for signal transduction research and as modulators of cyclic nucleotide-regulated binding proteins and isoenzymes thereof, and as ligands for affinity chromatography, for antibody production or for diagnostic applications e.g. on chip surfaces.

BACKGROUND OF THE INVENTION

Guanosine-3',5'-cyclic monophosphate (cGMP) is a purine nucleobase-containing cyclic nucleotide and was discovered as endogenous molecule in 1963. It is well known to act as a second messenger, wherein its intracellular level is altered as a response to (primary) signaling molecules such as toxins, hormones or nitric oxide, which in turn induces diverse cellular processes, such as gene control, chemotaxis, proliferation, differentiation, and apoptosis. Several diseases like retinal degeneration, cardiovascular diseases, asthma or diabetes are associated with unusually high or low levels of cGMP.[1] The cGMP signaling cascade therefore has been recognized as a potential pharmacological target and is investigated by numerous academic groups and pharmaceutical companies. Research in this field demands for compounds that effectively modulate different targets of the said cascade. For this purpose, a number of cGMP analogues featuring cell permeability (in contrast to cGMP), enhanced activity and increased resistance to degradation by phosphodiesterases (PDE) have been established.

However, for the use as a drug and/or research tool cGMP analogues need to comply with a complex profile of characteristics that is unique for each biological system, to achieve a maximum effect. While applied compounds are usually selected for their ability to interfere with the main target of a studied mechanism of a disease, condition or disorder, there are always several required characteristics of a compound, that cannot be predicted and demand for testing a large set of analogues. Accordingly, for the increasing number of applications there is growing need for constantly expanding the group of available cGMP analogues with derivatives that feature another combination of characteristics as well as further improved activation potential, target specificity or multi target effects. Also, tailormade modifications such as reporting groups are desired variations for instance for research or diagnostic purposes. One of the targets addressed by cGMP and its analogues is the cGMP dependent protein kinase (PKG) from which three isoforms (Iα, Iβ and II) are known. Knowledge on the identity and presence of PKG substrates in different cells, tissues and organisms is restricted. Hence the physiological as well as pathological importance of the cGMP-PKG system is not well understood, which is likely to have reduced the general understanding of cGMP-related phenomena, as well as the development of therapies in diseases and conditions where such substrates are involved. Efficient and reliable PKG activators will make it possible to address this question much more sharply than what can be currently achieved.

Among the PKG isoforms compounds activating PKG Iα have been explored most widely, while far less derivatives targeting Iβ and even fewer interfering with PKG II are available. In fact, only a small number of compounds were reported to feature PKG II activation.[2,3] For biochemical assays the most potent and predominantly applied one is 8-pCPT-cGMP. A drawback of this compound, however, is associated with the substituent in the 8-position. The 8-pCPT-moiety has been reported to induce additional off target effects besides PKG activation.[4] Furthermore it is not suitable for assays involving UV light, as it is decomposed under these conditions. For some applications it is therefore desirable to have strong PKG II agonists that don't feature an 8-pCPT-group.

A desired selective biological effect is always also an issue of the activation potential. The less a compound activates a studied target, the larger amount of substance needs to be applied and thus the higher is the probability of off target effects such as extra cellular bindings.[4] In conclusion it is favorable to use agonists with improved activation potential, reasoning a constant need for such compounds.

A class of PKG agonists, which could offer superior activity, are polymer linked multimers (PLM) of cGMP analogues, including di-, tri- and tetramers. This concept comprises the idea of achieving a strong enhancement of activity through addressing multiple binding sites with a single molecule. Prior to the present invention, however, the concept had only been applied once on a dimeric compound[5] (tri- and tetrameric analogues have not been reported). Therein, just a single type of a polymer linked dimeric cGMP (PLD), or more precisely one homologous series, differing only in the spacer length, has been disclosed. The preparation of said homologues was described as a coupling via the 8-position by reacting 8-thio cGMP with bifunctional PEG vinyl sulfones (VS-PEG$_n$-VS) affording structures of general formula cGMP-8-S—(CH$_2$)$_2$—SO$_2$-PEG$_n$-SO$_2$—(CH$_2$)$_2$—S-8-cGMP (also see FIG. 1). Dependent on the length of the (PEG) spacer these PLDs displayed an increased activation potential for either PKG Iα (up to 30-fold) or cyclic-nucleotide-gated (CNG) channels (up to 1000-fold) compared to cGMP itself. The most potent commercially available monomeric PKG Iα agonist 8-(2-NH$_2$-Ph-S)-cGMP (8-APT-cGMP) in contrary exhibits only an about 15-fold higher activity than cGMP.[6]

Applicability of the PLM concept has been proposed for further targets,[8] but no concrete methods to generate PLMs with superior activating potential for PKG isoforms 1B and II were disclosed and no further coupling strategies or synthetic protocols were reported. Particularly the synthetic access, however, comprises a drawback of the reported PLDs. Applying the published protocol, the desired compound is obtained in poor yields only as a byproduct. This outcome results from a favored addition of vinyl sulfones to the 7-position of cGMP.[7] PLDs featuring a different coupling moiety, that supports a more reliable access as well as maintained or preferably increased PKG activation, are therefore needed.

In addition, compounds featuring a similarly increased PKG Iβ and/or PKG II activation potential as described for Iα targeting PLDs above, would be valuable tools for numerous research groups. The effects on these isoforms, however, have never been studied in connection with polymer linked di-, tri- or tetramers. Accordingly, it was desirable to provide polymer linked multimeric activators of PKG Iβ and II, but unknown, whether the concept could be transferred to these isoforms and if, what modifications would be necessary.

The effect of structural manipulations at the nucleobase in context with polymer linked multimers also has not been studied before. This in turn is especially important, though, as established compounds used as biochemical tools often require customized derivatization for specific applications. Among others introduction of a reporter moiety that facilitates a certain assay read out or detection method can be desirable. Coupling of the respective compound to a fluorescent dye, for instance, is a common strategy in this context. This dye in turn allows localizing the intracellular distribution of the compound and its binding proteins in living cells by means of microscopic or spectroscopic techniques. A frequently observed drawback of strategies that involve structural manipulation of an activator, however, is the change of nature of the parent compound. Even minor modifications can result in a significant shift of target affinity and specificity or even loss of activation potential.

In addition, compounds, which simultaneously activate multiple targets such as two or all three PKG isoforms, could be beneficial for some applications and unsolved problems in signal transduction research.

Supported by the results of the only homologous PLD series reported before (as stated above), however, the enhanced target activation of these compounds appeared to fundamentally depend on an optimum spacer length (between the cGMP units), which is unique for each addressed protein. Therefore, addressing two or more targets, with the same PLD, seemed, if feasible at all, only possible with an intermediate spacer length at which the activation potential for both targets would be significantly decreased.

Accordingly, there is a growing need for activators of the cGMP signaling cascade, tailormade for individual biochemical applications, featuring superior single or multiple target activation, with or without additional functionalization that for instance facilitates specific assay read outs. To combine all these features within a single monomeric structure can be very difficult to accomplish. On such relatively small compounds each of the multiple modifications necessary can have a significant influence on the original target binding properties.

The situation, however, changes when it comes to multimers, wherein each desired modification can be introduced on a different cGMP unit. Thus, the respective impact on the biochemical activation profile follows different rules. PLMs offer access to a highly potent, so far rarely studied class of compounds. The challenges of transferring their potential to further targets of the cGMP signal transduction cascade (in particular PKG Iβ and II) and addressing multiple targets simultaneously, while optionally featuring a reporting group, though, have not been mastered yet.

SUMMARY OF THE INVENTION

Therefore, the achieved objective of the present invention has been to provide new polymer linked multimeric analogues of guanosine-3',5'-cyclic monophosphate (PLMs) including di-, tri- and tetrameric derivatives, which are compared to monomeric analogues used so far, improved in terms of PKG Iβ and/or PKG II activation potential. Preferably the new PLMs additionally interfere with PKG Iα, wherein it is even more preferred that the activation potential for this isoform exceeds the previously reported one for a polymer linked dimer.[5] Another objective of the invention has been, to provide PKG activators, which can be functionalized (e.g., with a reporting group), while essentially maintaining their target affinity. A further objective of the invention has been to provide the new PLMs as pharmaceutically acceptable analogues for treating or diagnosing a disease, condition or disorder associated with dysregulation of a cGMP-effected cellular target, wherein additional targets can be, including, but not limited to, a hyperpolarization-activated cyclic nucleotide-gated (HCN) channel, a phosphodiesterase (PDE) and a cGMP-gated channel (CNGC). In another aspect, the objective of the invention has been to provide the new PLMs for application as research tool to identify and validate the cGMP-system in cell cultures or tissues or as a diagnostic tool. Embodiments of the invention are directed to new polymer linked multimeric guanosine-3',5'-cyclic monophosphate (cGMP) analogues that modulate the cGMP-signaling system, preferably having activating properties, and more preferably being activators of cGMP dependent protein kinase (PKG), and related monomeric precursors thereof.

Another achieved objective of the present invention has been to provide related monomeric compounds, which may serve as monomeric precursors of the multimers of the present invention and/or may also show modulating activity. Thus, another objective of the invention has been to provide related monomeric compounds as pharmaceutically acceptable analogues for treating or diagnosing a disease, condition or disorder associated with dysregulation of a cGMP-effected cellular target, wherein additional targets can be, including, but not limited to, a hyperpolarization-activated cyclic nucleotide-gated (HCN) channel, a phosphodiesterase (PDE) and a cGMP-gated channel (CNGC). In another aspect, the objective of the invention has been to provide the new related monomeric compounds for application as research tool to identify and validate the cGMP-system in cell cultures or tissues or as a diagnostic tool. Embodiments of the invention are directed to new related monomeric compound analogues that modulate the cGMP-signaling system, preferably having activating properties, and more preferably being activators of cGMP dependent protein kinase (PKG).

BRIEF DESCRIPTION OF THE FIGURES AND FORMULAS

Formula I General constitution of compounds of the invention (branched and linear analogues).

Formula Ib More detailed illustration of Formula I.

Formula II General constitution of compounds of the invention (linear analogues).

Formula IIb More detailed illustration of Formula II.

Formula III General constitution of G units as discrete compounds of the invention or units of compounds according to Formula I or II.

Formula IV and V General constitution of G units according to Formula III, featuring exemplary imidazolinone substitution.

FIG. 1 Previously reported polymer linked dimeric cGMP[5]

Legend: Guanosine-3',5'-cyclic monophosphate-[8-thioethylsulfonyl-(ethyloxy)$_n$-ethylsulfonylethylthio-8]-guanosine-3',5'-cyclic monophosphate (polydispers compound arising from synthesis with polydispers bis vinylsulfonyl-PEG$_n$ with M$_w$ of 800 g/mol, 1.2 kg/mol, 3.4 kg/mol or 20 kg/mol; or monodispers compound with n=6).

Figure 2:
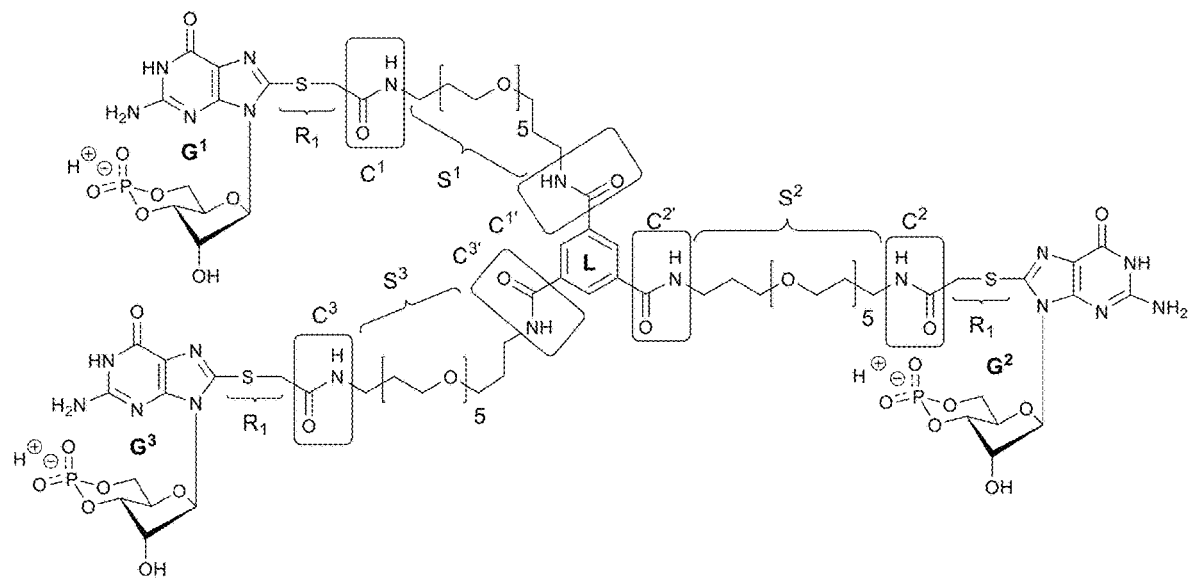

FIG. 2 Example of a trimeric compound according to the invention, illustrating the used variables.

FIG. 3 to 5 In vitro activation of PKG isoforms by polymer linked cGMP derivatives featuring different spacer lengths with and without PET-modification (FIG. 3), varied linking position (FIG. 4) and unequal cGMP (analogue) units with and without unequal linking positions (FIG. 5).

Legend: PKG isozymes Iα (0.2 nM), Iβ (0.15 nM) and II (0.5 nM) were incubated with different concentrations (10 pM to 6 µM) of compounds of the invention and cGMP as reference compound at room temperature for 60 min. The activation values of the compounds are expressed as relative PKG activation compared to cGMP with cGMP set as 1 for each kinase isozyme. The K$_a$-values of cGMP for half-maximal kinase activation were 28 nM for Iα, 425 nM for Iβ and 208 nM for II. Compound numbers refer to analogues displayed in Table 13.

Figure 6:
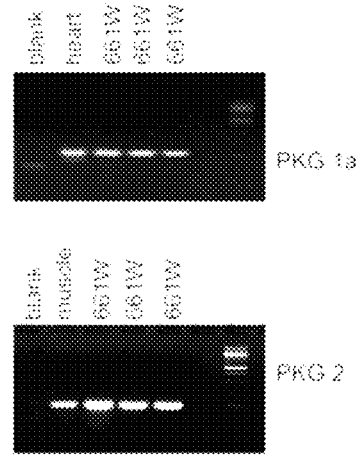

FIG. 6 Expression of PKG isoforms in 661W cells.
Legend: RT-PCR on cDNA from mRNA extracted from 661W cell. The 661W cell line expresses the PKG isoforms Iα and II. Heart and muscle tissues were used as positive controls.

Figure 7:
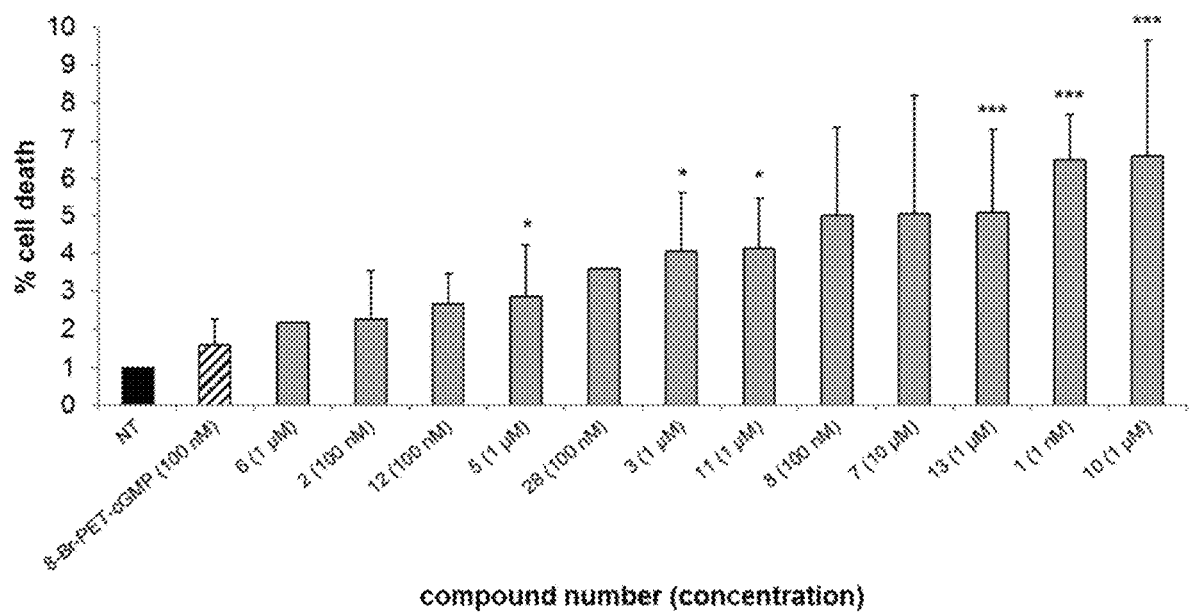

FIG. 7 Increased cell death in the 661W cell line after treatment with different polymer linked dimeric cGMP analogues.

Legend: 661W cells were exposed to compounds for 16 hours at different concentrations (1 nM to 10 µM) and percentage of dying cells was evaluated by Ethidium Homodimer assay. Untreated cells are shown as control sample (black bar). Reference compound 8-Br-PET-cGMP is shown as dashed bars. Data are presented as means±SD from at least three biological replicates. Results not including standard deviation refer to single measurements. Asterisks indicate the P value of the unpaired Student's t-test (* P≤0.05,  P≤0.01, * P≤0.001), statistically assessing significant differences between untreated and treated cells, wherein a p value≤0.05 was considered significant. Compound numbers refer to analogues displayed in Table 13.

SPECIFICATION OF STRUCTURES

The new polymer linked multimeric cGMP analogues of the invention are compounds having the formula (I) or (II)

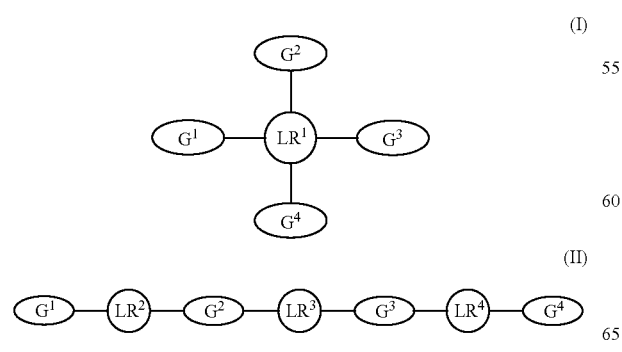

wherein:
G units $G^1$ and $G^2$ independently are compounds of formula (III) and G units $G^3$ and $G^4$ independently from $G^1$ and $G^2$ and independently from each other are compounds of formula (III) or absent, wherein in case of formula (II) $G^4$ is always absent if $G^3$ is absent,

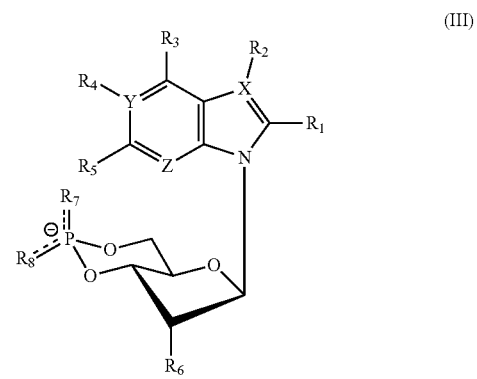

and wherein in formula (III)
X, Y and Z are N
$R_1$, $R_4$, $R_5$, $R_7$ and $R_8$ independently can be equal or individual for each G unit ($G^1$, $G^2$, $G^3$ and $G^4$), while
$R_1$ can independently be H, halogen, azido, cyano, acyl, aracyl, nitro, alkyl, aryl, aralkyl, OH, O-alkyl, O-aryl, O-aralkyl, O-acyl, O-aracyl, SH, S-alkyl, S-aryl, S-aralkyl, S-acyl, S-aracyl, S(O)-alkyl, S(O)-aryl, S(O)-aralkyl, S(O)-acyl, S(O)-aracyl, S(O)$_2$-alkyl, S(O)$_2$-aryl, S(O)$_2$-aralkyl, S(O)$_2$-acyl, S(O)$_2$-aracyl, SeH, Se-alkyl, Se-aryl, Se-aralkyl, NR9R10, SiR13R14R15 wherein R9, R10, R13, R14, R15 independently from each other can be H, alkyl, aryl, aralkyl;
$R_2$ is absent;
$R_3$ is OH;
$R_4$ can independently be absent, H, amino, alkyl, aralkyl, nitro, N-oxide, or can form together with $R_3$, Y and the carbon bridging Y and $R_3$ an imidazole ring which can be unsubstituted or substituted with alkyl, aryl or aralkyl, or can form together with Y and $R_5$ and the carbon bridging Y and $R_5$ an imidazole ring which can be unsubstituted or substituted with alkyl, aryl or aralkyl, or can form together with Y and $R_5$ and the carbon bridging Y and $R_5$ an imidazolinone as depicted (structure IV, V, n=1) or an homologous ring (n=2 to 8) which each can be unsubstituted or substituted (not depicted) with alkyl, aryl or aralkyl;

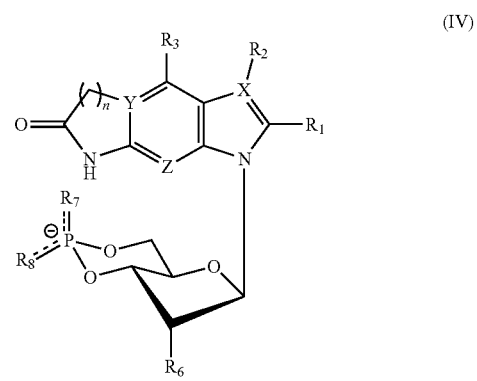

-continued

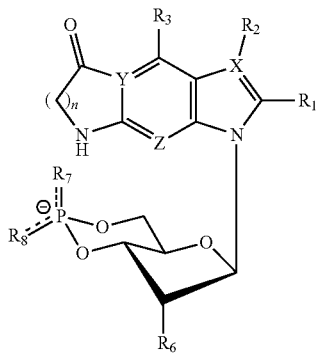

(V)

R$_5$ can independently be H, halogen, NR30R31, NH-carbamoylR32R33 wherein R30, R31, R32, R33, independently from each other can be H, alkyl, aryl, aralkyl, or can form together with R$_4$, Y and the carbon bridging Y and R$_5$ an imidazole ring which can be unsubstituted or substituted with alkyl, aryl or aralkyl, or can form together with R$_4$, Y and the carbon bridging Y and R$_5$ an imidazolinone ring as depicted (structure IV, V, n=1) or an homologous ring (n=2 to 8) which each can be unsubstituted or substituted (not depicted) with alkyl, aryl or aralkyl;

R$_6$ is OH;

R$_7$ is O-carbamoyl-alkyl, O-carbamoyl-aryl, O-carbamoyl-aralkyl, OH, O-alkyl, O-aryl, O-aralkyl, O-acyl, SH, S-alkyl, S-aryl, S-aralkyl, borano (BH$_3$), methylborano, dimethylborano, cyanoborano (BH$_2$CN), S-PAP, O-PAP, S-BAP, or O-BAP,
  wherein PAP is a photo-activatable protecting group with non limiting examples of, optionally, PAP=o-nitro-benzyl, 1-(o-nitrophenyl)-ethylidene, 4,5-dimethoxy-2-nitro-benzyl, 7-dimethylamino-coumarin-4-yl (DMACM-caged), 7-diethylamino-coumarin-4-yl (DEACM-caged) and 6,7-bis(carboxymethoxy)coumarin-4-yl)methyl (BCMCM-caged);
  and wherein BAP is a bio-activatable protecting group with non limiting examples of, optionally, BAP=methyl, acetoxymethyl, pivaloyloxymethyl, methoxymethyl, propionyloxymethyl, butyryloxymethyl, cyanoethyl, phenyl, benzyl, 4-acetoxybenzyl, 4-pivaloyloxybenzyl, 4-isobutyryloxybenzyl, 4-octanoyloxybenzyl, 4-benzoyloxybenzyl;

and

R$_8$ is O-carbamoyl-alkyl, O-carbamoyl-aryl, O-carbamoyl-aralkyl, OH, O-alkyl, O-aryl, O-aralkyl, O-acyl, O-PAP or O-BAP,
  wherein PAP is a photo-activatable protecting group with non limiting examples of, optionally, PAP=o-nitro-benzyl, 1-(o-nitrophenyl)-ethylidene, 4,5-dimethoxy-2-nitro-benzyl, 7-dimethylamino-coumarin-4-yl (DMACM-caged), 7-diethylamino-coumarin-4-yl (DEACM-caged) and 6,7-bis(carboxymethoxy)coumarin-4-yl)methyl (BCMCM-caged);
  and wherein BAP is a bio-activatable protecting group with non limiting examples of, optionally, BAP=methyl, acetoxymethyl, pivaloyloxymethyl, methoxymethyl, propionyloxymethyl, butyryloxymethyl, cyanoethyl, phenyl, benzyl, 4-acetoxybenzyl, 4-pivaloyloxybenzyl, 4-isobutyryloxybenzyl, 4-octanoyloxybenzyl, 4-benzoyloxybenzyl;

and wherein
linking residues LR$^1$, LR$^2$, LR$^3$ and LR$^4$ independently can replace or covalently bind to any of the particular residues R$_1$, R$_4$ and/or R$_5$ of the G units (G$^{1-4}$) they connect,
wherein in case they bind to any of the residues R$_1$, R$_4$ and/or R$_5$, an endstanding group of the particular residue (R$_1$, R$_4$ and/or R$_5$), as defined above, is transformed or replaced in the process of establishing the connection and is then further defined as part of the particular linking residue (LR$^{1-4}$) within the assembled compound,
while
LR$^1$ is (a) a tri- or tetravalent branched hydrocarbon moiety or (b) a divalent hydrocarbon moiety each with or without incorporated heteroatoms such as, but not limited to, O, N, S, Si, Se, B, wherein the backbone preferably contains 1 to 28 carbon atoms and can be saturated or unsaturated, substituted or unsubstituted,
while
each attachment point independently can be a substituted or unsubstituted carbon- or heteroatom
and
in case poly ethylene glycole (PEG) moieties are incorporated in accordance to the definition, the preferred number of carbon atoms can be exceeded by the number present in the PEG moieties, wherein all PEG moieties together can contain a total amount of
  1 to 500 ethylene glycol groups (—(CH$_2$CH$_2$O)$_n$— with n=1 to 500) in case of divalent linking residue (LR$^1$)
  or
  1 to 750 ethylene glycol groups (—(CH$_2$CH$_2$O)$_n$— with n=1 to 750) in case of trivalent linking residue (LR$^1$)
  or
  1 to 1000 ethylene glycol groups (—(CH$_2$CH$_2$O)$_n$— with n=1 to 1000) in case of tetravalent linking residue (LR$^1$),
and, if substituted,
substituents include, but are not limited to, optionally one or more alkyl groups, halogen atoms, haloalkyl groups, (un)substituted aryl groups, (un)substituted heteroaryl groups, amino, oxo, nitro, cyano, azido, hydroxy, mercapto, keto, carboxy, carbamoyl, expoxy, methoxy, ethynyl,
and/or substituents can further be connected to each other, forming a ringsystem with 1 to 4 rings, with or without incorporated heteroatoms, saturated or unsaturated, substituted or unsubstituted, aliphatic or aromatic;

LR$^2$ LR$^3$ and LR$^4$ are divalent hydrocarbon moieties with or without incorporated heteroatoms such as, but not limited to, optionally heteroatoms O, N, S, Si, Se, B, wherein the backbone preferably contains 1 to 28 carbon atoms and can be, saturated or unsaturated, substituted or unsubstituted,
while
each attachment point independently can be a substituted or unsubstituted carbon- or heteroatom
and
in case poly ethylene glycole (PEG) moieties are incorporated in accordance to the definition, the preferred number of carbon atoms can be exceeded by the number present in the PEG moieties, wherein all PEG moieties together can contain a total amount of 1 to 500 ethylene glycol groups (—(CH$_2$CH$_2$O)$_n$— with n=1 to 500)

and, if substituted, substituents include, but are not limited to, optionally one or more alkyl groups, halogen atoms, haloalkyl groups, (un)substituted aryl groups, (un)substituted heteroaryl groups, amino, oxo, nitro, cyano, azido, hydroxy, mercapto, keto, carboxy, carbamoyl, expoxy, methoxy, ethynyl, and/or substituents can further be connected to each other, forming a ringsystem with 1 to 4 rings, with or without incorporated heteroatoms, saturated or unsaturated, substituted or unsubstituted, aliphatic or aromatic;

wherein in case of formula (II) if G$^4$ is absent, LR$^4$ is absent, too, and wherein in case of formula (II) if G$^3$ and G$^4$ are absent, LR$^3$ and LR$^4$ are absent, too, and wherein G$^1$, G$^2$, G$^3$ and G$^4$ can further be salts and/or hydrates while, optionally, non limiting examples of suitable salts of the particular phosphate moiety are lithium, sodium, potassium, calcium, magnesium, zinc or ammonium, and trialkylammonium, dialkylammonium, alkylammonium, e.g., triethylammonium, trimethylammonium, diethylammonium and octylammonium;

and wherein

G$^1$, G$^2$, G$^3$ and G$^4$ can optionally be isotopically or radioactively labeled, be PEGylated, immobilized or be labeled with a dye or another reporting group, wherein the reporting group(s) and/or dye(s)

(a) are coupled to G$^1$, G$^2$, G$^3$ and/or G$^4$ via a linking residue (LR$^5$), bound covalently to or replacing any of the particular residues R$_1$, R$_4$ and/or R$_5$ independently for each G unit (G$^1$, G$^2$, G$^3$ and/or G$^4$) while LR$^5$ can be as defined for LR$^Z$ or (b) in case of formula (I) can replace G$^3$ and/or G$^4$ and wherein examples of optionally suitable dyes include, but are not limited to, fluorescent dyes such as fluorescein, anthraniloyl, N-methylanthraniloyl, dansyl or the nitro-benzofurazanyl (NBD) system, rhodamine-based dyes such as Texas Red or TAMRA, cyanine dyes such as Cy™ 3, Cy™ S, Cy™ 7, EVOblue™ 10, EVOblue™ 30, EVOblue™ 90, EVOblue™ 100 (EVOblue™-family), the BODIPY™-family, Alexa Fluor™-family, the DY-family, such as DY-547P1, DY-647P1, coumarines, acridines, oxazones, phenalenones, fluorescent proteins such as GFP, BFP and YFP, and near and far infrared dyes and wherein reporting groups optionally include, but are not limited to, quantum dots, biotin and tyrosylmethyl ester;

and wherein

PEGylated refers to the attachment of a single or multiple LR$^{PEG}$ group(s) independently, wherein LR$^{PEG}$ can be as defined for LR$^2$, with the provisos that in this case (i) of LR$^2$ only one terminus is connected to a G unit (G$^1$, G$^2$, G$^3$ and/or G$^4$) by covalently binding to or replacing any of the particular residues R$_1$, R$_4$, and/or R$_5$ independently for each G unit (G$^1$, G$^2$, G$^3$ and/or G$^4$), and (ii) the other terminus of LR$^2$ is either an alkyl group or a reactive group that allows for conjugation reactions and/or hydrogen bonding while, optionally, non limiting examples of reactive groups are, —NH$_2$, —SH, —OH, —COOH, —N$_3$, —NHS-ester, halogen group, epoxide, ethynyl, allyl and with the proviso (iii) that LR$^{PEG}$ has incorporated ethylene glycol moieties (—(CH$_2$CH$_2$O)$_n$— with n=2 to 500)

with the proviso that the compound of formula (I) and/or (II), is not selected from structures depicted in FIG. 1; Guanosine-3',5'-cyclic monophosphate-[8-thioethylsulfonyl-(ethyloxy)$_n$-ethylsulfonylethylthio-8]-guanosine-3',5'-cyclic monophosphate (polydispers compound arising from synthesis with polydispers bis vinylsulfonyl-PEGn with Mw of 800 g/mol, 1.2 kg/mol, 3.4 kg/mol or 20 kg/mol; or monodispers compound with n=6).

In a particular embodiment, the precedingly defined compound of formula (I) and/or (II) may be a compound, wherein at least two G units are unequally substituted.

In another particular embodiment, the precedingly defined compound of formula (I) and/or (II) may be a compound, wherein in case of formula (I) G$^3$ and G$^4$ are absent, or in case of formula (II) G$^3$, G$^4$, LR$^3$ and LR$^4$ are absent; and wherein R$_4$ is not H and/or R$_5$ is not NH$_2$.

In a particular variant embodiment, the precedingly defined compound of formula (I) and/or (II) may be a compound, wherein at least one G unit is linked via a position other than R$_1$.

In a further particular embodiment, the precedingly defined compound of formula (I) and/or (II) may be a compound, wherein in case of formula (I) G$^3$ and G$^4$ are absent, or in case of formula (II) G$^3$, G$^4$, LR$^3$ and LR$^4$ are absent.

In still another particular embodiment, any of the precedingly defined compounds of formula (I) and/or (II) may be a compound, wherein all R$_7$ are SH and all R$_8$ are O, or all R$_7$ are O and all R$_8$ are OH.

Any reasonable combination of the before embodiments is possible, too, according to the invention.

Chemical Definitions

Listed below are the definitions of various terms and phrases used to describe the compounds of the present invention. These definitions apply to the terms as they are used throughout the specification.

Halogen refers to F, Cl, Br, and I.

Alkyl refers to an alkyl group, which is a hydrocarbon moiety with 1 to 28, preferably 1 to carbon atoms, with or without (integrated) heteroatoms such as but not limited to O, S, Si, N, Se, B, wherein the point of attachment unless specified otherwise is a carbon atom. Its constitution can be Linear saturated hydrocarbon moiety—including, but not limited to, methyl, ethyl, propyl, butyl and pentyl or Linear unsaturated hydrocarbon moiety—containing more preferably 2 to 20 carbon atoms, including, but not limited to, ethylen, propylen, butylen and pentylen or Branched saturated hydrocarbon moiety—deviating from the general alkyl definition by containing at least 3 carbon atoms and including, but not limited to, isopropyl, sec.-butyl and tert.-butyl or Branched unsaturated hydrocarbon moiety—deviating from the general alkyl definition by containing at least 3 carbon atoms and including, but not limited to, isopropenyl, isobutenyl, isopentenyl and 4-methyl-3-pentenyl or Cyclic saturated hydrocarbon moiety—containing more preferably 3 to 8 ring atoms and including, but not limited to, cyclopentyl, cyclohexyl, cycloheptyl, piperidino, piperazino or Cyclic unsaturated hydrocarbon moiety—containing more preferably 3 to 8 ring atoms.

Herein the term saturated means the group has no carbon-carbon double and no carbon-carbon triple bonds. However, in the substituted case of saturated groups one or more carbon-oxygen or carbon-nitrogen double bonds may be present, which may occur as part of keto-enol and imine-enamine tautomerisation respectively. Independent from its constitution, an alkyl group, as defined herein, can be substituted or unsubstituted. Substituents include, but are not limited to, one or more alkyl groups, halogen atoms, haloalkyl groups, (un)substituted aryl groups, (un)substituted heteroaryl groups, amino, oxo, nitro, cyano, azido, hydroxy, mercapto, keto, carboxy, carbamoyl, expoxy, methoxy, ethynyl. In case alkyl, as defined herein, contains a poly ethylene glycol (PEG) moiety, the preferred number of carbon atoms can be exceeded by the number present in the PEG moiety, wherein the PEG moiety can contain a total amount of 1 to 500 ethylene glycol groups (—($CH_2CH_2O$)$_n$— with n=1 to 500).

It has to be noted, that -(EO)$_n$— is used as an abbreviated expression for —($CH_2CH_2O$)$_n$— with n indicating the number of ethylene glycol groups. The number of ethylene glycol groups especially may be n=1-500 or as stated in the particular example.

Aralkyl refers to an alkyl group as described above, that connects to an unsubstituted or substituted aromatic or heteroaromatic hydrocarbon moiety, consisting of one or more aromatic or heteroaromatic rings with 3-8 ring atoms each. Substituents for both the alkyl and aryl part include, but are not limited to, one or more halogen atoms, alkyl or haloalkyl groups, substituted or unsubstituted aryl groups, substituted or unsubstituted heteroaryl groups, amino, nitro, cyano, hydroxy, mercapto, carboxy, azido, methoxy, methylthio.

Aryl refers to an aryl group, which is an unsubstituted or substituted aromatic or heteroaromatic hydrocarbon moiety, consisting of one or more aromatic or heteroaromatic rings with 3-8 ring atoms each. Substituents include, but are not limited to, one or more halogen atoms, haloalkyl groups, substituted or unsubstituted aryl groups, substituted or unsubstituted heteroaryl groups, amino, nitro, cyano, hydroxy, mercapto, carboxy, azido, methoxy, methylthio.

Acyl refers to a —C(O)-alkyl group, wherein the alkyl group is as defined above.

Aracyl refers to a —C(O)-aryl group, wherein the aryl group is as defined above.

Carbamoyl refers to a —C(O)—$NH_2$ group, wherein the hydrogens can independently from each other be substituted with an alkyl group, aryl group or aralkyl group, wherein alkyl group, aryl group or aralkyl group are as defined above.

O-acyl refers to an —O—C(O)-alkyl group, wherein the alkyl group is as defined above.

O-alkyl refers to an alkyl group, which is bound through an O-linkage, wherein the alkyl group is as defined above.

O-aracyl refers to a —O—C(O)-aryl group, wherein the aryl group is as defined above.

O-aralkyl refers to an aralkyl group, which is bound through an O-linkage, wherein the aralkyl group is as defined above.

O-aryl refers to an aryl group, which is bound through an O-linkage, wherein the aryl group is as defined above.

O-carbamoyl refers to a carbamoyl group, which is bound through an O-linkage, wherein the carbamoyl group is as defined above.

S-alkyl refers to an alkyl group, which is bound through a S-linkage, wherein the alkyl group is as defined above.

S-aryl refers to an aryl group, which is bound through a S-linkage, wherein the aryl group is as defined above.

S-aralkyl refers to an aralkyl group, which is bound through a S-linkage, wherein the aralkyl group is as defined above.

S-aralkyl refers to an aralkyl group, which is bound through an S-linkage, wherein the aralkyl group is as defined above.

Se-alkyl refers to an alkyl group, which is bound through a Se-linkage, wherein the alkyl group is as defined above.

Se-aryl refers to an aryl group, which is bound through a Se-linkage, wherein the aryl group is as defined above.

Se-aralkyl refers to an aralkyl group, which is bound through a Se-linkage, wherein the aralkyl group is as defined above. NH-alkyl and N-bisalkyl refer to alkyl groups, which are bound through an N linkage, wherein the alkyl groups are as defined above.

NH-aryl and N-bisaryl refer to aryl groups, which are bound through an N linkage, wherein the aryl groups are as defined above.

NH-carbamoyl refers to a carbamoyl group, which is bound through an N-linkage, wherein the carbamoyl group is as defined above.

Amido-alkyl refers to an alkyl group, which is bound through a NH—C(O)— linkage, wherein the alkyl group is as defined above.

Amido-aryl refers to an aryl group, which is bound through a NH—C(O)— linkage, wherein the aryl group is as defined above.

Amido-aralkyl refers to an aralkyl group, which is bound through a NH—C(O)— linkage, wherein the aralkyl group is as defined above.

Endstanding group refers to a group of a particular residue ($R_1$, $R_4$ and/or $R_5$) which is (sterically) accessible and capable for covalently binding to a particular linking residue ($LR^{1-4}$). This may be a group at the actual terminal end of the residue ($R_1$, $R_4$ and/or $R_5$) or at any terminal end of any sidechain of the residue ($R_1$, $R_4$ and/or $R_5$), or which is otherwise located in the residue ($R_1$, $R_4$ and/or $R_5$) and sufficiently (sterically) accessible and capable for covalently binding to a particular linking residue ($LR^{1-4}$). The definition of the term endstanding group, if applicable, is independently also valid for the residues $LR^5$ and/or $LR^{PEG}$. Further, the term terminus refers to an endstanding group which is actually a terminal end of the concerned residue.

The person skilled in the art is well aware that a particular linking residue ($LR^{1-4}$) may represent a radical depending on the number of particular G units it binds to. Thus, in compounds of formula (II), the particular linking residue ($LR^{1-4}$) may be a biradical, or in case it is (intermediary) bound to only one particular G unit it may be a monoradical. Similarly, in case of compounds formula (I), depending on the number of particular G units it binds to, the particular linking residue ($LR^1$) may be a biradical, triradical, or tetraradical, or in case it is (intermediary) bound to only one particular G unit it may be a monoradical.

If an otherwise considered monovalent group is used with the modifier "divalent" as in "divalent alkyl" then this adds a second attachment point. Non limiting examples of divalent alkyl would be —$CH_2$—, —$CH_2CH_2$—, —$CH_2C(CH_3)_2CH_2$—.

Whenever side chains or residues are depicted as "floating groups" on a ring system, for example, in the formula:

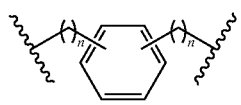

then these side chains (or residues) may replace any hydrogen atom attached to any of the ring atoms, including depicted, implied, or expressly defined hydrogen, as long as a stable structure is formed. All resulting substitution patterns are thus included. For the given example, this corresponds to

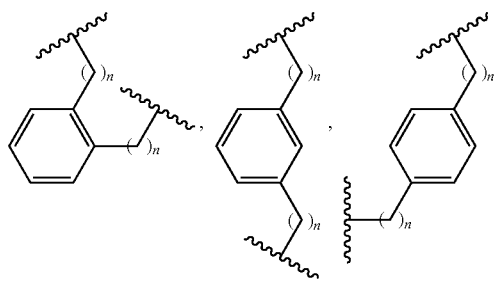

The person skilled in the art understands that many compounds that fall under formula III as defined above have tautomeric forms. It has to be noted that according to this specification all tautomeric forms fall under formula III if at least one of the tautomers falls under formula III as defined above.

In the chair form of saturated six-membered rings, bonds to ring atoms, and the molecular entities attached to such bonds, are termed "axial" or "equatorial" according to whether they are located about the periphery of the ring ("equatorial"), or whether they are orientated above or below the approximate plane of the ring ("axial"). Due to the given stereochemistry of the cyclic phosphate ring, the axial position can only be above the approximate plane of the ring.

In naturally occurring cyclic nucleotide monophosphates (cNMP), both R7 and R8 are oxygen, and the phosphorus double bond is "distributed or dislocated" between both atoms. In water at physiological pH, the compound has a negative charge between both oxygens, and a corresponding cation, such as H+ or Na+. The corresponding compound structures herein are presented as charged compounds with a dislocated double bond at the phosphorus, as long as this is in accordance with valency rules. This style is chosen to account for, depict and disclose all possible "locations" of the phosphorous double bond and distribution of electron density or charge each within a single structure. The dislocated double bond, as used herein, depending on the nature of the particular R7 and R8, however, does not necessarily refer to an equally distributed charge or electron density between R7 and R8.

The term PLM, as used herein, stands for polymer linked multimeric guanosine-3',5'-cyclic monophosphate (cGMP) analogue, wherein the term "multimeric" can refer to di-, tri- or tetrameric. To ease understanding of definitions and descriptions the term PLD (polymer linked dimeric cGMP analogue) is used as an equivalent to specifically refer to dimeric compounds. The term polymer, as used herein, refers to a moiety consisting of at least two (equal) units or monomers.

If R7 and R8 are not equal, the phosphorus atom has four different ligands and becomes chiral resulting in two stereoisomeric forms. To describe the configuration of the chiral phosphorus, the Rp/Sp-nomenclature is used. Therein R/S follows the Cahn-Ingold-Prelog rules while "p" stands for phosphorus.

To give an example: if the equatorial residue $R_8$ is oxygen (while axial $R_7$ is sulphur), the corresponding cyclic guanosine-3',5'-monophosphorothioate compound (cGMPS-analogue) is Sp-configured at phosphorus.

The person skilled in the art knows, that for the use in the field of the medicine especially as part of medicaments certainly only physiologically acceptable salts of the compounds according to the invention may be used.

Further Specification of Structures

In an embodiment the invention relates to a compound according to the definition hereinabove, wherein in case of formula (I) $G^4$ is absent, or, wherein in case of formula (II) $G^4$ and $LR^4$ are absent.

In another embodiment the invention relates to a compound according to the definition hereinabove, wherein in case of formula (I) $G^3$ and $G^4$ are absent, or, wherein in case of formula (II) $G^3$, $G^4$, $LR^3$ and $LR^4$ are absent.

In an embodiment the invention relates to a compound according to any definition hereinabove, wherein all $R_7$ are O and all $R_5$ are OH.

According to the invention it is preferred, that linking residues $LR^1$, $LR^2$, $LR^3$ and $LR^4$ are further subdivided as depicted in formula (Ib) and (IIb), (Ib)
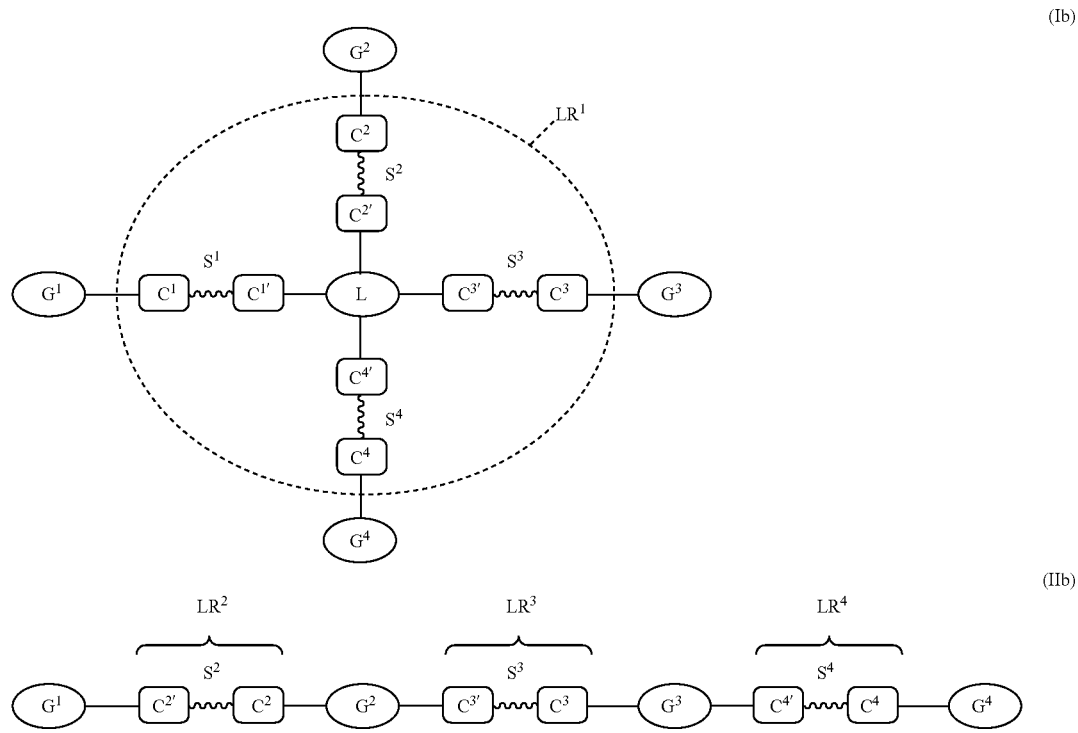
(IIb)
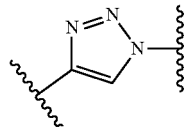
wherein:
coupling functions $C^1$, $C^{1'}$, $C^2$, $C^{2'}$, $C^3$, $C^{3'}$, $C^4$ and $C^{4'}$ independently from each other can be absent or as defined by structures selected from the group consisting of
-continued
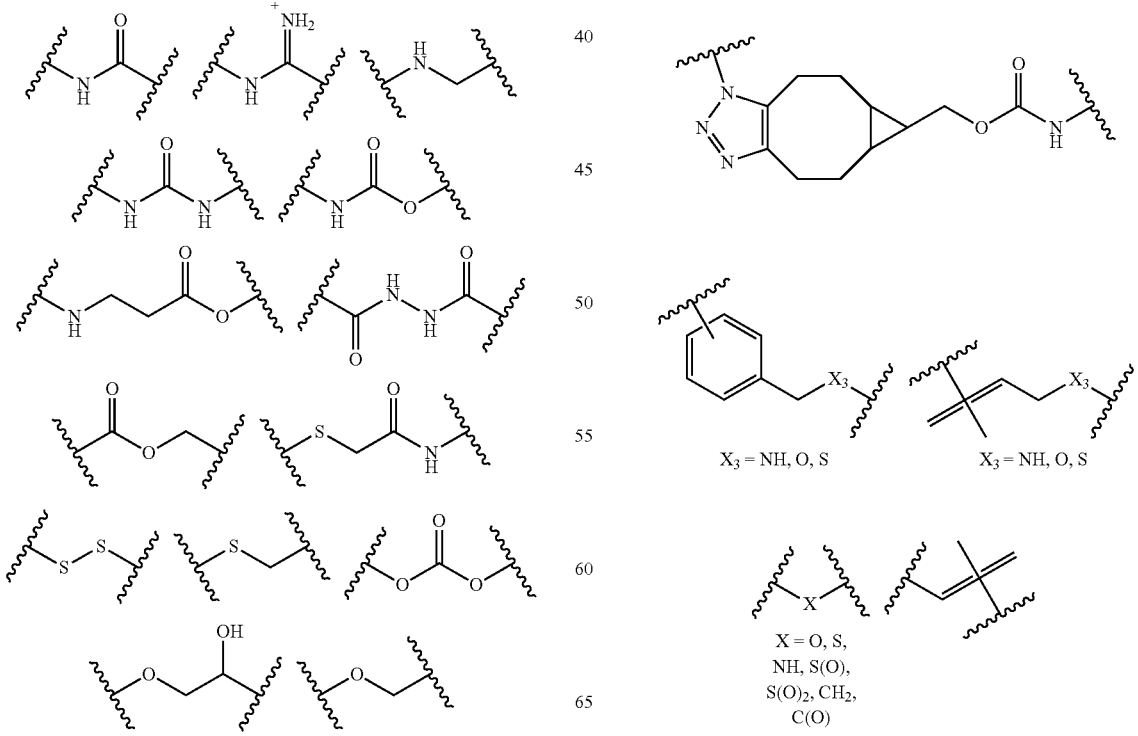

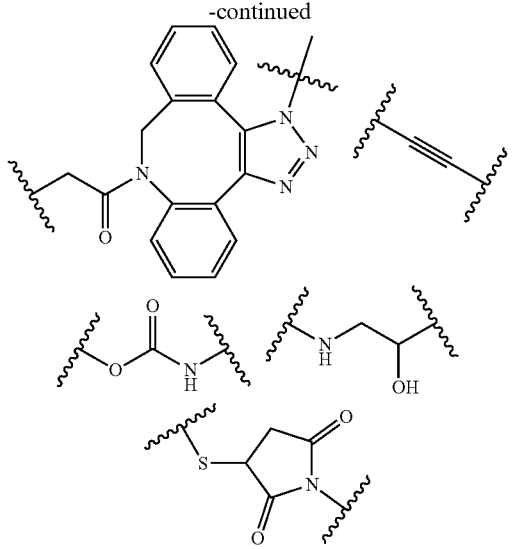

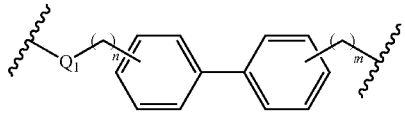

n = 0-4; m = 0-4;
Q₁ = absent, S, NH, O, C(O), S(O), S(O)₂;

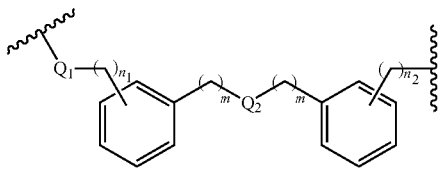

n1 = 0-4, n2 = 0-4; m = 0-4;
Q₁ = absent, S, NH, O, C(O), S(O), S(O)₂;
Q₂ = CH₂, O, NH, S;

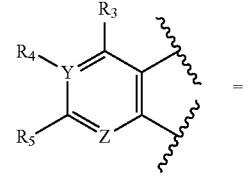

while connectivity can be as depicted or reversed as exemplified by

G¹-O—C(O)—NH—S² versus G¹-NH—C(O)—O—S² and wherein
in case the coupling function (C¹, C¹', C², C²', C³, C³', C⁴ and/or C⁴') does not replace the residue of the G unit (R₁, R₄ and/or R₅ of G¹⁻⁴) but bind to it, the particular residue (R₁, R₄ and/or R₅) involved in coupling of G units (or G unit with dye(s) or other reporting group(s)) independently from each other is as defined further above, wherein an endstanding group is replaced by or transformed to a coupling function
or
selected from the group depicted hereinafter (wherein if present, Q1 connects to the G unit)

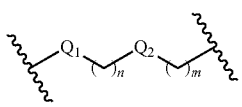

n = 0-6; m = 0-6;
Q₁ = absent, S, NH, O, C(O), S(O), S(O)₂;
Q₂ = NH, S, O, C(O), CH₂, OC(O), NC(O);

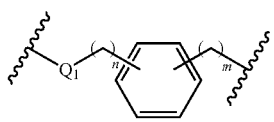

n = 0-4, m = 0-4
Q₁ = absent, S, NH, O, C(O), S(O), S(O)₂;

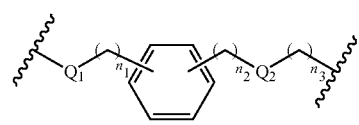

n₁ = 0-4, n₂ = 0-4, n₃ = 0-4,
Q₁ = absent, S, NH, O, C(O), S(O), S(O)₂;
Q₂ = NH, S, O, C(O), CH₂, OC(O), NC(O);

and wherein
the linker (L) is selected from the group consisting of

| Dimeric Linkers |
| --- |
|  |
| n = 0-4 |
| 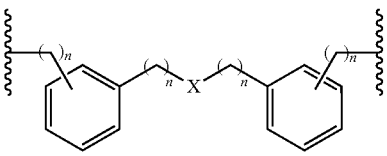 |
| X = CH₂, O, NH, S, S—S, C(O); n = 0-4 |

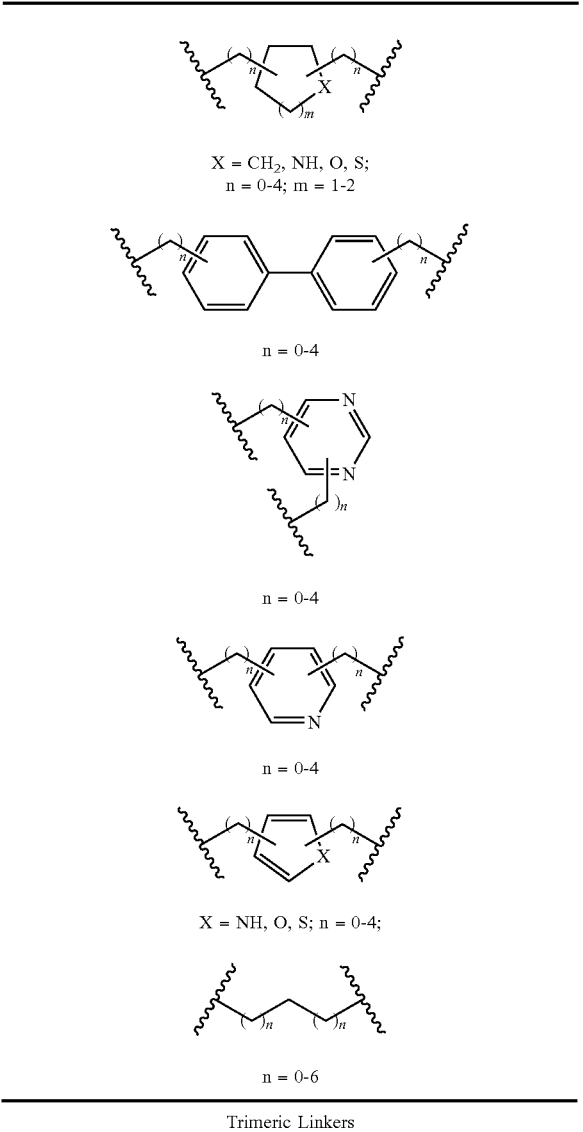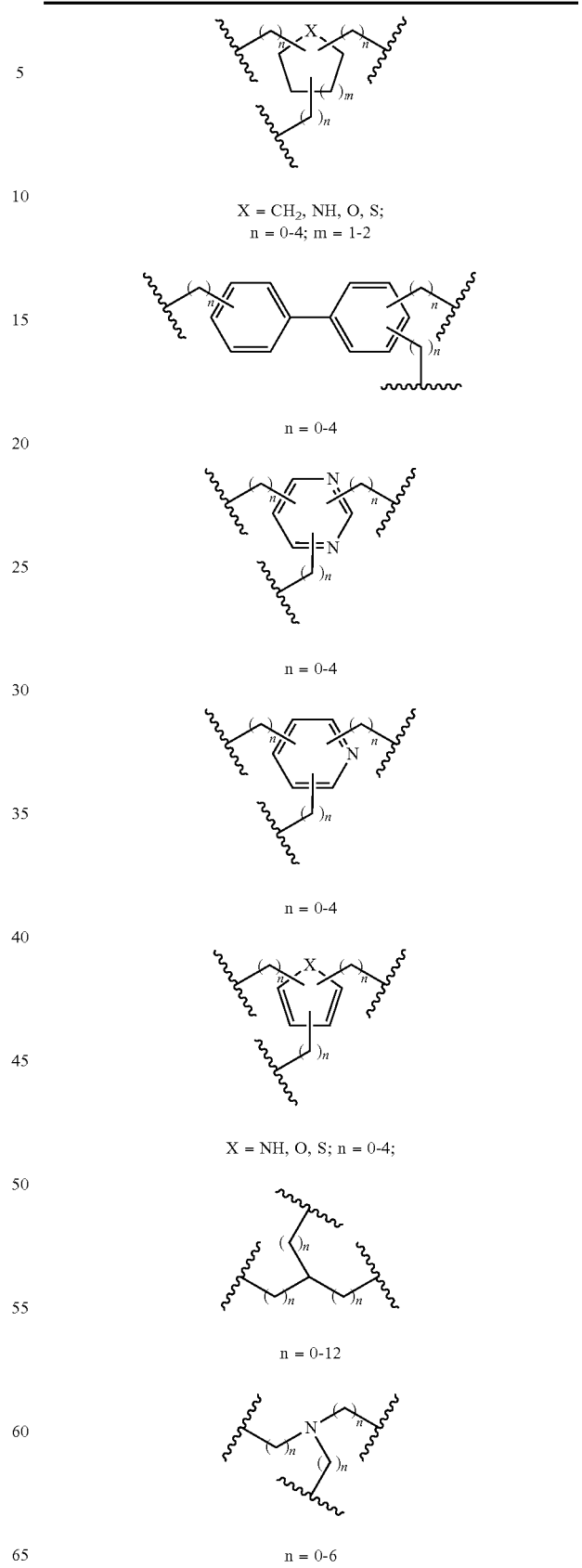

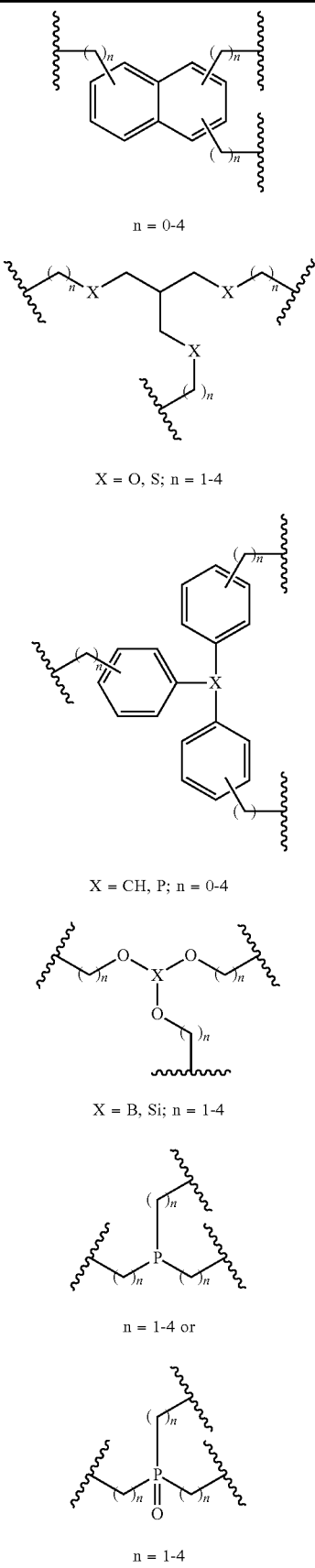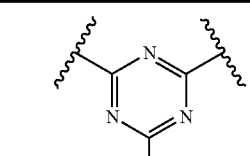
Tetrameric linkers

-continued
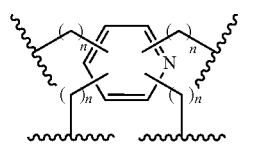
n = 0-4
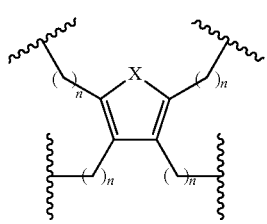
X = NH, O, S; n = 0-4;
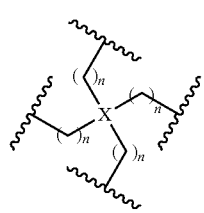
X = C, Si; n = 0-6 or
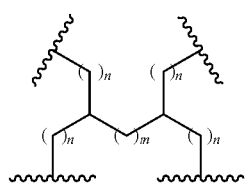
m = 0-24, n = 0-6
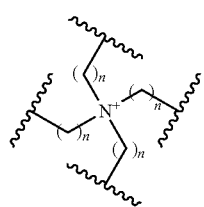
n = 0-6
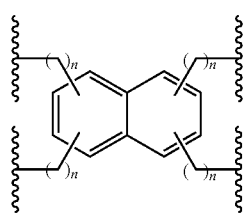
n = 0-4
-continued
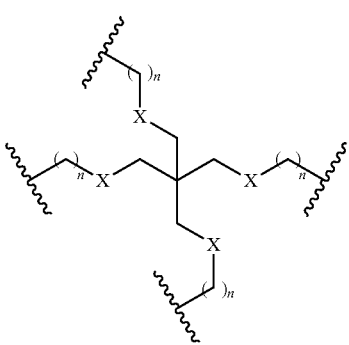
X = O, S; n = 1-4
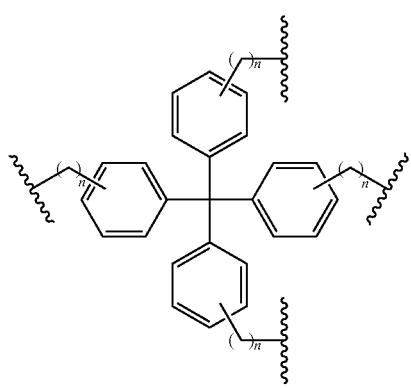
n = 0-4
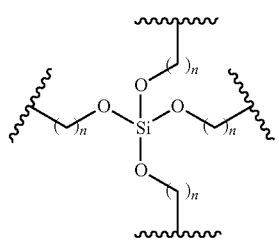
n = 1-4
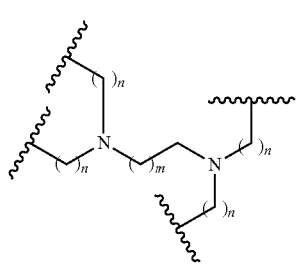
n = 1-6; m = 1-11

-continued

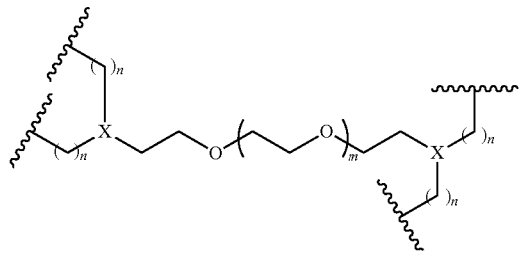

X = N, CH; n = 1-6; m = 0-10

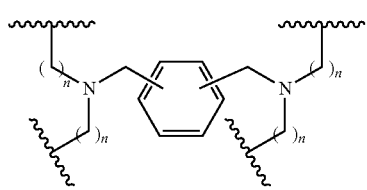

n = 0-6 while
- n for each sidechain within a particular linker of the list herebefore can have an equal or individual value as defined and
- all chiral, diastereomeric, racemic, epimeric, and all geometric isomeric forms of linkers (L) of the list herebefore, though not explicitly depicted, are included herein and
- cationic linkers (L) such as ammonium-derivatives are salts containing chloride-, bromide-, iodide-phosphate-, carbonate-, sulfate-, acetate- or any other physiologically accepted counterion and wherein
spacers ($S^1$, $S^2$, $S^3$ and $S^4$) can be equal or individual within a particular compound, be absent or be —$(CH_2)_{n1}$—$(CH_2CH_2\beta)_m$—$(CH_2)_{n2}$— (with $\beta$=O, S or NH; m=1 to 500, n1=0 to 8, n2=0 to 8, while both n1 and n2 can independently be equal or individual), or —$(CH_2)_n$— (with n=1 to 24).

Particularly, in the preferred embodiment of the invention, wherein it is preferred, that linking residues $LR^1$, $LR^2$, $LR^3$ and $LR^4$ are further subdivided as depicted in formula (Ib) and (IIb), containing spacer moieties ($S^{1-4}$), coupling functions ($C^{1-4}$, $C^{1'-4'}$) and a linker (L, only multimers of structure Ib), coupling functions ($C^{1-4}$, $C^{1'-4'}$) establish covalent bonds between the spacer and a G unit ($G^{1-4}$) by connecting to or replacing any of the residues $R_1$, $R_4$ and/or $R_5$ (compare formula structure III)

and/or
the spacer and a linker (L), dye or another reporting group and/or
(in case the particular spacer is absent) a G unit ($G^{1-4}$) and a dye or another reporting group by connecting to or replacing any of the residues $R_1$, $R_4$ and/or $R_5$ and/or
(in case the particular spacer is absent and/or a G unit is replaced by a dye or other reporting group) the linker (L) and a dye or another reporting group or a G unit ($G^{1-4}$, by connecting to or replacing any of the residues $R_1$, $R_4$ and/or $R_5$).

Coupling functions ($C^{1-4}$, $C^{1'-4'}$) are generated in a reaction between endstanding groups of the particular precursor parts according to well established methods of the art. Non limiting examples of precursor endstanding groups (of monomeric G units and (commercially available) linkers, dyes, reporting groups and spacers) and the corresponding coupling functions ($C^{1-4}$, $C^{1'-4'}$), to which they are transformed within the assembled (mono- or multimeric) compound according to the invention, are as depicted in Table 1. Coupling functions ($C^{1-4}$, $C^{1'-4'}$) can independently further be absent or be equal or individual within a particular mono- or multimeric compound.

TABLE 1

Endstanding groups and corresponding coupling functions ($C^{1-4}$, $C^{1'-4'}$)

| Entry | Endstanding Group of Monomeric G unit ($R_1$, $R_4$, $R_5$), L, dye, reporting group | Spacer ($S^1$, $S^2$, $S^3$, $S^4$) | (Corresponding) Coupling Function ($C^1$, $C^{1'}$, $C^2$, $C^{2'}$, $C^3$, $C^{3'}$, $C^4$, $C^{4'}$) |
|---|---|---|---|
| 1 | —NH$_2$ | HO–C(=O)– | –C(=O)–NH– |
| 2 | —NH$_2$ | CH$_3$O–C(=$^+$NH$_2$)– | –NH–C(=$^+$NH$_2$)– |
| 3 | —NH$_2$ | Br–CH$_2$– | –NH–CH$_2$– |

TABLE 1-continued

Endstanding groups and corresponding coupling functions ($C^{1-4}$, $C^{1'-4'}$)

| Entry | Endstanding Group of Monomeric G unit ($R_1$, $R_4$, $R_5$), L, dye, reporting group | Spacer ($S^1$, $S^2$, $S^3$, $S^4$) | (Corresponding) Coupling Function ($C^1$, $C^{1'}$, $C^2$, $C^{2'}$, $C^3$, $C^{3'}$, $C^4$, $C^{4'}$) |
|---|---|---|---|
| 4 | –NH₂ | O=C=N– | –NH–C(O)–NH– |
| 5 | –NH₂ | epoxide | –NH–CH₂–CH(OH)– |
| 6 | –NH₂ | 4-nitrophenyl carbonate | –NH–C(O)–O– |
| 7 | –NH₂ | acrylate | –NH–CH₂CH₂–C(O)–O– |
| 8 | –COOH | H₂N–NH–C(O)– | –C(O)–NH–NH–C(O)– |
| 9 | –COOH | Br–CH₂– | –C(O)–O–CH₂– |
|  | –C(O)–OMe | HO– |  |
| 10 | –SH | maleimide | thiosuccinimide |
| 11 | –SH | I–CH₂–C(O)–NH– | –S–CH₂–C(O)–NH– |
| 12 | –SH | 2-pyridyl-S–S– | –S–S– |
| 13 | –SH | Br–CH₂– | –S–CH₂– |

TABLE 1-continued
Endstanding groups and corresponding coupling functions ($C^{1-4}$, $C^{1'-4'}$)
| Entry | Endstanding Group of Monomeric G unit ($R_1$, $R_4$, $R_5$), L, dye, reporting group | Spacer ($S^1$, $S^2$, $S^3$, $S^4$) | (Corresponding) Coupling Function ($C^1$, $C^{1'}$, $C^2$, $C^{2'}$, $C^3$, $C^{3'}$, $C^4$, $C^{4'}$) |
|---|---|---|---|
| 14 | 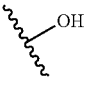 | 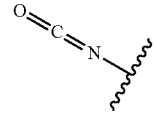 [SMILES: *N=C=O] | 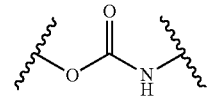 |
| 15 |  | 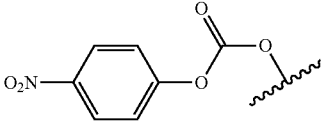 [SMILES: *OC(=O)Oc1ccc([N+](=O)[O-])cc1] | 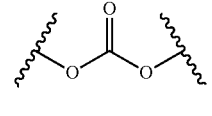 |
| 16 |  |  | 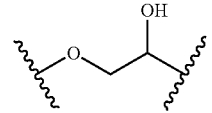 |
| 17 |  | 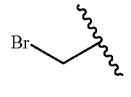 | 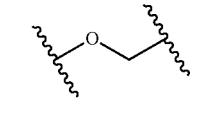 [SMILES: *CO*] |
| 18 |  |  | 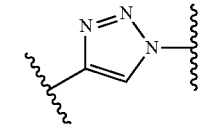 [SMILES: *c1cn(*)nn1] |
| 19 | 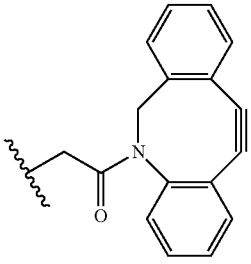 [SMILES: *CC(=O)N1Cc2ccccc2C#Cc2ccccc21] |  | 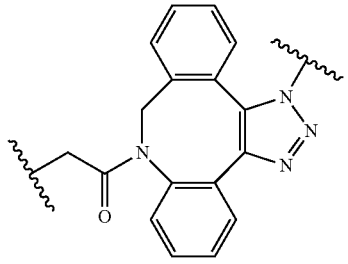 [SMILES: *CC(=O)N1Cc2ccccc2-c2c(nnn2*)-c2ccccc21] |
| 20 |  | 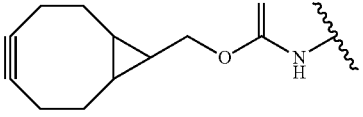 | 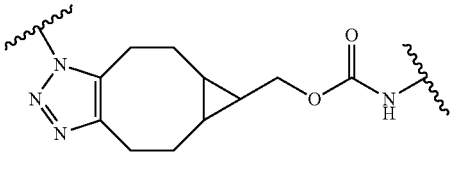 [SMILES: *NC(=O)OCC1C2CCc3nnn(*)c3CCC21] |
| 21 |  $X_1$ = Br, I bound to aryl, heteroaryl, alkenyl | 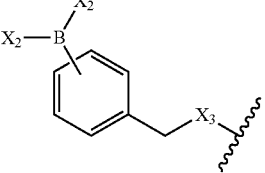 $X_2$ = alkyl, OH, O-alkyl $X_3$ = NH, O, S | 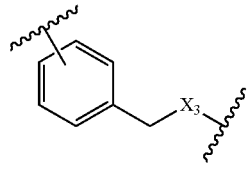 $X_3$ = NH, O, S |

TABLE 1-continued

Endstanding groups and corresponding coupling functions ($C^{1-4}$, $C^{1'-4'}$)

| Entry | Endstanding Group of Monomeric G unit ($R_1$, $R_4$, $R_5$), L, dye, reporting group | Spacer ($S^1$, $S^2$, $S^3$, $S^4$) | (Corresponding) Coupling Function ($C^1$, $C^{1'}$, $C^2$, $C^{2'}$, $C^3$, $C^{3'}$, $C^4$, $C^{4'}$) |
|---|---|---|---|
| 22 | 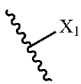 $X_1$ = Br, I bound to aryl, heteroaryl, alkenyl | 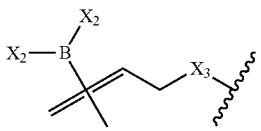 $X_2$ = alkyl, OH, O-alkyl $X_3$ = NH, O, S | 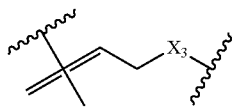 $X_3$ = NH, O, S |
| 23 |  $X_1$ = Br, I bound to aryl, heteroaryl, alkenyl | 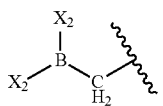 $X_2$ = alkyl, OH, O-alkyl | 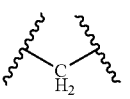 |
| 24 |  $X_1$ = Cl, Br, I, OTf bound to aryl, heteroaryl, alkenyl | 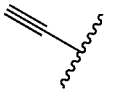 [SMILES: *C#C] | 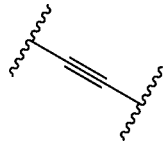 [SMILES: *C#C*] |
| 25 | 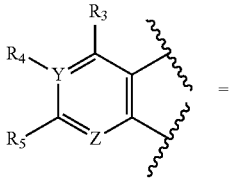 | 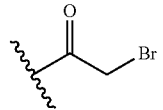 [SMILES: *C(=O)CBr] | 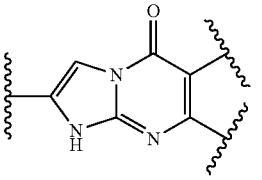 [SMILES: *c1cn2c(=O)c(*)c(*)nc2[nH]1] |
| 26 | 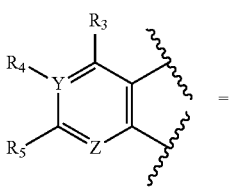 | 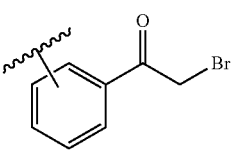 | 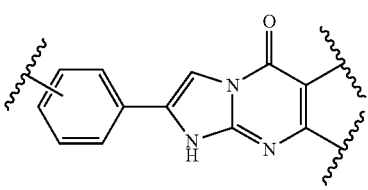 |

TABLE 1-continued

Endstanding groups and corresponding coupling functions ($C^{1-4}$, $C^{1'-4'}$)

| Entry | Endstanding Group of Monomeric G unit ($R_1$, $R_4$, $R_5$), L, dye, reporting group | Spacer ($S^1$, $S^2$, $S^3$, $S^4$) | (Corresponding) Coupling Function ($C^1$, $C^{1'}$, $C^2$, $C^{2'}$, $C^3$, $C^{3'}$, $C^4$, $C^{4'}$) |
|---|---|---|---|
| 27 | [pyrimidine with $R_3$, $R_4$-Y, $R_5$-Z] = [pyrimidinone with H-N, $H_2N$] | Br— | [N-alkyl pyrimidinone with $H_2N$] |

A person skilled in the art understands, that synthetic equivalents of the precursor endstanding groups of Table 1, such as but not limited to NHS esters instead of carboxylic acids or triflates instead of halogens can be used as well to generate the particular corresponding coupling function. A person skilled in the art further understands, that endstanding groups of the synthetic precursors (residues $R_1$, $R_4$ and/or $R_5$, linker (L), dye, reporting group and spacer ($S^{1-4}$)) can be interchanged amongst each other, resulting in reversed connectivity of the coupling function within the mono- or multimeric analogue.

A non limiting example of a multimeric compound according to the invention, illustrating the used and defined variables above is given in FIG. 2.

DETAILED DESCRIPTION OF THE INVENTION

Embodiments of the invention are directed to new polymer linked multimeric guanosine-3',5'-cyclic monophosphate (cGMP) analogues that modulate the cGMP-signaling system, preferably having activating properties, and more preferably being activators of cGMP dependent protein kinase (PKG), and related monomeric precursors thereof. The invention is also directed to related monomeric compounds, which may also show modulating activity and/or may serve as monomeric precursors of the multimers.

The idea of addressing more than one binding site of a target protein simultaneously with a single molecule has been reported once before using a polymer linked dimeric cGMP analogue (PLD).[5] Therein a homologous series of one PLD (FIG. 1), differing only in the length of the PEG spacer, was synthesized and tested for the ability to activate cGMP-dependent protein kinase Iα (PKG Iα) and cyclic nucleotide-gated ion channels (CNG channels). The results suggested, that PLDs feature an enhanced activatory potential compared to monomeric cGMP, while this enhancement, however, fundamentally depends on an optimum spacer length (between the cGMP units), which is unique for each addressed protein. Thus with increasing deviation from this optimum spacer length the effect was reported to decrease and eventually to disappear. In particular the only studied PLD gave best PKG Iα activation with a PEG-spacer of 282 Da. The same compound carrying a PEG-spacer of 2000 Da on the other hand displayed very strong activation of CNG channels but virtually no increased effect on PKG Iα (compared to monomeric cGMP). Accordingly, addressing both PKG Iα and CNG channels (or multiple targets in general), with the same PLD, appeared, if feasible at all, only possible with an intermediate spacer length at which the activation potential for both targets would be significantly decreased. Furthermore, the impact of PLDs or other multimeric cGMP analogues on PKG isoforms Iβ and II had not been studied before. In a quest to discover multimeric cGMP analogues, that would give similar results on PKG Iβ and/or PKG II, optionally with additional PKG Iα and/or CNGC interaction, a corresponding PLD (with a PEG 2000 Da spacer) was synthesized as part of the invention (PET-cGMP-8-TMAmd-(PEG pd 2000)-AmdMT-8-cGMP-PET, Table 13, compound 13). Said compound features an amide—instead of the reported sulfonyl coupling function as well as an additional β-phenyl-1, $N^2$-etheno (PET) function at both nucleobases. Unexpectedly, the PKG Iβ activation potential determined for this new PLD is the strongest so far observed (≥1735-fold activity of cGMP) while PKG II is rather poorly activated (2.5-fold activity of cGMP). Very surprisingly and contrary to previously reported results of the comparable sulfonyl coupled PLD[5], where superior PKG Iα activation disappeared at this spacer length, this compound not only causes increased PKG Iα activation but the effect is also more than 4-fold greater (≥140-fold potential of cGMP) as determined for the best PLD agonist (PEG-spacer of 282 Da) described before.

PKG activation values of the compounds of the invention are expressed as multiple of the cGMP activation with the cGMP activation value set as 1 for each isozyme. It has to be noted, that the applied standard assay conditions only allowed to determine increased activation potencies of up to 140-fold for PKG Iα, 2832-fold for PKG Iβ and 408-fold for PKG II, which is due to the employed enzyme concentration in the assays and the phenomenon that the isozymes were activity-titrated in some cases by the highly active compounds of the invention. The actual PKG activation potentials of these particular compounds of the invention appear to be significantly higher and are therefore expressed as ≥140-fold for PKG Iα, ≥2832-fold for PKG Iβ and ≥408-fold for PKG II.

Very surprisingly, for the analogue of compound 13 lacking the PET moiety (cGMP-8-TMAmd-(PEG pd 2000)-AmdMT-8-cGMP, Table 13, compound 10) the relative enhancement of PKG isoform activity (compared to cGMP) is almost the other way around. Thus it features the so far strongest reported PKG II activation potential (243-fold activity of cGMP) but shows a far less pronounced enhancement on relative PKG Iα and 1B activation (37-fold and 69-fold activity of cGMP). Accordingly, nucleobase manipulation of PLDs and/or variation of the coupling function, which both has not been studied before, surprisingly, overrules the so far proposed target selectivity induced by spacer length.[8][5] In particular, variations at $R_4$ and/or $R_5$ (such as the PET moiety) and/or exchange of the sulfonyl coupling function, which overlaps with modifications of the $R_1$ moiety, have a very significant impact on PKG activation. This was especially surprising and not foreseeable, as the monomeric precursors of the two PLD compounds, 8-Br-PET-cGMP and 8-Br-cGMP, differing only in the PET moiety, at least with respect to their PKG Iα and II activatory potential are very alike.[2] Yet, as described above, when coupled to a PLD, their PKG activation profile differs significantly. Accordingly, the PKG isoform activation profile of the PLD so far cannot be predicted from the one determined for the corresponding monomers. However, as described above, structural modifications were found to be essential parameters to estimate and manipulate the increasing effects of PLDs on relative PKG isoform activation.

PLDs of the present invention feature a variety of different spacer lengths, as the results described above were also reproduced with homologues PLDs. For instance shorter spacers (19 and 8 ethylene glycol units (-(EO)$_{19}$— and -(EO)$_8$—), see Table 13, compounds 12, 5, 8, 3) gave similar results, wherein in several cases the PKG enzyme was titrated (FIG. 3). As mentioned above, a titrated enzyme corresponds to a value beyond the measurement limit, indicating a very strong activation potential. The substantial major effect of nucleobase manipulation, in particular $R_4/R_5$ substitution, can again be observed by comparing for instance compounds 3 and 5 (FIG. 3). Therein compound 3 is identical to 5 but lacks the PET moiety. It gives a more than 51-fold decreased relative PKG Iβ activation compared to compound 5, while relative PKG II activation in turn is increased by a factor of 30. Thus, the described enhancing effect of $R_4/R_5$ transformations on relative PKG isoform activation is not restricted to a particular spacer length.

Furthermore, the present invention comprises PLDs containing standard coupling moieties other than amide groups, as the superior activity of new PLDs according to the invention is not limited to this particular type of coupling function. Dimers linked via a triazole group (e.g. compound 23 with ≥2832-fold activity of cGMP for PKG Iβ, also see FIG. 4) or featuring no additional coupling function besides the thio ether group directly connected to the nucleobase (e.g. compound 1 with 231-fold activity of cGMP for PKG II), as two random non limiting examples of the present invention, gave comparable results. Both of these optional coupling strategies as well as amide type of coupling in addition avoid regiochemical issues during synthesis, proofed to be beneficially robust and provided beneficially high yields. Furthermore, all tested PLDs linked via the $R_1$ position at all tested spacer lengths, wherein $R_4$ is absent and $R_5$ is $NH_2$ (according to formula III), were highly potent activators of PKG II.

Another structural aspect of PLDs according to the invention concerns the linkage position at which the two cGMP analogues are coupled to each other. The observed activity enhancement of PLDs is not restricted to linkage via the $R_1$ position. It is still present, when linkage is varied along the G unit. Thus, as a non limiting example, PLDs coupled via the PET-moiety (at $R_4+R_5$), displayed a similarly increased PKG agonist potential as PET-substituted derivatives tethered via the $R_1$-position (compound 6 and 23, FIG. 4). Accordingly PLDs of the invention comprise a variety of possible linking positions as defined further above.

The nature of the spacer moiety is another motive that affects PLD induced PKG activation. PEG (spacer) units used on the PLD derivatives mentioned so far, can be replaced by or combined with other functionalities such as peptides or alkanes, included in the present invention. Alkanes in particular, however, are restricted in size, as solubility decreases significantly with growing alkyl spacer length. Still alkyl spacers with moderate size (compounds 16, 19 and 21 as non limiting examples of the present invention) are tolerated with respect to maintaining sufficient water solubility. In addition a PKG activation screening performed with compound 16 indicated that such compounds can show an activity increasing effect (PKG II activation approx. 22-fold higher than for cGMP). This effect is less pronounced than for derivatives linked via PEG-spacers but alkyl chain tethered PLDs benefit from increased lipophilicity, which should support better cell permeability. Hence, making them useful tools for biochemical assays and for pharmacological applications.

As stated above, previously established and supported by the work of the inventors linkage to a second cGMP analogue unit appears to be essential to obtain significantly enhanced PKG activation. Moreover, prior to this invention just one type of PLD (FIG. 1) had been studied and its increased activation of PKG (tested only for the Iα isoform) was proposed to be connected to a simultaneous binding to homologous sites at two different PKG subunits (reasoned by the rather short observed optimal spacer length).[5] It was thus not foreseeable, that mixed (heterogenous) PLDs of the invention, featuring two unequal G units (e.g. containing one PET-cGMP unit and one that lacks the PET moiety, e.g. compound 11) with different binding affinities would give a PKG (isoform) activation profile, that to a large extend resembles the characteristics of both G units in their corresponding homogenous PLDs (in the exemplary case compound 12 and 8, FIG. 5). Mixed PLDs of the invention that additionally contain mixed linking positions (e.g. PET-cGMP analogue unit linked via the $R_4+R_5$-PET-moiety and unit lacking the PET-moiety linked via the $R_1$-position, e.g. 22) behaved similarly (FIG. 5). The latter non limiting example of mixed PLDs compound 22, which can be seen as a hybrid of the homogenous PLDs 6 and 18, particularly demonstrates the implied potential of mixed PLDs. Therein, compound 18 is a strong activator of PKG II (381-fold activity of cGMP) while 6 shows virtually no increased effect on this isoform (1.3-fold activity of cGMP). Even though 6 or this type of G unit respectively therefore appears to be unable to contribute to PKG II activation, the mixed PLD hybrid 22 still is a very strong activator of PKG II (194-fold activity of cGMP). These surprising results indicate, that linkage to a second cGMP (analogue) is required to obtain strongly enhanced PKG activity, the second G unit, however, does not necessarily need to be of the same kind. As described, the second G unit can even be a significantly less effective activator of PKG (observed for the respective homogenous PLD) while the superior PKG activation of the first G unit (again observed for the respective homogenous PLD) is substantially preserved within the mixed PLD hybrid.

These unexpected findings reveal another new great potential of (mixed) PLDs. As stated above, established effector compounds often need to be derivatized for specific biochemical applications. For instance, introduction of a fluorescent dye, to enable intracellular localization by means of microscopic or spectroscopic techniques, is a very common strategy. In order to obtain representative results, ideally such transformations, meant to facilitate assay read out, should have no impact on the target activation profile. However, these structural manipulations of the original compound frequently do result in a significant shift of target affinity and specificity or even loss of activation potential. This is especially the case, when the particular functionality can only be introduced at a pharmacophoric group or when it inhibits or weakens binding to the target protein due to steric hindrance. For applications that benefit from the use of multiple target compounds, in turn, a change in (or extension of) the target activation profile obviously can also be desirable. Developing a multi target compound, though, sometimes can be just as difficult as producing a target specific one. This is the case, whenever a modification, needed to address one target, inhibits binding to the second. Mixed PLDs as disclosed within the present invention, provide an improved solution to both of these problems. Their advantage springs from the fact, that two cGMP units (instead of one for monomers) contribute to the overall PKG activation profile. As described above, even such modifications, that would give a completely different target affinity (observed for the monomer or the homogeneous PLD), do not erase the enhanced activation characteristics of the parent compound, as long as they are performed at only one cGMP unit. In this respect, the effect of structural manipulation at a single cGMP unit is buffered within mixed PLDs. Thus, mixed PLDs allow a much broader diversity of modifications (at one cGMP unit), while the undesired decrease of PKG activation, caused by these modifications, is much less pronounced if present at all. On the other hand, mixed PLDs also support the design of multi target compounds. Functional groups (e.g., PET-group), intended to address different targets (e.g. different PKG isoform) apparently can be installed at one cGMP unit, giving an extended target activation spectrum of the mixed PLD.

The present invention also comprises the extension of the described concept of polymer linked cGMP analogues from dimers to tri- and tetramers. Therein linkage of the particular G units is accomplished either in a linear or branched fashion (see formula I and II). Compounds 14 and (Table 13) are two non limiting examples of the latter case, featuring particularly strong PKG II activation as predicted from analogues PLD derivatives lacking the PET-moiety (≥416-fold activity of cGMP for compound 14). The increased number of G units within tri- and tetramers results in even more diverse opportunities to combine (different) activator and target independent functionalized G units. While dimeric analogues only allow linkage of an activator G unit to either another one or a target independent functionalized G unit, for tri- and tetramers both can be provided within a single compound. Accordingly, compared to PLDs, they offer a broader scope of applications.

In summary the present invention has established the first activators of PKG Iβ and PKG II with PLM structure, which are furthermore significantly improved when compared to state of the art compounds. Among the new PLM are also derivatives, which in addition activate PKG Iα, and mixed PLM, which amongst others are beneficial for functionalization and/or addressing all three PKG isoforms. Nucleobase modifications at $R_4/R_5$ and $R_1$ position as a key part of the invention, thereby proved to be powerful modifiers of PKG activation potential. These modifications were shown herein to be able to exceed and overrule the effect of varying spacer lengths, which before was suggested to be the main effector of target selectivity and activity increase (compared to the monomer).[5, 8] As an exemplary embodiment of the present invention, PLMs coupled via the $R_1$ position, which overlaps with a nucleobase modification at $R_1$, wherein in addition $R_4$ is absent and $R_5$ is $NH_2$ (according to formula III), were found to feature strongly increased PKG II activation potential (compared to the monomer). Prior art PLD compounds[5] (see FIG. 1) also fall under the scope of this general structural paradigm, however, only by coincidence, and are expressively disclaimed from the present invention. Their appearance in the art was connected to a different question, wherein a different target (PKG Iα and CNGC) was addressed and the crucial role of a different modifier (spacer length instead of nucleobase modification) was concluded. The new PLM compounds of the present invention, furthermore differ in and benefit from improved synthetic coupling strategies. Prior art synthetic protocol for PLDs involved coupling of a thiol-group in the 8-($R_1$) position with a bifunctional PEG vinylsulfone.[5] The reported conditions, as published later[7] and in accordance with our own experience, however, favour addition at the 7-($R_2$) instead of the 8-($R_1$)position. To replace the insufficient coupling strategy of prior art, various more robust, regioselective and higher yielding methods were developed for the present invention, involving for instance peptide (amid)- and click chemistry.

To test the effect of the new PKG activators of the invention in a cellular system, the 661W cell line was used and increase in cell death after treatment was assessed (for more details see examples section). The 661W cell line is a photoreceptor precursor cell line, which expresses PKG (FIG. 6). This makes them a suitable model for examining PKG activity using cell death as readout since increased PKG activity was previously associated with increased cell death.[9] Results were compared to untreated cells and to incubation with 8-Br-PET-cGMP as reference. 8-Br-PET-cGMP is a well established commercially available PKG activator, which has been applied in various cellular systems and is furthermore a synthetic precursor of some of the exemplary PLDs of the invention. All 12 exemplary tested PLDs led to increased cell death at one or more concentrations when compared to untreated cells as well as the reference compound 8-Br-PET-cGMP (FIG. 7). Therein the most potent PLDs of the invention display a 5-6 fold increase in cell death when compared to untreated cells and 3-4 fold increase in cell death when compared to the reference 8-Br-PET-cGMP.

Compounds that are selected based on effects on 661W cells are promising tools for research studies on the intracellular signaling pathways mediated by cGMP. Such studies should not be restricted to retinal cells but also include other cell lines sensitive to changes in cGMP levels or activating cGMP targets.[10]

The present invention as summarized above and defined in the claims, which are particularly incorporated into this description by reference in their entirety, shall be exemplified in the following in more detail by preferred embodiments.

Preferred Compounds According to the Invention

According the invention it is preferred that R1 is selected from group consisting of H, halogen, azido, nitro, alkyl, acyl, aryl, OH, O-alkyl, O-aryl, SH, S-alkyl, S-aryl, S-aralkyl, S(O)-alkyl, S(O)-aryl, S(O)-aralkyl, S(O)-benzyl, S(O)$_2$-alkyl, S(O)$_2$-aryl, S(O)$_2$-aralkyl, amino, NH-alkyl, NH-aryl, NH-aralkyl, NR9R10, SiR13R14R15 wherein R9, R10, R13, R14, R15 are alkyl.

According to the invention it is further preferred that R1 is selected from the group consisting of H, Cl, Br, I, F, N$_3$, NO$_2$, OH, SH, NH$_2$, CF$_3$, 2-furyl, 3-furyl, 2-bromo-5-furyl, (2-furyl)thio, (3-(2-methyl)furyl)thio, (3-furyl)thio, 2-thienyl, 3-thienyl, (5-(1-methyl)tetrazolyl)thio, 1,1,2-trifluoro-1-butenthio, (2-(4-phenyl)imidazolyl)thio, (2-benzothiazolyl)thio, (2,6-dichlorophenoxypropyl)thio, 2-(N-(7-nitrobenz-2-oxa-1,3-diazol-4-yl)amino)ethylthio, (4-bromo-2,3-dioxobutyl)thio, [2-[(fluoresceinylthioureido)amino]ethyl]thio, 2,3,5,6-tetrafluorophenylthio, (7-(4-methyl)coumarinyl)thio, (4-(7-methoxy)coumarinyl)thio, (2-naphtyl)thio, (2-(1-bromo)naphtyl)thio, benzimidazolyl-2-thiobenzothiazolylthio, 4-pyridyl, (4-pyridyl)thio, 2-pyridylthio, 5-amino-3-oxopentylamino, 8-amino-3,6-dioxaoctylamino, 19-amino-4,7,10,13,16-pentaoxanonadecylamino, 17-amino-9-aza-heptadecylamino, 4-(N-methyl anthranoyl)aminobutyl amino, dimethylamino, diethylamino, 4-morpholino, 1-piperidino, 1-piperazino, triphenyliminophosphoranyl or as depicted in Table 2.

TABLE 2

Residue R$_1$.

| Entry | Residue |
|---|---|
| 1 | 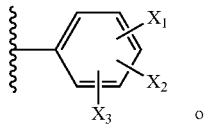 or 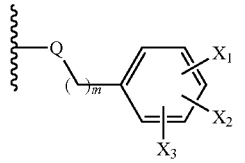 or 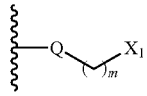 | wherein
m = 0-6.
Q = S, S(O), S(O)$_2$, O, NH, Se, CH$_2$, C(O).
X$_1$, X$_2$ and X$_3$ can be equal or independently be H, OH, NH$_2$, N$_3$, SH, CN, NO$_2$, F, Cl, Br, I, (CH$_2$)$_n$CH$_3$ (with n = 0-5), i-Pr, t-Bu, (CH$_2$)$_n$C≡CH (with n = 0-5), (CH$_2$)$_n$C=CH$_2$ (with n = 0-5), CH$_2$OH, (CH$_2$)$_n$OCH$_3$ (with n = 1-2), CH$_2$N(CH$_3$)$_2$, O(CH$_2$)$_n$CH$_3$ (with n = 0-5), Oi-Pr, OCy, OCyp, OBn, OC(O)CH$_3$, OC(O)Ph, OCF$_3$, N(CH$_3$)$_2$, NH(CH$_2$)$_n$CH$_3$ (with n = 0-5), NHC(O)t-Bu, NHC(O)Ph, NHC(O)Ot-Bu, NHC(O)CH$_3$, NHC(O)CH$_2$N$_3$, B(OH)$_2$, CF$_3$, C(O)OH, C(O)OCH$_3$, C(O)Oi-Pr, C(O)Ot-Bu, C(O)OPh, C(O)OBn, C(O)NH$_2$, C(O)N(CH$_3$)$_2$, C(O)NHPh, C(O)NHBn, C(O)CF$_3$, CH$_2$C(O)OH, CH$_2$C(O)OCH$_3$, CH$_2$C(O)Oi-Pr, CH$_2$C(O)Ot-Bu, CH$_2$C(O)OBn, S(CH$_2$)$_n$CH$_3$ (with n = 0-5), S(CH$_2$)$_n$OEt (with n = 1-4), SBn, SO$_2$CH$_3$, SO$_2$CF$_3$,

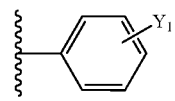

(with Y$_1$ = H, SH, CN, Ph, F, CH$_3$, OCH$_3$, SCH$_3$, 4-thiophenyl, NO$_2$, pentyl),

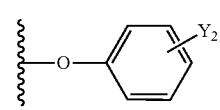

(with Y$_2$ = H, SH, F),

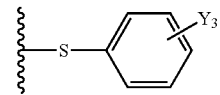

(with Y$_3$ = H, SH),

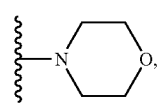

TABLE 2-continued

Residue R$_1$.

| Entry | Residue |
|---|---|
| 2 | 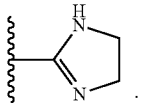 or 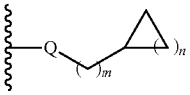<br>wherein<br>m = 0-6.<br>n = 1-6.<br>Q = S, S(O), S(O)$_2$, O, NH, Se. |

According to the invention it is especially preferred that R1 is selected from the group consisting of H, Cl, Br, I, F, N$_3$, NO$_2$, OH, SH, NH$_2$, CF$_3$, 2-furyl, 3-furyl, (2-furyl)thio, (3-(2-methyl)furyl)thio, (3-furyl)thio, 2-thienyl, 3-thienyl, (5-(1-methyl)tetrazolyl)thio, 1,1,2-trifluoro-1-butenthio, (2-(4-phenyl)imidazolyl)thio, (2-benzothiazolyl)thio, (2,6-dichlorophenoxypropyl)thio, 2-(N-(7-nitrobenz-2-oxa-1,3-diazol-4-yl)amino)ethylthio, (4-bromo-2,3-dioxobutyl)thio, [2-[(fluoresceinylthioureido)amino]ethyl]thio, 2,3,5,6-tetrafluorophenylthio, (7-(4-methyl)coumarinyl)thio, (4-(7-methoxy)coumarinyl)thio, (2-naphtyl)thio, (2-(1-bromo)naphtyl)thio, benzimidazolyl-2-thio, benzothiazolylthio, 4-pyridyl, (4-pyridyl)thio, 2-pyridylthio, 5-amino-3-oxopentylamino, 8-amino-3,6-dioxaoctylamino, 19-amino-4,7,10,13,16-pentaoxanonadecylamino, 17-amino-9-aza-heptadecylamino, 4-(N-methylanthranoyl)aminobutylamino, dimethylamino, diethylamino, 4-morpholino, 1-piperidino, 1-piperazino, triphenyliminophosphoranyl or as depicted in Table 3.

TABLE 3

Residue R$_1$.

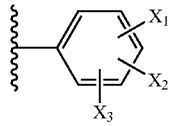 or

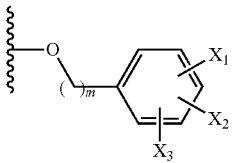 or

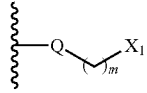

wherein
m = 0-6.
Q = S, S(O), S(O)$_2$, NH.
X$_1$, X$_2$ and X$_3$ can be equal or independently be H, OH, NH$_2$, N$_3$, SH, CN, NO$_2$, F, Cl, Br, I, (CH$_2$)$_n$CH$_3$ (with n = 0-5), i-Pr, t-Bu, Ph, (CH$_2$)$_n$C≡CH (with n = 0-5), (CH$_2$)$_n$C═CH$_2$ (with n = 0-5), CH$_2$OH, (CH$_2$)$_n$OCH$_3$ (with n = 1-2), CH$_2$N(CH$_3$)$_2$, O(CH$_2$)$_n$CH$_3$ (with n = 0-5), Oi-Pr, OCy, OCyp, OPh, OBn, OC(O)CH$_3$, OC(O)Ph, OCF$_3$, N(CH$_3$)$_2$, NH(CH$_2$)$_n$CH$_3$ (with n = 0-5), NHC(O)t-Bu, NHC(O)Ph, NHC(O)Ot-Bu, NHC(O)CH$_3$, NHC(O)CH$_2$N$_3$, B(OH)$_2$, CF$_3$, C(O)OH, C(O)OCH$_3$, C(O)Oi-Pr, C(O)Ot-Bu, C(O)OPh, C(O)OBn, C(O)NH$_2$, C(O)N(CH$_3$)$_2$, C(O)NHPh, C(O)NHBn, C(O)CF$_3$, CH$_2$C(O)OH, CH$_2$C(O)OCH$_3$, CH$_2$C(O)Oi-Pr, CH$_2$C(O)Ot-Bu, CH$_2$C(O)OBn, S(CH$_2$)$_n$CH$_3$ (with n = 0-5), S(CH$_2$)$_n$OEt (with n = 1-4), SBn, SPh,

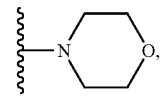

TABLE 3-continued

Residue $R_1$.

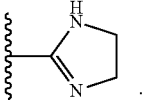

or

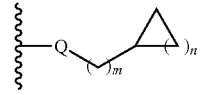

wherein
m = 0-6.
n = 1-6.
Q = S, S(O), S(O)$_2$, NH.

According to the invention it is even more preferred that R1 is selected from the group consisting of H, Cl, Br, SH, 2-furyl, 3-furyl, (2-furyl)thio, (3-(2-methyl)furyl)thio, (3-furyl)thio, 2-thienyl, 3-thienyl, (5-(1-methyl)tetrazolyl)thio, 1,1,2-tri fluoro-1-butenthio, (2-(4-phenyl)imidazolyl)thio, (2-benzothiazolyl)thio, (2,6-dichlorophenoxypropyl)thio, 2-(N-(7-nitrobenz-2-oxa-1,3-diazol-4-yl)amino)ethylthio, (4-bromo-2,3-dioxobutyl)thio, [2-[(fluoresceinylthioureido)amino]ethyl]thio, 2,3,5,6-tetrafluorophenylthio, (7-(4-methyl)coumarinyl)thio, (4-(7-methoxy)coumarinyl)thio, (2-naphtyl)thio, (2-(1-bromo)naphtyl)thio, benzimidazolyl-2-thio, benzothiazolylthio, 4-pyridyl, (4-pyridyl)thio, 2-pyridylthio, triphenyliminophosphoranyl or as depicted in Table 4.

TABLE 4

Residue $R_1$.

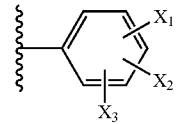

or

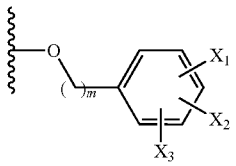

or

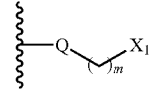

wherein
m = 0-3.
Q = S.
$X_1$, $X_2$ and $X_3$ can be equal or independently be H, OH, NH$_2$, N$_3$, SH, CN, NO$_2$, F, Cl, Br, I, (CH$_2$)$_n$CH$_3$ (with n = 0-5), i-Pr, t-Bu, Ph, (CH$_2$)$_n$C≡CH (with n = 0-5), (CH$_2$)$_n$C═CH$_2$ (with n = 0-5), CH$_2$OH, (CH$_2$)$_n$OCH$_3$ (with n = 1-2), CH$_2$N(CH$_3$)$_2$, O(CH$_2$)$_n$CH$_3$ (with n = 0-5), Oi-Pr, OCy, OCyp, OPh, OBn, OC(O)CH$_3$, OC(O)Ph, OCF$_3$, N(CH$_3$)$_2$, NH(CH$_2$)$_n$CH$_3$ (with n = 0-5), NHC(O)t-Bu, NHC(O)Ph, NHC(O)Ot-Bu, NHC(O)CH$_3$, NHC(O)CH$_2$N$_3$, B(OH)$_2$, CF$_3$, C(O)OH, C(O)OCH$_3$, C(O)Oi-Pr, C(O)Ot-Bu, C(O)OPh, C(O)OBn, C(O)NH$_2$, C(O)N(CH$_3$)$_2$, C(O)NHPh, C(O)NHBn, C(O)CF$_3$, CH$_2$C(O)OH, CH$_2$C(O)OCH$_3$, CH$_2$C(O)Oi-Pr, CH$_2$C(O)Ot-Bu, CH$_2$C(O)OBn, S(CH$_2$)$_n$CH$_3$ (with n = 0-5), S(CH$_2$)$_n$OEt (with n = 1-4), SBn, SPh,

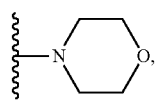 [SMILES: *N1CCOCC1]

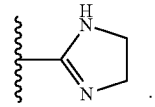

TABLE 4-continued

Residue $R_1$.

or

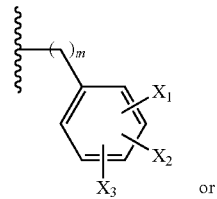

wherein
m = 0-6.
n = 1-6.
Q = S.

In addition to the above or independent to the above it is preferred that according the invention that R4 is selected from group consisting of H, amino, alkyl, aralkyl, nitro, N-oxide or R4 can form together with Y and $R_5$ and the carbon bridging Y and $R_5$ an imidazole ring which can be unsubstituted or substituted with alkyl, aryl or aralkyl, or can form together with Y and $R_5$ and the carbon bridging Y and $R_5$ an imidazolinone as depicted above (structure IV, V, n=1) or an homologous ring (n=2 to 8) which each can be unsubstituted or substituted (not depicted) with alkyl, aryl or aralkyl.

According to the invention it is further preferred that R4 is absent or selected from the group consisting of amino, N-oxide or as depicted in Table 5.

TABLE 5

Residue $R_4$.

| Entry | Residue |
|---|---|
| 1 | 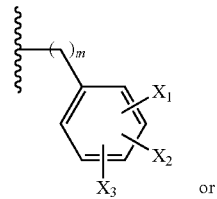 or | wherein
m = 1-6.
$X_1$, $X_2$ and $X_3$ can be equal or independently be H, $N_3$, CN, $NO_2$, F, Cl, Br, I, $(CH_2)_nCH_3$ (with n = 0-5), i-Pr, t-Bu, $(CH_2)_nC\equiv CH$ (with n = 0-5), $(CH_2)_nC=CH_2$ (with n = 0-5), $(CH_2)_nOCH_3$ (with n = 1-2), $CH_2N(CH_3)_2$, $O(CH_2)_nCH_3$ (with n = 0-5), Oi-Pr, OBn, OC(O)$CH_3$, OC(O)Ph, $OCF_3$, $N(CH_3)_2$, NHC(O)t-Bu, NHC(O)Ph, NHC(O)Ot-Bu, NHC(O)$CH_3$, NHC(O)$CH_2N_3$, $CF_3$, C(O)O$CH_3$, C(O)Oi-Pr, C(O)Ot-Bu, C(O)OPh, C(O)OBn, C(O)$NH_2$, C(O)N(CH$_3$)$_2$, C(O)NHPh, C(O)NHBn, C(O)$CF_3$, $CH_2$C(O)O$CH_3$, $CH_2$C(O)Oi-Pr, $CH_2$C(O)Ot-Bu, $CH_2$C(O)OBn, S(CH$_2$)$_n$CH$_3$ (with n = 0-5), S(CH$_2$)$_n$OEt (with n = 1-4), SBn, SPh, $SO_2CF_3$,

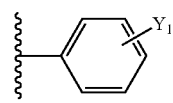

(with $Y_1$ = H, CN, Ph, F, $CH_3$, $OCH_3$, $SCH_3$, $NO_2$, pentyl),

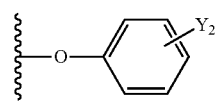

(with $Y_2$ = H, F),

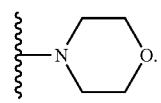

TABLE 5-continued

Residue R$_4$.

| Entry | Residue |
|---|---|

2 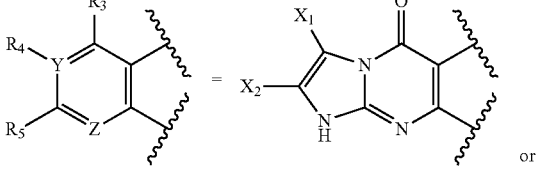 = 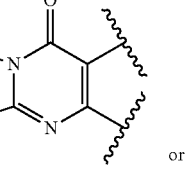 or

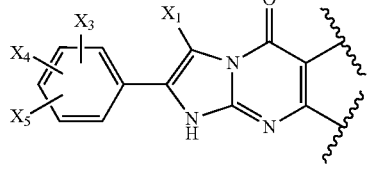

wherein
X$_1$ can be H, CH$_3$, Ph.
X$_2$ can be H, Ph, 2-naphtyl, 9-phenanthryl, 1-pyrenyl, 2,3-dihydro-1,4-benzodioxin-6-yl, dibenzo[b,d]furan-2-yl, 2,3-dihydro-1-benzofuran-5-yl, 1-benzothien-5-yl, 1-benzofuran-5-yl, cycopropyl, 1-adamantyl, C(Ph)$_3$, 2-thienyl, 3-chloro-2-thienyl, 3-thienyl, 1,3-thiazol-2-yl, 2-pyridinyl, 5-chloro-2-thienyl, 1-benzofuran-2-yl,
X$_3$, X$_4$ and X$_5$ can independently be H, OH, NH, CH$_3$, Cl, Br, F, CN, N$_3$, CF$_3$, OCF$_3$, NO$_2$, C(O)OH, C(O)OCH$_3$, OCH$_3$, OBn, O-benzoyl, SCH$_3$, t-Bu, N(CH$_3$)$_2$, S-phenyl, Ph, S(O)$_2$CH$_3$, C(O)NH$_2$, NHS(O)$_2$CH$_3$, 3 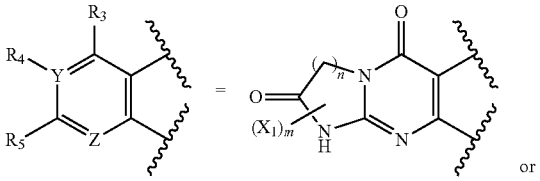 = 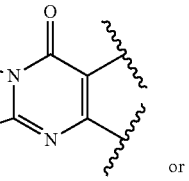 or

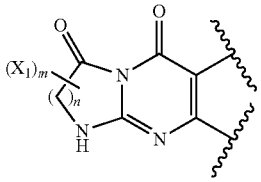

wherein deviating from the definition above, any hydrogen atom attached to any of the ring carbon atoms including depicted, implied, or expressly defined hydrogen, or both hydrogen atoms (m = 2) attached to the same particular carbon atom, can be replaced by one or two (equal) "floating groups" X$_1$ respectively, as long as a stable structure is formed.
while m = 1 or 2.
n = 1-4.
X$_1$ can be H, CH$_3$, Et, Pr, i-Pr, Bu, F, Ph, (CH$_2$)$_2$OH*
*Only for first case.

4 or

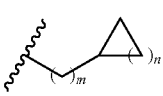

wherein
m = 1-6.
n = 1-6.

According to the invention it is especially preferred that R4 is absent or selected from the group consisting of amino, N-oxide or as depicted in Table 6.

TABLE 6

Residue R₄.

| Entry | Residue |
|---|---|
| 1 | 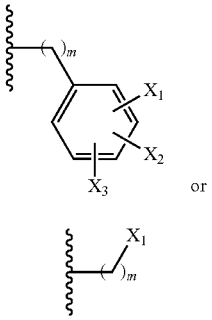 or 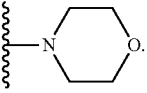<br>wherein<br>m = 1-3.<br>X₁, X₂ and X₃ can be equal or independently be H, N₃, CN, NO₂, F, Cl, Br, I, (CH₂)$_n$CH₃ (with n = 0-5), i-Pr, t-Bu, Ph, (CH₂)$_n$C≡CH (with n = 0-5), (CH₂)$_n$C=CH₂ (with n = 0-5), (CH₂)$_n$OCH₃ (with n = 1-2), CH₂N(CH₃)₂, O(CH₂)$_n$CH₃ (with n = 0-5), Oi-Pr, OPh, OBn, OC(O)CH₃, OC(O)Ph, OCF₃, N(CH₃)₂, NHC(O)t-Bu, NHC(O)Ph, NHC(O)Oy-Bu,NHC(O)CH₃, NHC(O)CH₂N₃, CF₃, C(O)OCH₃, C(O)Oi-Pr, C(O)Ot-Bu, C(O)OPh, C(O)OBn, C(O)NH₂, C(O)N(CH₃)₂, C(O)NHPh, C(O)NHBn, C(O)CF₃, CH₂C(O)OCH₃, CH₂C(O)Oi-Pr, CH₂C(O)Ot-Bu, CH₂C(O)OBn, S(CH₂)$_n$CH₃ (with n = 0-5), S(CH₂)$_n$OEt (with n = 1-4), SBn, SPh, SO₂CF₃,<br>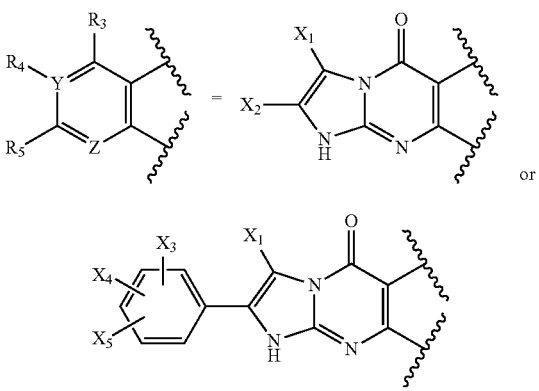 |
| 2 | 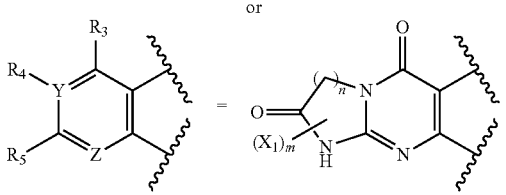<br>wherein<br>X₁ can be H, CH₃, Ph.<br>X₂ can be H, Ph, 2-naphtyl, 9-phenanthryl, 1-pyrenyl, 2,3-dihydro-1,4-benzodioxin-6-yl, dibenzo[b,d]furan-2-yl, 2,3-dihydro-1-benofuran-5-yl, 1-benzothien-5-yl, 1-benzofuran-5-yl, cycopropyl, 1-adamantyl, C(Ph)₃, 2-thienyl, 3-chloro-2-thienyl, 3-thienyl, 1,3-thiazol-2-yl, 2-pyridinyl, 1-benzofuran-2-yl;<br>X₃, X₄ and X₅ can independently be H, OH, NH, CH₃, Cl, Br, F, CN, N₃, CF₃, OCF₃, NO₂, C(O)OH, C(O)OCH₃, OCH₃, OBn, O-benzoyl, SCH₃, t-Bu, N(CH₃)₂, S-phenyl, Ph, S(O)₂CH₃, C(O)NH₂, NHS(O)₂CH₃, |
| 3 | or |

TABLE 6-continued

Residue $R_4$.

| Entry | Residue |
|---|---|
| | wherein deviating from the definition above, any hydrogen atom attached to any of the ring carbon atoms including depicted, implied, or expressly defined hydrogen, or both hydrogen atoms (m = 2) attached to the same particular carbon atom, can be replaced by one or two (equal) "floating groups" $X_1$ respectively, as long as a stable structure is formed.<br>while m = 1 or 2.<br>n = 1-4.<br>$X_1$ can be H, $CH_3$, Et, Pr, i-Pr, Bu, F, Ph, $(CH_2)_2OH$*<br>*Only for first case. |
| 4 | or<br>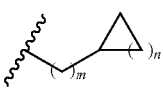<br>wherein<br>m = 1-6.<br>n = 1-6. |

According to the invention it is even more preferred that R4 is absent or as depicted in Table 7.

TABLE 7

Residue $R_4$.

| Entry | Residue |
|---|---|
| 1 | 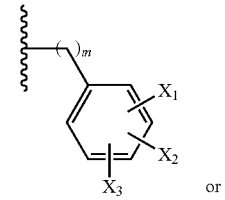 or 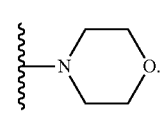<br>wherein<br>m = 1-3.<br>$X_1$, $X_2$ and $X_3$ can be equal or independently be H, $N_3$, CN, $NO_2$, F, Cl, Br, I, $(CH_2)_nCH_3$ (with n = 0-5), i-Pr, t-Bu, Ph, $(CH_2)_nC\equiv CH$ (with n = 0-5), $(CH_2)_nC=CH_2$ (with n = 0-5), $(CH_2)_nOCH_3$ (with n = 1-2), $CH_2N(CH_3)_2$, $O(CH_2)_nCH_3$ (with n = 0-5), Oi-Pr, OPh, OBn, OC(O)$CH_3$, OC(O)Ph, $OCF_3$, N$(CH_3)_2$, NHC(O)t-Bu, NHC(O)Ph, NHC(O)Ot-Bu, NHC(O)$CH_3$, NHC(O)$CH_2N_3$, $CF_3$, C(O)O$CH_3$, C(O)Oi-Pr, C(O)Ot-Bu, C(O)OPh, C(O)OBn, C(O)$NH_2$, C(O)N$(CH_3)_2$, C(O)NHPh, C(O)NHBn, C(O)$CF_3$, $CH_2$C(O)O$CH_3$, $CH_2$C(O)Oi-Pr, $CH_2$C(O)Ot-Bu, $CH_2$C(O)OBn, S$(CH_2)_nCH_3$ (with n = 0-5), S$(CH_2)_n$OEt (with n = 1-4), SBn, SPh, $SO_2CF_3$,<br>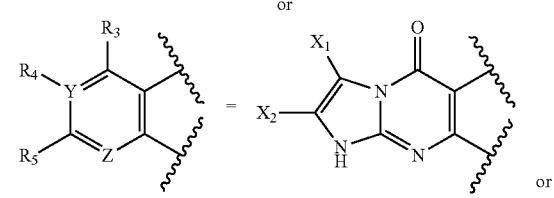 |
| 2 | or<br>(structures) or |

TABLE 7-continued

Residue R$_4$.

| Entry | Residue |
|---|---|
| 3 | 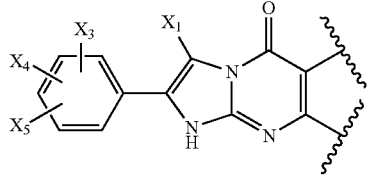<br>wherein<br>X$_1$ can be H, CH$_3$, Ph.<br>X$_2$ can be H, Ph, 2-naphtyl, 9-phenanthryl, 1-pyrenyl, 2,3-dihydro-1,4-benzodioxin-6-yl, dibenzo[b,d]furan-2-yl, 2,3-dihydro-1-benofuran-5-yl, 1-benzothien-5-yl, 1-benzofuran-5-yl, cycopropyl, 1-adamantyl, C(Ph)$_3$, 2-thienyl, 3-chloro-2-thienyl, 3-thienyl, 1,3-thiazol-2-yl, 2-pyridinyl, 1-benzofuran-2-yl;<br>X$_3$, X$_4$ and X$_5$ can independently be H, OH, NH, CH$_3$, Cl, Br, F, CN, N$_3$, CF$_3$, OCF$_3$, NO$_2$, C(O)OH, C(O)OCH$_3$, OCH$_3$, OBn, O-benzoyl, SCH$_3$, t-Bu, N(CH$_3$)$_2$, S-phenyl, Ph, S(O)$_2$CH$_3$, C(O)NH$_2$, NHS(O)$_2$CH$_3$,<br>or |
| 4 | 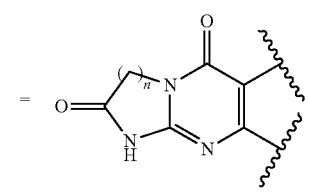<br>wherein<br>n = 1-4.<br>or<br>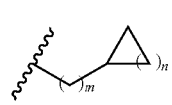<br>wherein<br>m = 1-3.<br>n = 1-6. |

In addition to the above or independent to the above it is preferred that according the invention that R5 is selected from the group consisting of H, halogen, NH-carbamoyl-alkyl, NH-carbamoyl-aryl, NH-carbamoyl-aralkyl, amino, NH-alkyl, NH-aryl, NH-aralkyl, NR30R31 wherein R30 and R31 are alkyl, or can form together with R$_4$, Y and the carbon bridging Y and R$_5$ an imidazole ring which can be unsubstituted or substituted with alkyl, aryl or aralkyl, or can form together with R$_4$, Y and the carbon bridging Y and R$_5$ an imidazolinone ring as depicted above (structure IV, V, n=1) or an homologous ring (n=2 to 8) which each can be unsubstituted or substituted (not depicted) with alkyl, aryl or aralkyl.

According to the invention it is further preferred that R5 is selected from the group consisting of H, NH$_2$, F, Cl, Br, I, methylamino, NH-benzyl, NH-phenyl, NH-4-azidophenyl, NH-phenylethyl, NH-phenylpropyl, 2-aminoethylamino, n-hexylamino, 6-amino-n-hexylamino, 8-amino-3,6-dioxaoctylamino, dimethylamino, 1-piperidino, 1-piperazino or can form together with R$_4$, Y and the carbon bridging Y and R$_5$ a ring system as depicted in Table 5 (entry 2 and 3).

According to the invention it is especially preferred that R5 is selected from the group consisting of H, NH$_2$, F, Cl, Br, I, methylamino, NH-benzyl, NH-phenyl, NH-4-azidophenyl, NH-phenylethyl, NH-phenylpropyl, 2-aminoethylamino, n-hexylamino, 6-amino-n-hexylamino, 8-amino-3,6-dioxaoctylamino, dimethylamino, 1-piperidino, 1-piperazino or can form together with R$_4$, Y and the carbon bridging Y and R$_5$ a ring system as depicted in Table 6 (entry 2 and 3).

According to the invention it is even more preferred that R5 is NH$_2$, or can form together with R$_4$, Y and the carbon bridging Y and R$_5$ a ring system as depicted in Table 7 (entry 2 and 3).

In addition to the above or independent to the above it is preferred that according the invention that R7 is selected from group consisting of OH, O-alkyl, O-aryl, O-aralkyl, O-acyl, SH, S-alkyl, S-aryl, S-aralkyl, borano (BH$_3$), methylborano, dimethylborano, cyanoborano (BH$_2$CN), S-PAP, O-PAP, S-BAP, or O-BAP
  wherein PAP is a photo-activatable protecting group with PAP=o-nitro-benzyl, 1-(o-nitrophenyl)-ethylidene, 4,5-dimethoxy-2-nitro-benzyl, 7-dimethylamino-coumarin-4-yl (DMACM-caged), 7-diethylamino-coumarin-4-yl (DEACM-caged) and 6,7-bis(carboxymethoxy)coumarin-4-yl)methyl (BCMCM-caged).
  and wherein BAP is a bio-activatable protecting group with BAP=methyl, acetoxymethyl, pivaloyloxymethyl, methoxymethyl, propionyloxymethyl, butyryloxymethyl, cyanoethyl, phenyl, benzyl, 4-acetoxybenzyl, 4-pivaloyloxybenzyl, 4-isobutyryloxybenzyl, 4-octanoyloxybenzyl, 4-benzoyloxybenzyl.

According to the invention it is further preferred that R7 is selected from the group consisting of OH, methyloxy, ethyloxy, cyanoethyloxy, acetoxymethyloxy, pivaloyloxymethyloxy, methoxymethyloxy, propionyloxymethyloxy, butyryloxymethyloxy, acetoxyethyloxy, acetoxybutyloxy, acetoxyisobutyloxy, phenyloxy, benzyloxy, 4-acetoxybenzyloxy, 4-pivaloyloxybenzyloxy, 4-isobutyryloxybenzyloxy, 4-octanoyloxybenzyloxy, 4-benzoyloxybenzyloxy, acetyloxy, propionyloxy, benzoyloxy, SH, methylthio, acetoxymethylthio, pivaloyloxymethylthio, methoxymethylthio, propionyloxymethylthio, butyryloxymethylthio, cyanoethylthio, phenylthio, benzylthio, 4-acetoxybenzylthio, 4-pivaloyloxybenzylthio, 4-isobutyryloxybenzylthio, 4-octanoyloxybenzylthio, 4-benzoyloxybenzylthio, borano (BH$_3$), methylborano, dimethylborano, cyanoborano (BH$_2$CN).

According to the invention it is further more preferred that R7 is selected from the group consisting of OH, methyloxy, ethyloxy, cyanoethyloxy, acetoxymethyloxy, pivaloyloxymethyloxy, methoxymethyloxy, propionyloxymethyloxy, butyryloxymethyloxy, acetoxyethyloxy, acetoxybutyloxy, acetoxyisobutyloxy, phenyloxy, benzyloxy, 4-acetoxybenzyloxy, 4-pivaloyloxybenzyloxy, 4-isobutyryloxybenzyloxy, 4-octanoyloxybenzyloxy, 4-benzoyloxybenzyloxy, acetyloxy, propionyloxy, benzoyloxy, SH, methylthio, acetoxymethylthio, pivaloyloxymethylthio, methoxymethylthio, propionyloxymethylthio, butyryloxymethylthio, cyanoethylthio, phenylthio, benzylthio, 4-acetoxybenzylthio, 4-pivaloyloxybenzylthio, 4-isobutyryloxybenzylthio, 4-octanoyloxybenzylthio, 4-benzoyloxybenzylthio.

According to the invention it is even more preferred that R7 is OH.

In addition to the above or independent to the above it is preferred that according the invention that R8 is selected from group consisting of OH, O-alkyl, O-aryl, O-aralkyl, O-acyl, O-PAP or O-BAP,
  wherein PAP is a photo-activatable protecting group with non limiting examples of, optionally, PAP=o-nitrobenzyl, 1-(o-nitrophenyl)-ethylidene, 4,5-dimethoxy-2-nitro-benzyl, 7-dimethylamino-coumarin-4-yl (DMACM-caged), 7-diethylamino-coumarin-4-yl (DEACM-caged) and 6,7-bis(carboxymethoxy)coumarin-4-yl)methyl (BCMCM-caged);
  and wherein BAP is a bio-activatable protecting group with non limiting examples of, optionally, BAP=methyl, acetoxymethyl, pivaloyloxymethyl, methoxymethyl, propionyloxymethyl, butyryloxymethyl, cyanoethyl, phenyl, benzyl, 4-acetoxybenzyl, 4-pivaloyloxybenzyl, 4-isobutyryloxybenzyl, 4-octanoyloxybenzyl, 4-benzoyloxybenzyl;

According to the invention it is further preferred that R8 is selected from the group consisting OH, methyloxy, ethyloxy, cyanoethyloxy, acetoxymethyloxy, pivaloyloxymethyloxy, methoxymethyloxy, propionyloxymethyloxy, butyryloxymethyloxy, acetoxyethyloxy, acetoxybutyloxy, acetoxyisobutyloxy, phenyloxy, benzyloxy, 4-acetoxybenzyloxy, 4-pivaloyloxybenzyloxy, 4-isobutyryloxybenzyloxy, 4-octanoyloxybenzyloxy, 4-benzoyloxybenzyloxy, acetyloxy, propionyloxy, benzoyloxy;

According to the invention it is further even more preferred that R8 is OH.

In addition to the above or independent to the above it is preferred that according the invention residues involved in connecting a G unit with another G unit or a dye or another reporting group can be $R_1$, $R_4$ and/or $R_5$, in which case the particular residue is
  as defined for the preferred embodiment above, wherein an endstanding group is replaced by or transformed to a coupling function
or
selected from the group depicted in Table 8 (wherein if present, Q1 connects to the G unit)

TABLE 8

Residues R1, R4 and R5 involved in connecting a G unit with another G unit or a dye or another reporting group (if present Q$_1$ connects to the G unit).

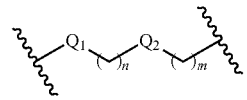

n = 0-6; m = 0-6;
Q1 = absent, S, NH, O;
Q2 = NH, S, O, C(O), CH$_2$, OC(O), NC(O);

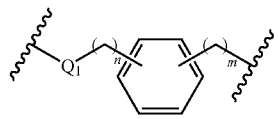

n = 0-4, m = 0-4
Q1 = absent, S, NH, O;

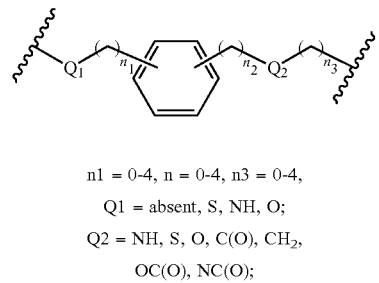

n1 = 0-4, n = 0-4, n3 = 0-4,
Q1 = absent, S, NH, O;
Q2 = NH, S, O, C(O), CH$_2$, OC(O), NC(O);

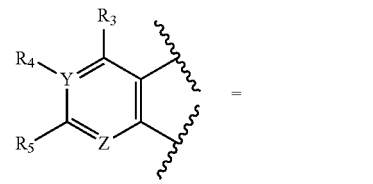

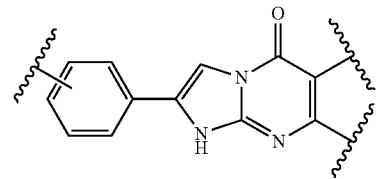

TABLE 8-continued

Residues R1, R4 and R5 involved in connecting a G unit with another G unit or a dye or another reporting group (if present Q₁ connects to the G unit).

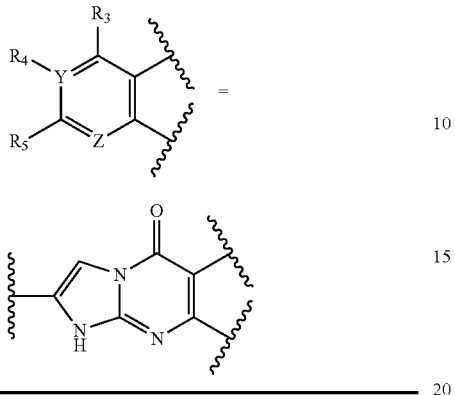

According to the invention it is further preferred that residues involved in connecting a G unit with another G unit or a dye or another reporting group can be $R_1$, $R_4$ and/or $R_5$, in which case the particular residue is
- as defined for its preferred ordinary embodiment, wherein an endstanding group is replaced by or transformed to the coupling function or

- selected from the group depicted in Table 9 (wherein if present, Q1 connects to the G unit)

In addition to the above or independent to the above it is preferred that according the invention that coupling functions ($C^{1-4}$ and $C^{1'-4'}$) are absent or selected from the group depicted in Table 10.

TABLE 10

Coupling functions ($C^{1-4}$ and $C^{1'-4'}$).

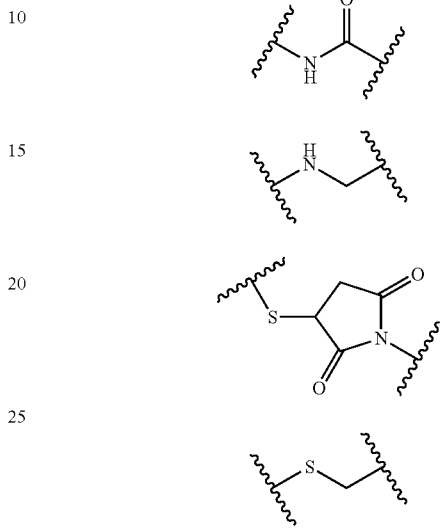

TABLE 9

Residues $R_1$, $R_4$ and $R_5$ involved in connecting a G unit with another G unit or a dye or another reporting group (if present $Q_1$ connects to the G unit)

| $R_1$ | $R_4$ | | $R_4 + R_5$ |
|---|---|---|---|
| n = 0-4, m = 0-4  Q₁ = absent, S; | n = 0-4, m = 0-4 | | = |
| n₁ = 0-4, n₂ = 0-4, n₃ = 0-4, Q₁ = absent (for n₁ = 0), S; Q₂ = NH, S, O, CH₂, NC(O); | n = 0-6, m = 0-6 | | = |
| n = 0-6; m = 0-6; Q1 = S; Q2 = NH, S, O, CH₂, NC(O); | | | |

TABLE 10-continued

Coupling functions ($C^{1-4}$ and $C^{1'-4'}$).

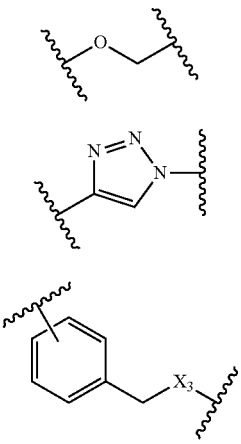

$X_3$ = NH, O, S

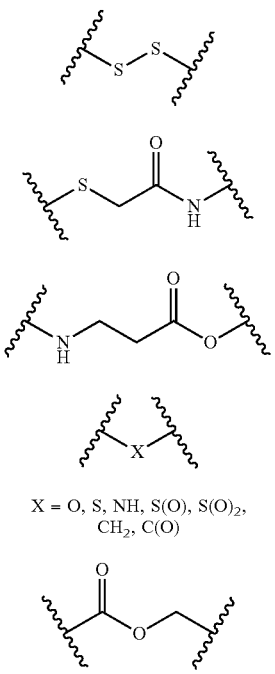

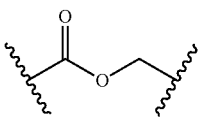 [SMILES: *COC(*)=O]

X = O, S, NH, S(O), S(O)$_2$, CH$_2$, C(O)

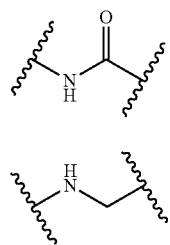

According to the invention it is further preferred that coupling functions ($C^{1-4}$ and $C^{1'-4'}$) are absent or selected from the group depicted in Table 11.

TABLE 11

Coupling functions ($C^{1-4}$ and $C^{1'-4'}$).

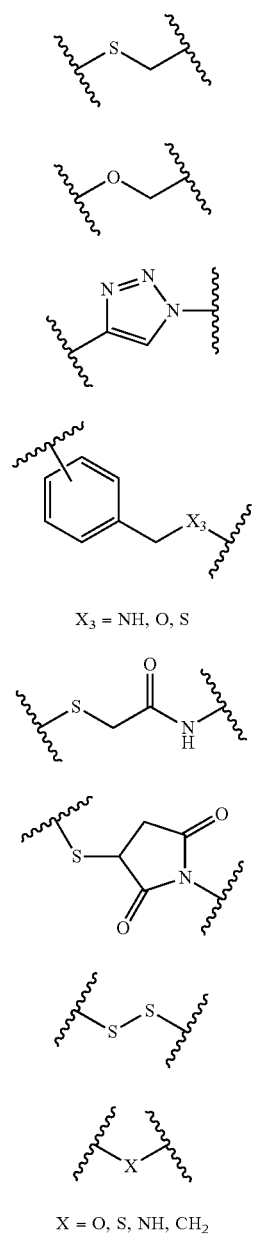

TABLE 11-continued

Coupling functions ($C^{1-4}$ and $C^{1'-4'}$).

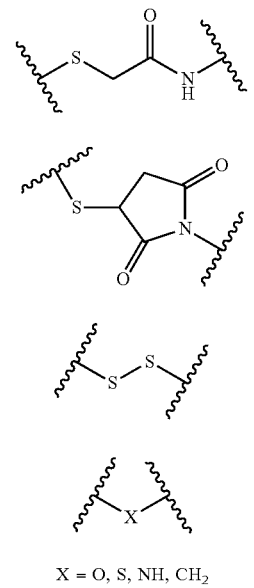

$X_3$ = NH, O, S

X = O, S, NH, CH$_2$

In addition to the above or independent to the above it is preferred that according the invention the linker (L) is absent or selected from the group depicted in Table 12.

TABLE 12

Linker (L).

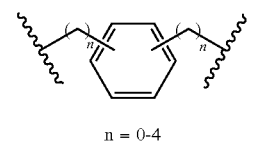

n = 0-4

TABLE 12-continued
Linker (L).
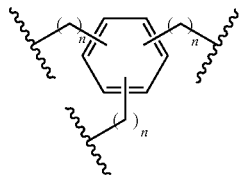
n = 0-4
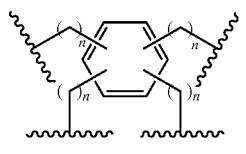
n = 0-4
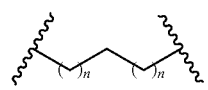
n = 0-6
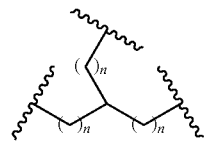
n = 0-12
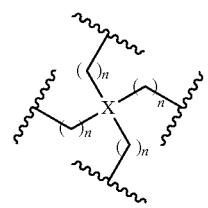
X = C, Si; n = 0-6
or
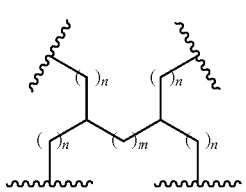
m = 0-24, n = 0-6
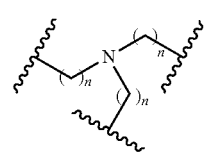
n = 0-6
TABLE 12-continued
Linker (L).
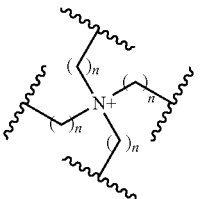
n = 0-6
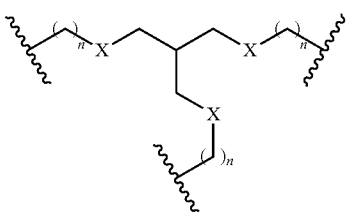
X = O, S; n = 1-4
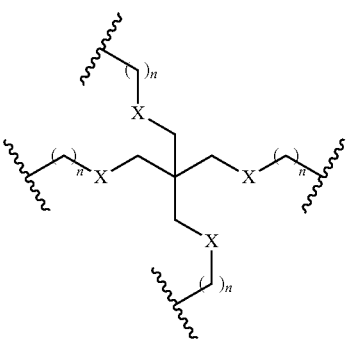
X = O, S; n = 1-4
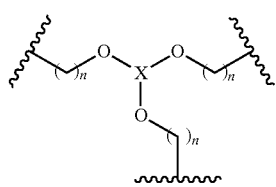
X = B, Si; n = 1-4

TABLE 12-continued

Linker (L).

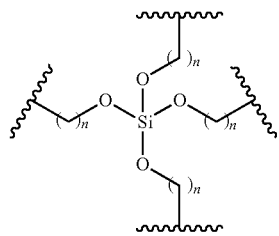

n = 1-4

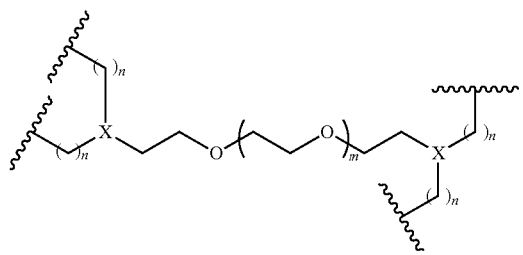

X = N, CH; n = 1-6; m = 0-10

TABLE 12-continued

Linker (L).

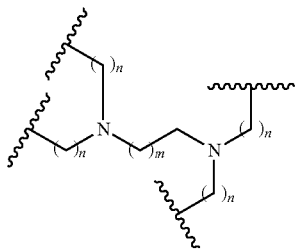

n = 1-6; m = 1-11

While n for each sidechain within a particular linker can have an equal or individual value as defined.

In addition to the above or independent to the above it is preferred that in case of formula (I) according to the invention $G^4$ or $G^4$ and $G^3$ are absent or in case of formula (II) $G^4$ and $LR^4$ or $G^4$, $LR^4$, $G^3$ and $LR^3$ are absent.

According to the invention it is even more preferred that in case of formula (I) $G^4$ and $G^3$ are absent or in case of formula (II) $G^4$, $LR^4$, $G^3$ and $LR^3$ are absent.

Particularly preferred embodiments of the invention based on the above exemplifications, are as defined in anyone of the claims 6, 7, 8 and 9.

Especially preferred according to the invention are the compounds of Table 13, and as defined in claim 10. It has to be noted that in case of doubt the chemical structure as depicted in the formula is the valid one. It further has to be noted, that the compounds of Table 13 are displayed as the free acid. The present invention, however, also comprises salts of these compounds, featuring cations such as but not limited to $Na^+$, $Li^+$, $NH_4^+$, $Et_3NH^+$ and $(i-Pr)_2EtNH^+$.

TABLE 13

Structures of novel compounds according to the invention.

| # | Compound | Structure |
|---|----------|-----------|
| 1 | Guanosine-3',5'-cyclic monophosphate-[8-thio-(pentaethoxy)-ethylthio-8]-guanosine-3',5'-cyclic monophosphate | cGMP-8-T-(EO)5-ET-8-cGMP |
| 2 | Guanosine-3',5'-cyclic monophosphate-[8-thiomethylamidomethyl-(pentaethoxy)-propylamidomethylthio-8]-guanosine-3',5'-cyclic monophosphate | cGMP-8-TMAmdM-(EO)5-PrAmdMT-8-cGMP |

TABLE 13-continued

Structures of novel compounds according to the invention.

| # | Compound | Structure |
|---|---|---|
| 3 | Guanosine-3',5'-cyclic monophosphate-[8-thiomethylamido-(octaethoxy)-ethylamidomethylthio-8]-guanosine-3',5'-cyclic monophosphate | cGMP-8-TMAmd-(EO)$_8$-EAmdMT-8-cGMP 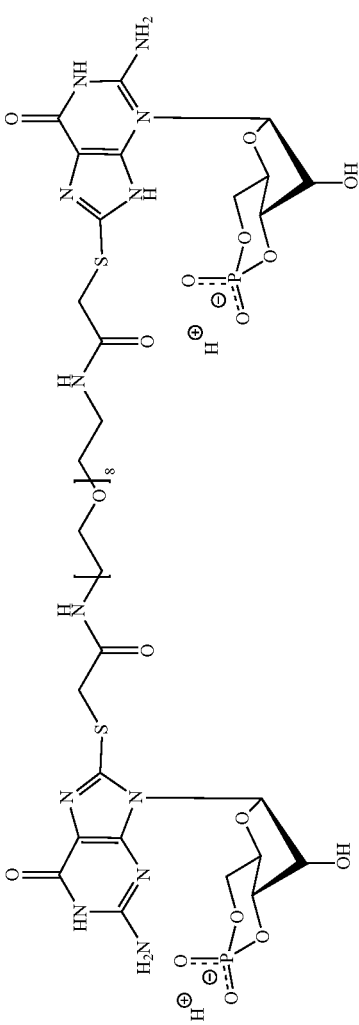 |
| 4 | Guanosine-3',5'-cyclic monophosphate-[8-(4-thiophenylthio)-(pentaethoxy)-ethyl-(4-thiophenylthio)-8]-guanosine-3',5'-cyclic monophosphate | cGMP-8-pTPT-(EO)$_5$-EpTPT-8-cGMP 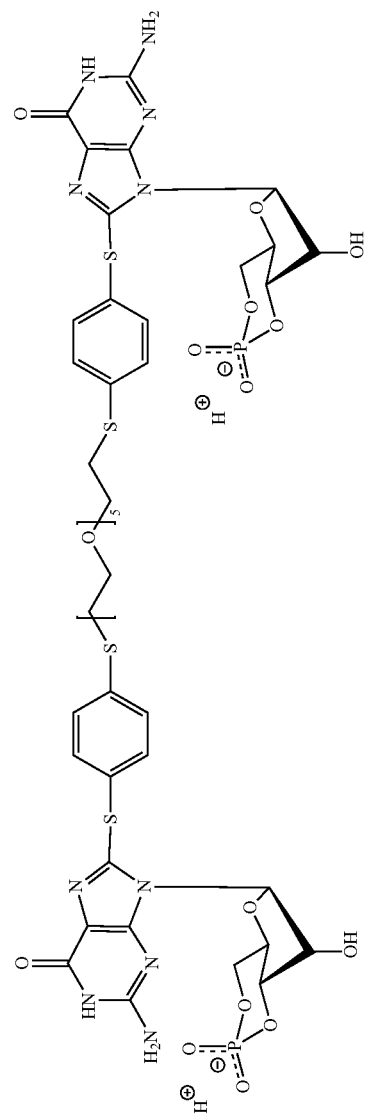 |

TABLE 13-continued

Structures of novel compounds according to the invention.

| # | Compound | Structure |
|---|---|---|
| 5 | β-Phenyl-1, N²-ethenoguanosine-3',5'-cyclic monophosphate-[8-thiomethylamido-(octaethoxy)-ethylamidomethylthio-8]-β-phenyl-1, N²-ethenoguanosine-3',5'-cyclic monophosphate | 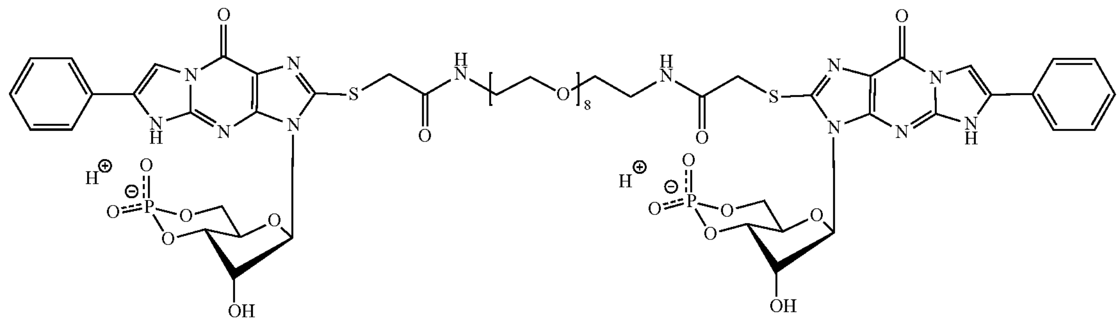 |
| 6 | 8-Bromoguanosine-3',5'-cyclic monophosphate-[1, N²-etheno-β-phenyl-4-yl-(1-[1,2,3]-triazole-4-yl)-methoxy-(hexaethoxy)-methyl-(4-(4-[1,2,3]-triazole-1-yl)-β-phenyl-1, N²-etheno]-8-bromoguanosine-3',5'-cyclic monophosphate | 8-Br-cGMP-ETP-p(1-[1,2,3]-Tz-4)-MeO-(EO)₆-Me-p(4-[1,2,3]-Tz-1)-PET-cGMP-8-Br |

PET-cGMP-8-TMAmd-(EO)₈-EAmdMT-8-cGMP-PET

TABLE 13-continued

Structures of novel compounds according to the invention.

| # | Compound | Structure |
|---|---|---|
| 7 | Guanosine-3',5'-cyclic monophosphate-[8-thiomethylamido-(octaethoxy)-ethylamidomethylthio-8]-β-phenyl-1, N²-ethenoguanosine-3',5'-cyclic monophosphate | cGMP-8-TMAmd-(EO)₈-EAmdMT-8-cGMP-PET |
| 8 | Guanosine-3',5'-cyclic monophosphate-[8-thiomethylamido-(nonadecaethoxy)-ethylamidomethylthio-8]-guanosine-3',5'-cyclic monophosphate | cGMP-8-TMAmd-(EO)₁₉-EAmdMT-8-cGMP |

TABLE 13-continued

Structures of novel compounds according to the invention.

| # | Compound | Structure |
|---|---|---|
| 9 | Guanosine-3′,5′-cyclic monophosphate-[8-(1-[1,2,3]-triazole-4-yl)-methoxy-(hexaethoxy)-methyl-(4-[1,2,3]-triazole-1-yl)-8]-guanosine-3′,5′-cyclic monophosphate | 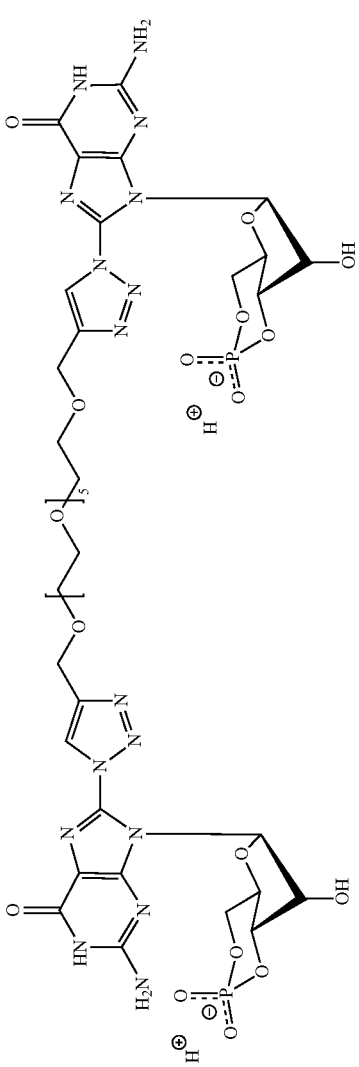 cGMP-8-(1-[1,2,3]-Tz-4)-MeO-(EO)₆-Me-(4-[1,2,3]-Tz-1)-8-cGMP |
| 10 | Guanosine-3′,5′-cyclic monophosphate-[8-thiomethylamido-(PEG pd 2000)-amidomethylthio-8]-guanosine-3′,5′-cyclic monophosphate | 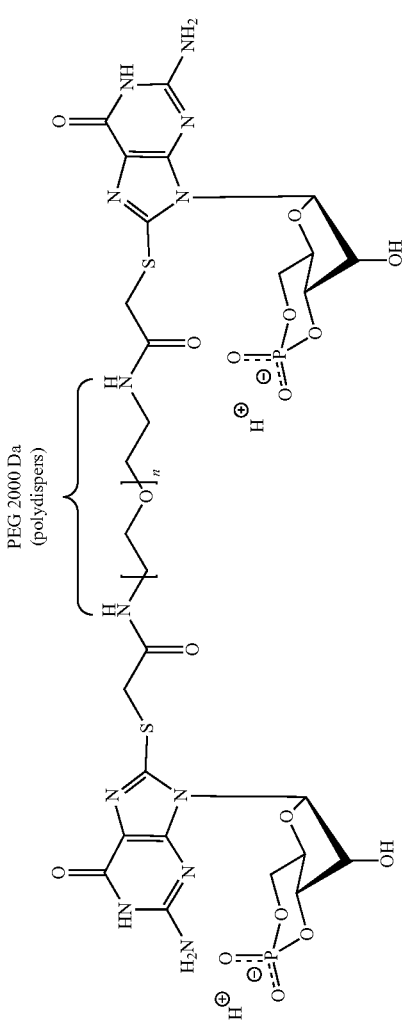 cGMP-8-TMAamd-(PEG pd 2000)-AmdMT-8-cGMP |

TABLE 13-continued

Structures of novel compounds according to the invention.

| # | Compound | Structure |
|---|---|---|
| 11 | β-Phenyl-1, N²-ethenoguanosine-3',5'-cyclic monophosphate-[8-thiomethylamido-(nonadecaethoxy)-ethylamidomethylthio-8]-guanosine-3',5'-cyclic monophosphate | PET-cGMP-8-TMAmd-(EO)₁₉-EAmdMT-8-cGMP |
| 12 | β-Phenyl-1, N²-ethenoguanosine-3',5'-cyclic monophosphate-[8-thiomethylamido-(nonadecaethoxy)-ethylamidomethylthio-8]-β-phenyl-1, N²-ethenoguanosine-3',5'-cyclic monophosphate | PET-cGMP-8-TMAmd-(EO)₁₉-EAmdMT-8-cGMP-PET |

TABLE 13-continued
Structures of novel compounds according to the invention.
| # | Compound | Structure |
|---|----------|-----------|
| 13 | β-Phenyl-1, N²-ethenoguanosine-3',5'-cyclic monophosphate-[8-thiomethylamido-(PEG pd 2000)-amidomethylthio-8]-β-phenyl-1, N²-ethenoguanosine-3',5'-cyclic monophosphate | 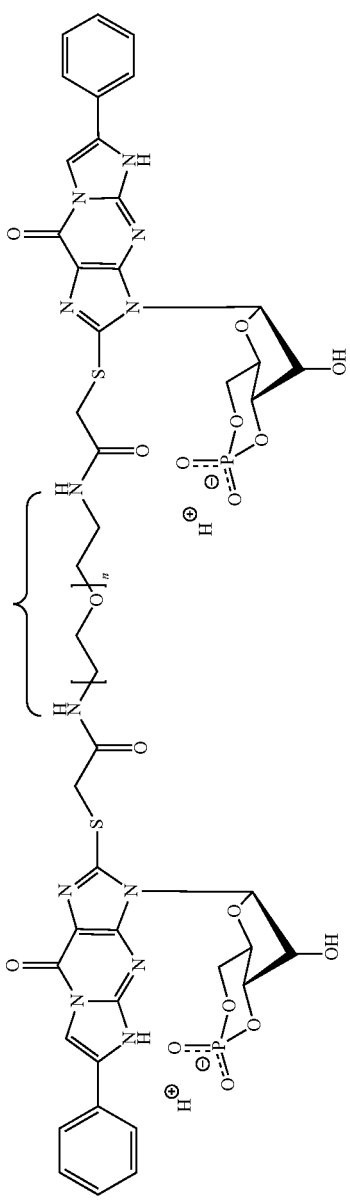 PET-cGMP-8-TMAmd-(PEG pd 2000)-AmdMT-8-cGMP-PET |

TABLE 13-continued
Structures of novel compounds according to the invention.
| # | Compound | Structure |
|---|---|---|
| 14 | Benzene-1,3,5-tri-[(8-amidomethyl-(pentaethoxy)-propylamidomethylthio)guanosine-3',5'-cyclic monophosphate] | 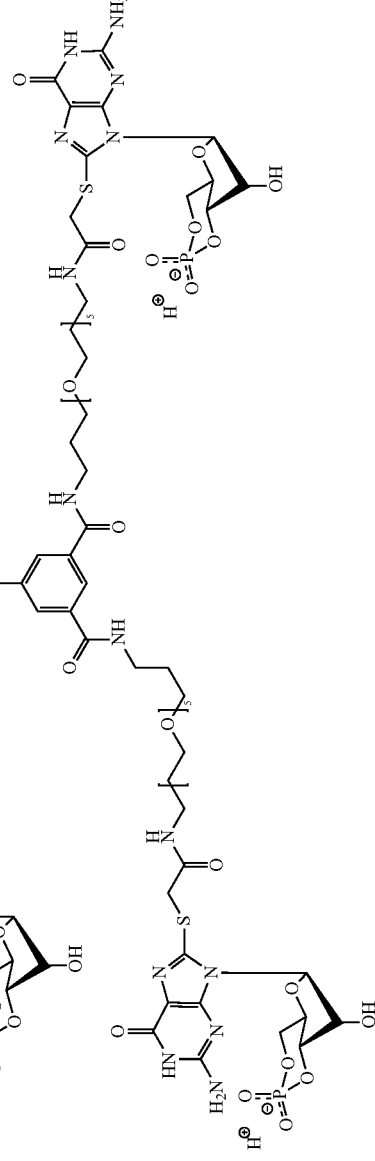 Bn-1,3,5-tri(AmdPr-(OE)₅-MAmdMT-8-cGMP |

TABLE 13-continued

Structures of novel compounds according to the invention.

| # | Compound | Structure |
|---|---|---|
| 15 | Ethylene glycol-bis(2-aminoethylether)-N,N,N',N'-tetra-[(8-methylamidoethylthio)guanosine-3',5'-cyclic monophosphate] | EG-N,N,N',N'-tetra(8-MAmdET-cGMP) |

TABLE 13-continued

Structures of novel compounds according to the invention.

| # | Compound | Structure |
|---|---|---|
| 16 | Guanosine-3',5'-cyclic monophosphate-[8-thio-(dodecanyl)-thio-8]-guanosine-3',5'-cyclic monophosphate | 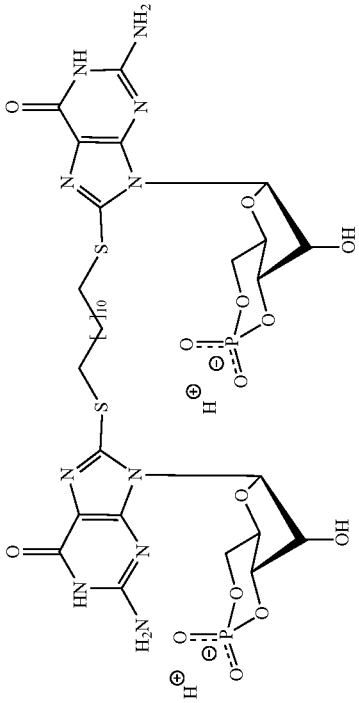 cGMP-8-T-(CH$_2$)$_{12}$-T-8-cGMP |
| 17 | β-Phenyl-1, N$^2$-ethenoguanosine-3',5'-cyclic monophosphate-[8-thio-(dodecanyl)-thio-8]-β-phenyl-1, N$^2$-ethenoguanosine-3',5'-cyclic monophosphate, triethyl ammonium salt | 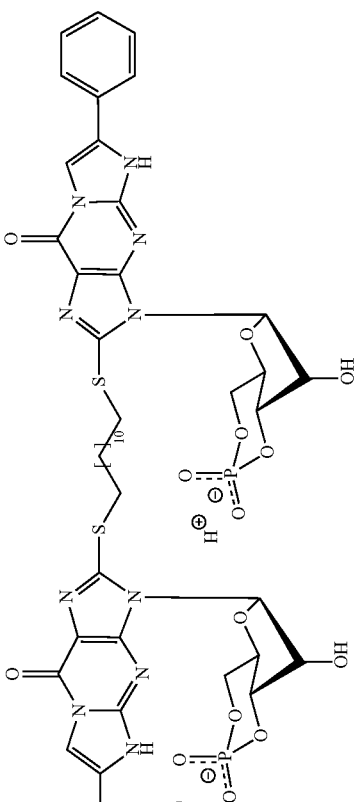 PET-cGMP-8-T-(CH$_2$)$_{12}$-T-8-cGMP-PET |

TABLE 13-continued

Structures of novel compounds according to the invention.

| # | Compound | Structure |
|---|----------|-----------|
| 18 | Guanosine-3',5'-cyclic monophosphate-[8-thioethylamidomethyl-(1-[1,2,3]-triazole-4-yl)-methoxy-(hexaethoxy)-methyl-(4-[1,2,3]-triazole-1-yl)-methylamidoethylthio-8]-guanosine-3',5'-cyclic monophosphate | 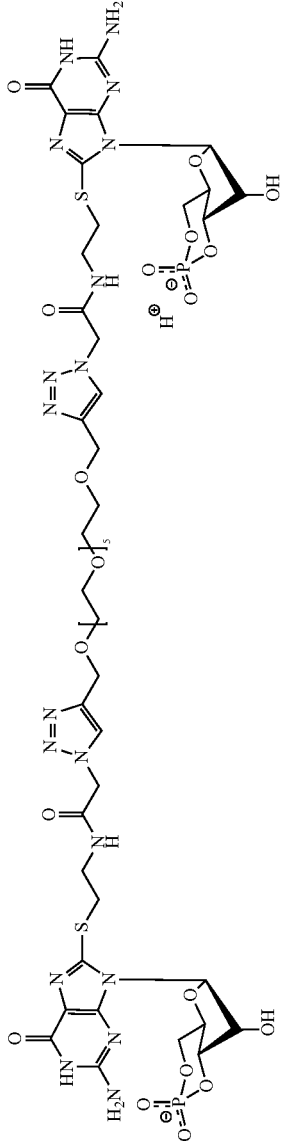 cGMP-8-TEAmdM-(1-[1,2,3]-Tz-4)-MeO-(EO)₆-Me-(4-[1,2,3]-Tz-1)-MAmdET-8-cGMP |
| 19 | Guanosine-3',5'-cyclic monophosphate-[8-thioethylthio-8]-guanosine-3',5'-cyclic monophosphate | 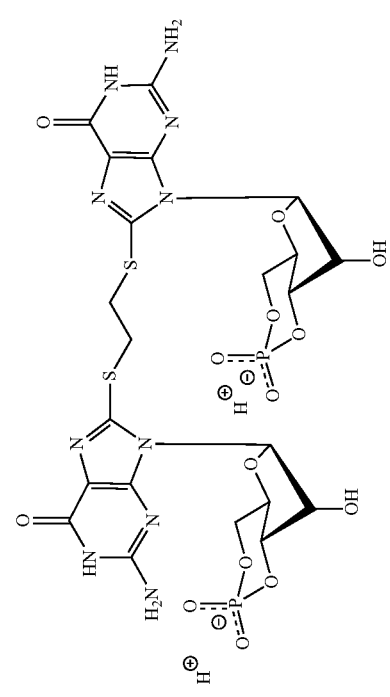 cGMP-8-TET-8-cGMP |

TABLE 13-continued

Structures of novel compounds according to the invention.

| # | Compound | Structure |
|---|---|---|
| 20 | Guanosine-3',5'-cyclic monophosphate-[8-thioethyl-(1-[1,2,3]-triazole-4-yl)-methoxy-(hexaethoxy)-methyl-(4-[1,2,3]-triazole-1-yl)-ethylthio-8]-guanosine-3',5'-cyclic monophosphate | 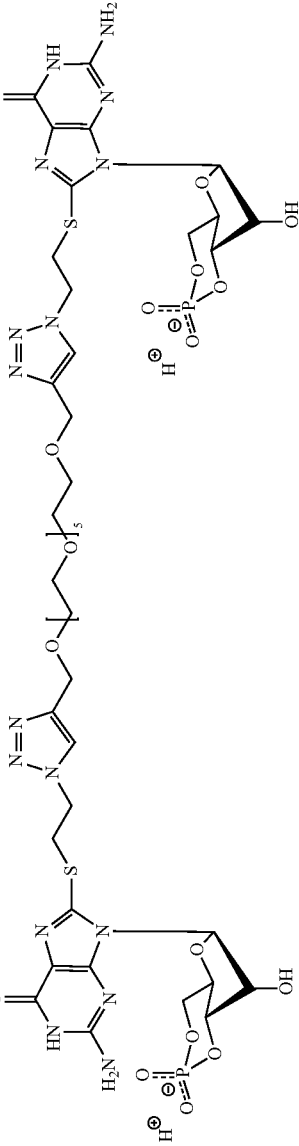 cGMP-8-TE-(1-[1,2,3]-Tz-4)-MeO-(EO)₆-Me-(4-[1,2,3]-Tz-1)-ET-8-cGMP |
| 21 | Guanosine-3',5'-cyclic monophosphate-[8-thio-(dodecanyl)-(4-thiophenyl-4''-thiophenylthio)-(dodecanyl)-thio-8]-guanosine-3',5'-cyclic monophosphate | 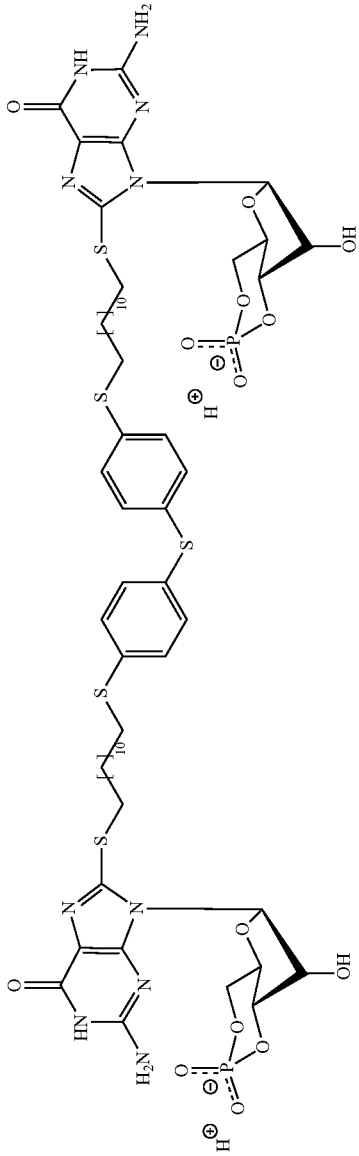 cGMP-8-T-(CH₂)₁₂-pTPpTPT-(CH₂)₁₂-T-8-cGMP |

TABLE 13-continued

Structures of novel compounds according to the invention.

| # | Compound | Structure |
|---|---|---|
| 22 | Guanosine-3′,5′-cyclic monophosphate-[8-thioethylamidomethyl-(1-[1,2,3]-triazole-4-yl)-methoxy-(hexaethoxy)-methyl-(4-(4-[1,2,3]-triazole-1-yl)-β-phenyl-1, N²-etheno)]-8-bromoguanosine-3′,5′-cyclic monophosphate | cGMP-8-TEAmdM-(1-[1,2,3]-Tz-4)-MeO-(EO)₆-Me-(4-[1,2,3]-Tz-1)-PET-8-Br-cGMP |
| 23 | β-Phenyl-1, N²-ethenoguanosine-3′,5′-cyclic monophosphate-[8-thioethyl-(1-[1,2,3]-triazole-4-yl)-methoxy-(hexaethoxy)-methyl-(4-[1,2,3]-triazole-1-yl)-ethylthio-8]-β-phenyl-1, N²-ethenoguanosine-3′,5′-cyclic monophosphate | PET-cGMP-8-TE-(1-[1,2,3]-Tz-4)-MeO-(EO)₆-Me-(4-[1,2,3]-Tz-1)-ET-8-cGMP-PET |

TABLE 13-continued

Structures of novel compounds according to the invention.

| # | Compound | Structure |
|---|---|---|
| 24 | 8-Bromoguanosine-3',5'-cyclic monophosphate-[1-propylamidomethyl-(pentaethoxy)-propylamidomethylthio-8]-β-phenyl-1, N²-ethenoguanosine-3',5'-cyclic monophosphate | 8-Br-cGMP-1-PrAmdM-(EO)₅-PrAmdMT-8-cGMP-PET |
| 25 | 8-Bromoguanosine-3',5'-cyclic monophosphate-[1-(pentaethoxy)-ethyl-1]-8-bromoguanosine-3',5'-cyclic monophosphate | 8-Br-cGMP-1-(EO)₅-E-1-cGMP-8-Br |

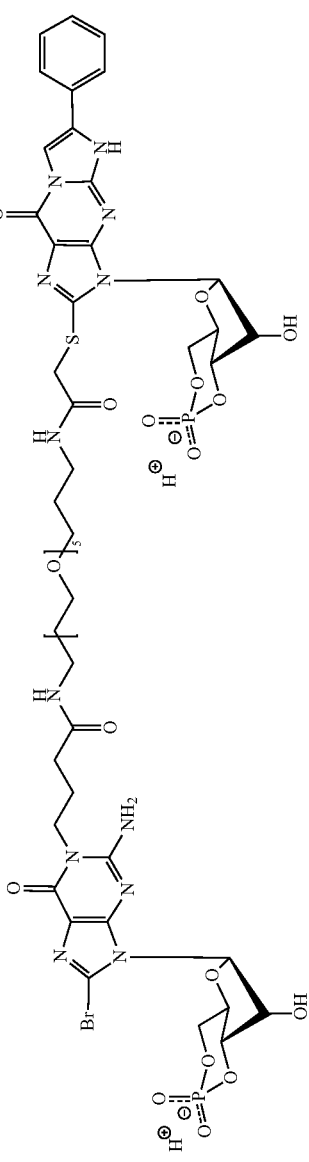
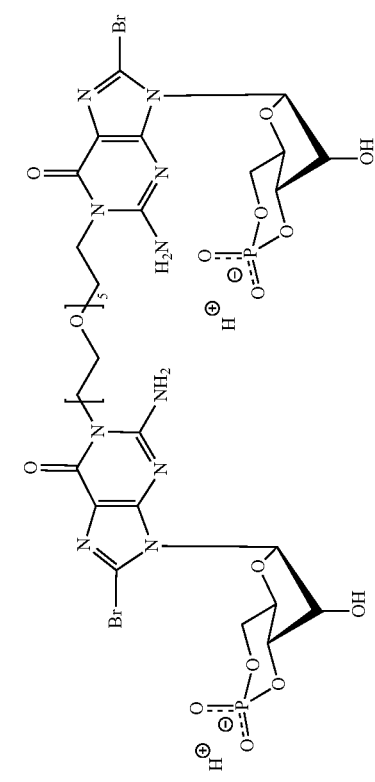

TABLE 13-continued

Structures of novel compounds according to the invention.

| # | Compound | Structure |
|---|---|---|
| 26 | 8-Bromoguanosine-3',5'-cyclic monophosphate-[1-propylamidomethyl-(pentaethoxy)-propylamidopropyl-1]-8-bromoguanosine-3',5'-cyclic monophosphate | 8-Br-cGMP-1-PrAmdM-(EO)$_5$-PrAmdPr-1-cGMP-8-Br |
| 27 | 8-Bromoguanosine-3',5'-cyclic monophosphate-[1-propylamidomethyl-(pentaethoxy)-propylamidomethylthio-8]-guanosine-3',5'-cyclic monophosphate | 8-Br-cGMP-1-PrAmdM-(EO)$_5$-PrAmdMT-8-cGMP |

TABLE 13-continued

Structures of novel compounds according to the invention.

| # | Compound | Structure |
|---|---|---|
| 28 | Guanosine-3',5'-cyclic monophosphate-[8-(phenyl-4-thio)-(pentaethoxy)-ethyl-(4-thiophenyl)-8]-guanosine-3',5'-cyclic monophosphate | 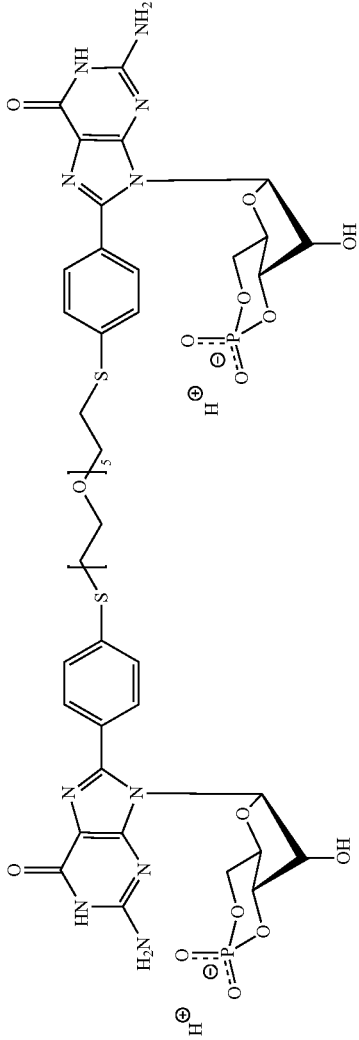 cGMP-8-PpT-(EO)₅-EpTP-8-cGMP |
| 29 | β-1, N²-Acetyl-guanosine-3',5'-cyclic monophosphate-[8-thiomethylamido-(octaethoxy)-ethylamidomethylthio-8]-β-1,N²-acetyl-guanosine-3',5'-cyclic monophosphate | 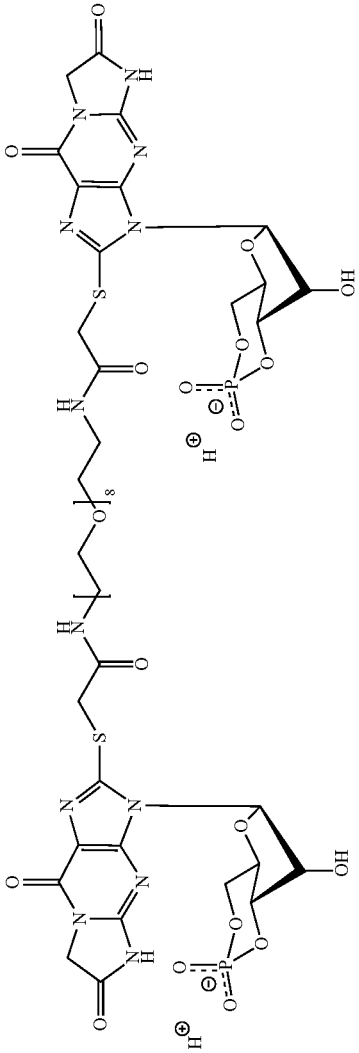 β-1,N²-Ac-cGMP-8-TMAmd-(EO)₈-EAmdMT-8-cGMP-β-1,N²-Ac |

TABLE 13-continued
Structures of novel compounds according to the invention.
| # | Compound | Structure |
|---|---|---|
| 30 | 8-Phenylguanosine-3′,5′-cyclic monophosphate-[1, N²-etheno-β-phenyl-4-yl-(1-[1,2,3]-triazole-4-yl)-methoxy-(hexaethoxy)-methyl-(4-[1,2,3]-triazole-1-yl)-β-phenyl-1, N²-etheno)]-8-phenylguanosine-3′,5′-cyclic monophosphate | 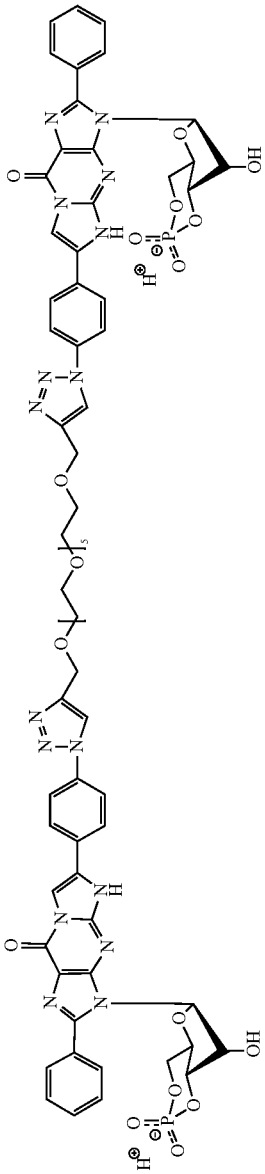 8-Phe-cGMP-ETP-p(1-[1,2,3]-Tz-4)-MeO-(EO)₆-Me-p(4-[1,2,3]-Tz-1)-cGMP-8-Phe |

Monomeric precursor cGMP analogues (G units) for the synthesis of polymer linked multimeric cGMP analogues (PLMs) are compounds of formula (III). As described above, the PKG activation potential is strongly increased, once the monomeric precursor is linked to additional one(s) within a PLM, wherein particularly enhanced PKG isoform activation can be related to a certain extend to structural parameters. Non limiting examples of methods for the transformation of monomeric precursors into exemplary PLMs are given in the examples section. In addition Table 1 gives an overview of exemplary endstanding groups, that can be used for coupling reactions and the corresponding coupling functions within the PLM, to which they are transformed according to established methods of the art.

The invention in one aspect also relates to monomeric compounds of formula (III) and/or monomeric precursors according to formula (III), of any compound of the invention as described herein above, wherein the monomeric compound of formula (III) and/or the monomeric precursor of formula (III) is defined in the context of any said compounds herein above, and preferably wherein the monomeric compound of formula (III) and/or monomeric precursor of formula (III) complies with the following proviso:

$R_7$ is O and $R_8$ is OH and further complies with at least one of the following provisos:

$R_4$ is not H and $R_5$ is $NH_2$
wherein $R_4$ is attached via a —$CH_2$— bridge, which is part of $R_4$ or $R_5$ together with $R_4$, Y and the carbon bridging Y and $R_5$ form a ring system, which can be
  a) an imidazolinone ring as depicted hereinafter (n=1) or an homologous ring (n=2 to 8)

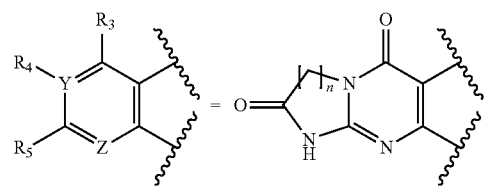

b) an imidazole ring, which can be unsubstituted or substituted as depicted hereinafter as residue entry 1 and 2
     residue entry 1

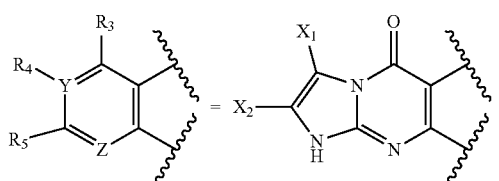

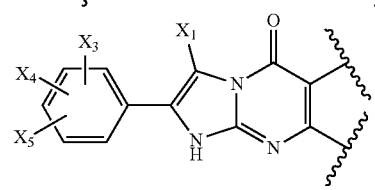

Wherein $X_1$ is H;

$X_2$ can be H, 2-naphtyl, 9-phenanthryl, 1-pyrenyl, 2,3-dihydro-1,4-benzodioxin-6-yl, dibenzo[b,d]furan-2-yl, 2,3-dihydro-1-benzofuran-5-yl, 1-benzothien-5-yl, 1-benzofuran-5-yl, cyclopropyl, 1-adamantyl, C(Ph)$_3$, 2-thienyl, 3-chloro-2-thienyl, 3-thienyl, 1,3-thiazol-2-yl, 2-pyridinyl, 5-chloro-2-thienyl, 1-benzofuran-2-yl;

$X_3$, $X_4$ and $X_5$ can independently be OH, NH, $CH_3$, Cl, Br, F, CN, $N_3$, $CF_3$, $OCF_3$, $NO_2$, C(O)OH, C(O)OCH$_3$, OCH$_3$, OBn, O-benzoyl, SCH$_3$, t-Bu, N(CH$_3$)$_2$, S-phenyl, Ph, S(O)$_2$CH$_3$, C(O)NH$_2$, NHS(O)$_2$CH$_3$, while $X_4$ and $X_5$ can also independently be H;

residue entry 2

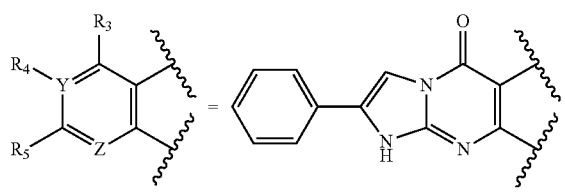

while $R_1$ is as in any of the compounds 31 to 107.

or $R_1$ is attached via a —S(O)— or —S(O)$_2$— bridge or via a carbon atom of an aromatic ring system, which in each case is part of $R_1$ while $R_4$ is H and $R_5$ is $NH_2$ and in addition complies with the proviso that the monomeric compound of formula (III) and/or the monomeric precursor compound of formula (III) is not selected from the group of compounds consisting of

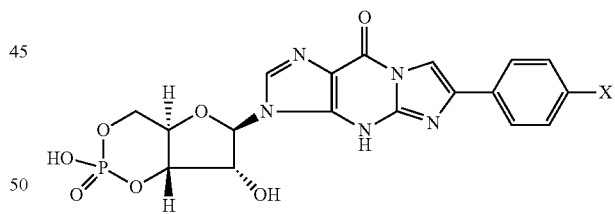

with X = OMe or Cl

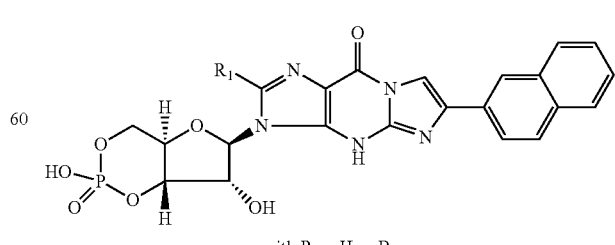

with $R_1$ = H or Br

101

-continued

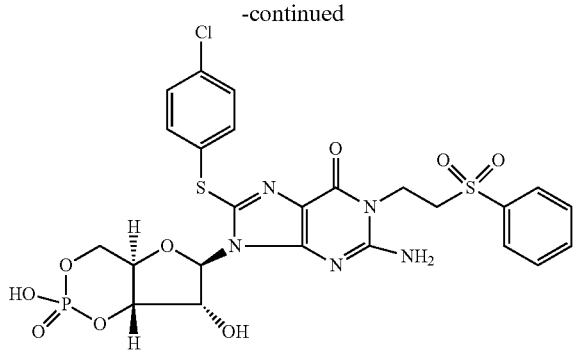

with X = O, S or Se

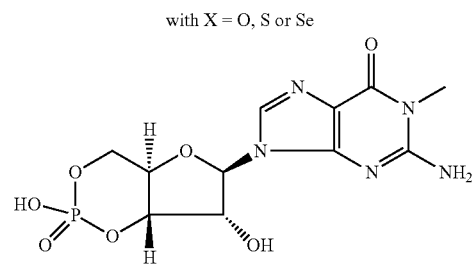

102

-continued

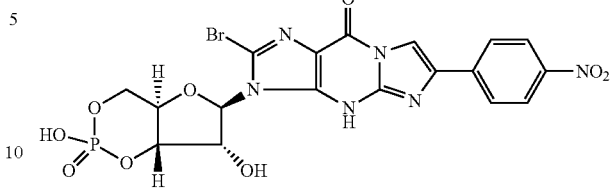

and/or
the monomeric compound of formula (III) and/or the monomeric precursor of the invention is selected from the group depicted in Table 14.

TABLE 14

Structures of novel monomeric precursor compounds according to the invention.

| # | Compound | Structure |
|---|---|---|
| 31 | 8-Amidomethylthioguanosine-3',5'-cyclic monophosphate | 8-AmdMT-cGMP |
| 32 | 8-(4-Boronatephenylthio)-guanosine-3',5'-cyclic monophosphate | 8-pB(OH)₂PT-cGMP |

TABLE 14-continued

Structures of novel monomeric precursor compounds according to the invention.

| # | Compound | Structure |
|---|---|---|
| 33 | 8-(4-Cyanobenzylthio)guanosine-3',5'-cyclic monophosphate | 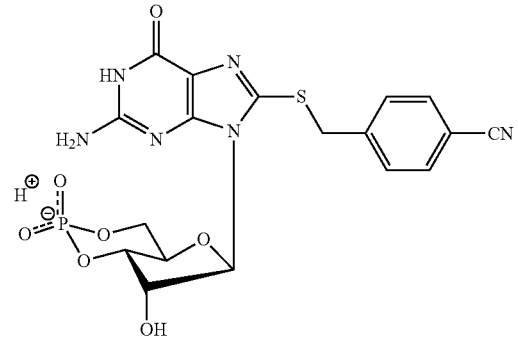<br>8-pCNBT-cGMP |
| 34 | 8-(4-(2-Cyanophenyl)-benzylthio)guanosine-3',5'-cyclic monophosphate | 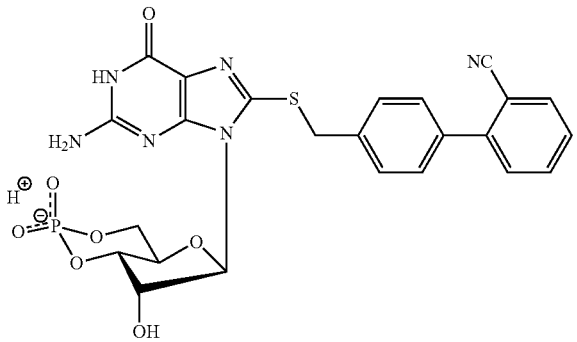<br>8-p(2-CNPhe)BT-cGMP |
| 35 | 8-Cyclohexylmethyl-thioguanosine-3',5'-cyclic monophosphate | 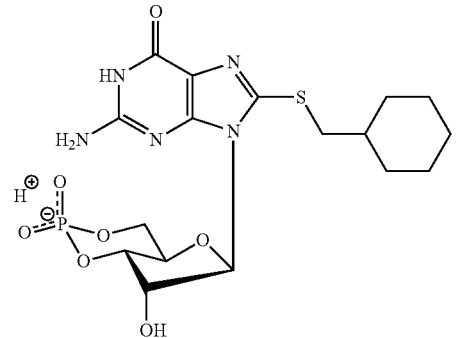<br>8-cHeMT-cGMP |
| 36 | 8-(2,4-Dichlorophenylthio)guanosine-3',5'-cyclic monophosphate | 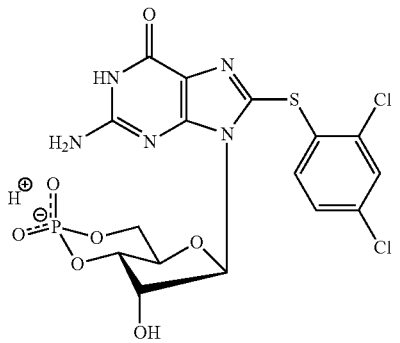<br>8-o,pDClPT-cGMP |

TABLE 14-continued

Structures of novel monomeric precursor compounds according to the invention.

| # | Compound | Structure |
|---|---|---|
| 37 | 8-Diethylphos-phonoethylthio-guanosine-3',5'-cyclic monophosphate | 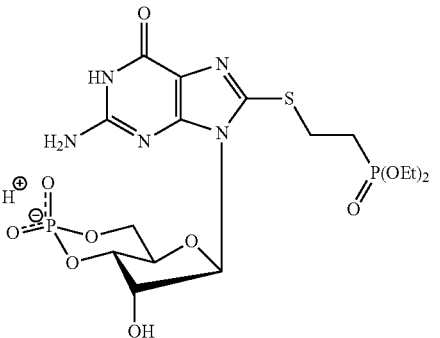 8-DEPET-cGMP |
| 38 | 8-Ethylthioguanosine-3',5'-cyclic monophosphate | 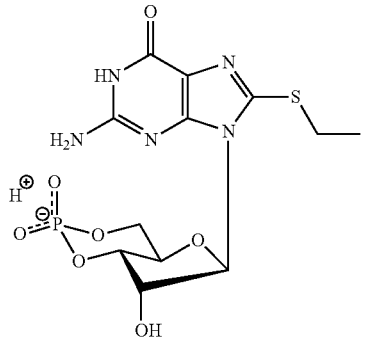 8-ET-cGMP |
| 39 | 8-Hexylthioguanosine-3',5'-cyclic monophosphate | 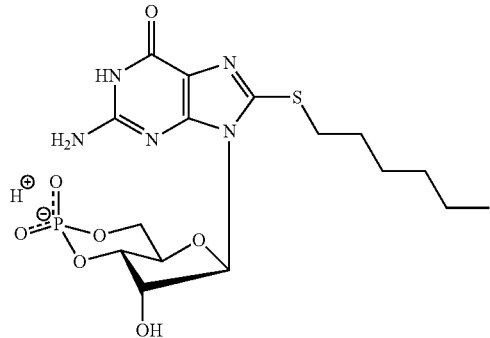 8-HT-cGMP |
| 40 | 8-(4-Isopropylphenylthio)guanosine-3',5'-cyclic monophosphate | 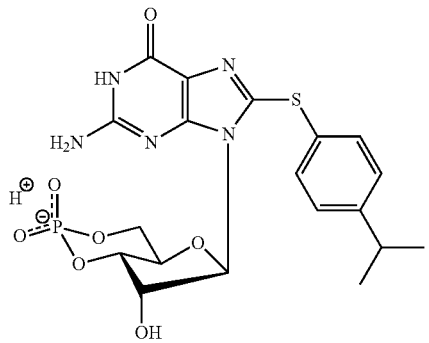 8-pIPrPT-cGMP |

TABLE 14-continued

Structures of novel monomeric precursor compounds according to the invention.

| # | Compound | Structure |
|---|---|---|
| 41 | 8-(3-(2-Methyl)furanyl)thioguanosine-3',5'-cyclic monophosphate | 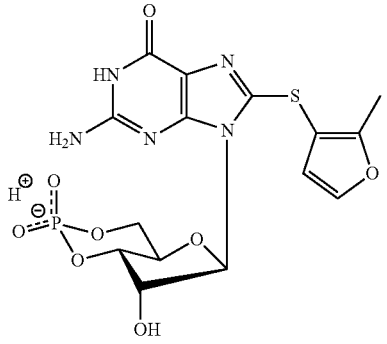<br>8-(3-(2-Me)-FU)T-cGMP |
| 42 | 8-(5-(1-Methyl)tetrazolyl)thioguanosine-3',5'-cyclic monophosphate | 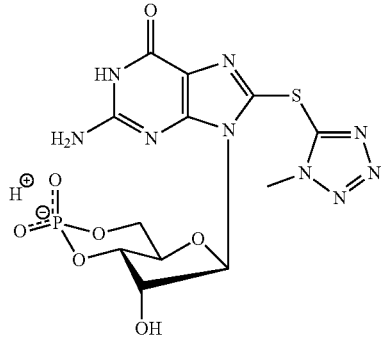<br>8-(5-(1-Me)-Tet)T-cGMP |
| 43 | 8-(4-Methoxybenzylthio)guanosine-3',5'-cyclic monophosphate | 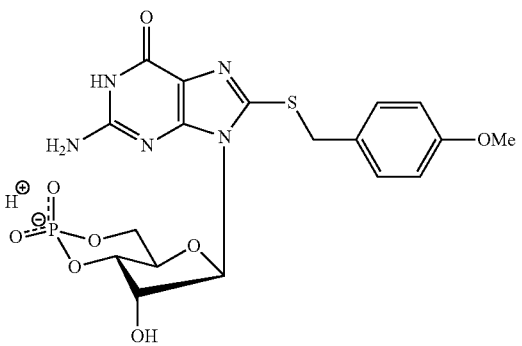<br>8-pMeOBT-cGMP |
| 44 | 8-(7-(4-Methyl)coumarinyl)thioguanosine-3',5'-cyclic monophosphate | 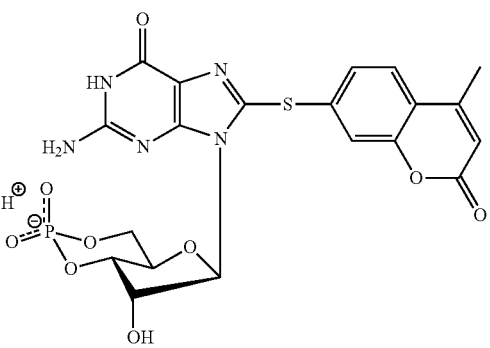<br>8-(7-(4-Me)-Cou)T-cGMP |

TABLE 14-continued

Structures of novel monomeric precursor compounds according to the invention.

| # | Compound | Structure |
|---|---|---|
| 45 | 8-Methylacetyl-thioguanosine-3',5'-cyclic monophosphate | 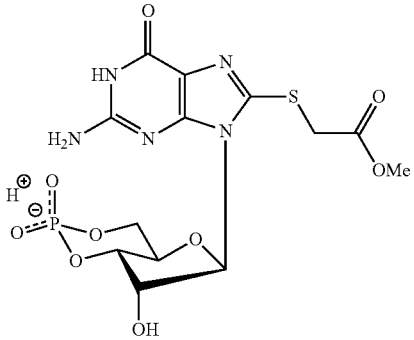<br>8-MAcT-cGMP |
| 46 | 8-(5-(1-Phenyl)tetrazolyl)thioguanosine-3',5'-cyclic monophosphate | 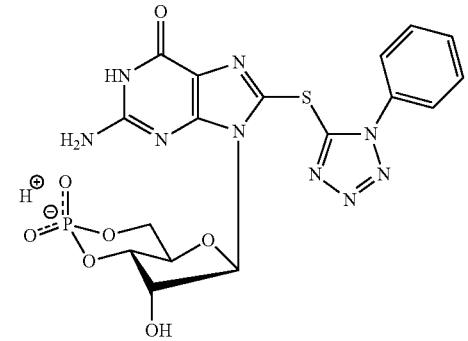<br>8-(5-(1-Phe)-Tet)T-cGMP |
| 47 | 8-(2-Phenylethyl)thioguanosine-3',5'-cyclic monophosphate | 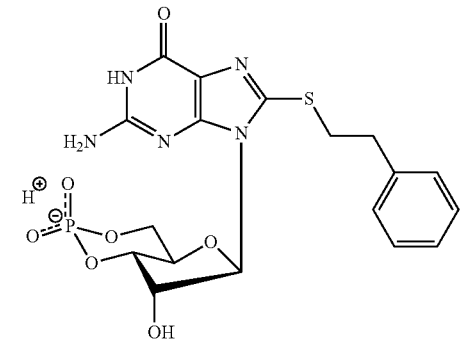<br>8-PhEtT-cGMP |
| 48 | 8-(2-(4-Phenyl)imidazolyl)thioguanosine-3',5'-cyclic monophosphate | 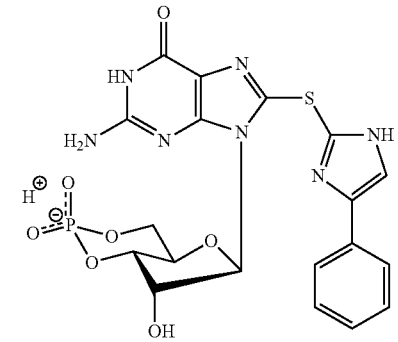<br>8-(2-(4-Phe)-Im)T-cGMP |

TABLE 14-continued

Structures of novel monomeric precursor compounds according to the invention.

| # | Compound | Structure |
|---|----------|-----------|
| 49 | 8-(2-Thiophenyl)thioguanosine-3',5'-cyclic monophosphate | 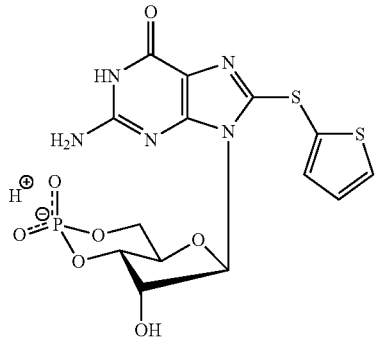<br>8-(2-Tp)T-cGMP |
| 50 | 8-(1,1,2-Trifluoro-1-butenthio)guanosine-3',5'-cyclic monophosphate | 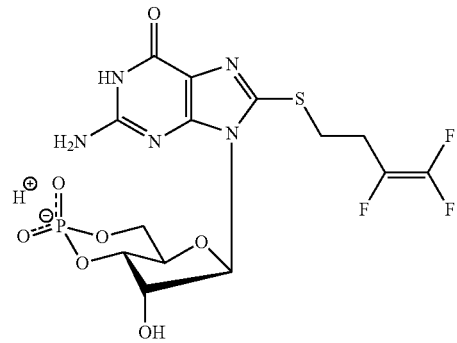<br>8-(1,1,2-TF-Bu(1-en))T-cGMP |
| 51 | 8-Amidopropyl-thioguanosine-3',5'-cyclic monophosphate | 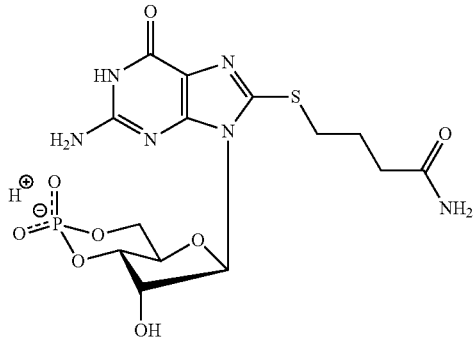<br>8-AmdPrT-cGMP |
| 52 | 8-Amidoethyl-thioguanosine-3',5'-cyclic monophosphate | 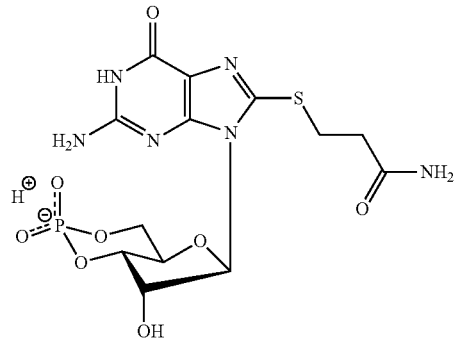<br>8-AmdET-cGMP |

TABLE 14-continued

Structures of novel monomeric precursor compounds according to the invention.

| # | Compound | Structure |
|---|---|---|
| 53 | 8-Amidobutyl-thioguanosine-3',5'-cyclic monophosphate | 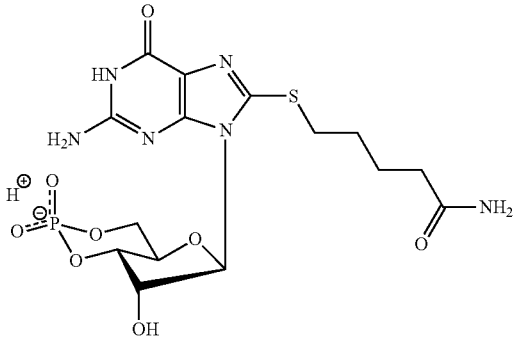<br>8-AmdBuT-cGMP |
| 54 | 8-Acetamidoethyl-thioguanosine-3',5'-cyclic monophosphate | 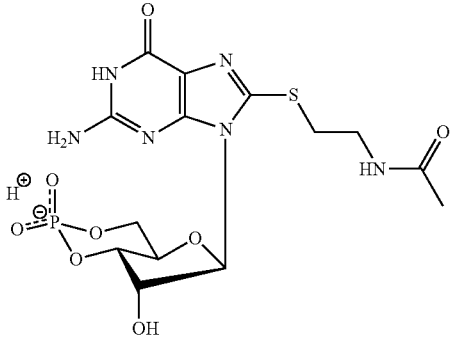<br>8-AcAmdET-cGMP |
| 55 | 8-(2-Benzothiazolyl)thioguanosine-3',5'-cyclic monophosphate | 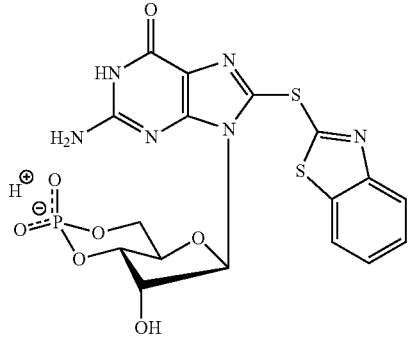<br>8-(2-BT)T-cGMP |
| 56 | 8-(2-Boronatebenzylthio)guanosine-3',5'-cyclic monophosphate | 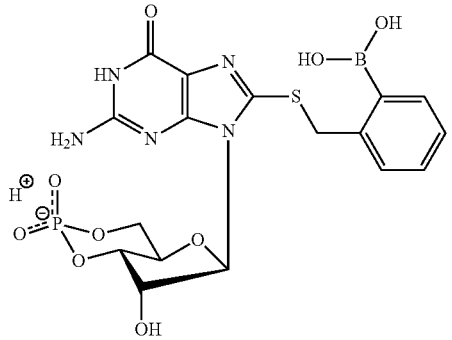<br>8-(oB(OH)₂Bn)T-cGMP |

TABLE 14-continued

Structures of novel monomeric precursor compounds according to the invention.

| # | Compound | Structure |
|---|---|---|
| 57 | 8-(4-Boronatebutylthio)guanosine-3',5'-cyclic monophosphate | 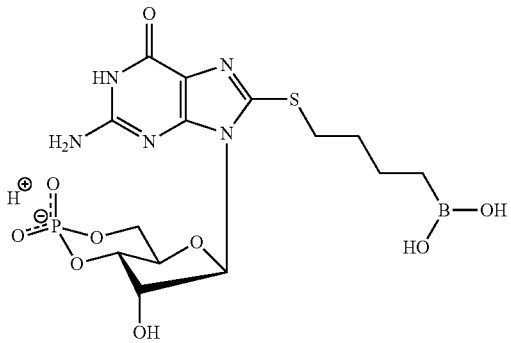<br>8-(pB(OH)₂Bu)T-cGMP |
| 58 | 8-(4-Boronatebenzylthio)guanosine-3',5'-cyclic monophosphate | 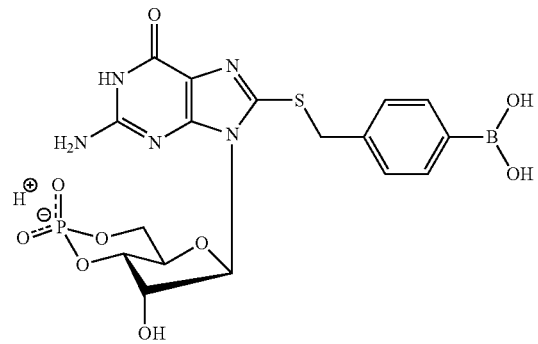<br>8-(pB(OH)₂Bn)T-cGMP |
| 59 | 8-(3-Boronatebenzylthio)guanosine-3',5'-cyclic monophosphate | 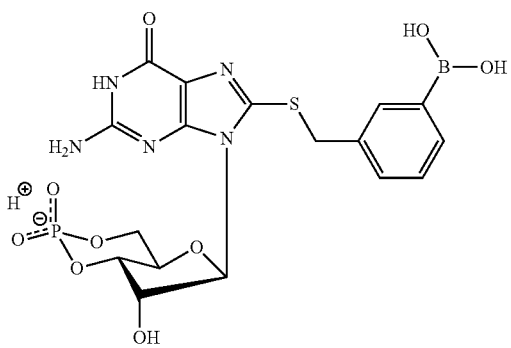<br>8-(mB(OH)₂Bn)T-cGMP |
| 60 | 8-Azidomethyl-amidoethylthio-guanosine-3',5'-cyclic monophosphate | 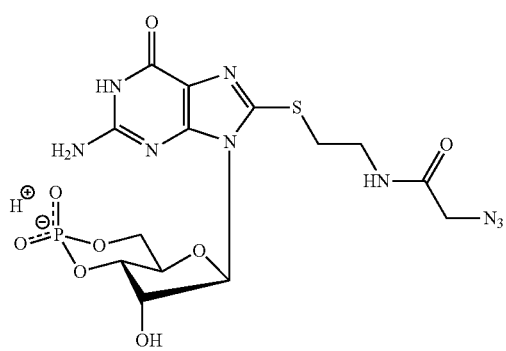<br>8-N₃-MAmdET-cGMP |

TABLE 14-continued

Structures of novel monomeric precursor compounds according to the invention.

| # | Compound | Structure |
|---|---|---|
| 61 | 8-(3-Boronatephenyl) amidobutylthio-guanosine-3',5'-cyclic monophosphate | 8-(mB(OH)₂PAmdBu)T-cGMP |
| 62 | 8-Benzylamidobutyl-thioguanosine-3',5'-cyclic monophosphate | 8-BnAmdBuT-cGMP |
| 63 | 8-Benzamidoethyl-thioguanosine-3',5'-cyclic monophosphate | 8-BAmdET-cGMP |
| 64 | 8-(3-Boronatephenyl) amidomethyl-thioguanosine-3',5'-cyclic monophosphate | 8-mB(OH)₂PAmdMT-cGMP |

TABLE 14-continued

Structures of novel monomeric precursor compounds according to the invention.

| # | Compound | Structure |
|---|----------|-----------|
| 65 | 8-Benzylamidomethylthio-guanosine-3',5'-cyclic monophosphate | 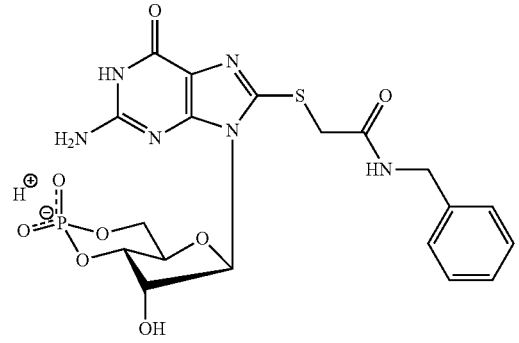<br>8-BnAmdMT-cGMP |
| 66 | 8-(3-Boronatephenyl)amidoethylthio-guanosine-3',5'-cyclic monophosphate | 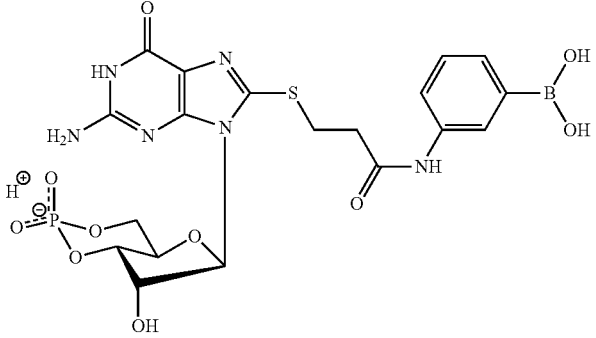<br>8-mB(OH)$_2$PAmdET-cGMP |
| 67 | 8-(3-Boronatephenyl)amidopropylthio-guanosine-3',5'-cyclic monophosphate | 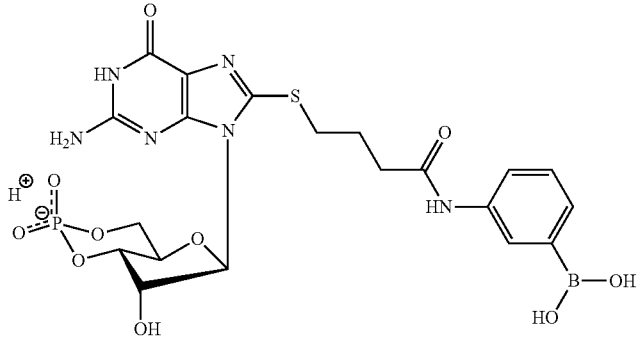<br>8-mB(OH)$_2$PAmdPrT-cGMP |
| 68 | 8-Carboxypropyl-thioguanosine-3',5'-cyclic monophosphate | 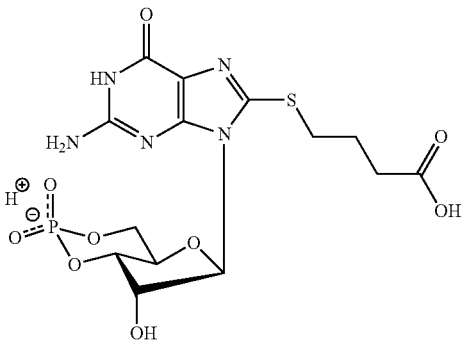<br>8-CPrT-cGMP |

TABLE 14-continued

Structures of novel monomeric precursor compounds according to the invention.

| # | Compound | Structure |
|---|----------|-----------|
| 69 | 8-Carboxybutyl-thioguanosine-3',5'-cyclic monophosphate | 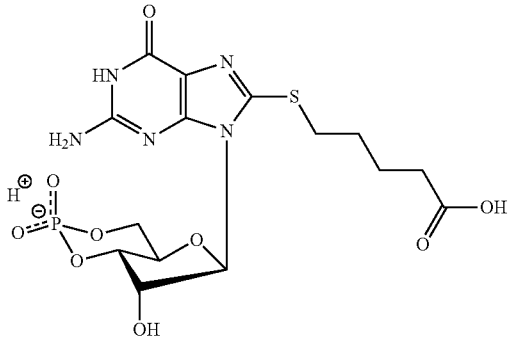<br>8-CBuT-cGMP |
| 70 | 8-(2,6-Dichlorophenoxy-propyl)thio-guanosine-3',5'-cyclic monophosphate | 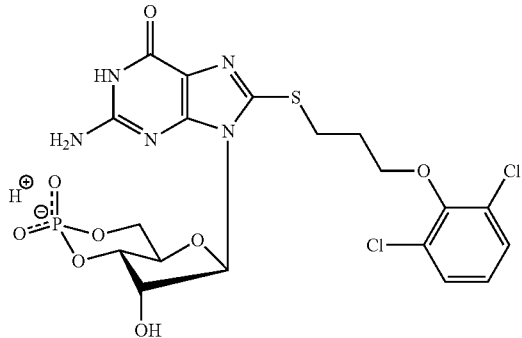<br>8-(2,6-DClPheoPr)T-cGMP |
| 71 | 8-(4-Dimethylamino-phenyl)amido-methylthioguanosine-3',5'-cyclic monophosphate | 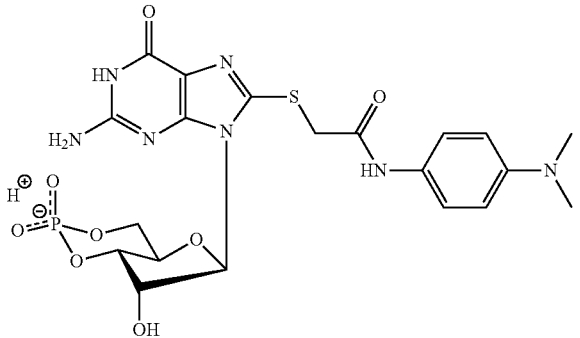<br>8-pDMAPAmdMT-cGMP |
| 72 | 8-(4-Dimethylamino-phenyl)amido-butylthioguanosine-3',5'-cyclic monophosphate | 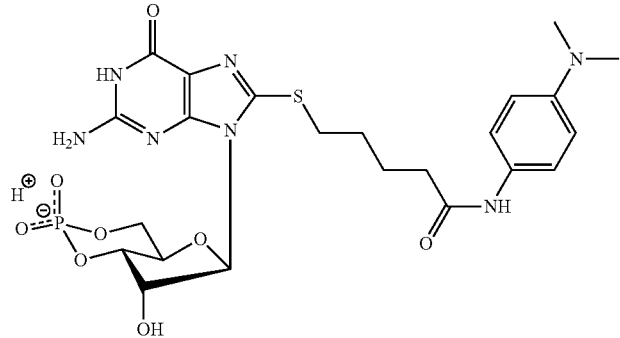<br>8-pDMAPAmdBuT-cGMP |

TABLE 14-continued

Structures of novel monomeric precursor compounds according to the invention.

| # | Compound | Structure |
|---|----------|-----------|
| 73 | 8-Ethylbutyrylthio-guanosine-3',5'-cyclic monophosphate | 8-EButT-cGMP |
| 74 | 8-Methylpropionyl-thioguanosine-3',5'-cyclic monophosphate | 8-MPT-cGMP |
| 75 | 8-Methylvalerianyl-thioguanosine-3',5'-cyclic monophosphate | 8-MValT-cGMP |
| 76 | 8-Methoxyethyl-amidobutylthio-guanosine-3',5'-cyclic monophosphate | 8-MeOEAmdBuT-cGMP |

TABLE 14-continued

Structures of novel monomeric precursor compounds according to the invention.

| # | Compound | Structure |
|---|---|---|
| 77 | 8-Methoxyethyl-amidomethylthio-guanosine-3',5'-cyclic monophosphate | 8-MeOEAmdMT-cGMP |
| 78 | 8-Methoxyethyl-amidoethylthio-guanosine-3',5'-cyclic monophosphate | 8-MeOEAmdET-cGMP |
| 79 | 8-Phenylamidomethylthio-guanosine-3',5'-cyclic monophosphate | 8-PAmdMT-cGMP |
| 80 | 8-Phenylpropylthio-guanosine-3',5'-cyclic monophosphate | 8-PPrT-cGMP |

TABLE 14-continued

Structures of novel monomeric precursor compounds according to the invention.

| # | Compound | Structure |
|---|----------|-----------|
| 81 | 8-(3-Butynylthio) guanosine-3',5'-cyclic monophosphate | 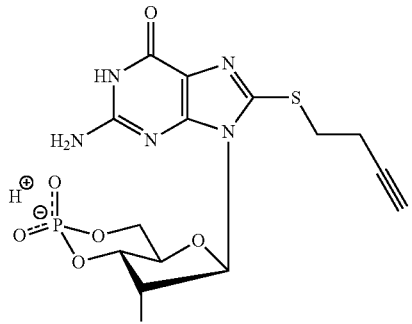<br>8-Bu(3-yne)T-cGMP |
| 82 | 8-(4-Acetamidophenylthio) guanosine-3',5'-cyclic monophosphate | 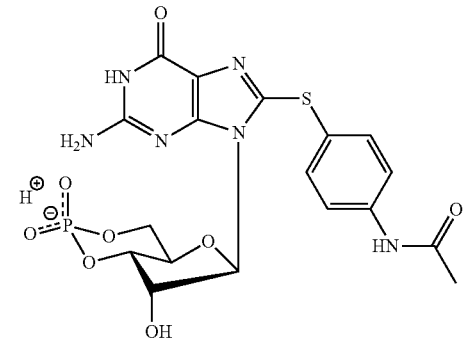<br>8-pAcAmdPT-cGMP |
| 83 | 8-(4-Chlorophenylsulfonyl) guanosine-3',5'-cyclic monophosphate | 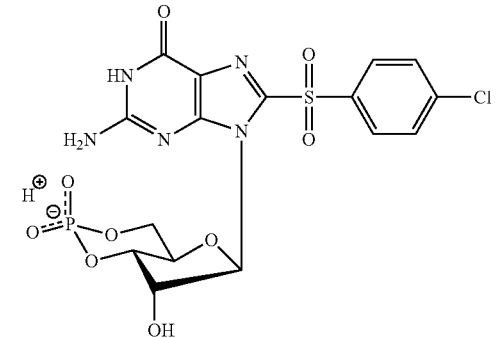<br>8-pCPS-cGMP |
| 84 | 8-(4-Chlorophenyl-sulfoxide)-guanosine-3',5'-cyclic monophosphate | 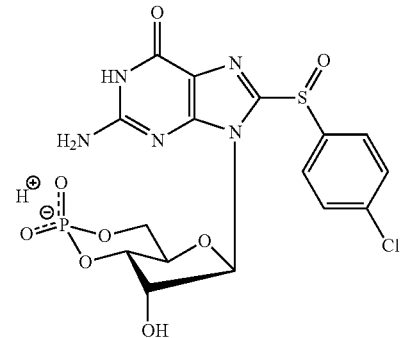<br>8-pCPS(O)-cGMP |

TABLE 14-continued

Structures of novel monomeric precursor compounds according to the invention.

| # | Compound | Structure |
|---|---|---|
| 85 | 8-((2-Ethoxyethyl)-4-thiophenylthio)guanosine-3',5'-cyclic monophosphat | 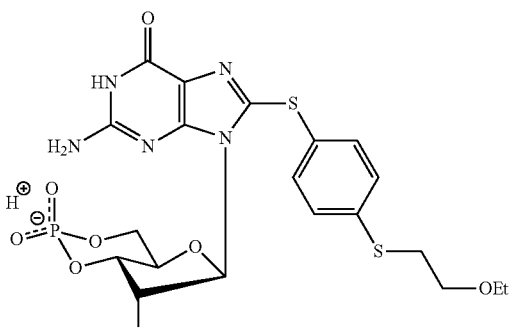<br>8-(2-EOE)-pTPT-cGMP |
| 86 | 8-(4-Thiophenyl-4''-thiophenylthio)guanosine-3',5'-cyclic monophosphate | 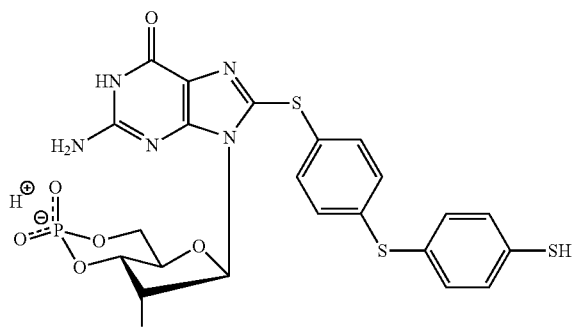<br>8-pTP-pTPT-cGMP |
| 87 | 8-(2-Azidoethylthio)guanosine-3',5'-cyclic monophosphate | 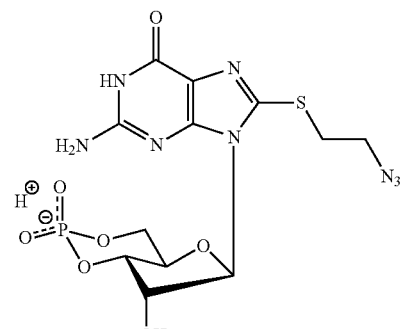<br>8-N$_3$-ET-cGMP |
| 88 | 8-(3-Aminopropyl)-(pentaethoxy)-methylamidomethylthio-guanosine-3',5'-cyclic monophosphate | 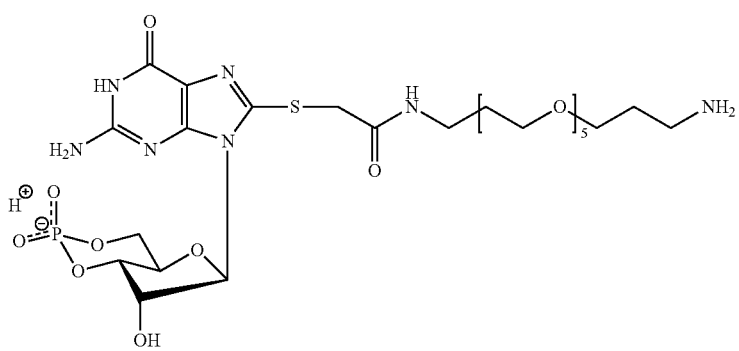<br>8-APr-(EO)$_5$-MAmdMT-cGMP |

TABLE 14-continued

Structures of novel monomeric precursor compounds according to the invention.

| # | Compound | Structure |
|---|---|---|
| 89 | 8-(2-Aminoethyl)-(octaethoxy)-amidomethylthio-guanosine-3',5'-cyclic monophosphate | 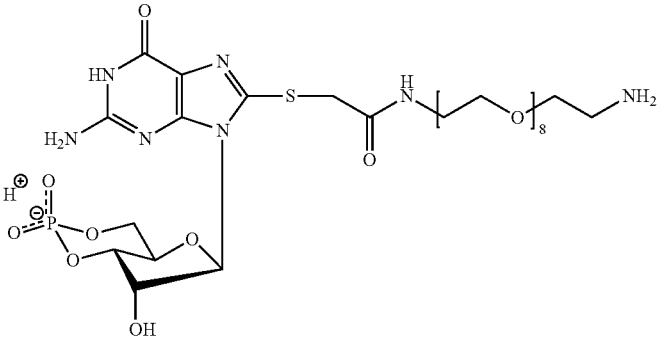  8-AE-(EO)₈-AmdMT-cGMP |
| 90 | 8-(2-Bromoethyl)-(pentaethoxy)-(4-thiophenylthio)guanosine-3',5'-cyclic monophosphate | 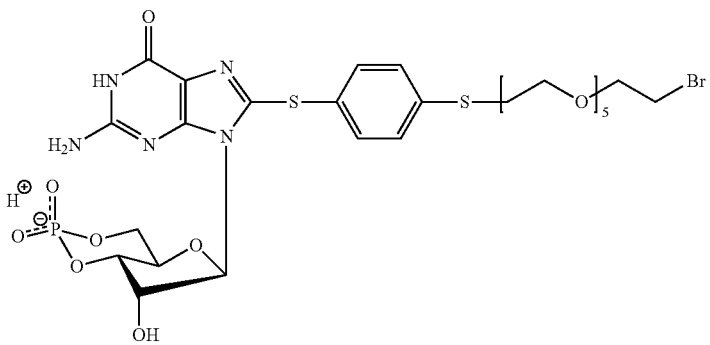  8-BrE-(EO)₅-pTPT-cGMP |
| 91 | 8-(4-(Propargyloxy-(hexaethoxy)-methyl)-[1,2,3]-triazole-1-yl)-methylamidoethylthio-guanosine-3',5'-cyclic monophosphate | 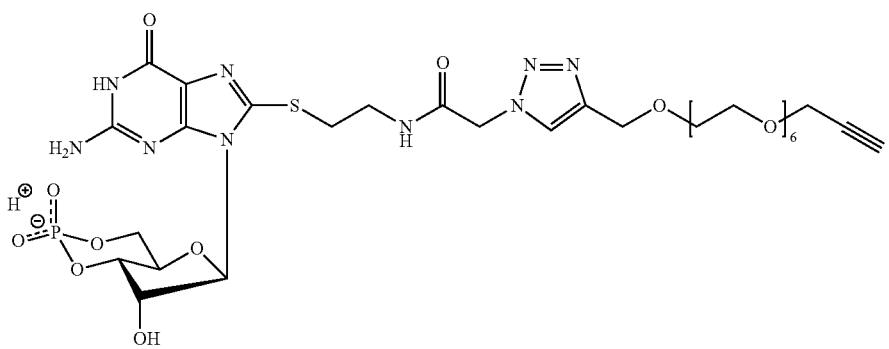  8-(4-(PargO-(EO)₆-Me)-[1,2,3]-Tz-1)-MAmdET-cGMP |
| 92 | 8-(4-Carboxyphenylthio)guanosine-3',5'-cyclic monophosphate | 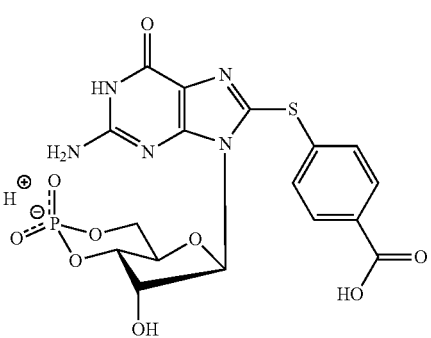  8-pCarbPT-cGMP |

TABLE 14-continued

Structures of novel monomeric precursor compounds according to the invention.

| # | Compound | Structure |
|---|----------|-----------|
| 93 | 8-(4-Hydroxy-phenylsulfonyl)-guanosine-3',5'-cyclic monophosphate | 8-pHPS-cGMP |
| 94 | 8-(4-Isopropyl-phenylsulfonyl)-guanosine-3',5'-cyclic monophosphate | 8-pIPrPs-cGMP |
| 95 | 8-(4-Methyl-carboxyphenylthio)-guanosine-3',5'-cyclic monophosphate | 8-pMeCarbPT-cGMP |
| 96 | 8-Methylsulfonyl-guanosine-3',5'-cyclic monophosphate | 8-MSulf-cGMP |

TABLE 14-continued

Structures of novel monomeric precursor compounds according to the invention.

| # | Compound | Structure |
|---|---|---|
| 97 | 8-(1-Bromo-2-naphthyl)methyl-thioguanosine-3',5'-cyclic monophosphate | 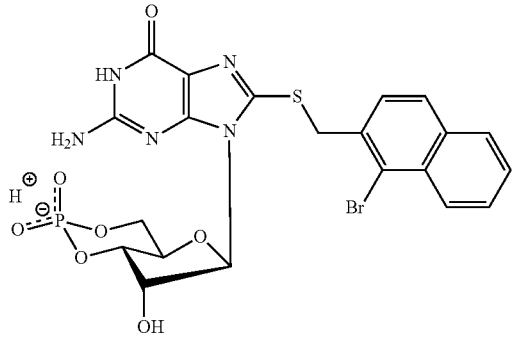<br>8-(1-Br-2-N)MT-cGMP |
| 98 | 8-(2-(1-Benzyl-[1,2,3]-triazole-4-yl)-ethylthio) guanosine-3',5'-cyclic monophosphate | 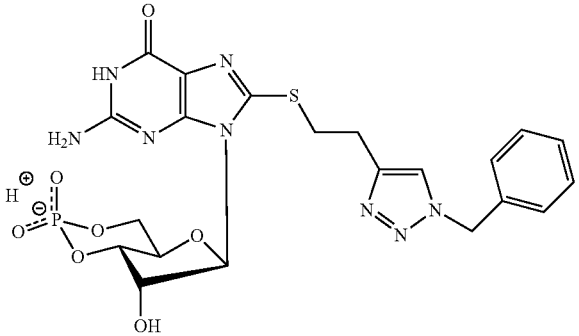<br>8-(1-Bn-[1,2,3]-Tz-4)-ET-cGMP |
| 99 | 8-(3-Fluoro-5-methoxybenzylthio) guanosine-3',5'-cyclic monophosphate | 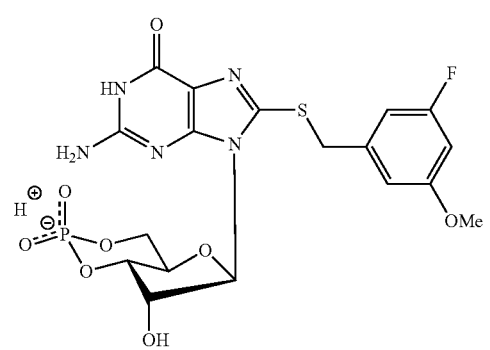<br>8-(3-F-5-MeO)BT-cGMP |
| 100 | 8-Pentafluorobenzyl-thioguanosine-3',5'-cyclic monophosphate | 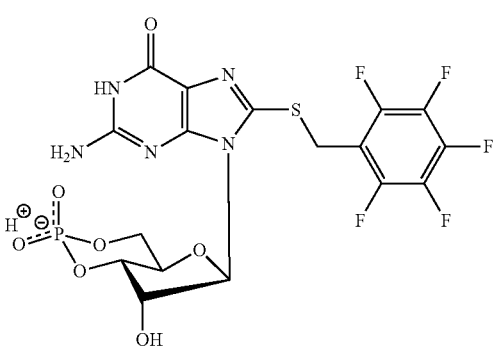<br>8-PFBT-cGMP |

TABLE 14-continued

Structures of novel monomeric precursor compounds according to the invention.

| # | Compound | Structure |
|---|---|---|
| 101 | 8-Triphenyliminophosphoranyl-guanosine-3',5'-cyclic monophosphate | 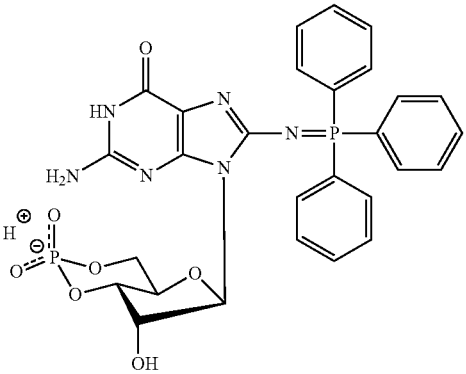<br>8-Ph₃PN-cGMP |
| 102 | 8-(4-Chlorophenyl)guanosine-3',5'-cyclic monophosphate | 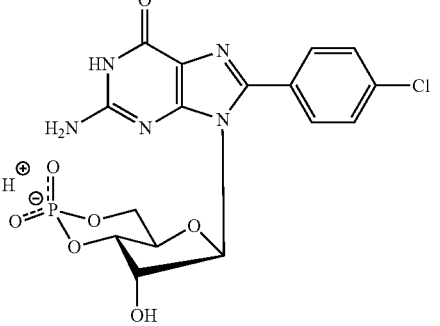<br>8-pCP-cGMP |
| 103 | 8-(4-Fluorophenyl)guanosine-3',5'-cyclic monophosphate | 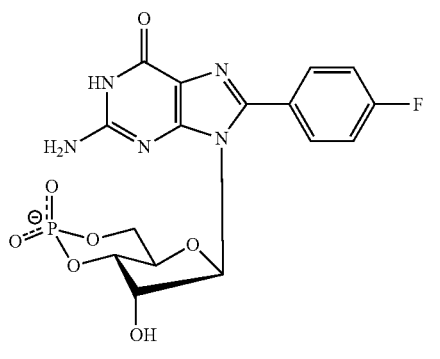<br>8-pFP-cGMP |
| 104 | 8-(2-Furyl)guanosine-3',5'-cyclic monophosphate | 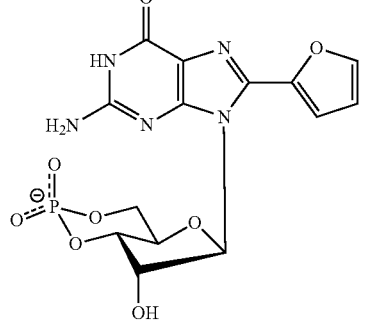<br>8-(2-Fur)-cGMP |

TABLE 14-continued

Structures of novel monomeric precursor compounds according to the invention.

| # | Compound | Structure |
|---|----------|-----------|
| 105 | 8-(4-Hydroxyphenyl)guanosine-3',5'-cyclic monophosphate | 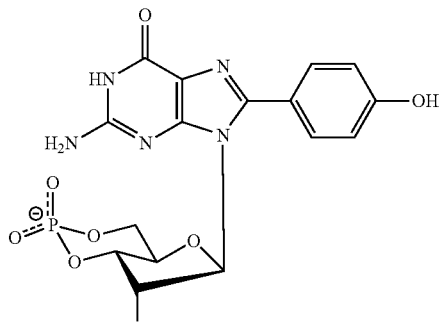<br>8-pHP-cGMP |
| 106 | 8-(4-Isopropylphenyl)guanosine-3',5'-cyclic monophosphate | 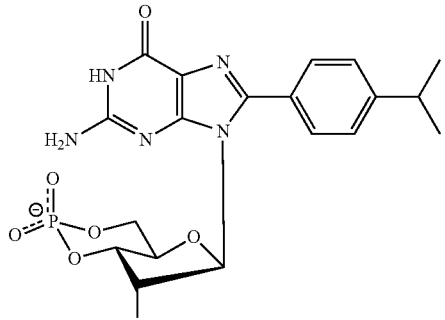<br>8-pIPrP-cGMP |
| 107 | 8-Phenylguanosine-3',5'-cyclic monophosphate | 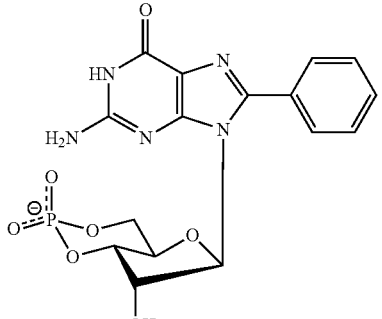<br>8-Phe-cGMP |
| 108 | β-Phenyl-1, N²-etheno-8-thioguanosine-3',5'-cyclic monophosphate | 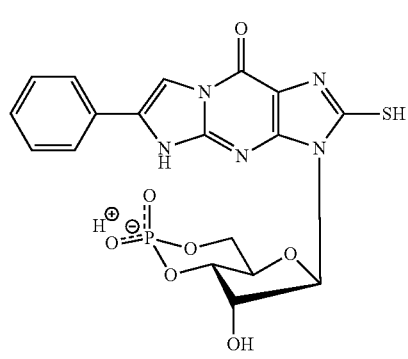<br>PET-8-T-cGMP |

TABLE 14-continued

Structures of novel monomeric precursor compounds according to the invention.

| # | Compound | Structure |
|---|---|---|
| 109 | 8-(2-Aminophenyl-thio)-ß-phenyl-1, N²-ethenoguanosine-3',5'-cyclic monophosphate | 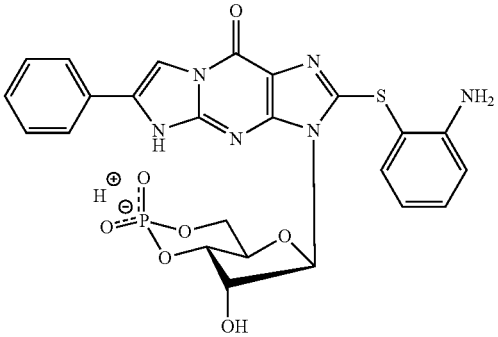<br>8-oAPT-PET-cGMP |
| 110 | 8-Cyclohexylthio-ß-phenyl-1, N²-ethenoguanosine-3',5'-cyclic monophosphate | 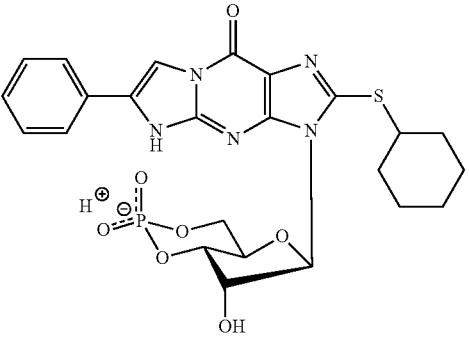<br>8-cHeT-PET-cGMP |
| 111 | 8-Cyclopentylthio-ß-phenyl-1, N²-ethenoguanosine-3',5'-cyclic monophosphate | 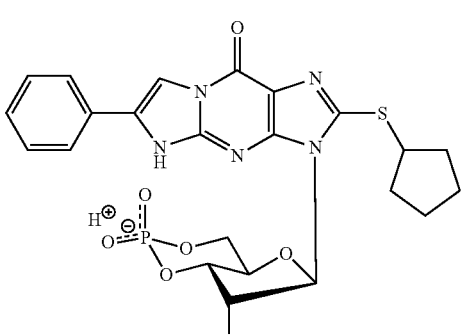<br>8-cPeT-PET-cGMP |
| 112 | 8-(4-Methylphenylthio)-ß-phenyl-1, N²-ethenoguanosine-3',5'-cyclic monophosphate | 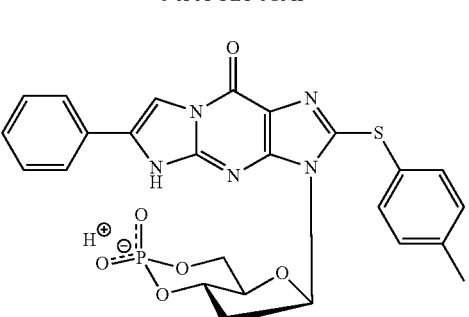<br>8-pMePT-PET-cGMP |

TABLE 14-continued

Structures of novel monomeric precursor compounds according to the invention.

| # | Compound | Structure |
|---|---|---|
| 113 | 8-(4-Methoxyphenylthio)-ß-phenyl-1, N²-ethenoguanosine-3',5'-cyclic monophosphate | 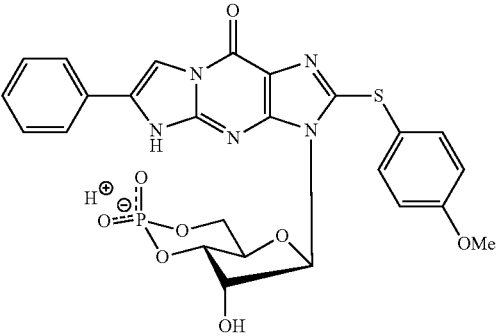<br>8-pMeOPT-PET-cGMP |
| 114 | 8-(3-(2-Methyl)furanyl)thio-ß-phenyl-1, N²-ethenoguanosine-3',5'-cyclic monophosphate | 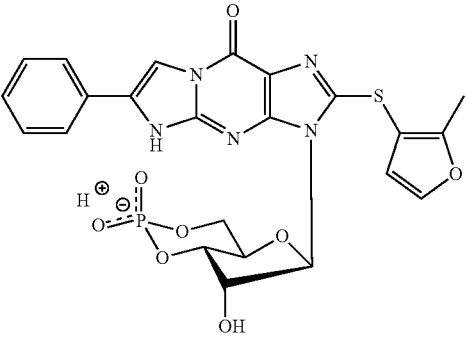<br>8-(3-(2-Me)-FU)T-PET-cGMP |
| 115 | 8-(7-(4-Methyl)coumarinyl)thio-ß-phenyl-1, N²-ethenoguanosine-3',5'-cyclic monophosphate | 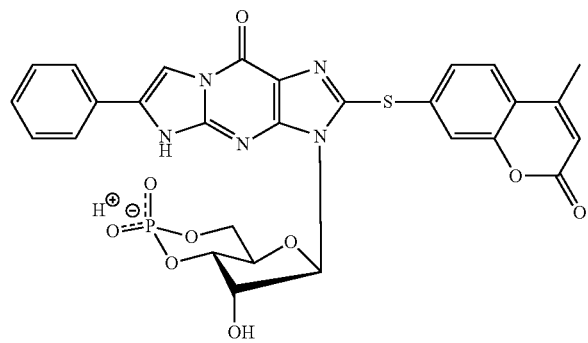<br>8-(7-(4-Me)-Cou)T-PET-cGMP |
| 116 | 8-(2-Naphthyl)thio-ß-phenyl-1, N²-ethenoguanosine-3',5'-cyclic monophosphate | 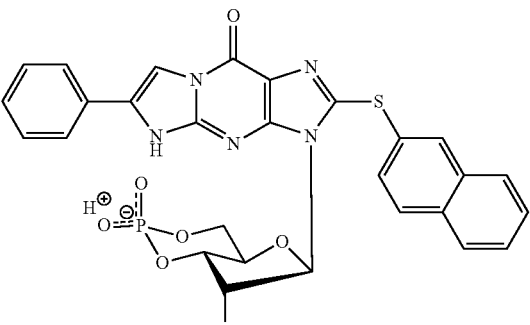<br>8-(2-N)T-PET-cGMP |

TABLE 14-continued

Structures of novel monomeric precursor compounds according to the invention.

| # | Compound | Structure |
|---|---|---|
| 117 | ß-Phenyl-1, N²-etheno-8-(2-thiophenyl)thioguanosine-3',5'-cyclic monophosphate | 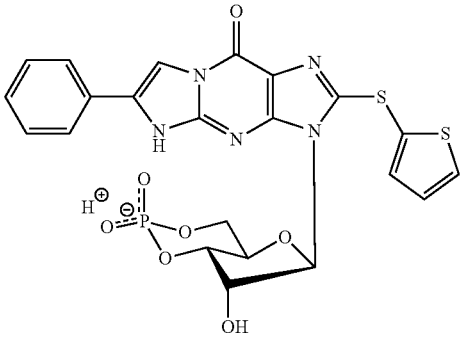<br>PET-8-(2-Tp)T-cGMP |
| 118 | ß-Phenyl-1, N²-etheno-8-(2-phenylethyl)thioguanosine-3',5'-cyclic monophosphate | 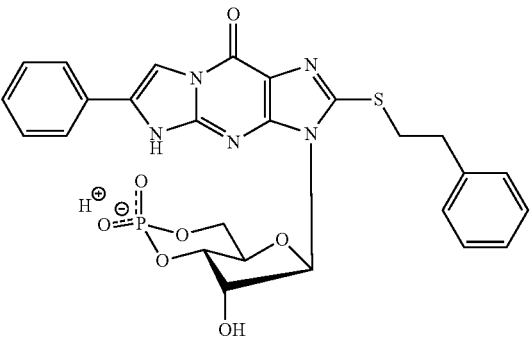<br>PET-8-PhEtT-cGMP |
| 119 | 8-Amidomethylthio-ß-phenyl-1, N²-ethenoguanosine-3',5'-cyclic monophosphate | 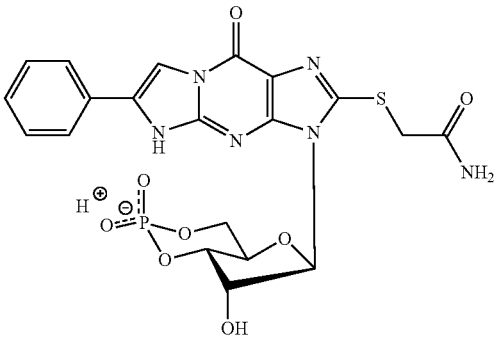<br>8-AmdMT-PET-cGMP |
| 120 | 8-Carboxymethylthio-β-phenyl-1, N²-ethenoguanosine-3',5'-cyclic monophosphate | 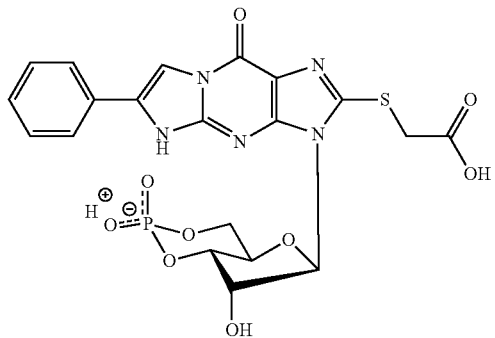<br>8-CMT-PET-cGMP |

TABLE 14-continued

Structures of novel monomeric precursor compounds according to the invention.

| # | Compound | Structure |
|---|---|---|
| 121 | 8-(4-Boronate-phenylthio)-ß-phenyl-1, $N^2$-ethenoguanosine-3',5'-cyclic monophosphate | 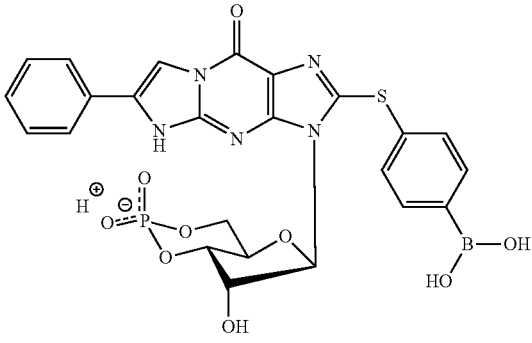<br>8-(pB(OH)$_2$P)T-PET-cGMP |
| 122 | 8-Ethylthio-ß-phenyl-1, N2-ethenoguanosine-3',5'-cyclic monophosphate | 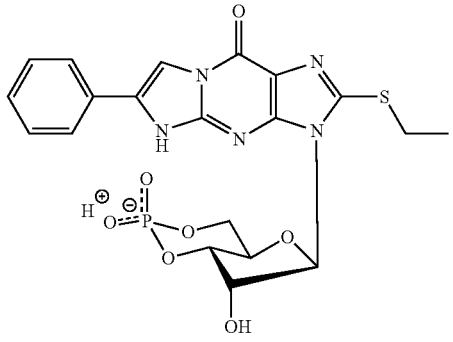<br>8-ET-PET-cGMP |
| 123 | 8-(4-Fluorophenyl-thio)-ß-phenyl-1, $N^2$-ethenoguanosine-3',5'-cyclic monophosphate | 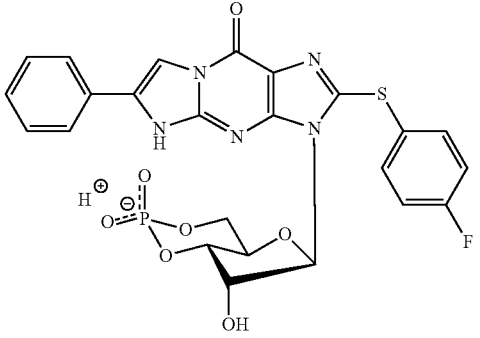<br>8-pFPT-PET-cGMP |
| 124 | 8-Methylthio-ß-phenyl-1, $N^2$-ethenoguanosine-3',5'-cyclic monophosphate | 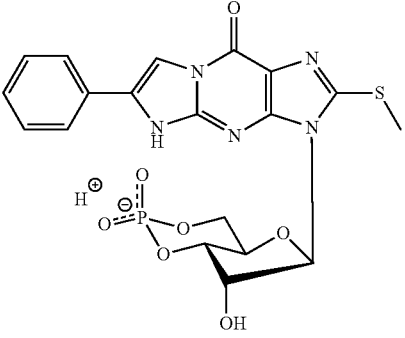<br>8-MeS-PET-cGMP |

TABLE 14-continued

Structures of novel monomeric precursor compounds according to the invention.

| # | Compound | Structure |
|---|---|---|
| 125 | ß-Phenyl-1, $N^2$-etheno-8-propylthio-guanosine-3',5'-cyclic monophosphate | 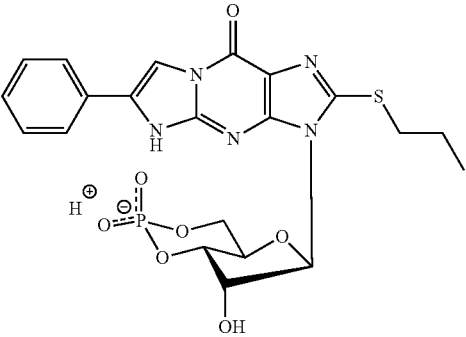<br>PET-8-PrT-cGMP |
| 126 | 8-Azidoethylthio-β-phenyl-1, $N^2$-ethenoguanosine-3',5'-cyclic monophosphate | 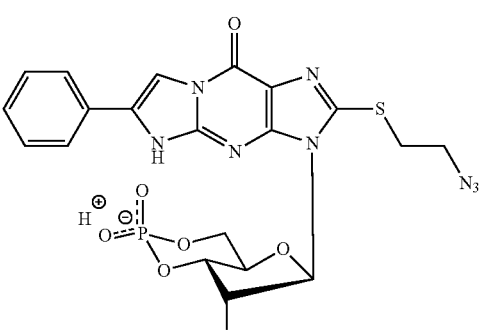<br>8-N$_3$-ET-PET-cGMP |
| 127 | ß-Phenyl-1, $N^2$-etheno-8-(4-trifluoromethylphenyl-thio)guanosine-3',5'-cyclic monophosphate | 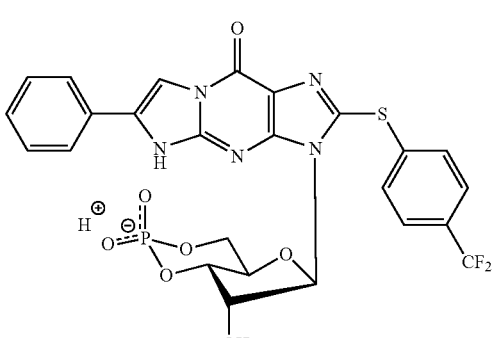<br>PET-8-pTFMePT-cGMP |
| 128 | 8-(4-Chlorophenyl-sulfonyl)-β-phenyl-1, $N^2$-ethenoguanosine-3',5'-cyclic monophosphate | 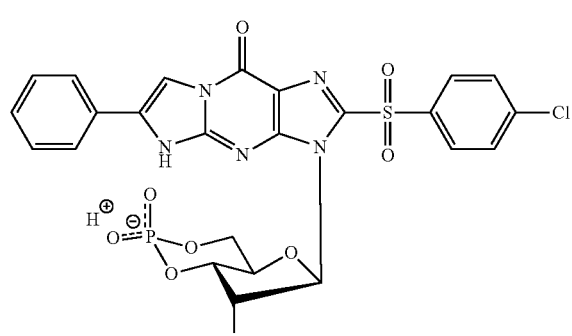<br>8-pCPS-PET-cGMP |

TABLE 14-continued

Structures of novel monomeric precursor compounds according to the invention.

| # | Compound | Structure |
|---|---|---|
| 129 | 8-(4-Isopropyl-phenylthio)-β-phenyl-1, $N^2$-ethenoguanosine-3',5'-cyclic monophosphate | 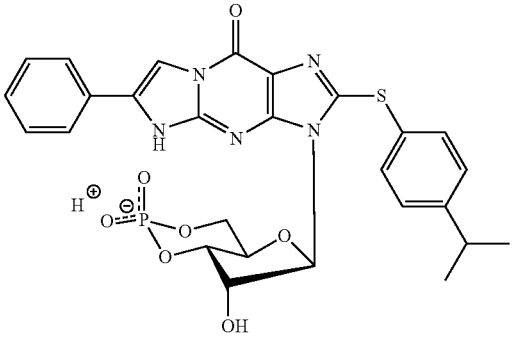<br>8-pIPrPT-PET-cGMP |
| 130 | 8-(4-Isopropyl-phenylsulfonyl)-β-phenyl-1, $N^2$-ethenoguanosine-3',5'-cyclic monophosphate | 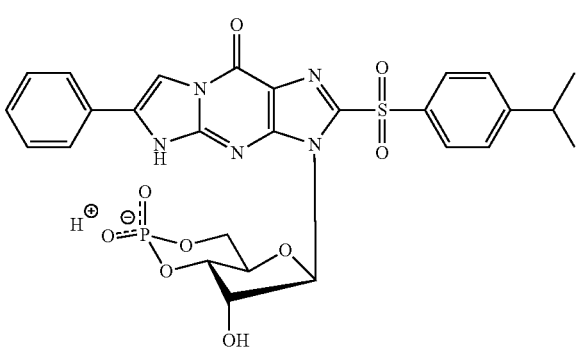<br>8-pIPrPS-PET-cGMP |
| 131 | 8-(4-Chlorophenyl)-β-phenyl-1, $N^2$-ethenoguanosine-3',5'-cyclic monophosphate | 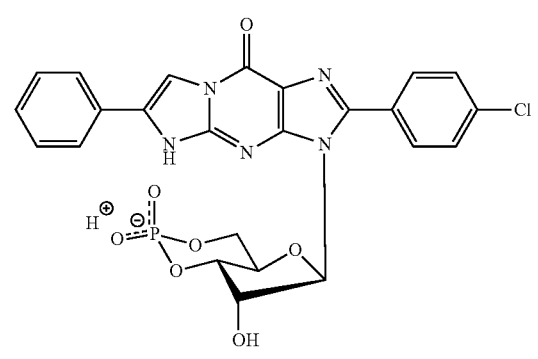<br>8-pCP-PET-cGMP |
| 132 | 8-(4-Hydroxyphenyl)-β-phenyl-1, $N^2$-ethenoguanosine-3',5'-cyclic monophosphate | 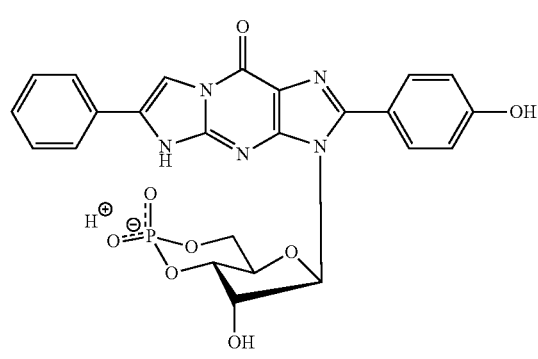<br>8-pHP-PET-cGMP |

TABLE 14-continued

Structures of novel monomeric precursor compounds according to the invention.

| # | Compound | Structure |
|---|----------|-----------|
| 133 | 8-(4-Isopropylphenyl)-β-phenyl-1, N²-ethenoguanosine-3',5'-cyclic monophosphate | 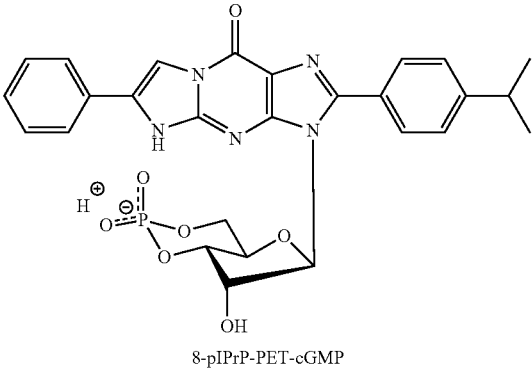<br>8-pIPrP-PET-cGMP |
| 134 | 8-Bromo-(4-methoxy-ß-phenyl-1, N2-etheno)guanosine-3',5'-cyclic monophosphate | 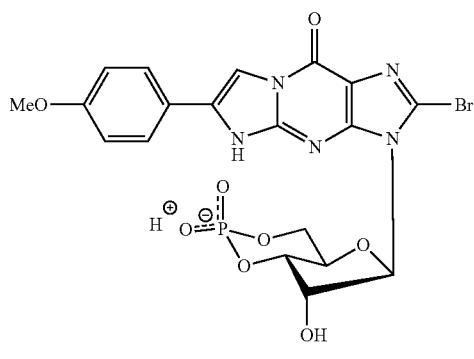<br>8-Br-pMeO-PET-cGMP |
| 135 | 8-Bromo-(4-methyl-ß-phenyl-1, N2-etheno)guanosine-3',5'-cyclic monophosphate | 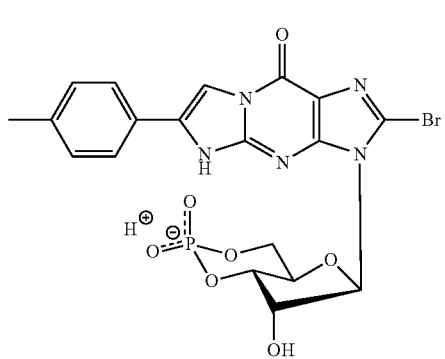<br>8-Br-pMe-PET-cGMP |
| 136 | alpha-Benzoyl-beta-phenyl-1, N2-etheno-8-bromoguanosine-3',5'-cyclic monophosphate | 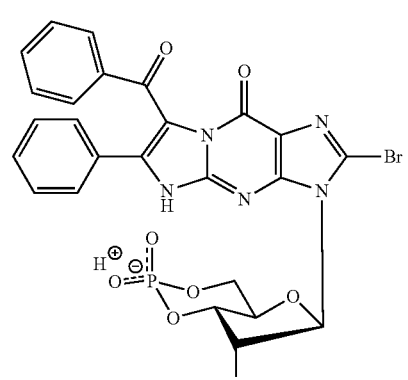<br>Bnz-PET-8-Br-cGMP |

TABLE 14-continued

Structures of novel monomeric precursor compounds according to the invention.

| # | Compound | Structure |
|---|---|---|
| 137 | 8-Bromo-(4-chloro-ß-phenyl-1, N2-etheno)guanosine-3',5'-cyclic monophosphate | 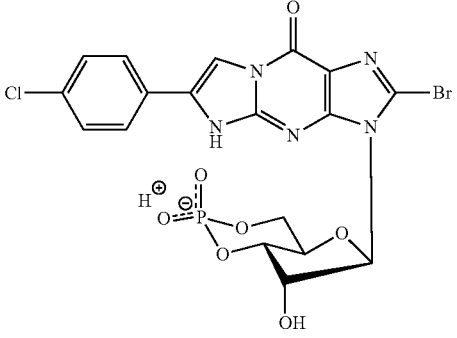<br>8-Br-pCl-PET-cGMP |
| 138 | 8-Bromo-(3-nitro-ß-phenyl-1, N2-etheno)guanosine-3',5'-cyclic monophosphate | 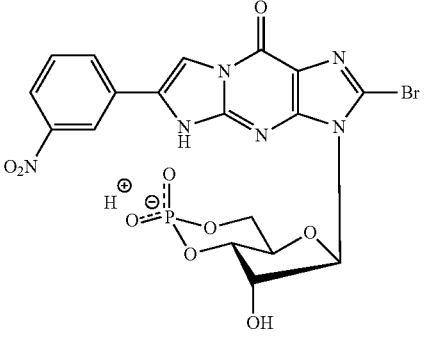<br>8-Br-mN-PET-cGMP |
| 139 | 8-Bromo-(ß-tert.-butyl-1, N2-etheno)guanosine-3',5'-cyclic monophosphate | 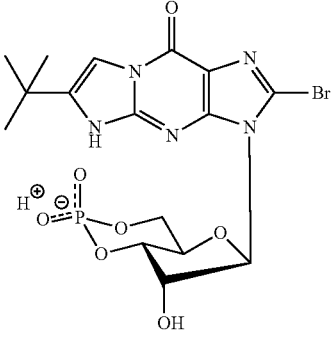<br>8-Br-tBuET-cGMP |
| 140 | 8-Bromo-(2-methoxy-ß-phenyl-1, N2-etheno)guanosine-3',5'-cyclic monophosphate | 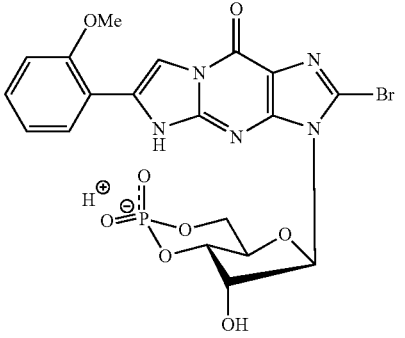<br>8-Br-oMeO-PET-cGMP |

TABLE 14-continued

Structures of novel monomeric precursor compounds according to the invention.

| # | Compound | Structure |
|---|----------|-----------|
| 141 | 8-Bromo-(3-methoxy-ß-phenyl-1, N2-etheno)guanosine-3',5'-cyclic monophosphate | 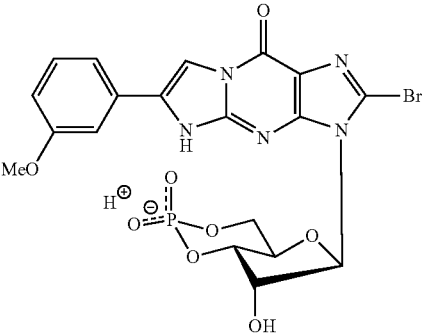<br>8-Br-mMeO-PET-cGMP |
| 142 | 8-Bromo-(2,4-dimethoxy-ß-phenyl-1, N2-etheno)guanosine-3',5'-cyclic monophosphate | 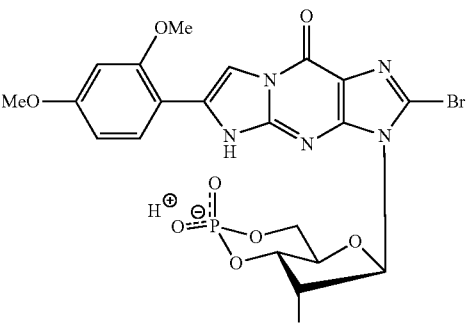<br>8-Br-o,pDMeO-PET-cGMP |
| 143 | 8-Bromo-(4-pyridinyl-1, N2-etheno)guanosine-3',5'-cyclic monophosphate | 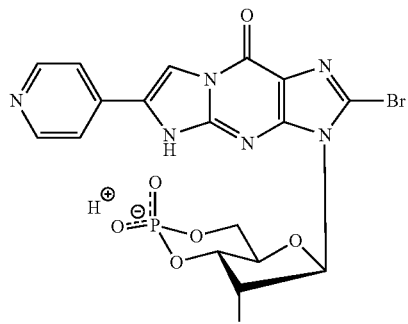<br>8-Br-(4-Pyr)ET-cGMP |
| 144 | 8-Bromo-(3-thiophen-yl-1, N2-etheno)guanosine-3',5'-cyclic monophosphate | 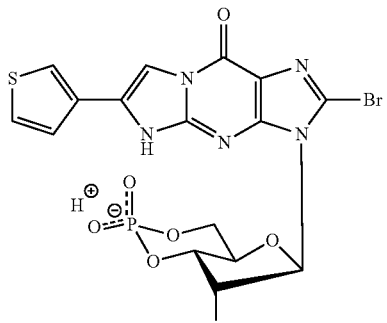<br>8-Br-(3-Tp)ET-cGMP |

TABLE 14-continued

Structures of novel monomeric precursor compounds according to the invention.

| # | Compound | Structure |
|---|----------|-----------|
| 145 | 8-Bromo-(4-fluoro-ß-phenyl-1, N2-etheno)guanosine-3',5'-cyclic monophosphate | 8-Br-pF-PET-cGMP |
| 146 | 8-Bromo-1, N2-ethenoguanosine-3',5'-cyclic monophosphate | 8-Br-ET-cGMP |
| 147 | 8-Bromo-(3-hydroxy-ß-phenyl-1, N2-etheno)guanosine-3',5'-cyclic monophosphate | 8-Br-mH-PET-cGMP |
| 148 | 8-Bromo-(4-hydroxy-ß-phenyl-1, $N^2$-etheno)guanosine-3',5'-cyclic monophosphate | 8-Br-pHPET-cGMP |

TABLE 14-continued

Structures of novel monomeric precursor compounds according to the invention.

| # | Compound | Structure |
|---|----------|-----------|
| 149 | 8-Bromo-(ß-(2,3-dihydro-1,4-benzodioxin)-1, N2-etheno)guanosine-3',5'-cyclic monophosphate | 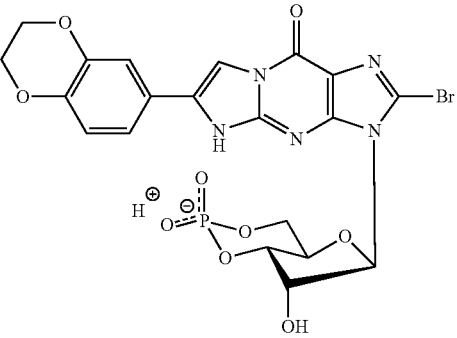<br>8-Br-(2,3-DHy-1,4-BnzDiox)-ET-cGMP |
| 150 | 8-Bromo-(4-methylsulfonamido-ß-phenyl-1, N2-etheno)guanosine-3',5'-cyclic monophosphate | 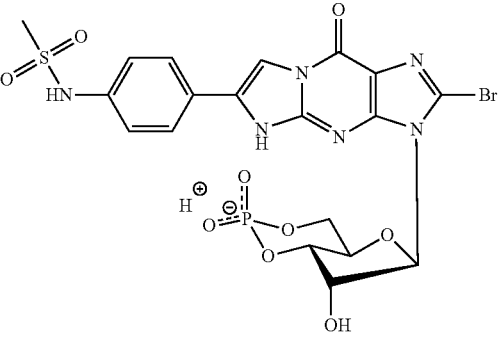<br>8-Br-pMSulfAmd-PET-cGMP |
| 151 | 8-Bromo-(4-cyano-β-phenyl-1, $N^2$-etheno)guanosine-3',5'-cyclic monophosphate | 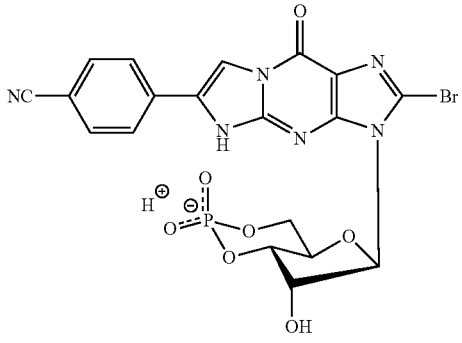<br>8-Br-pCN-PET-cGMP |
| 152 | 8-Bromo-(α-phenyl-β-methyl-1, $N^2$-etheno)guanosine-3',5'-cyclic monophosphate | 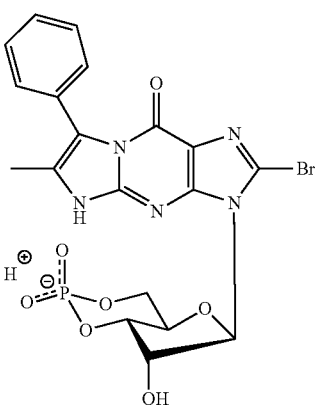<br>8-Br-alpha-Phe-beta-Me-ET-cGMP |

TABLE 14-continued

Structures of novel monomeric precursor compounds according to the invention.

| # | Compound | Structure |
|---|---|---|
| 153 | β-(4-Aminophenyl)-1, N²-etheno-8-bromoguanosine-3',5'-cyclic monophosphate | pNH₂-PET-8-Br-cGMP |
| 154 | 8-Bromo-(6-methoxy-2-naphthyl-1, N²-etheno) guanosine-3',5'-cyclic monophosphate | 8-Br-(6-MeO-2-N)ET-cGMP |
| 155 | 8-Bromo-(9-phenanthrenyl-1, N²-etheno)guanosine-3',5'-cyclic monophosphate | 8-Br-(9-Phethr)ET-cGMP |
| 156 | 8-Bromo-(4-trifluoromethyl-β-phenyl-1, N²-etheno) guanosine-3',5'-cyclic monophosphate | 8-Br-pTFMe-PET-cGMP |

TABLE 14-continued

Structures of novel monomeric precursor compounds according to the invention.

| # | Compound | Structure |
|---|---|---|
| 157 | (4-Fluoro-ß-phenyl-1, N2-etheno)-8-methyl-thioguanosine-3',5'-cyclic monophosphate | 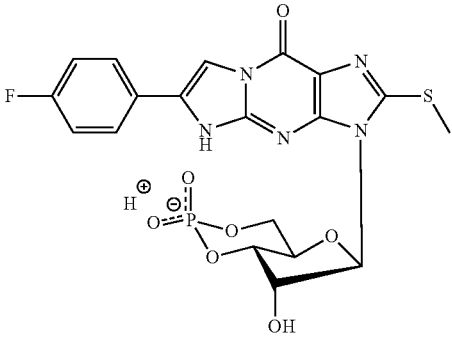<br>pF-PET-8-MeS-cGMP |
| 158 | (4-Methoxy-ß-phenyl-1, N2-etheno)-8-methyl-thioguanosine-3',5'-cyclic monophosphate | 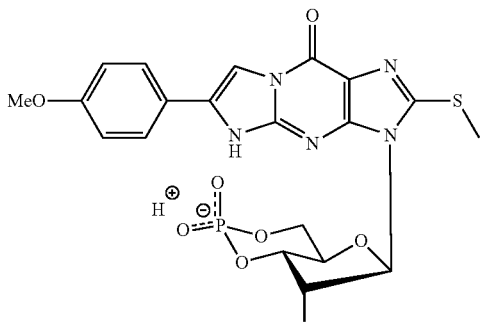<br>pMeO-PET-8-MeS-cGMP |
| 159 | 1, $N^2$-Etheno-8-(2-phenylethyl)thioguanosine-3',5'-cyclic monophosphate | 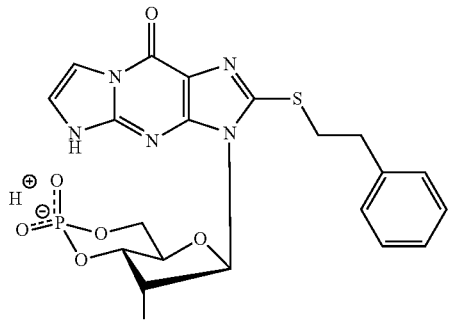<br>ET-8-PhEtT-cGMP |
| 160 | (4-Methoxy-ß-phenyl-1, N2-etheno)-8-propylthio-guanosine-3',5'-cyclic monophosphate | 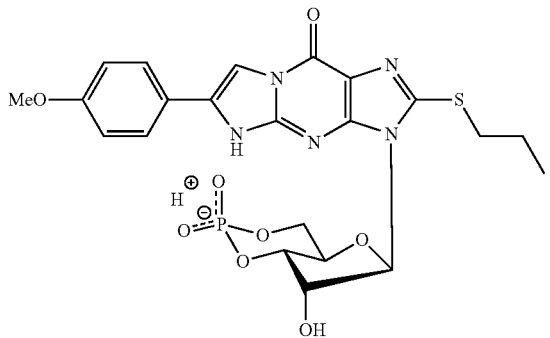<br>pMeO-PET-8-PrT-cGMP |

TABLE 14-continued

Structures of novel monomeric precursor compounds according to the invention.

| # | Compound | Structure |
|---|---|---|
| 161 | β-1, N²-Acetyl-8-bromoguanosine-3',5'-cyclic monophosphate | 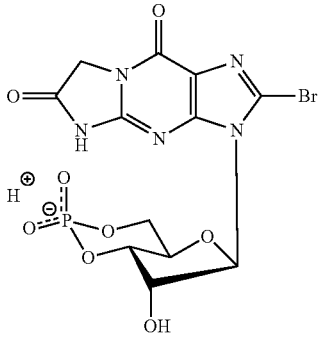<br>β-1,N²-Ac-8-Br-cGMP |
| 162 | 8-Bromo-δ-1, N²-butyrylguanosine-3',5'-cyclic monophosphate | 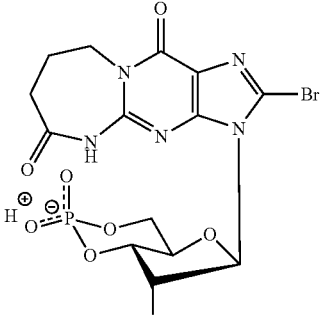<br>8-Br-δ-1,N²-But-cGMP |
| 163 | 8-Bromo-1-(3-carboxypropyl)guanosine-3',5'-cyclic monophosphate | 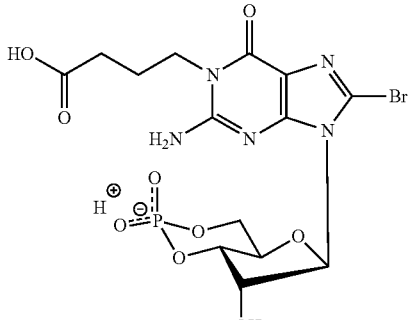<br>8-Br-1-CPr-cGMP |
| 164 | 1-[Aminomethyl-(pentaethoxy)-propylamidopropyl]-8-bromoguanosine-3',5'-cyclic monophosphate | 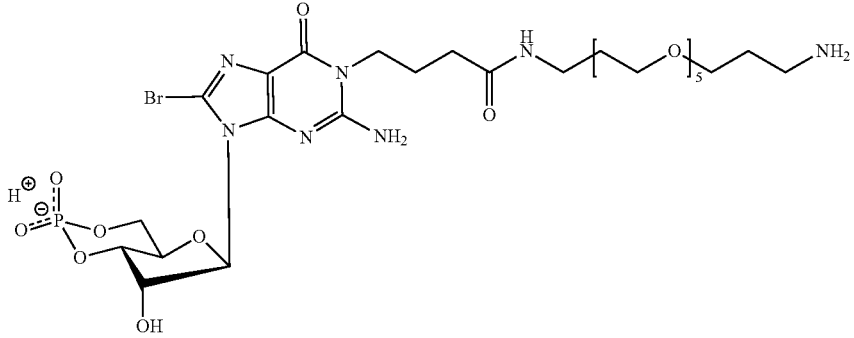<br>1-AM-(EO)₅-PrAmdPr-8-Br-cGMP |

TABLE 14-continued

Structures of novel monomeric precursor compounds according to the invention.

| # | Compound | Structure |
|---|---|---|
| 165 | 1-Benzyl-8-bromo-guanosine-3',5'-cyclic monophosphate | 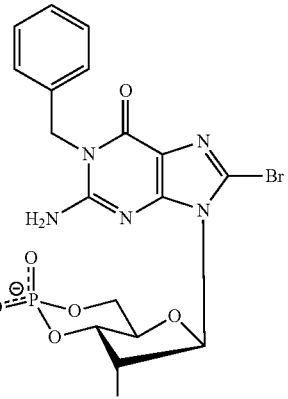<br>1-Bn-8-Br-cGMP |
| 166 | 2'-O-(2-Azidoacetyl)-8-bromo-β-phenyl-1, $N^2$-ethenoguanosine-3',5'-cyclic monophosphate | 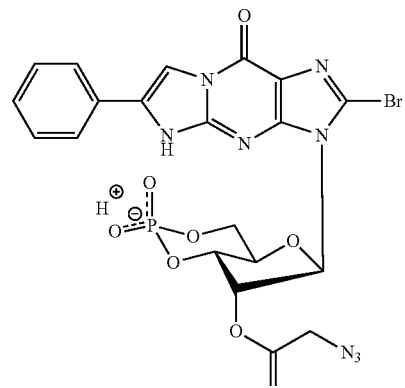<br>2'-O-(2-N$_3$Ac)-8-Br-PET-cGMP |

As described above, the compounds according to the present invention may further be labelled, according to well-known labelling techniques. For example, fluorescent dyes may be coupled to the compounds in order to, but not limited to, localize the intracellular distribution of cyclic nucleotide binding proteins in living cells by means of confocal microscopy, for fluorescence correlation spectrometry, for fluorescence energy transfer studies, or for determination of their concentration in living cells.

It should be understood that hydrates of the compounds are also within the scope of the present invention.

Instead of or additional to fluorescent dyes the compounds according to the inventions may be labelled with (radio) nuclides. The person skilled in the art knows many techniques and suitable isotopes that can be used for this.

As described above, the invention also comprises PEGylated forms of the specified compounds, wherein PEGylation is generally known to greatly improve water solubility, pharmacokinetic and biodistribution properties.

The invention further comprises modifications wherein $R_7$ (according to formula III) can be an unsubstituted or substituted thio- or borano function. Both modifications are known in the art to improve resistance towards metabolic degradation.[1a, 14]

The invention also comprises prodrug forms of the described compounds, wherein the negative charge of the (modified or unmodified) phosphate moiety is masked by a bioactivatable protecting group. It is widely accepted that such structures increase lipophilicity and with that, membrane-permeability and bioavailability resulting in a 10-1000 fold enhanced potency compared to the mother-compound. Such bioactivatable protecting groups can be introduced according to well known techniques of the art and include, but are not limited to acetoxymethyl, propionyloxymethyl, butyryloxymethyl, pivaloyloxymethyl, acetoxyethyl, acetoxybutyl, acetoxyisobutyl. Non limiting examples of corresponding residues R7 and/or R8 according to the invention are acetoxymethyloxy, propionyloxymethyloxy and butyryloxymethyloxy. More labile examples of protecting groups include alkyl or aryl groups as well as substituted alkyl or aryl groups. Non limiting examples for chemically labile protection groups of the R7 and/or R8 position are methyl, ethyl, 2-cyanoethyl, propyl, benzyl, phenyl and polyethylene glycol. These compounds are inactive per se, but extremely membrane-permeable, leading to strongly increased intracellular concentrations. Upon hydrolysis of the ester bond, the biologically active mother compounds are released.

Compounds according to the invention can also feature a photolysable group (also-called "caged"- or photo-activatable protecting group), which can be introduced according to well known techniques of the art. For example, but not limited to, caged groups may be coupled to an R8 oxo-function, leading to compounds with significantly increased lipophilicity and bioavailability. Non limiting examples for caged groups are o-nitro-benzyl, 1-(o-nitrophenyl)-ethyl-idene, 4,5-dimethoxy-2-nitro-benzyl, 7-dimethylamino-coumarin-4-yl (DMACM-caged), 7-diethylamino-coumarin-4-yl (DEACM-caged) and 6,7-bis(carboxymethoxy)coumarin-4-yl)methyl (BCMCM-caged).

The compounds according to the present invention can also be immobilized to insoluble supports, such as, but not limited to, agarose, dextran, cellulose, starch and other carbohydrate-based polymers, to synthetic polymers such as polacrylamide, polyethyleneimine, polystyrol and similar materials, to apatite, glass, silica, gold, graphene, fullerenes, carboranes, titania, zirconia or alumina, to the surface of a chip suitable for connection with various ligands.

The compounds according to the present invention can also be encapsulated within nanoparticles or liposomes for directed or non-directed delivery and release purposes of the compounds as described in the literature.[11]

Preferably, the new polymer linked multimeric cGMP analogues of the invention, or the related monomeric compounds of formula (III) of the present invention, respectively, are used for treating or preventing a disease or condition that is associated with low cGMP signaling activity.

Diseases and conditions are preferably treated with polymer linked multimeric cGMP analogues, or the related monomeric compounds of formula (III) of the present invention, respectively, that activate the disease-related unbalanced cGMP-system, and include[1c]:

- neurodegenerative diseases associated with insufficient synaptic function and learning and memory defects.
- neuromuscular junction defects including motor neuron diseases (e.g. Amyotrophic lateral sclerosis (ALS), Primary lateral sclerosis), also forms caused by certain infectious diseases (e.g. paralytic Poliomyelitis)
- cancer, including the initiation of cancer cell apoptosis and the prevention of metastasis
- cardiovascular diseases, including hypertension, cardiac hypertrophy, angina pectoris, ischemia and stroke
- parasitic diseases caused by trypanosomes, including Malaria, Chagas, sleeping sickness
- borelliosis (lyme disease)
- pulmonary diseases and conditions, such as pulmonary fibrosis and pulmonary hypertension
- osteoporosis
- Autoimmune diseases associated with an excessive proliferation of B- and T-cells including but not limited to: multiple sclerosis, Crohn's disease, Hashimoto's disease, juvenile arthritis, myocarditis, and rheuma.

It is to be understood herein that the treatment of a pathology, condition or disorder also includes the prevention thereof, even if not explicitly mentioned, unless specifically otherwise indicated.

In another aspect, the invention relates to a method for treating or preventing any of the above pathologies, conditions or disorders by administration of a therapeutically or prophylactically effective amount of an equatorially modified cGMP-analogue of the invention to a subject in need of prophylaxis or therapy.

The compounds according to the present invention, including the related monomeric compounds of formula (III) of the present invention, respectively, can also be used as research tool compound, preferably as research tool compound in regard of a disease or disorder related to an unbalanced cGMP-system, preferably a disease or disorder selected from the group consisting of cancer, cardiovascular disease or disorder, or autoimmune disease or disorder, or neurodegenerative disease or disorder.

The invention is further illustrated by the following figures and examples describing preferred embodiments of the present invention which are, however, not intended to limit the invention in anyway.

EXAMPLES

1. Compound Synthesis
General Experimental Methods

All applied solvents and reagents were available from commercial suppliers. 8-Br-cGMP, 8-Br-PET-cGMP and 4-N$_3$-PET-8-Br-cGMP were available from Biolog Life Science Institute (Bremen, Germany). 8-T-cGMP is established in the literature and was prepared analogously to PET-8-T-cGMP (see examples below). Solvents used were specified as analytical or hplc grade. Dimethyl sulfoxide was stored over activated molecular sieves for at least two weeks before use. Chromatographic operations were performed at ambient temperature. Both reaction progress and purity of isolated products were determined by reversed phase hplc (RP-18, ODS-A-YMC, 120-S-11, 250×4 mm, 1.5 mL/min), wherein UV detection was performed either at 263 nm, an intermediate wavelength suitable to detect most cyclic GMP products and—impurities, or at the $\lambda_{max}$ of the particular starting material or product. Syntheses were typically performed in a 20-200 µmol scale in 2 mL polypropylene reaction vials with screw cap (reactions requiring inert gas atmosphere and/or degassing were performed in round bottom flasks (typically 10 or 25 mL)). Dissolution of poorly soluble reactants was achieved through sonification or heating (70° C.) prior to addition of reagents. In case dissolution was not elicited by these techniques, which mainly applied to some cGMP analogues carrying a PET-moiety, the suspension was used. Purification of products was accomplished by preparative reversed phase hplc (RP-18, ODS-A-YMC, 12 nm-S-10, 250×16 mm, UV 254 nm). The eluent composition is described in the particular synthetic example and, unless stated otherwise, can be used for analytical purposes as well. Desalting of products was accomplished by repeatedly freeze-drying or by preparative reversed phase hplc (RP-18, ODS-A-YMC, 12 nm-S-10, 250×16 mm, UV 254 nm) according to standard procedures for nucleotides. Solutions were frozen at −70° C. for 15 min prior to evaporation, in case a speedvac concentrator was used to remove the solvent. Products were either isolated as sodium or triethylammonium salt, depending on the applied buffer. Yields refer to the fraction of isolated product featuring the reported purity. They were calculated from UV-absorbance at the $\lambda_{max}$, measured on a JASCO V-650 Spectrophotometer (JASCO Germany GmbH, Gross-Umstadt, Germany) according to Lambert-Beer's law. Extinction coefficients were estimated from literature known values of structurally related compounds. Mass spectra were obtained with an Esquire LC 6000 spectrometer (Bruker Daltronics, Bremen, Germany) in the ESI-MS mode with 50% water/50% methanol as matrix.

Experimental Procedures for the Preparation of 8-Thio-Modified Guanosine-3',5'-Cyclic Monophosphate Analogues General Procedure A:

In a typical experiment the corresponding thiol reactant (8 eq) and NaOH (2 M, 4 eq) were added successively to a solution of the corresponding 8-Br-substituted cGMP analogue (sodium salt, 65 mM, 1 eq) in $H_2O$/i-PrOH (1:1, v/v). The reaction mixture was heated to 90° C. and stirred until the bromide starting material was completely consumed or no further reaction progress was observed. The solution was then allowed to reach room temperature, neutralized with HCl (1 M) and the solvent was removed through high vacuum evaporation with a speedvac concentrator. The residue was dissolved in water (1 mL) and washed with MTBE (3x).* The aqueous phase was evaporated under reduced pressure using a rotary evaporator, the residue redissolved in water, subjected to preparative reversed phase hplc and desalted, giving the 8-thio-modified cGMP analogue.

*In case the residue was not soluble in water, the obtained suspension was washed with MTBE and (if necessary) diluted with MeOH to dissolve remaining precipitate.

General Procedure A2:

In a typical experiment the corresponding thiol(ate) reactant (4.5 eq) was added to a solution of the corresponding 8-Br-substituted cGMP analogue (sodium salt, 65 mM, 1 eq) in $H_2O$/i-PrOH (1:1, v/v). The reaction mixture was stirred at room temperature until the bromide starting material was completely consumed or no further reaction progress was observed. The solution was then adjusted to pH 6 with NaOH (10%) and the solvent was removed through high vacuum evaporation with a speedvac concentrator. The residue was dissolved in water (1 mL) and washed with $CH_2Cl_2$ (3x). The aqueous phase was evaporated under reduced pressure using a rotary evaporator, the residue redissolved in water, subjected to preparative reversed phase hplc and desalted, giving the 8-thio-modified cGMP analogue.

General Procedure B:

In a typical experiment a solution of the 8-Br-substituted cGMP analogue (sodium salt, 87 mM, 1 eq) was added portionwise over 2 h to a suspension of the corresponding dithiol (50 mM in water/i-PrOH, 2:3, v/v, 10 eq) and NaOH (2 M, 5 eq). The reaction mixture was heated to 90° C. and stirred until the bromide starting material was completely consumed or no further reaction progress was observed. The solvent was removed through high vacuum evaporation with a speedvac concentrator. The residue was suspended in water (1 mL), neutralized with HCl (1 M) and filtered. The crude product solution was subjected to preparative reversed phase hplc and desalted, giving the thiol analogue.

General Procedure C:

In a typical experiment NaOH (2 M, 16 eq) and the corresponding thiol reactant (8 eq) were added successively to a solution of the 8-Br-substituted cGMP analogue (sodium salt, 200 mM, 1 eq) in borate buffer (100 mM, pH 12). The reaction mixture was heated to 90° C. and stirred until the bromide starting material was completely consumed or no further reaction progress was observed. The solution was then allowed to reach room temperature and neutralized with HCl (1 M). The solvent was removed under reduced pressure using a rotary evaporator. The residue was dissolved in water (1 mL), subjected to preparative reversed phase hplc and desalted.

General Procedure D:

In a typical experiment N,N-diisopropylethylamine (2 eq) and the corresponding bromide (1 eq) were added successively to a solution of the 8-SH-substituted cGMP analogue (sodium or triethylammonium salt, 100 mM, 1 eq) in DMSO. The reaction mixture was stirred until the thiol starting material was completely consumed or no further reaction progress was observed. The solvent was removed through high vacuum evaporation with a speedvac concentrator. The residue was dissolved in water (1 mL), washed with ethyl acetate (3x), subjected to preparative reversed phase hplc and desalted.

General Procedure E:

For the formation of dimeric cGMP analogues general Procedure D was followed using N,N-diisopropylethylamine (2 eq), the corresponding bis-bromide spacer (0.5 eq) and the 8-SH-substituted cGMP analogue (sodium or triethylammonium salt, 100 mM, 1 eq) in DMSO.

Experimental Procedure for the Transformation of Carboxylic Acid Ester Functionalized Guanosine-3',5'-Cyclic Monophosphate Analogues into the Corresponding Carboxylic Acid or Amide General Procedure F:

In a typical experiment NaOH (2 M, 10 eq) was added to a solution of the corresponding ester (80 mM, 1 eq) in water/MeOH (1:1, v/v). The reaction mixture was stirred until the ester starting material was completely consumed or no further reaction progress was observed. The solution was then neutralized with HCl (1 M) and the solvent was removed under reduced pressure using a rotary evaporator. The residue was dissolved in water (1 mL), subjected to preparative reversed phase hplc and desalted, giving the carboxylic acid analogue.

General Procedure G:

In a typical experiment the corresponding ester (1 eq) was dissolved in excess methanolic ammonia (4.2 M, 200 eq). The reaction mixture was stirred until the starting material was completely consumed or no further reaction progress was observed. The solvent was removed through high vacuum evaporation with a speedvac concentrator. The residue was dissolved in water (1 mL), neutralized with HCl (1 M) and filtered through a syringe filter. The crude product was subjected to preparative reversed phase hplc and desalted, giving the carboxylic acid amide analogue.

Experimental Procedures for the Formation of Amide Bonds with Guanosine-3',5'-Cyclic Monophosphate Analogues General Procedure H:

In a typical experiment HOBt (1.1 eq), N,N-diisopropylethylamine (2.2 eq) and EDC (1.1 eq) were added successively to a solution of the corresponding acid-substituted cGMP analogue (100 mM in DMSO, 1 eq) and the corresponding amine (1.1 eq)*. The reaction mixture was stirred until the starting material was completely consumed or no further reaction progress was observed. The solvent was removed through high vacuum evaporation with a speedvac concentrator. The residue was dissolved in water (1 mL) and washed with ethyl acetate (5x). The aqueous phase was evaporated under reduced pressure using a rotary evaporator, redissolved in water, subjected to preparative reversed phase hplc and desalted, giving the coupled cGMP analogue.

*The less valuable reactant was added in slight excess, thus for the reaction with reversed functions the amine-substituted cGMP analogue (100 mM in DMSO, 1 eq) and the acid reactant (1.1 eq) were used.

General Procedure I:

In a typical experiment HOBt (1.1 eq), N,N-diisopropylethylamine (2.2 eq) and EDC (1.1 eq) were added successively to a solution of the corresponding acid-substituted cGMP analogue (100 mM in DMSO, 1 eq) and the corresponding bis-amino spacer (0.5 eq). Workup was performed as described in general procedure H, giving the dimeric cGMP analogue.

General Procedure J:

In a typical experiment N,N-diisopropylethylamine (2.2 eq) and PyBOP (1.1 eq) were added successively to a solution of the corresponding carboxylic acid-substituted cGMP analogue (100 mM in DMSO, 1 eq) and the corresponding amine (1.1 eq)*. The reaction mixture was stirred until the starting material was completely consumed or no further reaction progress was observed (usually <10 min). Water (100 µL) was added, stirring was continued for 10 min and the solvent was removed through high vacuum evaporation with a speedvac concentrator. The residue was dissolved in water (1 mL), if necessary the pH was adjusted to 6 with NaOH (2 M) or HCl (1 M) and the solution washed with ethyl acetate (5×). The aqueous phase was evaporated under reduced pressure using a rotary evaporator, redissolved in water, subjected to preparative reversed phase hplc and desalted, giving the coupled cGMP analogue.

*The less valuable reactant was added in slight excess, thus for the reaction with reversed functions the amine-substituted cGMP analogue (100 mM in DMSO, 1 eq) and the acid reactant (1.1 eq) were used.

General Procedure K:

In a typical experiment a solution of the corresponding carboxylic acid-substituted cGMP analogue (100 mM in DMSO, 1 eq) was added portionwise over 40 min to a solution of the bis-amino spacer (400 mM in DMSO, 5 eq), N,N-diisopropylethylamine (2.2 eq) and PyBOP (1.1 eq). More PyBOP (1 eq) was added and the reaction mixture was stirred until the starting material was completely consumed or no further reaction progress was observed (usually <10 min). Workup was performed as described in general procedure J, giving the monomeric cGMP analogue coupling product.

General Procedure L:

General procedure J was followed using the corresponding acid-substituted cGMP analogue (100 mM in DMSO, 1 eq), the bis-amino spacer (0.5 eq), N,N-diisopropylethylamine (2.2 eq) and PyBOP (1.1 eq) to obtain the dimeric cGMP analogue.

General Procedure M:

General procedure J was followed using the corresponding amine-substituted cGMP analogue (33 mM in DMSO, 1 eq), the linker tri-acid (0.3 eq), N,N-diisopropylethylamine (2 eq) and PyBOP (1.3 eq) to obtain the trimeric cGMP analogue.

General Procedure N:

General procedure J was followed using the corresponding amine-substituted cGMP analogue (diisopropylethylammonium salt, 50 mM in DMSO, 1 eq)*, the linker tetra-acid (tetra-diisopropylethylammonium salt, 0.25 eq)*, N,N-diisopropylethylamine (3 eq) and PyBOP (1.3 eq) to obtain the tetrameric cGMP analogue.

*To transform the reactants into the diisopropylethylammonium salt they were subjected to N,N-diisopropylethylamine (3 eq per acidic function) in water (0.1-0.3 M) and evaporated to dryness using a speedvac concentrator at high vacuum.

Experimental Procedures for the Preparation of 8-Sulfonyl- and 8-Sulfoxide-Modified Guanosine-3',5'-Cyclic Monophosphate Analogues General Procedure O:

In a typical experiment a solution of OXONE® (180 mM, 5 eq) in NaOAc buffer (2 M, pH 4.2) was added dropwise to a solution of the corresponding 8-thio-substituted cGMP analogue (40 mM, 1 eq) in water/MeOH (1:1, v/v). The reaction mixture was stirred until the thio starting material was completely consumed or no further reaction progress was observed. The solution was then neutralized with NaOH (2 M) and filtered through a syringe filter. The solvent was removed under reduced pressure using a rotary evaporator. The residue was dissolved in water (1 mL), subjected to preparative reversed phase hplc and desalted, giving the 8-sulfonyl-substituted cGMP analogue.

Derivatives featuring a modified phosphate function, sensitive to oxidation reactions, such as a phosphorothioate, were synthesized starting from the corresponding guanosine, while the (modified) phosphate group was then introduced according to well established methods of the art (e.g. thiophosphorylation protocol[12]) after oxidation of the 8-thio function.

General Procedure P:

General procedure O was followed, favoring the formation of the 8-sulfoxide-substituted cGMP analogue through shorter reaction time and decreased equivalents of oxidizing agent OXONE® (1.5 eq).

Experimental Procedure for the Generation of 8-Azidoalkylthio-Substituted Guanosine-3',5'-Cyclic Monophosphate Analogues General Procedure Q:

In a typical experiment $NaN_3$ (22.5 eq) was added portionwise over 5 h to a solution of 1,2-dibromoalkane (1.5 M, 15 eq) in DMF in an amber flask. The reaction mixture was stirred for 23 h and the 8-SH-substituted cGMP analogue (triethylammonium salt, 1 eq) as well as N,N-diisopropylethylamine (1 eq) were added successively. Stirring was continued until the cGMP analogue starting material was completely consumed or no further reaction progress was observed (usually about 1 h). The solvent was removed through high vacuum evaporation with a speedvac concentrator. The residue was dissolved in water (1 mL) and washed with MTBE (5×). The aqueous phase was evaporated under reduced pressure using a rotary evaporator, the residue was redissolved in water, subjected to preparative reversed phase hplc and desalted, giving the 8-azidoalkyl-thio-substituted analogue.

Experimental Procedures for the [3+2] Cycloaddition of Azides and Terminal Alkynes on Guanosine-3',5'-Cyclic Monophosphate Analogues General Procedure R:

In a typical experiment a solution of the corresponding azide (0.5 M in $CH_2Cl_2$, 1.1 eq) was added to the alkyne-substituted cGMP analogue (40 mM in $H_2O$, 1 eq) in an amber flask. Bromotris(triphenylphosphine)copper(I) ([Cu(PPh$_3$)$_3$Br]) (0.05 eq) was added and the reaction mixture was stirred until the alkyne starting material was completely consumed or no further reaction progress was observed. The mixture was diluted with water (to 1.5 mL) and washed with $CH_2Cl_2$ (3×). The aqueous phase was evaporated under reduced pressure using a rotary evaporator, the residue was redissolved in water, subjected to preparative reversed phase hplc and desalted, giving the triazole addition product.

General Procedure S:

In a typical experiment Cu(PPh$_3$)$_3$Br (0.05 eq) was added to a solution of the corresponding azide (13 mM, 1 eq) and the corresponding alkyne (13 mM, 1 eq) in water/N,N-diisopropylethylamine (7:1, v/v) in an amber flask. The reaction mixture was stirred at 65° C. until the starting material was completely consumed or no further reaction progress was observed. The solvent was removed through high vacuum evaporation with a speedvac concentrator. The residue was dissolved in water (1 mL) and washed with $CH_2Cl_2$ (3×). The aqueous phase was evaporated under reduced pressure using a rotary evaporator, the residue was redissolved in water, subjected to preparative reversed phase hplc and desalted, giving the triazole-containing product.

General Procedure T:

General Procedure S was followed, using Cu(PPh$_3$)$_3$Br (0.05 eq), the corresponding azide-substituted cGMP analogue (23 mM, 1 eq) and the corresponding bis-alkyne (12 mM, 2 eq) in water/N,N-diisopropylethylamine (8:1, v/v). Conditions were chosen to obtain both the monomeric and the dimeric triazole-containing product.

General Procedure U:

General Procedure S was followed, using [Cu(PPh$_3$)$_3$Br] (0.05 eq), the corresponding azide-substituted cGMP analogue (33 mM, 1 eq) and the corresponding bis-alkyne (16 mM, 0.5 eq) in water/N,N-diisopropylethylamine (10:1, v/v) to obtain the dimeric triazole-containing product.

Experimental Procedure for the Transformation of Azido-Substituted Guanosine-3',5'-Cyclic Monophosphate Analogues into the Corresponding Amines General Procedure V:

In a typical experiment a solution of the azido-substituted cGMP analogue (2.5 mM in water, 1 eq) in an amber flask was adjusted to pH 10 by addition of triethylamine and cooled to 10° C. DL-Dithiothreitol (5 eq) was added and the reaction mixture was stirred until the azide starting material was completely consumed or no further reaction progress was observed (usually <20 min). The mixture was evaporated to dryness under reduced pressure using a rotary evaporator. The residue was dissolved in water (1 mL), subjected to preparative reversed phase hplc and desalted, giving the amine-substituted cGMP analogue.

Experimental Procedures for the Transformation of 8-Azido-Substituted Guanosine-3',5'-Cyclic Monophosphate Analogues into the Corresponding Iminophosphoranyl Analogue General Procedure W:

In a typical experiment PPh$_3$ (1.75 eq) and water (100 µL) were added to a solution of 8-azido-substituted cGMP analogue (100 mM, 1 eq) in DMF in an amber flask. The reaction mixture was stirred until the azide starting material was completely consumed or no further reaction progress was observed. The solvent was removed through high vacuum evaporation with a speedvac concentrator. The residue was suspended in water (1 mL) and washed with toluene (5×). The aqueous phase was evaporated under reduced pressure using a rotary evaporator, the residue was redissolved in water/MeOH (4:1), subjected to preparative reversed phase hplc and desalted, giving the iminophosphoranyl analogue.

Experimental Procedure for the Suzuki Cross-Coupling of Br-Substituted Guanosine-3',5'-Cyclic Monophosphate Analogues with Organoboronic Acids General Procedure X:

In a typical experiment aqueous K$_2$CO$_3$ (2 M, 3 eq) and Pd(dppf)Cl$_2$ (0.05 eq) were added successively to a solution of the Br-substituted cGMP analogue (52 mM, 1 eq) and the boronic acid (72 mM, 1.4 eq) in EtOH/H$_2$O (1:1, v/v). The reaction mixture was immediately degassed applying three cycles of freeze-pump-thaw technique and stirred at 90° C. under argon until the bromide starting material was completely consumed or no further reaction progress was observed. The solvent was removed through high vacuum evaporation with a speedvac concentrator. The residue was suspended in water and washed with CHCl$_3$ (3×). Methanol was added until dissolution of the precipitate (up to H$_2$O/MeOH=1:1). If an organic phase, containing residual CHCl$_3$, emerged from this composition, it was separated. The aqueous phase was then filtered through a Macherey-Nagel Chromafix C 18 (S) 270 mg cartridge (preconditioned with 10 mL of MeOH, 50% MeOH and 30% MeOH respectively) and rinsed with 30% MeOH (6 mL). The solvent was removed under reduced pressure using a rotary evaporator. The residue was dissolved in water (1 mL), subjected to preparative reversed phase hplc and desalted, giving the cross-coupling product.

* All solvents used, were degassed through sonication under reduced pressure prior to the experiment.

General Procedure X2 (Preparation of Bis Boronic Acid Reagent 4-B(OH)$_2$PhS-PEG$_5$-(CH$_2$)$_2$-4-SPhB(OH)$_2$):

In a typical experiment N,N-diisopropylethylamine (2 eq) was added to a solution of 4-mercaptophenylboronic acid (0.2 M, 1 eq) and Br-(EO)$_5$—(CH$_2$)$_2$—Br (0.5 eq) in DMF. The reaction mixture was stirred until the boronic acid starting material was completely consumed or no further reaction progress was observed. The solvent was removed through high vacuum evaporation with a speedvac concentrator. The residue was dissolved in methanol (1 mL) and subjected to preparative reversed phase hplc (62% MeOH) giving 4-B(OH)$_2$PhS-PEG$_5$-(CH$_2$)$_2$-4-SPhB(OH)$_2$ (34% yield).

Experimental Procedure for the Preparation of 1, N$^2$-functionalized Guanosine-3',5'-Cyclic Monophosphate Analogues General Procedure Y:

In a typical experiment DBU (7 eq) and the corresponding 2-bromo-aceto-reactant (3.5 eq) were added successively to a solution of the corresponding cGMP analogue (50 mM, 1 eq) in DMSO. The reaction mixture was stirred under exclusion of light until the cGMP analogue starting material was completely consumed or no further reaction progress was observed. Water (100 µL) was added, stirring was continued for 10 min and the solvent was removed through high vacuum evaporation with a speedvac concentrator. The residue was dissolved in methanol (0.5 mL) and the pH adjusted to 6-7 with HCl (1 M). In case a precipitate was formed thereby, methanol was added to redissolve it. Otherwise, water was slowly added until all components just remained soluble (max. H$_2$O/MeOH=5:1). The solution was subjected to preparative reversed phase hplc and desalted, giving the 1, N$^2$-etheno-functionalized cGMP analogue.

General Procedure Y2:

In a typical experiment DBU (2 eq) and the corresponding alkyl bromoacetate-reactant (1.1 eq) were added successively to a solution of the corresponding cGMP analogue (100 mM, 1 eq) in DMSO. The reaction mixture was stirred until the cGMP analogue starting material was completely consumed or no further reaction progress was observed. Water (100 µL) was added, stirring was continued for 10 min and the solvent was removed through high vacuum evaporation with a speedvac concentrator. The residue was dissolved in H$_2$O (0.5 mL) and the pH adjusted to 6-7 with HCl (1 M). The solution was subjected to preparative reversed phase hplc and desalted, giving the 1, N$^2$-acyl-functionalized cGMP analogue.

General Procedure Y3:

In a typical experiment N,N-diisopropylethylamine (2 eq) and PyBOP (1.1 eq) were added successively to a solution of the corresponding 1-carboxyalkyl-substituted cGMP analogue (10 mM in DMSO, 1 eq). The reaction mixture was stirred until the cGMP analogue starting material was completely consumed or no further reaction progress was observed. Water (100 µL) was added, stirring was continued for 10 min and the solvent was removed through high vacuum evaporation with a speedvac concentrator. The residue was dissolved in water (1 mL), the pH adjusted to 5-6 with NaOH (2 M) and the solution washed with ethyl acetate (5×). The aqueous phase was evaporated under reduced pressure using a rotary evaporator, redissolved in water, subjected to preparative reversed phase hplc and desalted, giving the 1, N²-acyl-functionalized cGMP analogue.

Experimental Procedures for the Preparation of 1-Substituted Guanosine-3',5'-Cyclic Monophosphate Analogues General Procedure Z:

In a typical experiment DBU (4 eq) and the corresponding bromide-(or iodide) reactant (4 eq) were added successively to a solution of the corresponding cGMP analogue (50-300 mM, 1 eq) in DMSO. The reaction mixture was stirred until the cGMP analogue starting material was completely consumed or no further reaction progress was observed. The solvent was removed through high vacuum evaporation with a speedvac concentrator. The residue was dissolved in H$_2$O (0.5 mL) and, in case the resulting solution was not neutral, the pH was adjusted to 7 with HCl (1 M). The solution was washed with ethyl acetate (4×). The aqueous phase was evaporated under reduced pressure using a rotary evaporator, the residue was redissolved in water, subjected to preparative reversed phase hplc and desalted, giving the 1-substituted cGMP analogue.

General Procedure Z2:

In a typical experiment DBU (2 eq) and the corresponding dibromide-reactant (0.5 eq) were added successively to a solution of the corresponding cGMP analogue (15 mM, 1 eq) in DMSO. The reaction mixture was stirred at 90° C. until the cGMP analogue starting material was completely consumed or no further reaction progress was observed. The solvent was removed through high vacuum evaporation with a speedvac concentrator. The residue was dissolved in H$_2$O (0.5 mL), the pH adjusted to 5-7 with HCl (1 M) and the solution was washed with ethyl acetate (4×). The aqueous phase was evaporated under reduced pressure using a rotary evaporator, the residue was redissolved in water, subjected to preparative reversed phase hplc and desalted, giving the 1-substituted dimeric cGMP analogue.

Experimental Procedures for the Preparation of 2'-OR Substituted Guanosine-3',5'-Cyclic Monophosphate Analogues General Procedure ZZ:

In a typical experiment 2-azidoacetic anhydride (32 eq, prepared according to Freudenberg[13]) and 4-dimethylaminopyridine (1 eq) were added successively to the corresponding cGMP analogue (1 eq). The reaction mixture was stirred under exclusion of light until the cGMP analogue starting material was completely consumed or no further reaction progress was observed. The mixture was separated between MTBE and H$_2$O, the organic phase was decanted off and the aqueous phase washed with MTBE (2×). A precipitate was dissolved by adding methanol to the aqueous layer. The solution was subjected to preparative reversed phase hplc and desalted, giving the 2'-O-(2-azidoacetyl)-substituted cGMP analogue.

Synthesis of previously established precursors is described in the following:

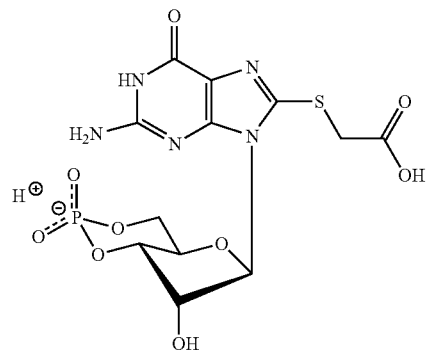

8-Carboxymethylthioguanosine-3',5'-cyclic monophosphate (8-CMT-cGMP)

Using general procedure C, 8-Br-cGMP was reacted with mercaptoacetic acid to give the title compound.

Yield (Purity): 66% (>99%).

HPLC: (5% MeCN, 100 mM TEAF buffer, pH 6.8).

UV-VIS: $\lambda_{max}$=275 nm (pH 7), ε=13700 (est.).

ESI-MS (+): m/z calculated for C$_{12}$H$_{15}$N$_5$O$_9$PS ([M+H]$^+$): 436.03, found: 436.

ESI-MS (−): m/z calculated for C$_{12}$H$_{13}$N$_5$O$_9$PS ([M−H]$^−$): 434.02, found: 434.

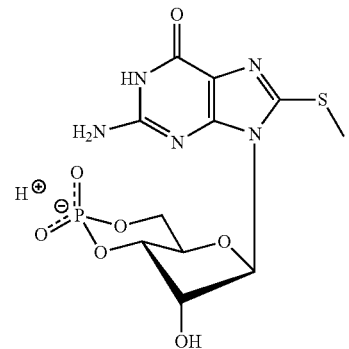

8-Methylthioguanosine-3',5'-cyclic monophosphate (8-MeS-cGMP)

Using general procedure A, 8-Br-cGMP (1 eq) was reacted with sodium methanethiolate (4 eq) to give the title compound.

Yield (Purity): 50% (>99%).

HPLC: (9% MeCN, 20 mM TEAF buffer, pH 6.8).

UV-VIS: $\lambda_{max}$=274 nm (pH 7), ε=14000 (est.).

ESI-MS (+): m/z calculated for C$_{11}$H$_{15}$N$_5$O$_7$PS ([M+H]$^+$): 392.04, found: 392.

ESI-MS (−): m/z calculated for C$_{11}$H$_{13}$N$_5$O$_7$PS ([M−H]$^−$): 390.03, found: 390.

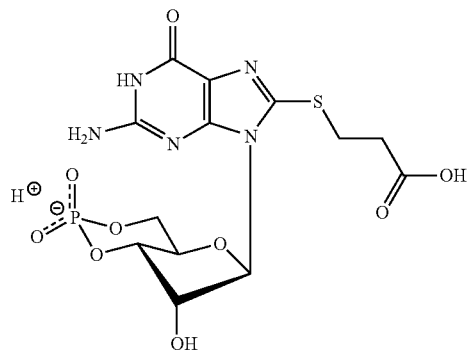

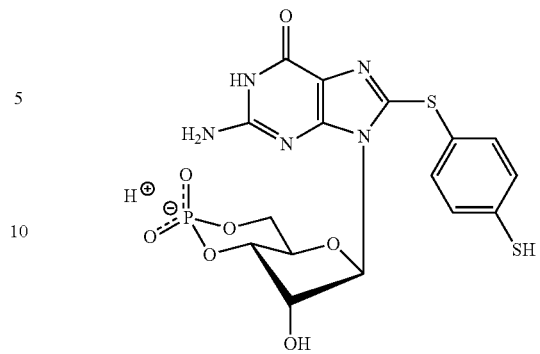

8-(4-Thiophenylthio)guanosine-3',5'-cyclic monophosphate (8-pTPT-cGMP)

Using general procedure B, 8-Br-cGMP was reacted with 1,4-benzenedithiol to give the title compound.

Yield (Purity): 41% (>99%).

HPLC: (32% MeOH, 10 mM TEAF buffer, pH 6.8).

UV-VIS: λmax=286 nm (pH 7), ε=21500 (est.).

ESI-MS (+): m/z calculated for $C_{16}H_{17}N_5O_7PS_2$ ([M+H]+): 486.03, found: 486.

ESI-MS (−): m/z calculated for $C_{16}H_{15}N_5O_7PS_2$ ([M−H]−): 484.02, found: 484.

8-Carboxyethylthioguanosine-3',5'-cyclic monophosphate (8-CET-cGMP)

The title compound was synthesized from 8-MPT-cGMP using general procedure F.

Yield (Purity): 56% (>99%).

HPLC: (5% MeCN, 10 mM TEAF buffer, pH 6.8).

UV-VIS: $\lambda_{max}$=275 nm (pH 7), ε=13700 (est.).

ESI-MS (+): m/z calculated for $C_{13}H_{17}N_5O_9PS$ ([M+H]$^+$): 450.05, found: 450.

ESI-MS (−): m/z calculated for $C_{13}H_{15}N_5O_9PS$ ([M−H]$^-$): 448.33, found: 448.

The invention is further illustrated by the figures and examples of Table 15 describing preferred embodiments of the present invention which are, however, not intended to limit the invention in any way. Structural examples of novel compounds are depicted in the free acid form. After HPLC workup, compounds are obtained as salts of the applied buffer, but can be transformed to other salt forms or to the free acid by cation exchange according to standard procedures for nucleotides.

TABLE 15

Examples of novel polymer linked multimeric cGMP compounds.

| # | Compound/Structure |
|---|---|
| 1 | |

Guanosine-3',5'-cyclic monophosphate-[8-thio-(pentaethoxy)-ethylthio-8]-guanosine-3',5'-cyclic TABLE 15-continued Examples of novel polymer linked multimeric cGMP compounds.

| # | Compound/Structure |
|---|---| monophosphate (cGMP-8-T-(EO)$_5$-ET-8-cGMP)
Using general procedure E, 8-T-cGMP was reacted with Br—PEG$_5$—CH$_2$CH$_2$Br to give the title compound.
Yield (Purity): 51% (>99%).
HPLC: (30% MeOH, 10 mM TEAF buffer, pH 6.8).
UV-VIS: $\lambda_{max}$ = 274 nm (pH 7), $\varepsilon$ = 24660 (est.).
ESI-MS (+): m/z calculated for C$_{32}$H$_{46}$N$_{10}$O$_{19}$P$_2$S$_2$Na ([M + Na]$^+$): 1023.18, found: 1023.
ESI-MS (−): m/z calculated for C$_{32}$H$_{45}$N$_{10}$O$_{19}$P$_2$S$_2$ ([M − H]$^-$): 999.18, found: 999.

2 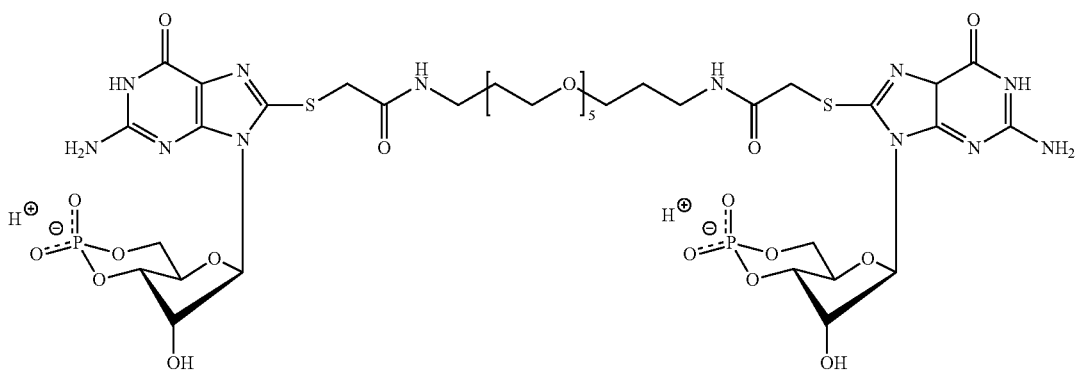

Guanosine-3',5'-cyclic monophosphate-[8-thiomethylamidomethyl-(pentaethoxy)-propylamidomethylthio-8]-guanosine-3',5'-cyclic monophosphate (cGMP-8-TMAmdM-(EO)$_5$-PrAmdMT-8-cGMP)
Using general procedure I, 8-CMT-cGMP was reacted with NH$_2$CH$_2$—PEG$_5$—(CH$_2$)$_3$NH$_2$ to give the title compound.
Yield (Purity): 42% (>99%).
HPLC: (27% MeOH, 10 mM TEAF buffer pH 6.8).
UV-VIS: $\lambda_{max}$ = 275 nm (pH 7), $\varepsilon$ = 24660 (est.).
ESI-MS (+): m/z calculated for C$_{38}$H$_{54}$N$_{12}$O$_{21}$P$_2$S$_2$Na$_3$ ([M − 2H + 3Na]$^+$): 1209.21, found: 1209.
ESI-MS (−): m/z calculated for C$_{38}$H$_{55}$N$_{12}$O$_{21}$P$_2$S$_2$ ([M − H]$^-$): 1141.25, found: 1141.

3 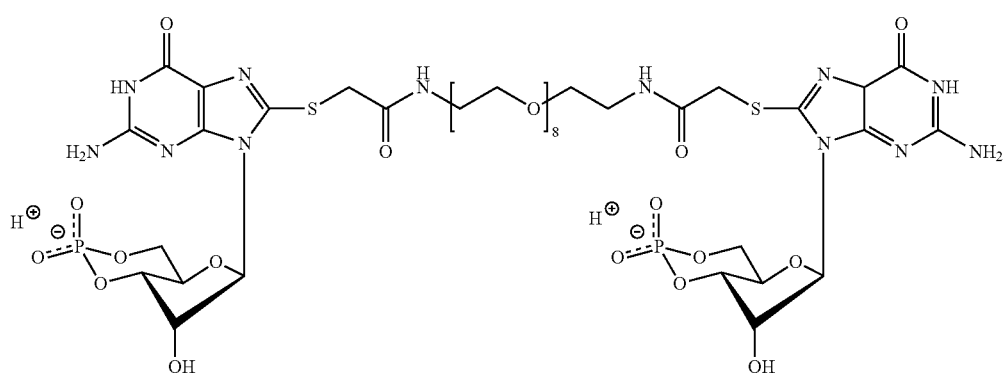

Guanosine-3',5'-cyclic monophosphate-[8-thiomethylamido-(octaethoxy)-ethylamidomethylthio-8]-guanosine-3',5'-cyclic monophosphate (cGMP-8-TMAmd-(EO)$_8$-EAmdMT-8-cGMP)
Using general procedure I, 8-CMT-cGMP was reacted with NH$_2$—(EO)$_8$—(CH$_2$)$_2$NH$_2$ to give the title compound.
Yield (Purity): 38% (>98%).
HPLC: (27% MeOH, 10 mM TEAF buffer, pH 6.8).
UV-VIS: $\lambda_{max}$ = 275 nm (pH 7), $\varepsilon$ = 24660 (est.).
ESI-MS (+): m/z calculated for C$_{42}$H$_{64}$N$_{12}$O$_{24}$P$_2$S$_2$Na ([M + Na]$^+$): 1269.30, found: 1269.
ESI-MS (−): m/z calculated for C$_{42}$H$_{63}$N$_{12}$O$_{24}$P$_2$S$_2$ ([M − H]$^-$): 1245.30, found: 1245.

TABLE 15-continued

Examples of novel polymer linked multimeric cGMP compounds.

| # | Compound/Structure |
|---|---|
| 4 | Guanosine-3',5'-cyclic monophosphate-[8-(4-thiophenylthio)-(pentaethoxy)-ethyl-(4-thiophenylthio)-8]-guanosine-3',5'-cyclic monophosphate (cGMP-8-pTPT-(EO)$_5$-EpTPT-8-cGMP)<br>Using general procedure E, 8-pTPT-cGMP was reacted with Br—PEG$_5$—CH$_2$CH$_2$Br to give the title compound.<br>Yield (Purity): 31% (>99%).<br>HPLC: (52% MeOH, 10 mM TEAF buffer, pH 6.8).<br>UV-VIS: $\lambda_{max}$ = 275 nm (pH 7), $\varepsilon$ = 38700 (est.).<br>ES-MS (+): m/z calculated for C$_{44}$H$_{54}$N$_{10}$O$_{19}$P$_2$S$_4$Na ([M + H]$^+$): 1239.18, found 1239.<br>ES-MS (−): m/z calculated for C$_{44}$H$_{53}$N$_{10}$O$_{19}$P$_2$S$_4$ ([M − H]$^-$): 1215.18, found 1215. |
| 5 | β-Phenyl-1,N$^2$-ethenoguanosine-3',5'-cyclic monophosphate-[8-thiomethylamido-(octaethoxy)-ethylamidomethylthio-8]-β-phenyl-1,N$^2$-ethenoguanosine-3',5'-cyclic monophosphate (PET-cGMP-8-TMAmd-(EO)$_8$-EAmdMT-8-cGMP-PET)<br>Using general procedure I, 8-CMT-PET-cGMP was reacted with NH$_2$—PEG$_8$—(CH$_2$)$_2$NH$_2$ to give the title compound.<br>Yield (Purity): 24% (>99%).<br>HPLC: (49% MeOH, 10 mM TEAF buffer, pH 6.8).<br>UV-VIS: $\lambda_{max}$ = 272 nm (pH 7), $\varepsilon$ = 72000 (est.).<br>ESI-MS (+): m/z calculated for C$_{58}$H$_{75}$N$_{12}$O$_{24}$P$_2$S$_2$ ([M + 2H]$^{2+}$): 724.70, found: 724.<br>ESI-MS (−): m/z calculated for C$_{58}$H$_{71}$N$_{12}$O$_{24}$P$_2$S$_2$ ([M − 2H]$^{2-}$): 722.68, found: 722. |
| 6 | 8-Bromoguanosine-3',5'-cyclic monophosphate-[1,N$^2$-etheno-β-phenyl-4-yl-(1-[1,2,3]-triazole-4-yl)-methoxy-(hexaethoxy)-methyl-(4-(4-[1,2,3]-triazole-1-yl)-β-phenyl-1,N$^2$-etheno)]-8-bromoguanosine-3',5'-cyclic monophosphate (8-Br-cGMP-ETP-p(1-[1,2,3]-Tz-4)-MeO-(EO)$_6$-Me-p(4-[1,2,3]-Tz-1)-PET-cGMP-8-Br)<br>Using general procedure U, 4-N$_3$-PET-8-Br-cGMP was reacted with Bis-Propargyl-PEG$_7$ to give the title compound.<br>Yield (Purity): 34% (>99%). |

TABLE 15-continued

Examples of novel polymer linked multimeric cGMP compounds.

| # | Compound/Structure |
|---|---|

HPLC: (20% MeCN, 50 mM $NaH_2PO_4$ buffer, pH 6.8).
UV-VIS: $\lambda_{max}$ = 270 nm (pH 7), $\varepsilon$ = 72000 (est.).
ESI-MS (+): m/z calculated for $C_{54}H_{59}Br_2N_{16}O_{21}P_2$ ([M + H]$^+$): 1487.19, found: 1487.
ESI-MS (−): m/z calculated for $C_{54}H_{57}Br_2N_{16}O_{21}P_2$ ([M − H]$^-$): 1485.17, found: 1485.

7

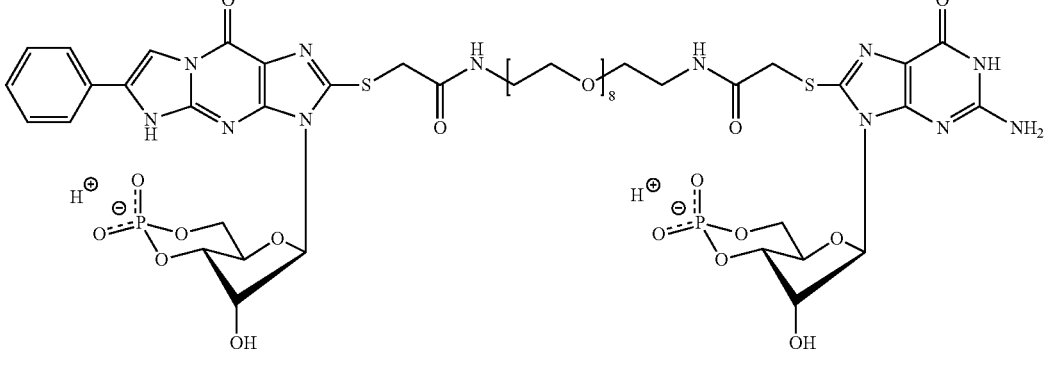

Guanosine-3',5'-cyclic monophosphate-[8-thiomethylamido-(octaethoxy)-
ethylamidomethylthio-8]-β-phenyl-1,$N^2$-ethenoguanosine-3',5'-cyclic
monophosphate (cGMP-8-TMAmd-(EO)$_8$-EAmdMT-8-cGMP-PET)
Using general procedure J, 8-CMT-PET-cGMP (C 169, 1 eq) was reacted with 8-AE-(EO)$_8$-
AmdMT-cGMP (A 240, 1 eq) to give the title compound.
Yield (Purity): 47% (>99%).
HPLC: (19% MeCN, 50 mM $NaH_2PO_4$ buffer, pH 6.8).
UV-VIS: $\lambda_{max}$ = 274 nm (pH 7), $\varepsilon$ = 48330 (est.).
ESI-MS (+): m/z calculated for $C_{50}H_{69}N_{12}O_{24}P_2S_2$ ([M + H]$^+$): 1347.35, found: 1347.
ESI-MS (−): m/z calculated for $C_{50}H_{67}N_{12}O_{24}P_2S_2$ ([M − H]$^-$): 1345.33, found: 1345.

8

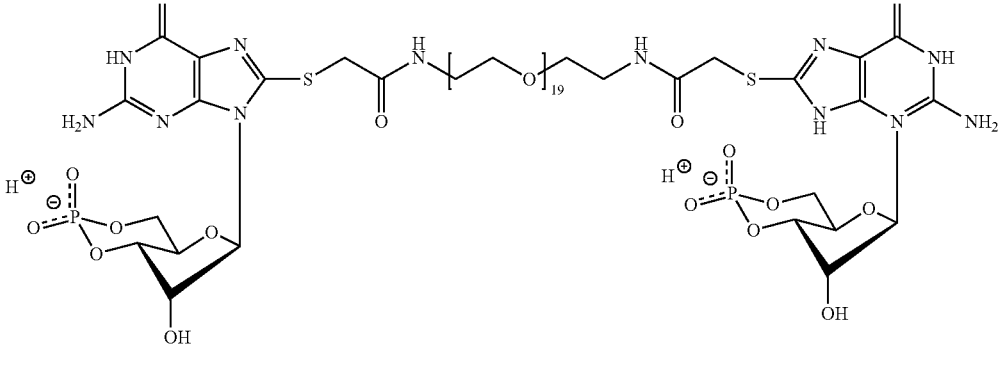

Guanosine-3',5'-cyclic monophosphate-[8-thiomethylamido-(nonadecaethoxy)-
ethylamidomethylthio-8]-guanosine-3',5'-cyclic monophosphate (cGMP-8-TMAmd-
(EO)$_{19}$-EAmdMT-8-cGMP)
Using general procedure L, 8-CMT-cGMP was reacted with $NH_2$—PEG$_{19}$—$(CH_2)_2NH_2$ to give
the title compound.
Yield (Purity): 47% (>97%).
HPLC (17% MeCN, 25 mM $NaH_2PO_4$ buffer, pH 6.8).
UV-VIS: $\lambda_{max}$ = 275 nm (pH 7), $\varepsilon$ = 24660 (est.).
ESI-MS (+): m/z calculated for $C_{64}H_{109}N_{12}O_{35}P_2S_2$ ([M + H]$^+$): 1731.60, found: 1732.
ESI-MS (−): m/z calculated for $C_{64}H_{107}N_{12}O_{35}P_2S_2$ ([M − H]$^-$): 1729.56, found: 1730.

TABLE 15-continued

Examples of novel polymer linked multimeric cGMP compounds.

| # | Compound/Structure |
|---|---|
| 9 | 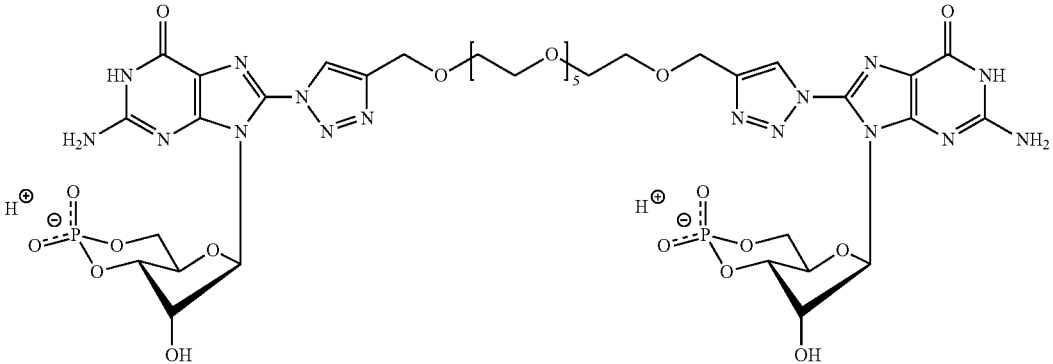 |

Guanosine-3',5'-cyclic monophosphate-[8-(1-[1,2,3]-triazole-4-yl)-methoxy-
(hexaethoxy)-methyl-(4-[1,2,3]-triazole-1-yl)-8]-guanosine-3',5'-cyclic
monophosphate (cGMP-8-(1-[1,2,3]-Tz-4-)-MeO-(EO)$_6$-Me-(4-[1,2,3]-Tz-1)-8-cGMP)

Using general procedure U, 8-N$_3$-cGMP was reacted with Bis-Propargly-PEG$_7$ to give the
title compound.

Yield (Purity): 4% (>99%).

HPLC: (13% MeCN, 50 mM NaH$_2$PO$_4$ buffer, pH 6.8).

UV-VIS: $\lambda_{max}$ = 277 nm (pH 7), $\varepsilon$ = 38700 (est.).

ESI-MS (+): m/z calculated for C$_{38}$H$_{53}$N$_{16}$O$_{21}$P$_2$ ([M + H]$^+$): 1131.30, found: 1131.

ESI-MS (−): m/z calculated for C$_{38}$H$_{51}$N$_{16}$O$_{21}$P$_2$ ([M − H]$^-$): 1129.29, found: 1129.

| 10 | 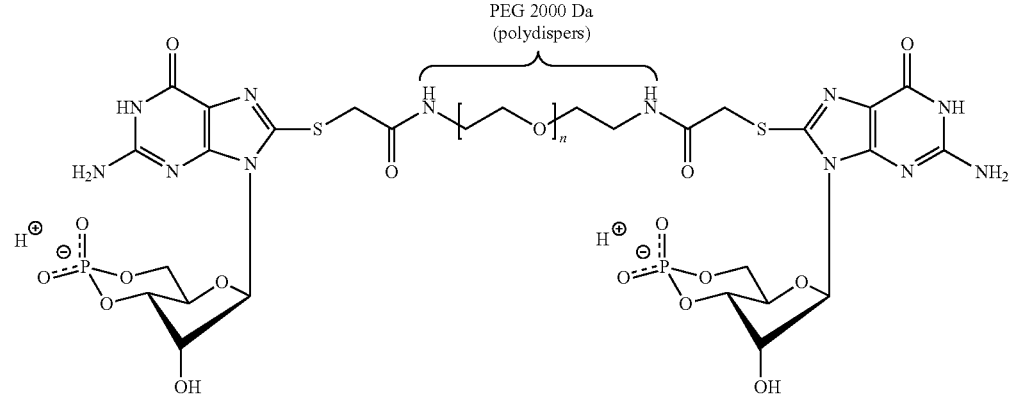 |

Guanosine-3',5'-cyclic monophosphate-[8-thiomethylamido-(PEG pd 2000)-
amidomethylthio-8]-guanosine-3',5'-cyclic monophosphate (cGMP-8-TMAmd-(PEG
pd 2000)-AmdMT-8-cGMP)

Using general procedure L, 8-CMT-cGMP was reacted with NH$_2$—PEG$_n$—(CH$_2$)$_2$NH$_2$
(2000 Da, polydispers) to give the title compound.

Yield (Purity): 47% (>95%).

HPLC: (Gradient, 21% then 24% MeCN, 50 mM NaH$_2$PO$_4$ buffer, pH 6.8).

UV-VIS: $\lambda_{max}$ = 275 nm (pH 7), $\varepsilon$ = 24660 (est.).

ESI-MS: (−): m/z calculated for C$_{114}$H$_{206}$N$_{12}$O$_{60}$P$_2$S$_2$ (n = 44, [M − 2H]$^{2-}$): 1414.62, found: 1414.

TABLE 15-continued

Examples of novel polymer linked multimeric cGMP compounds.

| # | Compound/Structure |
|---|---|

11

β-Phenyl-1,N²-ethenoguanosine-3',5'-cyclic monophosphate-[8-thiomethylamido-
(nonadecaethoxy)-ethylamidomethylthio-8]-guanosine-3',5'-cyclic monophosphate
(PET-cGMP-8-TMAmd-(EO)$_{19}$-EAmdMT-8-cGMP)

Using the procedure J, 8-CMT-cGMP (1 eq) and 8-CMT-PET-cGMP (1 eq) were
reacted with NH$_2$—PEG$_{19}$—(CH$_2$)$_2$NH$_2$ in the presence of N,N-diisopropylethylamine (4 eq) and
PyBOP (2.05 eq) to give the title compound. Conditions were chosen to additionally obtain
the symmetrically substituted dimeric analogues.
Yield (Purity): 35% (>99%).
HPLC: (Gradient, 21% then 23 the 24% MeCN, 50 mM NaH$_2$PO$_4$ buffer, pH 6.8).
UV-VIS: $\lambda_{max}$ = 274 nm (pH 7), ε = 49700 (est.).
ESI-MS (+): m/z calculated for C$_{72}$H$_{113}$N$_{12}$O$_{35}$P$_2$S$_2$ ([M + H]$^+$): 1831.63, found 1832.
ESI-MS (−): m/z calculated for C$_{72}$H$_{111}$N$_{12}$O$_{35}$P$_2$S$_2$ ([M − H]$^−$): 1829.62, found: 1830.

12

β-Phenyl-1,N²-ethenoguanosine-3',5'-cyclic monophosphate-[8-thiomethylamido-
(nonadecaethoxy)-ethylamidomethylthio-8]-β-phenyl-1,N²-ethenoguanosine-3',5'-
cyclic monophosphate (PET-cGMP-8-TMAmd-(EO)$_{19}$-EAmdMT-8-cGMP-PET)

Using general procedure J, 8-CMT-cGMP (1 eq) and 8-CMT-PET-cGMP (1 eq) were
reacted with NH$_2$—PEG$_{19}$—(CH$_2$)$_2$NH$_2$ in the presence of N,N-diisopropylethylamine (4 eq) and PyBOP (2.05 eq) to give
the title compound. Conditions were chosen to additionally obtain the symmetrically substituted dimeric analogues.
Yield (Purity): 22% (>99%).
HPLC: (Gradient, 21% then 23 then 24% MeCN, 50 mM NaH$_2$PO$_4$ buffer, pH 6.8).
UV-VIS: $\lambda_{max}$ = 272 nm (pH 7), ε = 72000 (est.).
ESI-MS (+): m/z calculated for C$_{80}$H$_{117}$N$_{12}$O$_{35}$P$_2$S$_2$ ([M + H]$^+$): 1931.67, found: 1932.
ESI-MS (−): m/z calculated for C$_{80}$H$_{115}$N$_{12}$O$_{35}$P$_2$S$_2$ ([M − H]$^−$): 1929.65, found: 1930.

TABLE 15-continued

Examples of novel polymer linked multimeric cGMP compounds.

| # | Compound/Structure |
|---|---|
| 13 | 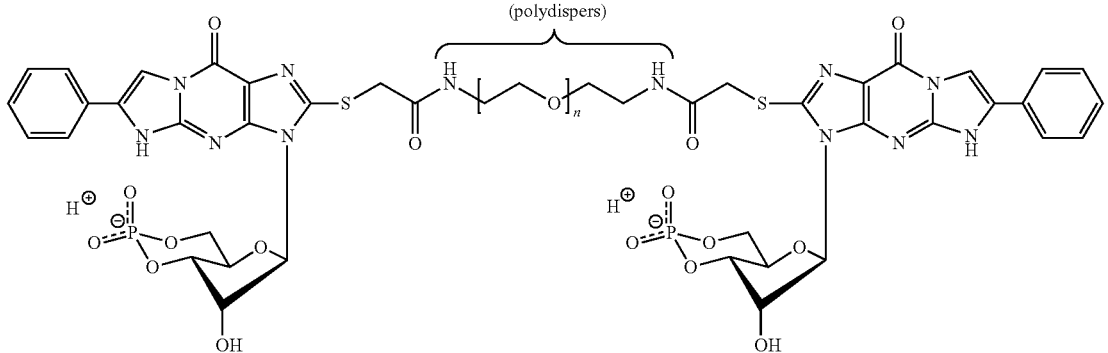
β-Phenyl-1,N²-ethenoguanosine-3',5'-cyclic monophosphate-[8-thiomethylamido-(PEG pd 2000)-amidomethylthio-8]-β-phenyl-1,N²-ethenoguanosine-3',5'-cyclic monophosphate (PET-cGMP-8-TMAmd-(PEG pd 2000)-AmdMT-8-cGMP-PET)
Using general procedure L, 8-CMT-PET-cGMP was reacted with $NH_2$—$PEG_n$—$(CH_2)_2NH_2$ (2000 Da, polydispers). More PyBOP (0.5 eq) was added stepwise to drive the reaction to completion and yield the title compound.
Yield (Purity): 35% (>95%).
HPLC: (28% MeCN, 25 mM $NaH_2PO_4$ buffer, pH 6.8).
UV-VIS: $\lambda_{max}$ = 272 nm (pH 7), ε = 72000 (est.).
ESI-MS: (−): m/z calculated for $C_{130}H_{214}N_{12}O_{60}P_2S_2$ (n = 44, $[M − 2H]^{2−}$): 1516.6, found: 1516. |
| 14 | 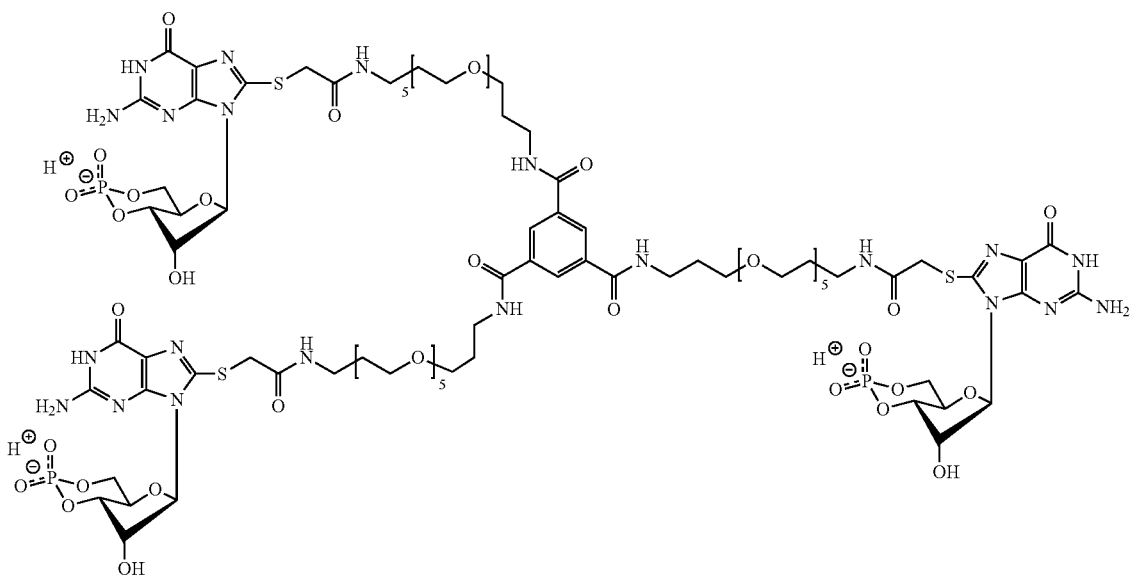
Benzene-1,3,5-tri-[(8-amidomethyl-(pentaethoxy)-propylamidomethylthio)guanosine-3',5'-cyclic monophosphate] (Bn-1,3,5-tri(AmdPr-(OE)₅-MAmdMT-8-cGMP)
Using general procedure M, 8-APr-(EO)₅-MAmdMT-cGMP was reacted with 1,3,5-benzenetricarboxylic acid to give the title compound.
Yield (Purity): 60% (>99%).
HPLC: (18% MeCN, 15 mM TEAF buffer, pH 6.8).
UV-VIS: $\lambda_{max}$ = 274 nm (pH 7), ε = 36990 (est.).
ESI-MS: (+): m/z calculated for $C_{87}H_{133}N_{21}O_{42}P_3S_3$ ($[M + H]^+$): 2332.73, found 2333.
ESI-MS: (−): m/z calculated for $C_{87}H_{131}N_{21}O_{42}P_3S_3$ ($[M − H]^−$): 2330.71, found: 2331. |

TABLE 15-continued

Examples of novel polymer linked multimeric cGMP compounds.

| # | Compound/Structure |
|---|---|
| 15 | 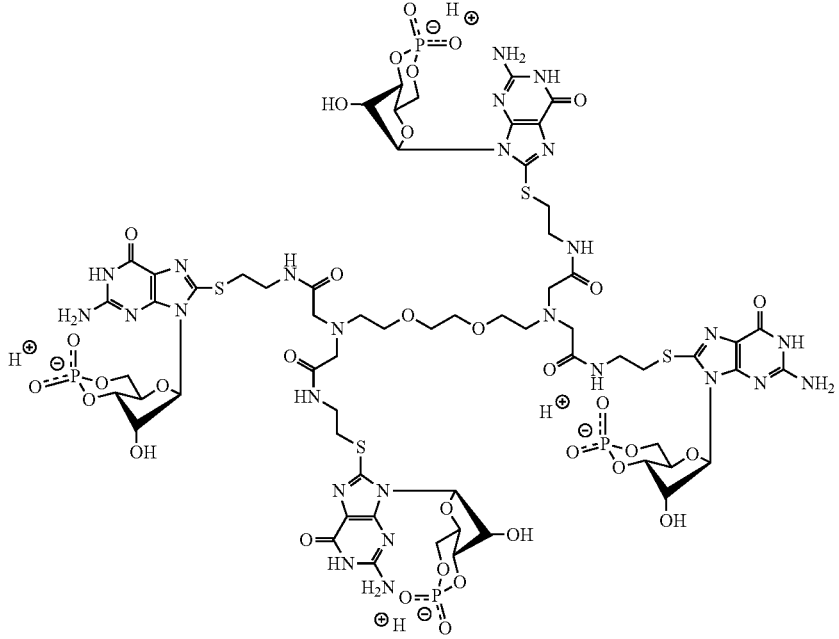 |

Ethylene glycol-bis(2-aminoethylether)-N,N,N',N'-tetra-[(8-methylamidoethylthio)guanosine-3',5'-cyclic monophosphate] (EG-N,N,N',N'-tetra(8-MAmdET-cGMP))

Using general procedure N, 8-AET-cGMP was reacted with Ethylene glycol-bis(2-aminoethylether)-N,N,N',N'-tetraacetic acid (EGTA) to give the title compound.

Yield (Purity): 15% (>99%).

HPLC: (28% MeOH, 10 mM TEAF buffer, pH 6.8).

UV-VIS: $\lambda_{max}$ = 274 nm (pH 7), ε = 49320 (est.).

ESI-MS (+): m/z calculated for $C_{62}H_{85}N_{26}O_{34}P_4S_4$ ([M + H]$^+$): 1989.36, found: 1989.
ESI-MS (−): m/z calculated for $C_{62}H_{83}N_{26}O_{34}P_4S_4$ ([M − H]$^-$): 1987.34, found: 1987.

| 16 | 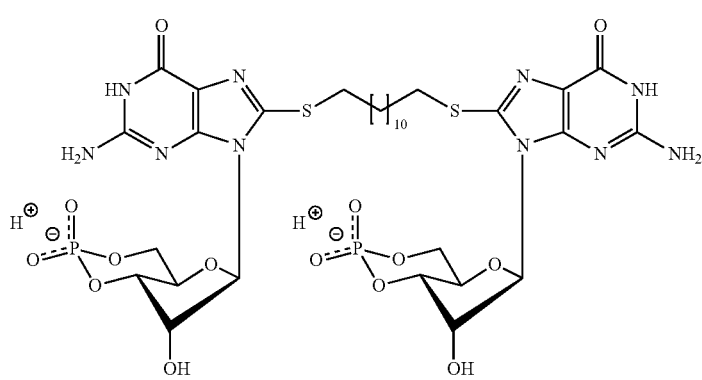 |

Guanosine-3',5'-cyclic monophosphate-[8-thio(dodecanyl)-thio-8]-guanosine-3',5'-cyclic monophosphate (cGMP-8-T-(CH$_2$)$_{12}$-T-8-cGMP)

Using general procedure E, 8-T-cGMP was reacted with 1,12-dibromdodecane to give the title compound.

Yield (Purity): 73% (>99%).

HPLC: (26% MeCN, 30 mM NaH$_2$PO$_4$ buffer, pH 6.8).

UV-VIS: $\lambda_{max}$ = 276 nm (pH 7), ε = 24660 (est.).

ESI-MS (+): m/z calculated for $C_{32}H_{47}N_{10}O_{14}P_2S_2$ ([M + H]$^+$): 921.22, found: 921.
ESI-MS (−): m/z calculated for $C_{32}H_{45}N_{10}O_{14}P_2S_2$ ([M − H]$^-$): 919.20, found: 919.

TABLE 15-continued

Examples of novel polymer linked multimeric cGMP compounds.

| # | Compound/Structure |
|---|---|
| 17 | 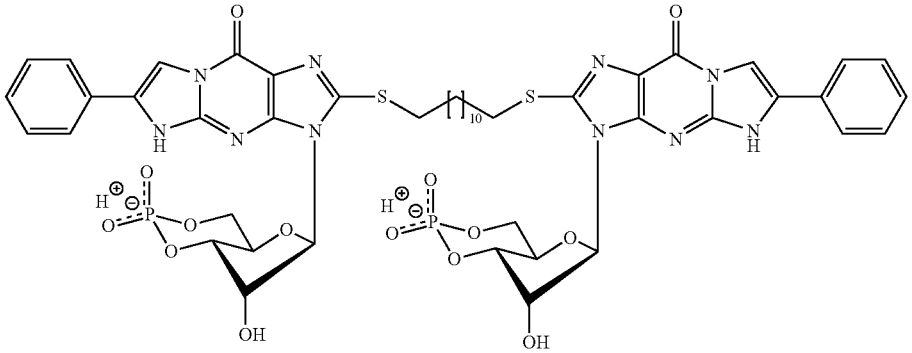<br>β-Phenyl-1,N²-ethenoguanosine-3',5'-cyclic monophosphate-[8-thio-(dodecanyl)-thio-8]-β-phenyl-1,N²-ethenoguanosine-3',5'-cyclic monophosphate (PET-cGMP-8-T-(CH₂)₁₂-T-8-cGMP-PET)<br>Using general procedure E, PET-8-T-cGMP was reacted with 1,12-dibromdodecane to give the title compound.<br>Yield (Purity): 24% (>99%).<br>HPLC: (36% MeCN, 20 mM TEAF buffer, pH 6.8).<br>UV-VIS: $\lambda_{max}$ = 275 nm (pH 7), $\varepsilon$ = 72000 (est.).<br>ESI-MS (−): m/z calculated for $C_{48}H_{53}N_{10}O_{14}P_2S_2$ ([M − H]⁻): 1019.27, found: 1019. |
| 18 | 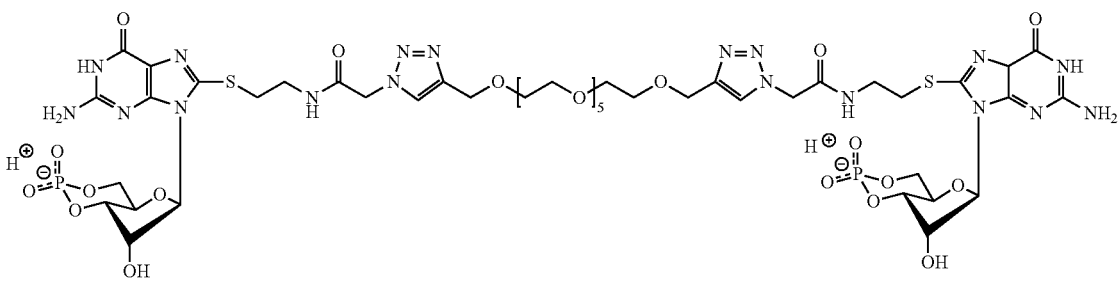<br>Guanosine-3',5'-cyclic monophosphate-[8-thioethylamidomethyl-(1-[1,2,3]-triazole-4-yl)-methoxy-(hexaethoxy)-methyl-(4-[1,2,3]-triazole-1-yl)-methylamidoethylthio-8]-guanosine-3',5'-cyclic monophosphate (cGMP-8-TEAmdM-(1-[1,2,3]-Tz-4)-MeO-(EO)₆-Me-(4-[1,2,3]-Tz-1)-MAmdET-8-cGMP)<br>Using general procedure S, 8-N3-MAmdET-cGMP (1 eq) was reacted with bis-propargyl-PEG₇ (2 eq) to give the title compound. Conditions were chosen to additionally obtain the pegylated monomeric analogue.<br>Yield (Purity): 23% (>99%).<br>HPLC: (14% MeCN, 30 mM TEAF buffer, pH 6.8).<br>UV-VIS: $\lambda_{max}$ = 274 nm (pH 7), $\varepsilon$ = 24660 (est.).<br>ESI-MS (+): m/z calculated for $C_{46}H_{67}N_{18}O_{23}P_2S_2$ ([M + H]⁺): 1365.35, found: 1365.<br>ESI-MS (−): m/z calculated for $C_{46}H_{65}N_{18}O_{23}P_2S_2$ ([M − H]⁻): 1363.34, found: 1363. |
| 19 | 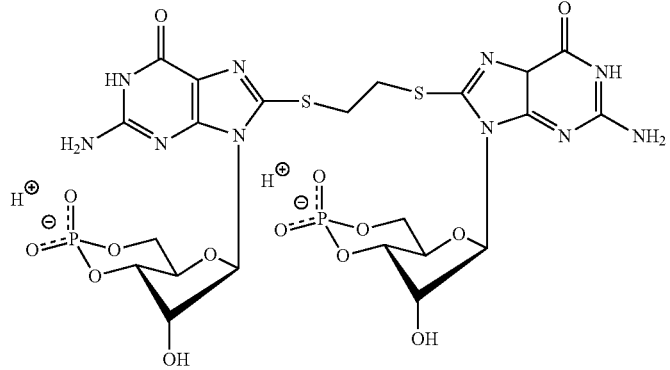<br>Guanosine-3',5'-cyclic monophosphate-[8-thioethylthio-8]-guanosine-3',5'-cyclic monophosphate (cGMP-8-TET-cGMP)<br>Using general method Q, the title compound was obtained beside monomeric azide |

TABLE 15-continued

Examples of novel polymer linked multimeric cGMP compounds.

| # | Compound/Structure |
|---|---| analogue starting from 8-T-cGMP.
Yield (Purity): 19% (>99%).
HPLC: (10% MeOH, 15 mM TEAF buffer, pH 6.8).
UV-VIS: $\lambda_{max}$ = 273 nm (pH 7), ε = 24660 (est.).
ESI-MS (+): m/z calculated for $C_{22}H_{27}N_{10}O_{14}P_2S_2$ ([M + H]$^+$): 78.06, found: 781.
ESI-MS (−): m/z calculated for $C_{22}H_{25}N_{10}O_{14}P_2S_2$ ([M − H]$^−$): 779.05, found: 779.

20

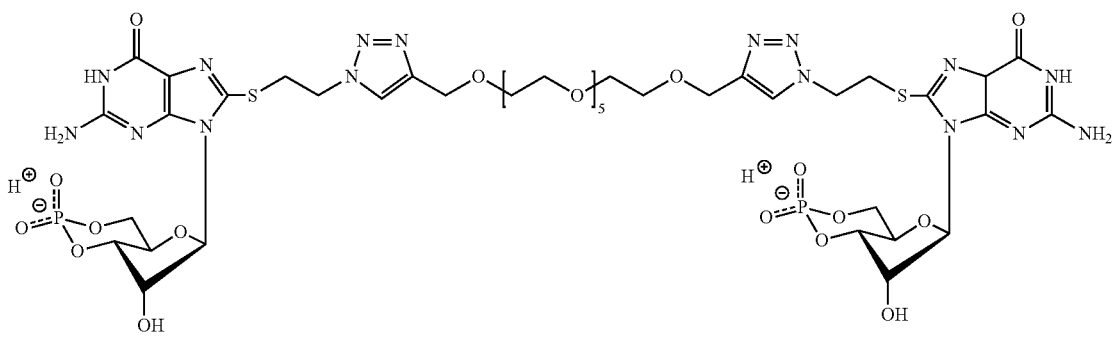

Guanosine-3',5'-cyclic monophosphate-[8-thioethyl-(1-[1,2,3]-triazole-4-yl)-
methoxy-(hexaethoxy)-methyl-(4-[1,2,3]-triazole-1-yl)-ethylthio-8]-guanosine-
3',5'-cyclic monophosphate (cGMP-8-TE-(1-[1,2,3]-Tz-4)-MeO-(EO)$_6$-Me-(4-[1,2,3]-Tz-
1)-ET-8-cGMP)
Using general procedure U, 8-N$_3$-ET-cGMP was reacted with bis-propargyl-PEG$_7$ to give the
title compound.
Yield (Purity): 61% (>99%).
HPLC: (14% MeCN, 20 mM TEAF buffer, pH 6.8).
UV-VIS: $\lambda_{max}$ = 276 nm (pH 7), ε = 24660 (est.).
ESI-MS: (+): m/z calculated for $C_{42}H_{61}N_{16}O_{21}P_2S_2$ ([M + H]$^+$): 1251.31, found: 1251.
ESI-MS: (−): m/z calculated for $C_{42}H_{59}N_{16}O_{21}P_2S_2$ ([M − H]$^−$): 1249.30, found: 1249.

21

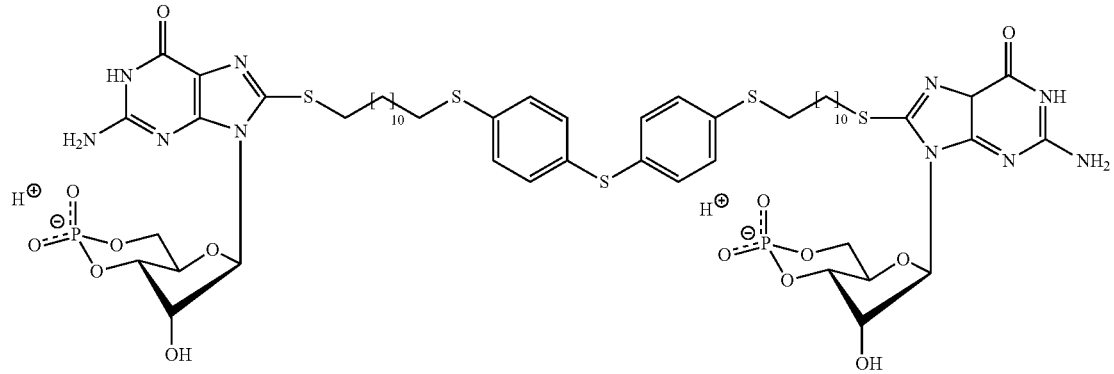

Guanosine-3',5'-cyclic monophosphate-[8-thio-(dodecanyl)-(4-thiophenyl-4''-
thiophenylthio)-(dodecanyl)-thio-8]-guanosine-3',5'-cyclic monophosphate
(cGMP-8-T-(CH$_2$)$_{12}$-pTPpTPT-(CH$_2$)$_{12}$-T-8-cGMP)
A solution of 8-T-cGMP (200 mM, 1 eq) and N,N-diisopropylethylamine (2 eq) in DMSO was
added portionwise over 30 min to a solution of 1,12-dibromdodecane (1.5M, 15 eq) in
DMSO at 40° C. The reaction mixture was stirred until no further reaction progress was
observed (<10% remaining starting material). The solvent was removed through high
vacuum evaporation with a speedvac concentrator. The residue was dissolved in
MeCN/water (8:1, v/v), washed with petroleum ether (3×) and the aqueous phase
evaporated to dryness using a rotary evaporator. The crude product was dissolved in DMF
(115 mM). 4,4'-Thiobisbenzenthiol (0.5 eq) and N,N-diisopropylethylamine (2.2 eq) were
added successively. The reaction mixture was stirred until the starting material was
completely consumed. The solvent was removed through high vacuum evaporation with a
speedvac concentrator. The residue was dissolved in water (1 mL), washed with ethyl
acetate (3 × 1 mL), subjected to preparative reversed phase hplc and desalted.
Yield (Purity): 26% (>99%).
HPLC: (57% MeCN, 30 mM NaH$_2$PO$_4$ buffer, pH 6.8).
UV-VIS: $\lambda_{max}$ = 275 nm (pH 7), ε = 24660 (est.).
ESI-MS (+): m/z calculated for $C_{56}H_{79}N_{10}O_{14}P_2S_5$ ([M + H]$^+$): 1337.39, found: 1337.
ESI-MS (−): m/z calculated for $C_{56}H_{77}N_{10}O_{14}P_2S_5$ ([M − H]$^−$): 1335.37, found: 1335.

TABLE 15-continued

Examples of novel polymer linked multimeric cGMP compounds.

| # | Compound/Structure |
|---|---|
| 22 | Guanosine-3',5'-cyclic monophosphate-[8-thioethylamidomethyl-(1-[1,2,3]-triazole-4-yl)-methoxy-(hexaethoxy)-methyl-(4-(4-[1,2,3]-triazole-1-yl)-β-phenyl-1,N$^2$-etheno)]-8-bromoguanosine-3',5'-cyclic monophosphate (cGMP-8-TEAmdM-(1-[1,2,3]-Tz-4)-MeO-(EO)$_6$-Me-(4-[1,2,3]-Tz-1)-PET-8-Br-cGMP)<br>Using general procedure S, 4-N$_3$-PET-8-Br-cGMP (1 eq) was reacted with 8-(4-(PargO-(EO)$_6$-Me)-[1,2,3]-Tz-1)-MAmdET-cGMP (1 eq) to give the title compound.<br>Yield (Purity): 26% (>99%).<br>HPLC: (57% MeCN, 30 mM NaH$_2$PO$_4$ buffer, pH 6.8).<br>UV-VIS: $\lambda_{max}$ = 275 nm (pH 7), ε = 24660 (est.).<br>ESI-MS (+): m/z calculated for C$_{56}$H$_{79}$N$_{10}$O$_{14}$P$_2$S$_5$ ([M + H]$^+$): 1337.39, found: 1337.<br>ESI-MS (−): m/z calculated for C$_{56}$H$_{77}$N$_{10}$O$_{14}$P$_2$S$_5$ ([M − H]$^-$): 1335.37, found: 1335. |
| 23 | β-Phenyl-1,N$^2$-ethenoguanosine-3',5'-cyclic monophosphate-[8-thioethyl-(1-[1,2,3]-triazole-4-yl)-methoxy-(hexaethoxy)-methyl-(4-[1,2,3]-triazole-1-yl)-ethylthio-8]-β-phenyl-1,N$^2$-ethenoguanosine-3',5'-cyclic monophosphate (PET-cGMP-8-TE-(1-[1,2,3]-Tz-4)-MeO-(EO)$_6$-Me-(4-[1,2,3]-Tz-1)-ET-8-cGMP-PET)<br>Using general procedure U, PET-8-N$_3$-ET-cGMP (A 257) was reacted with bis-propargyl-PEG$_7$ to give the title compound.<br>Yield (Purity): 23% (>99%).<br>HPLC: (56% MeOH, 30 mM TEAF buffer, pH 6.8).<br>UV-VIS: $\lambda_{max}$ = 273 nm (pH 7), ε = 72000 (est.).<br>ESI-MS (+): m/z calculated for C$_{58}$H$_{69}$N$_{16}$O$_{21}$P$_2$S$_2$ ([M + H]$^+$): 1451.37, found: 1451.<br>ESI-MS (−): m/z calculated for C$_{58}$H$_{67}$N$_{16}$O$_{21}$P$_2$S$_2$ ([M − H]$^-$): 1449.36, found: 1449. |
| 24 | 8-Bromoguanosine-3',5'-cyclic monophosphate-[1-propylamidomethyl-(pentaethoxy)-propylamidomethylthio-8]-β-phenyl-1,N$^2$-ethenoguanosine-3',5'-cyclic monophosphate (8-Br-cGMP-1-PrAmdM-(EO)$_5$-PrAmdMT-8-cGMP-PET)<br>Using general procedure J, 1-AM-(EO)$_5$-PrAmdPr-8-Br-cGMP was reacted with 8-CMT-PET-cGMP to give the title compound.<br>Yield (Purity): 20% (>99%).<br>HPLC: (48% MeOH, 50 mM TEAF buffer, pH 6.8). |

TABLE 15-continued

Examples of novel polymer linked multimeric cGMP compounds.

| # | Compound/Structure |
|---|---|

UV-VIS: $\lambda_{max}$ = 272 nm (pH 7), ε = 50580 (est.).

ESI-MS (+): m/z calculated for $C_{48}H_{64}N_{12}O_{21}P_2SBr$ ([M + H]$^+$): 1317.27, found: 1317.

ESI-MS (−): m/z calculated for $C_{48}H_{62}N_{12}O_{21}P_2SBr$ ([M − H]$^−$): 1315.25, found: 1315.

25 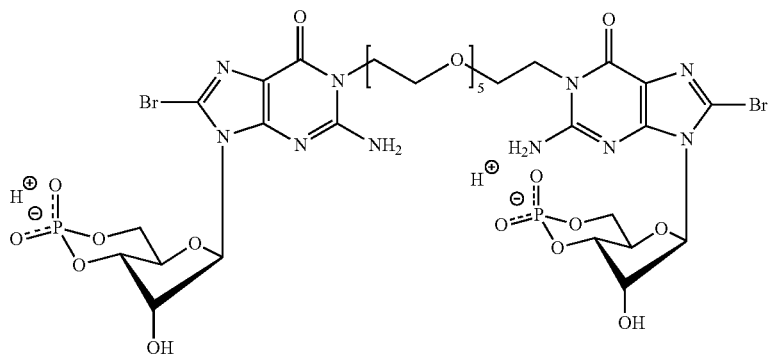

8-Bromoguanosine-3',5'-cyclic monophosphate-[1-(pentaethoxy)-ethyl-1]-8-bromoguanosine-3',5'-cyclic monophosphate (8-Br-cGMP-1-(EO)$_5$-E-1-cGMP-8-Br)

Using general procedure Z2, 8-Br-cGMP was reacted with Br—PEG$_5$—(CH$_2$)$_2$—Br to give the title compound.

Yield (Purity): 32% (>99%).

HPLC: (17% MeCN, 50 mM TEAF buffer, pH 6.8).

UV-VIS: $\lambda_{max}$ = 266 nm (pH 7), ε = 23400 (est.).

ESI-MS (+): m/z calculated for $C_{32}H_{45}N_{10}O_{19}P_2Br_2$ ([M + H]$^+$): 1095.07, found: 1095.

ESI-MS (−): m/z calculated for $C_{32}H_{43}N_{10}O_{19}P_2Br_2$ ([M − H]$^−$): 1093.05, found: 1093.

26 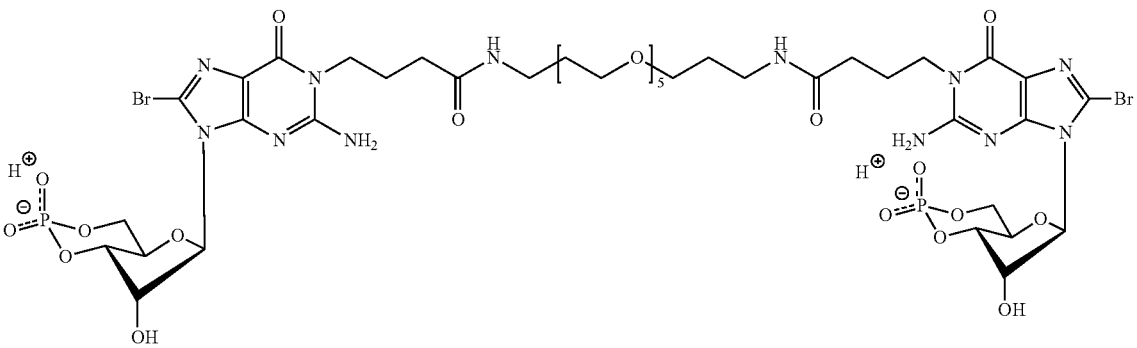

8-Bromoguanosine-3',5'-cyclic monophosphate-[1-propylamidomethyl-(pentaethoxy)-propylamidopropyl-1]-8-bromoguanosine-3',5'-cyclic monophosphate (8-Br-cGMP-1-PrAmdM-(EO)$_5$-PrAmdPr-1-cGMP-8-Br)

Using adapted general procedure L, 8-Br-1-CPr-cGMP was reacted with NH$_2$CH$_2$—PEG$_5$—(CH$_2$)$_3$—NH$_2$ (3 eq) to receive the title compound and the pegylated monomeric analogue.

Yield (Purity): 7% (>99%).

HPLC: (36% MeOH, 100 mM TEAF buffer, pH 6.8 then (after sepperation of monomer) 44% MeOH, 100 mM TEAF buffer, pH 6.8).

UV-VIS: $\lambda_{max}$ = 267 nm (pH 7), ε = 29160 (est.).

ESI-MS (+): m/z calculated for $C_{42}H_{63}N_{12}O_{21}P_2Br_2$ ([M + H]$^+$): 1293.21, found: 1293.

ESI-MS (−): m/z calculated for $C_{42}H_{61}N_{12}O_{21}P_2Br_2$ ([M − H]$^−$): 1291.19, found: 1291.

TABLE 15-continued

Examples of novel polymer linked multimeric cGMP compounds.

| # | Compound/Structure |
|---|---|
| 27 | 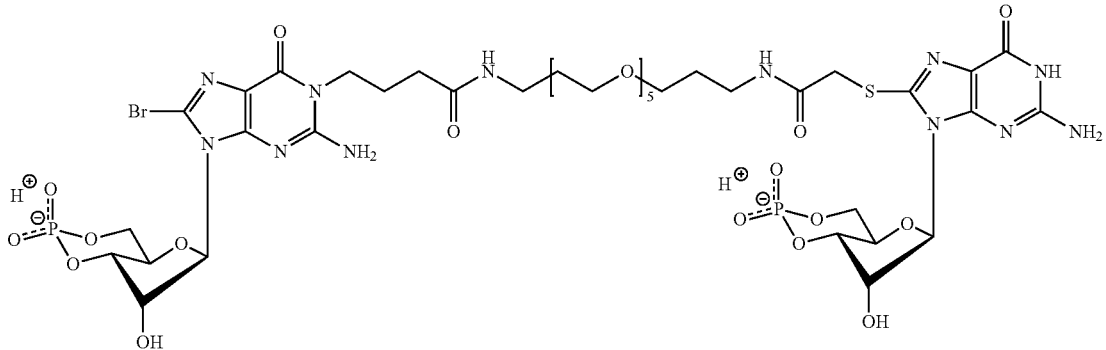 |

8-Bromoguanosine-3',5'-cyclic monophosphate-[1-propylamidoethyl-
(pentaethoxy)-propylamidomethylthio-8]-guanosine-3',5'-cyclic monophosphate
(8-Br-cGMP-1-PrAmdM-(EO)$_5$-PrAmdMT-8-cGMP)
Using general procedure J, 1-AM-(EO)$_5$-PrAmdPr-8-Br-cGMP was reacted with 8-CMT-
cGMP to give the title compound.
Yield (Purity): 32% (>99%).
HPLC: (36% MeOH, 50 mM TEAF buffer, pH 6.8).
UV-VIS: $\lambda_{max}$ = 272 nm (pH 7), $\varepsilon$ = 26910 (est.).
ESI-MS (+): m/z calculated for $C_{40}H_{60}N_{12}O_{21}P_2SBr$ ([M + H]$^+$): 1217.24, found: 1217.
ESI-MS (−): m/z calculated for $C_{40}H_{58}N_{12}O_{21}P_2SBr$ ([M − H]$^-$): 1215.22 found: 1215.

| 28 | 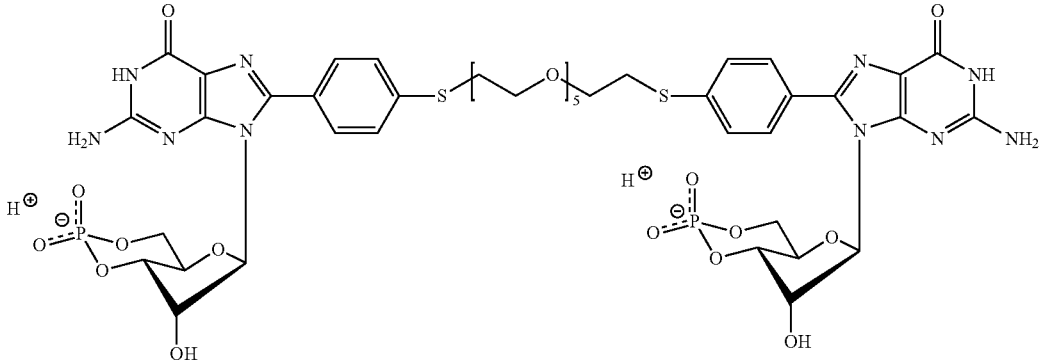 |

Guanosine-3',5'-cyclic monophosphate-[8-(phenyl-4-thio)-(pentaethoxy)-ethyl-
(4-thiophenyl)-8]-guanosine-3',5'-cyclic monophosphate (cGMP-8-PpT-(EO)$_5$-
EpTP-8-cGMP)
Using general procedure X, 8-Br-cGMP was reacted with 4-B(OH)$_2$PhS—PEG$_5$—(CH$_2$)$_2$—4-SPhB(OH)$_2$
(0.5 eq) to give the compound.
Yield (Purity): 11% (>99%).
HPLC: (23% MeCN, 10 mM TEAF buffer, pH 6.8).
UV-VIS: $\lambda_{max}$ = 296 nm (pH 7), $\varepsilon$ = 38700 (est.).
ESI-MS (+): m/z calculated for $C_{44}H_{55}N_{10}O_{19}P_2S_2$ ([M + H]$^+$): 1153.26, found: 1153.
ESI-MS (−): m/z calculated for $C_{44}H_{53}N_{10}O_{19}P_2S_2$ ([M − H]$^-$): 1151.24 found: 1151.

| 29 | 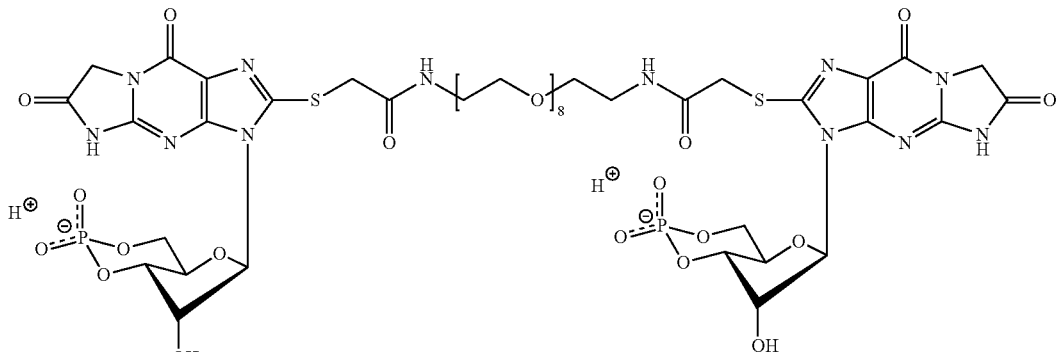 |

TABLE 15-continued

Examples of novel polymer linked multimeric cGMP compounds.

| # | Compound/Structure |
|---|---|
| 30 | β-1, N²-Acetyl-guanosine-3',5'-cyclic monophosphate-[8-thiomethylamido-(octaethoxy)-ethylamidomethylthio-8]-β-1,N²-acetyl-guanosine-3',5'-cyclic monophosphate (β-1,N²-Ac-cGMP-8-TMAmd-(EO)₈-EAmdMT-8-cGMP-β-1,N²-Ac) Using general procedure C, β-1,N²-Ac-8-Br-cGMP is reacted with mercaptoacetic acid to give the carboxymethyl thio substituted derivative, which is transformed to the title compound by reaction with NH₂—(EO)₈—(CH₂)₂NH₂ applying general procedure L.<br><br>8-Phenylguanosine-3',5'-cyclic monophosphate-[1,N²-etheno-β-phenyl-4-yl-(1-[1,2,3]-triazole-4-yl)-methoxy-(hexaethoxy)-methyl-(4-(4-[1,2,3]-triazole-1-yl)-β-phenyl-1,N²-etheno)]-8-phenylguanosine-3',5'-cyclic monophosphate (8-Phe-cGMP-ETP-p(1-[1,2,3]-Tz-4)-MeO-(EO)₆-Me-p(4-[1,2,3]-Tz-1)-PET-cGMP-8-Phe) Using general procedure Y, 8-Phe-cGMP is reacted with 4-azidophenacylbromide to give the 4-N₃-PET substituted derivative, which is transformed to the title compound by reaction with with bis-propargyl-(EO)₇ applying general procedure U. |

Monomeric precursors of the invention and/or monomeric compounds of the invention are further illustrated by the figures and examples of Table 16 describing preferred embodiments of the present invention which are, however, not intended to limit the invention in any way. Structural examples of novel compounds are depicted in the free acid form. After HPLC workup, compounds are obtained as salts of the applied buffer, but can be transformed to other salt forms or to the free acid by cation exchange according to standard procedures for nucleotides.

TABLE 16

Examples of monomeric precursors and/or monomeric compound of the invention.

| # | Compound/Structure |
|---|---|
| 31 | 8-Amidomethylthioguanosine-3',5'-cyclic monophosphate (8-AmdMT-cGMP)<br>Using general procedure D, 8-T-cGMP was reacted with 2-bromoacetamide to give the title compound.<br>Yield (Purity): 44% (>99%).<br>HPLC: (5% MeCN, 10 mM TEAF buffer, pH 6.8).<br>UV-VIS: $\lambda_{max}$ = 275 nm (pH 7), ε = 13700 (est.).<br>ESI-MS (+): m/z calculated for $C_{12}H_{16}N_6O_8PS$ ([M + H]⁺): 435.05, found: 435.<br>ESI-MS (−): m/z calculated for $C_{12}H_{14}N_6O_8PS$ ([M − H]⁻): 433.03, found: 433. |

TABLE 16-continued

Examples of monomeric precursors and/or monomeric compound of the invention.

| # | Compound/Structure |
|---|---|
| 32 | 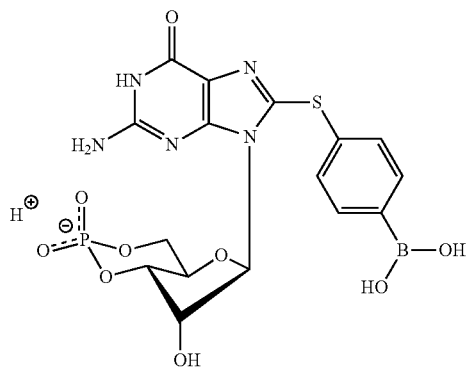<br>8-(4-Boronatephenylthio)-guanosine-3',5'-cyclic monophosphate<br>(8-pB(OH)$_2$PT-cGMP)<br>Using general procedure A, 8-Br-cGMP was reacted with 4-mercaptophenylboronic acid to give the title compound.<br>Yield (Purity): 71% (>99%).<br>HPLC: (32% MeOH, 10 mM TEAF buffer, pH 6.8).<br>UV-VIS: $\lambda_{max}$ = 276 nm (pH 7), $\varepsilon$ = 21500 (est.).<br>ESI-MS (+): m/z calculated for C$_{16}$H$_{17}$BN$_5$O$_9$PSNa ([M + H]$^+$): 520.05, found: 520.<br>ESI-MS (−): m/z calculated for C$_{16}$H$_{16}$BN$_5$O$_9$PS ([M − H]$^-$): 496.05, found: 496. |
| 33 | 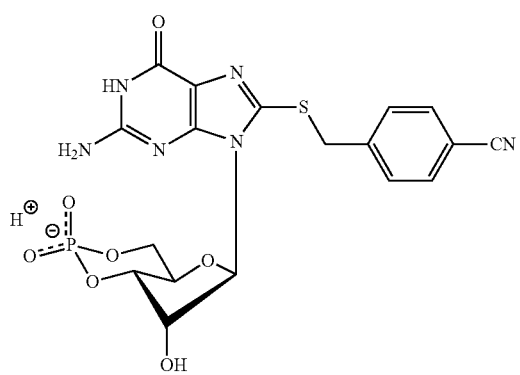<br>8-(4-Cyanobenzylthio)guanosine-3',5'-cyclic monophosphate<br>(8-pCNBT-cGMP)<br>Using general procedure D, 8-T-cGMP was reacted with 4-cyanobenzyl bromide to give the title compound.<br>Yield (Purity): 34% (>99%).<br>HPLC: (32% MeOH, 10 mM TEAF buffer, pH 6.8).<br>UV-VIS: $\lambda_{max}$ = 276 nm (pH 7), $\varepsilon$ = 13700 (est.).<br>ESI-MS (+): m/z calculated for C$_{18}$H$_{18}$N$_6$O$_7$PS ([M + H]$^+$): 493.07, found: 493.<br>ESI-MS (−): m/z calculated for C$_{18}$H$_{16}$N$_6$O$_7$PS ([M − H]$^-$): 491.05, found: 491. |
| 34 | 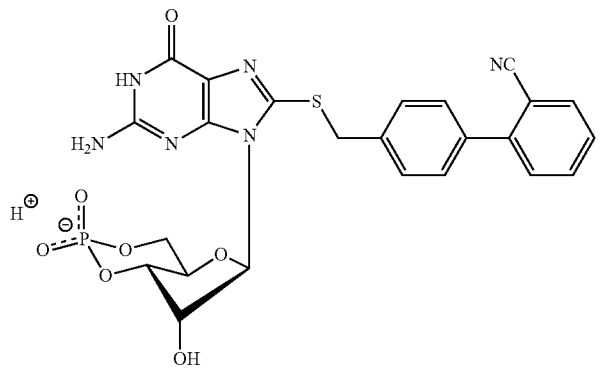<br>8-(4-(2-Cyanophenyl)-benzylthio)guanosine-3',5'-cyclic monophosphate<br>(8-(p(2-CNPhe)BT-cGMP |

TABLE 16-continued

Examples of monomeric precursors and/or monomeric compound of the invention.

| # | Compound/Structure |
|---|---|

Using general procedure D, 8-T-cGMP was reacted with 4-bromomethyl-2-cyanobiphenyl to give the title compound.
Yield (Purity): 16% (>99%).
HPLC: (52% MeOH, 10 mM TEAF buffer, pH 6.8).
UV-VIS: $\lambda_{max}$ = 260 nm (pH 7), $\varepsilon$ = 13700 (est.).
ESI-MS (+): m/z calculated for $C_{24}H_{22}N_6O_7PS$ ([M + H]$^+$): 569.10, found: 569.
ESI-MS (−): m/z calculated for $C_{24}H_{20}N_6O_7PS$ ([M − H]$^-$): 567.09, found: 567.

35

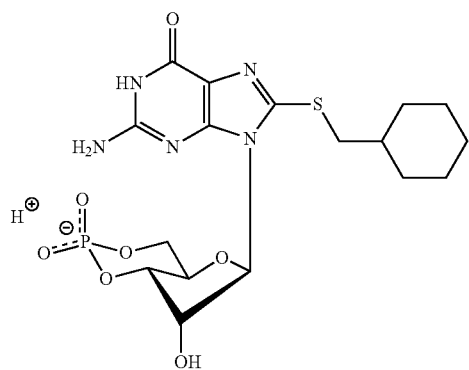

8-Cyclohexylmethylthioguanosine-3',5'-cyclic monophosphate (8-cHeMT-cGMP)
Using general procedure D, 8-T-cGMP (1 eq) was reacted with cyclohexylmethyl bromide (2 eq) at 90° C. to give the title compound.
Yield (Purity): 38% (>99%).
HPLC: (57% MeOH, 10 mM TEAF buffer, pH 6.8).
UV-VIS: $\lambda_{max}$ = 276 nm (pH 7), $\varepsilon$ = 13700 (est.).
ESI-MS (+): m/z calculated for $C_{17}H_{25}N_5O_7PS$ ([M + H]$^+$): 474.12, found: 474.
ESI-MS (−): m/z calculated for $C_{17}H_{23}N_5O_7PS$ ([M − H]$^-$): 472.11, found: 472.

36

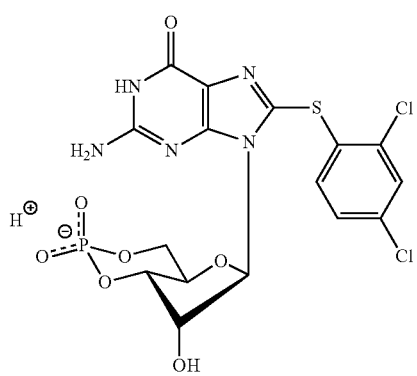

8-(2,4-Dichlorophenylthio)guanosine-3',5'-cyclic monophosphate (8-o,pDClPT-cGMP)
Using general procedure A, 8-Br-cGMP was reacted with 2,4-dichlorobenzenethiol to give the title compound.
Yield (Purity): 33% (>99%).
HPLC: (22% MeCN, 10 mM TEAF buffer, pH 6.8).
UV-VIS: $\lambda_{max}$ = 279 nm (pH 7), $\varepsilon$ = 21500 (est.).
ESI-MS (+): m/z calculated for $C_{16}H_{14}Cl_2N_5O_7PSNa$ ([M + Na]$^+$): 543.96, found: 544.
ESI-MS (−): m/z calculated for $C_{16}H_{13}Cl_2N_5O_7PS$ ([M − H]$^-$): 519.97, found: 520.

TABLE 16-continued

Examples of monomeric precursors and/or monomeric compound of the invention.

| # | Compound/Structure |
|---|---|
| 37 | 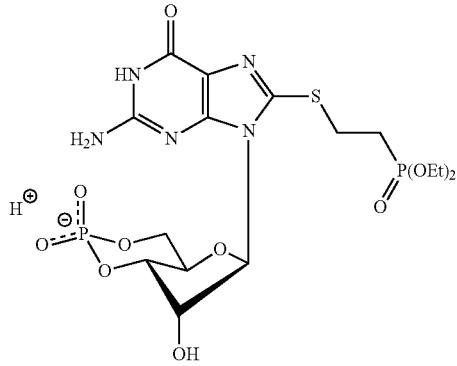<br>8-Diethylphosphonoethylthio-guanosine-3',5'-cyclic monophosphate (8-DEPET-cGMP)<br>Using general procedure D, 8-T-cGMP was reacted with diethyl 2-bromoethylphosphonat to give the title compound.<br>Yield (Purity): 20% (>99%).<br>HPLC: (32% MeOH, 10 mM TEAF buffer, pH 6.8).<br>UV-VIS: $\lambda_{max}$ = 275 nm (pH 7), $\varepsilon$ = 13700 (est.).<br>ESI-MS (+): m/z calculated for $C_{16}H_{26}N_5O_{10}P_2S$ ([M + H]$^+$): 542.09, found: 542.<br>ESI-MS (−): m/z calculated for $C_{16}H_{24}N_5O_{10}P_2S$ ([M − H]$^-$): 540.07, found: 540. |
| 38 | 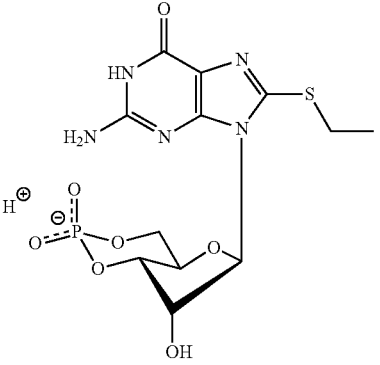<br>8-Ethylthioguanosine-3',5'-cyclic monophosphate (8-ET-cGMP)<br>Using general procedure A, 8-Br-cGMP was reacted with ethanethiol to give the title compound.<br>Yield (Purity): 30% (>99%).<br>HPLC: (10% MeCN, 10 mM NaH2PO4 buffer, pH 4.8).<br>UV-VIS: $\lambda_{max}$ = 275 nm (pH 7), $\varepsilon$ = 14000 (est.).<br>ESI-MS (+): m/z calculated for for $C_{12}H_{17}N_5O_7PS$ ([M + H]$^+$): 406.06, found: 406.<br>ESI-MS (−): m/z calculated for $C_{12}H_{15}N_5O_7PS$ ([M − H]$^-$): 404.04, found: 404. |
| 39 | 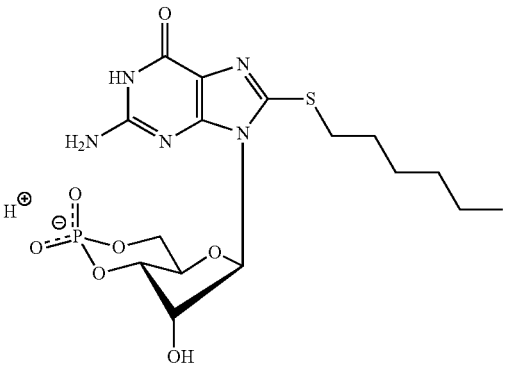<br>8-Hexylthioguanosine-3',5'-cyclic monophosphate (8-HT-cGMP)<br>Using general procedure A, 8-Br-cGMP was reacted with 1-hexanethiol to give the title compound. |

TABLE 16-continued

Examples of monomeric precursors and/or monomeric compound of the invention.

| # | Compound/Structure |
|---|---|

Yield (Purity): 50% (>99%).
HPLC: (21% MeCN, 20 mM TEAF buffer, pH 6.8).
UV-VIS: $\lambda_{max}$ = 276 nm (pH 7), $\epsilon$ = 14000 (est.).
ESI-MS (+): m/z calculated for $C_{16}H_{25}N_5O_7PS$ ($[M + H]^+$): 462.12, found: 462.
ESI-MS (−): m/z calculated for $C_{16}H_{23}N_5O_7PS$ ($[M − H]^-$): 460.11, found: 460.

40

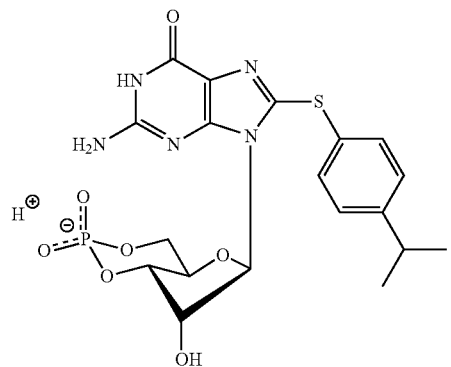

8-(4-Isopropylphenylthio)guanosine-3',5'-cyclic monophosphate
(8-pIPrPT-cGMP)
Using general procedure A, 8-Br-cGMP was reacted with 4-Isopropylthiophenol
to give the title compound.
Yield (Purity): 75% (>98%).
HPLC: (55% MeOH, 10 mM TEAF buffer, pH 6.8).
UV-VIS: $\lambda_{max}$ = 278 nm (pH 7), $\epsilon$ = 21500 (est.).
ESI-MS (+): m/z calculated for $C_{19}H_{23}N_5O_7PS$ ($[M + H]^+$): 496.11, found: 496.
ESI-MS (−): m/z calculated for $C_{19}H_{21}N_5O_7PS$ ($[M − H]^-$): 494.09, found: 494.

41

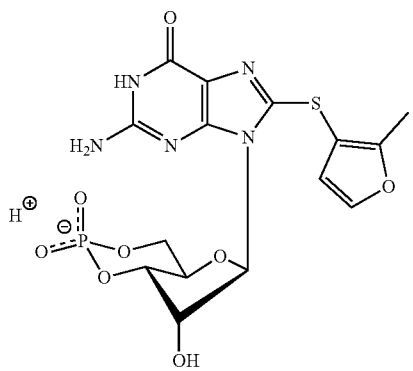

8-(3-(2-Methyl)furanyl)thioguanosine-3',5'-cyclic monophosphate
(8-(3-(2-Me)-FU)T-cGMP)
Using general procedure A, 8-Br-cGMP was reacted with 2-methyl-3-furanethiol
to give the title compound.
Yield (Purity): 32% (>99%).
HPLC: (37% MeOH, 10 mM TEAF buffer, pH 6.8).
UV-VIS: $\lambda_{max}$ = 275 nm (pH 7), $\epsilon$ = 21500 (est.).
ESI-MS (+): m/z calculated for $C_{15}H_{17}N_5O_8PS$ ($[M + H]^+$): 458.05, found: 458.
ESI-MS (−): m/z calculated for $C_{15}H_{15}N_5O_8PS$ ($[M − H]^-$): 456.04, found: 456.

TABLE 16-continued

Examples of monomeric precursors and/or monomeric compound of the invention.

| # | Compound/Structure |
|---|---|
| 42 | 8-(5-(1-Methyl)tetrazolyl)thioguanosine-3',5'-cyclic monophosphate (8-(5-(1-Me)-Tet)T-cGMP)<br>Using general procedure A, 8-Br-cGMP was reacted with 5-mercapto-1-methyltetrazole to give the title compound.<br>Yield (Purity): 29% (>95%).<br>HPLC: (7% MeCN, 10 mM TEAF buffer, pH 6.8).<br>UV-VIS: $\lambda_{max}$ = 276 nm (pH 7), $\varepsilon$ = 21500 (est.).<br>ESI-MS (+): m/z calculated for $C_{12}H_{15}N_9O_7PS$ ([M + H]$^+$): 460.06, found: 460.<br>ESI-MS (−): m/z calculated for $C_{12}H_{13}N_9O_7PS$ ([M − H]$^-$): 458.04, found: 458. |
| 43 | 8-(4-Methoxybenzylthio)guanosine-3',5'-cyclic monophosphate (8-pMeOBT-cGMP)<br>Using the general procedure A, 8-Br-cGMP (1 eq) was reacted with 4-methoxybenzyl mercaptan (4 eq) to give the title compound.<br>Yield (Purity): 37% (>99%).<br>HPLC: (21% MeCN, 20 mM TEAF buffer, pH 6.8.).<br>UV-VIS: $\lambda_{max}$ = 277 nm (pH 7), $\varepsilon$ = 21500 (est.).<br>ESI-MS (+): m/z calculated for $C_{18}H_{21}N_5O_8PS$ ([M + H]$^+$): 498.08, found: 498.<br>ESI-MS (−): m/z calculated for $C_{18}H_{19}N_5O_8PS$ ([M − H]$^-$): 496.07, found: 496. |
| 44 | 8-(7-(4-Methyl)coumarinyl)thio-guanosine-3',5'-cyclic monophosphate (8-(7-(4-Me)-Cou)T-cGMP) |

TABLE 16-continued

Examples of monomeric precursors and/or monomeric compound of the invention.

| # | Compound/Structure |
|---|---|

Using general procedure A, 8-Br-cGMP was reacted with 7-mercapto-4-methylcoumarin to give the title compound.
Yield (Purity): 77% (>99%).
HPLC: (35% MeOH, 10 mM TEAF buffer, pH 6.8).
UV-VIS: $\lambda_{max}$ = 281 nm (pH 7), $\varepsilon$ = 21500 (est.).
ESI-MS (+): m/z calculated for $C_{20}H_{19}N_5O_9PS$ ([M + H]$^+$): 536.06, found: 536.
ESI-MS (−): m/z calculated for $C_{20}H_{17}N_5O_9PS$ ([M − H]$^-$): 534.05, found: 534.

45

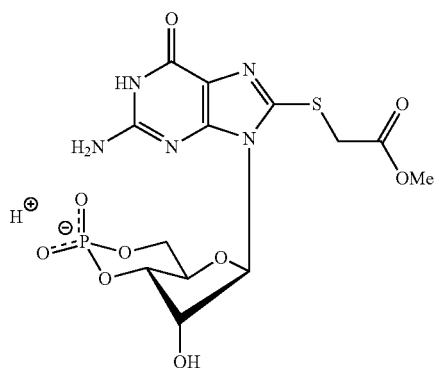

8-Methylacetylthioguanosine-3',5'-cyclic monophosphate (8-MAcT-cGMP)
Using general procedure D, 8-T-cGMP was reacted with methyl bromoacetate to give the title compound.
Yield (Purity): 35% (>98%).
HPLC: (25% MeOH, 10 mM TEAF buffer, pH 6.8).
UV-VIS: $\lambda_{max}$ = 274 nm (pH 7), $\varepsilon$ = 13700 (est.).
ESI-MS (+): m/z calculated for $C_{13}H_{17}N_5O_9PS$ ([M + H]$^+$): 450.05, found: 450.
ESI-MS (−): m/z calculated for $C_{13}H_{15}N_5O_9PS$ ([M − H]$^-$): 448.03, found: 448.

46

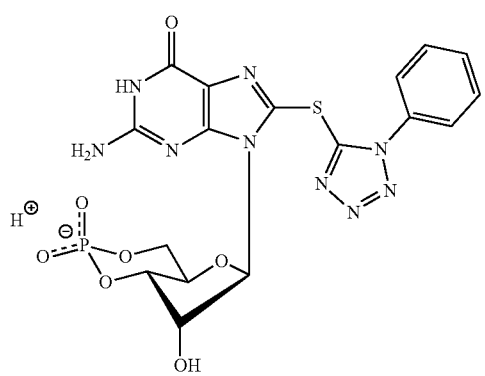

8-(5-(1-Phenyl)tetrazolyl)thioguanosine-3',5'-cyclic monophosphate (8-(5-(1-Phe)-Tet)T-cGMP)
Using general procedure A, 8-Br-cGMP was reacted with 5-mercapto-1-phenyl-1H-tetrazole to give the title compound.
Yield (Purity): 44% (>99%).
HPLC: (32% MeOH, 10 mM TEAF buffer, pH 6.8).
UV-VIS: $\lambda_{max}$ = 277 nm (pH 7), $\varepsilon$ = 21500 (est.).
ESI-MS (+): m/z calculated for $C_{17}H_{17}N_9O_7PS$ ([M + H]$^+$): 522.07, found: 522.
ESI-MS (−): m/z calculated for $C_{17}H_{15}N_9O_7PS$ ([M − H]$^-$): 520.06, found: 520.

TABLE 16-continued

Examples of monomeric precursors and/or monomeric compound of the invention.

| # | Compound/Structure |
|---|---|
| 47 | 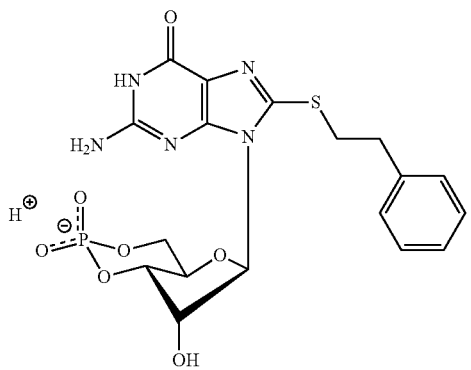<br>8-(2-Phenylethyl)thioguanosine-3',5'-cyclic monophosphate (8-PhEtT-cGMP)<br>Using general procedure A, 8-Br-cGMP (1 eq) was reacted with 2-phenylethanethiol (4 eq) to give the title compound.<br>Yield (Purity): 20% (>99%).<br>HPLC: (21% MeCN, TEAF buffer, pH 6.8).<br>UV-VIS: $\lambda_{max}$ = 277 nm (pH 7), $\varepsilon$ = 21500 (est.).<br>ESI-MS (+): m/z calculated for $C_{18}H_{21}N_5O_7PS$ ([M + H]$^+$): 482.09, found: 482.<br>ESI-MS (−): m/z calculated for $C_{18}H_{19}N_5O_7PS$ ([M − H]$^-$): 480.07, found: 480. |
| 48 | 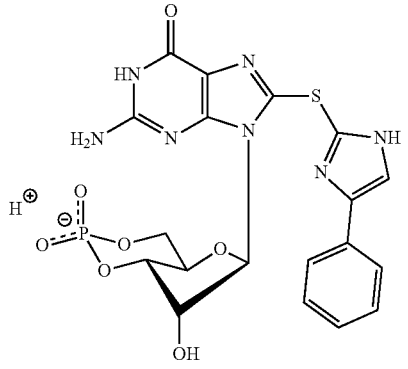<br>8-(2-(4-Phenyl)imidazolyl)thioguanosine-3',5'-cyclic monophosphate (8-(2-(4-Phe)-Im)T-cGMP)<br>Using general procedure A, 8-Br-cGMP was reacted with 4-phenylimidazole-2-thiol to give the title compound.<br>Yield (Purity): 26% (>99%).<br>HPLC: (35% MeOH, 10 mM TEAF buffer, pH 6.8).<br>UV-VIS: $\lambda_{max}$ = 276 nm (pH 7), $\varepsilon$ = 21500 (est.).<br>ESI-MS (+): m/z calculated for $C_{19}H_{19}N_7O_7PS$ ([M + H]$^+$): 520.08, found: 520.<br>ESI-MS (−): m/z calculated for $C_{19}H_{17}N_7O_7PS$ ([M − H]$^-$): 518.07, found: 518. |
| 49 | 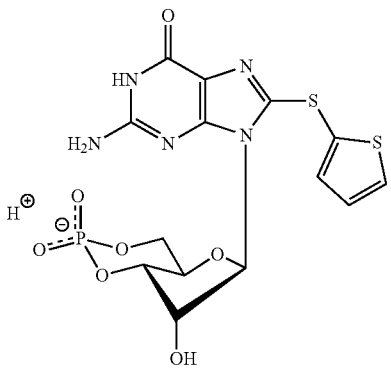<br>8-(2-Thiophenyl)thioguanosine-3',5'-cyclic monophosphate (8-(2-Tp)T-cGMP)<br>Using general procedure A, 8-Br-cGMP was reacted with 2-thiophenethiol to give the title compound. |

TABLE 16-continued

Examples of monomeric precursors and/or monomeric compound of the invention.

| # | Compound/Structure |
|---|---|

Yield (Purity): 21% (>98%.)

HPLC: (30% MeOH, 10 mM TEAF buffer, pH 6.8).

UV-VIS: $\lambda_{max}$ = 277 (pH 7), $\epsilon$ = 21500 (est.).

ESI-MS (+): m/z calculated for $C_{14}H_{15}N_5O_7PS_2$ ([M + H]$^+$): 460.02, found: 460.

ESI-MS (−): m/z calculated for $C_{14}H_{13}N_5O_7PS_2$ ([M − H]$^-$): 458.00, found: 458.

50

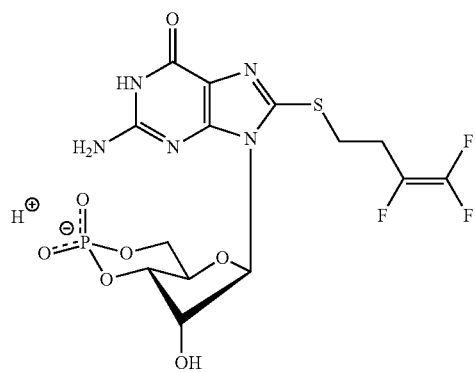

8-(1,1,2-Trifluoro-1-butenthio)guanosine-3',5'-cyclic monophosphate (8-(1,1,2-TF-Bu(1-en))T-cGMP)

Using general procedure D, 8-TcGMP was reacted with 4-bromo-1,1,2-trifluoro-1-butene to give the title compound.

Yield (Purity): 21% (>99%).

HPLC: (37% MeOH, 10 mM TEAF buffer, pH 6.8).

UV-VIS: $\lambda_{max}$ = 276 nm (pH 7), $\epsilon$ = 13700 (est.).

ESI-MS (+): m/z calculated for $C_{14}H_{16}F_3N_5O_7PS$ ([M + H]$^+$): 486.05, found: 486.

ESI-MS (−): m/z calculated for $C_{14}H_{14}F_3N_5O_7PS$ ([M − H]$^-$): 484.03, found: 484.

51

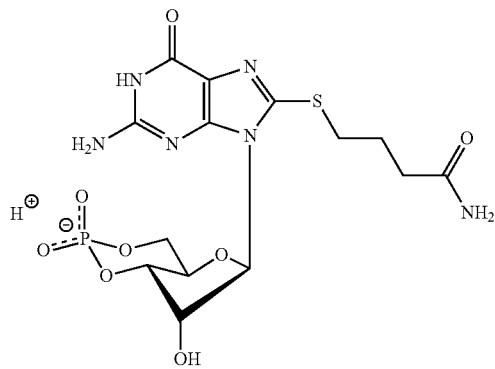

8-Amidopropylthioguanosine-3',5'-cyclic monophosphate (8-AmdPrT-cGMP)

The title compound was synthesized from 8-EButT-cGMP using general procedure G.

Yield (Purity): 18% (>99%).

HPLC: (32% MeOH, 10 mM TEAF buffer, pH 6.8).

UV-VIS: $\lambda_{max}$ = 274 nm (pH 7), $\epsilon$ = 13700 (est.).

ES-MS (+): m/z calculated for $C_{14}H_{20}N_6O_8PS$ ([M + H]$^+$): 463.08, found: 463.

ES-MS (−): m/z calculated for $C_{14}H_{18}N_6O_8PS$ ([M − H]$^-$): 461.06, found: 461.

TABLE 16-continued

Examples of monomeric precursors and/or monomeric compound of the invention.

| # | Compound/Structure |
|---|---|
| 52 | |

8-Amidoethylthioguanosine-3',5'-cyclic monophosphate (8-AmdET-cGMP)
The title compound was synthesized from 8-MPT-cGMP using general procedure G.
Yield (Purity): 57% (>99%).
HPLC: (6% MeCN, 10 mM TEAF buffer, pH 6.8).
UV-VIS: $\lambda_{max}$ = 275 nm (pH 7), $\varepsilon$ = 13700 (est.).
ESI-MS (+): m/z calculated for $C_{13}H_{18}N_6O_8PS$ ([M + H]$^+$): 449.06, found: 449.
ESI-MS (−): m/z calculated for $C_{13}H_{16}N_6O_8PS$ ([M − H]$^-$): 447.34, found:.

53

8-Amidobutylthioguanosine-3',5'-cyclic monophosphate (8-AmdBuT-cGMP)
The title compound was synthesized from 8-MVAlT-cGMP using general procedure G.
Yield (Purity): 24% (>99%).
HPLC: (6% MeCN, 10 mM TEAF buffer, pH 6.8).
UV-VIS: $\lambda_{max}$ = 275 nm (pH 7), $\varepsilon$ = 13700 (est.).
ESI-MS (+): m/z calculated for $C_{15}H_{22}N_6O_8PS$ ([M + H]$^+$): 477.10, found: 477.
ESI-MS (−): m/z calculated for $C_{15}H_{20}N_6O_8PS$ ([M − H]$^-$): 475.08, found: 475.

54

8-Acetamidoethylthioguanosine-3',5'-cyclic monophosphate (8-AcAmdET-cGMP)
Using general procedure H, 8-AET-cGMP was reacted with acetic acid to give the title
compound.
Yield (Purity): 34% (>98%).
HPLC: (6% MeCN, 10 mM TEAF buffer, pH 6.8).
UV-VIS: $\lambda_{max}$ = 275 nm (pH 7), $\varepsilon$ = 13700 (est.).

TABLE 16-continued

Examples of monomeric precursors and/or monomeric compound of the invention.

| # | Compound/Structure |
|---|---|

ESI-MS (+): m/z calculated for $C_{14}H_{20}N_6O_8PS$ ([M + H]$^+$): 463.08, found: 463.
ESI-MS (−): m/z calculated for $C_{14}H_{18}N_6O_8PS$ ([M − H]$^−$): 461.06, found:.

55

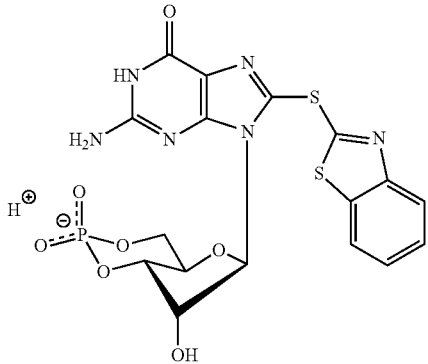

8-(2-Benzothiazolyl)thioguanosine-3',5'-cyclic monophosphate (8-(2-BT)T-cGMP)
Using general procedure A, 8-Br-cGMP was reacted with 2-mercaptobenzothiazole to give
the title compound.
Yield (Purity): 3% (>99%).
HPLC: (37% MeOH, 10 mM TEAF buffer, pH 6.8).
UV-VIS: $\lambda_{max}$ = 278 nm (pH 7), $\varepsilon$ = 21500 (est.).
ESI-MS (+): m/z calculated for $C_{17}H_{16}N_6O_7PS_2$ ([M + H]$^+$): 511.03, found: 511.
ESI-MS (−): m/z calculated for $C_{17}H_{14}N_6O_7PS_2$ ([M − H]$^−$): 509.01, found: 509.

56

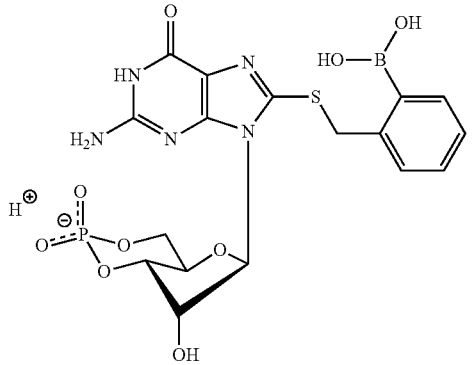

8-(2-Boronatebenzylthio)guanosine-3',5'-cyclic monophosphate
(8-(oB(OH)$_2$Bn)T-cGMP)
Using general procedure D, 8-T-cGMP was reacted with 2-
(bromomethyl)phenylboronic acid to give the title compound.
Yield (Purity): 37% (>99%).
HPLC: (32% MeOH, 10 mM TEAF buffer, pH 6.8).
UV-VIS: $\lambda_{max}$ = 278 nm (pH 7), $\varepsilon$ = 13700 (est.).
ESI-MS (+): m/z calculated for $C_{17}H_{19}BN_5O_9PSNa$ ([M + Na]$^+$): 534.06, found: 534.
ESI-MS (−): m/z calculated for $C_{17}H_{18}BN_5O_9PS$ ([M − H]$^−$): 510.07, found: 510.

57

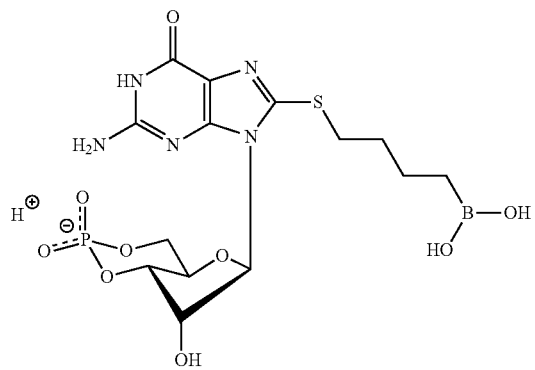

TABLE 16-continued

Examples of monomeric precursors and/or monomeric compound of the invention.

| # | Compound/Structure |
|---|---|
| | 8-(4-Boronatebutylthio)guanosine-3',5'-cyclic monophosphate (8-(pB(OH)$_2$Bu)T-cGMP)<br>Using general procedure D, 8-T-cGMP was reacted with 4-bromobutylboronic acid to give the title compound.<br>Yield (Purity): 43% (>99%).<br>HPLC: (30% MeOH, 10 mM TEAF buffer, pH 6.8).<br>UV-VIS: $\lambda_{max}$ = 275 nm (pH 7), ε = 13700 (est.).<br>ESI-MS (+): m/z calculated for C$_{14}$H$_{21}$BN$_5$O$_9$PSNa ([M + H]$^+$): 500.08, found: 500.<br>ESI-MS (−): m/z calculated for C$_{14}$H$_{20}$BN$_5$O$_9$PS ([M − H]$^−$): 476.08, found: 476. |
| 58 | 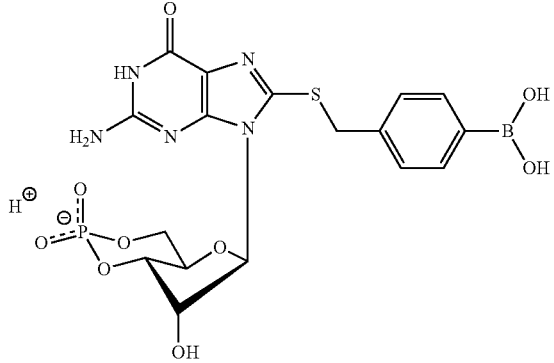<br>8-(4-Boronatebenzylthio)guanosine-3',5'-cyclic monophosphate (8-(pB(OH)$_2$Bn)T-cGMP)<br>Using general procedure D, 8-T-cGMP was reacted with 4-(bromomethyl)phenylboronic acid to give the title compound.<br>Yield (Purity): 67% (>99%).<br>HPLC: (30% MeOH, 10 mM TEAF buffer, pH 6.8).<br>UV-VIS: $\lambda_{max}$ = 278 nm (pH 7), ε = 13700 (est.).<br>ESI-MS (+): m/z calculated for C$_{17}$H$_{20}$BN$_5$O$_9$PS ([M + H]$^+$): 512.08, found: 512.<br>ESI-MS (−): m/z calculated for C$_{17}$H$_{18}$BN$_5$O$_9$PS ([M − H]$^−$): 510.07, found: 510. |
| 59 | 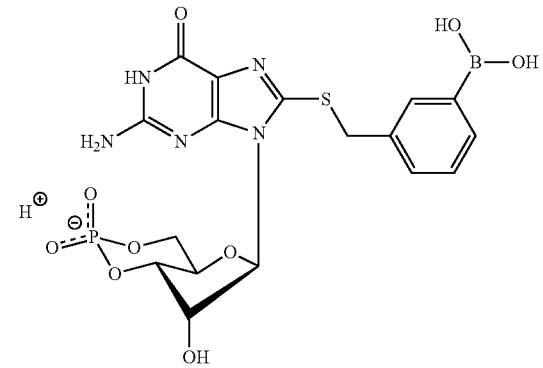<br>8-(3-Boronatebenzylthio)guanosine-3',5'-cyclic monophosphate (8-(mB(OH)$_2$Bn)T-cGMP)<br>Using general procedure D, 8-T-cGMP was reacted with 3-(bromomethyl)phenylboronic acid to give the title compound.<br>Yield (Purity): 54% (>99%).<br>HPLC: (30% MeOH, 10 mM TEAF buffer, pH 6.8).<br>UV-VIS: $\lambda_{max}$ = 278 nm (pH 7), ε = 13700 (est.).<br>ESI-MS (+): m/z calculated for C$_{17}$H$_{19}$BN$_5$O$_9$PSNa ([M + Na]$^+$): 534.06, found: 534.<br>ESI-MS (−): m/z calculated for C$_{17}$H$_{18}$BN$_5$O$_9$PS ([M − H]$^−$): 510.07, found: 510. |

TABLE 16-continued

Examples of monomeric precursors and/or monomeric compound of the invention.

| # | Compound/Structure |
|---|---|

60

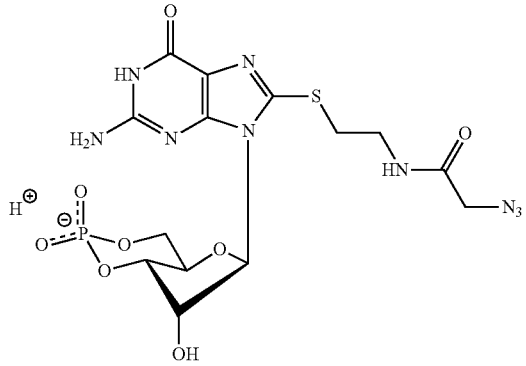

8-Azidomethylamidoethylthioguanosine-3',5'-cyclic monophosphate (8-N$_3$-MAmdET-cGMP)
Using general procedure J, 8-AET-cGMP was reacted with azidoacetic acid to give the title compound.
Yield (Purity): 62% (>98%).
HPLC: (21% MeOH, 20 mM TEAF buffer, pH 6.8).
UV-VIS: $\lambda_{max}$ = 276 nm (pH 7), $\varepsilon$ = 13700 (est.).
ESI-MS (+): m/z calculated for C$_{14}$H$_{19}$N$_9$O$_8$PS ([M + H]$^+$): 504.08, found: 504.
ESI-MS (−): m/z calculated for C$_{14}$H$_{17}$N$_9$O$_8$PS ([M − H]$^-$): 502.07, found: 502.

61

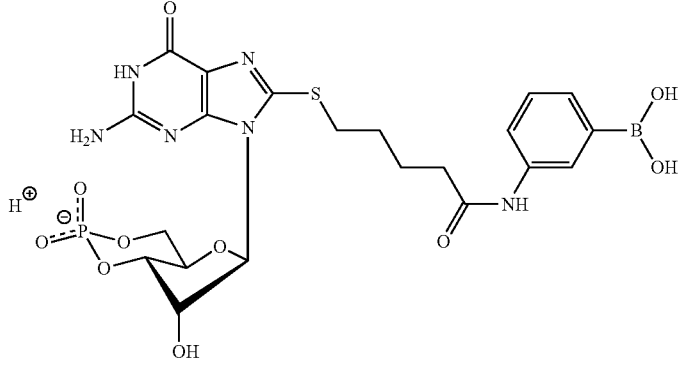

8-(3-Boronatephenyl)amidobutylthio-guanosine-3',5'-cyclic monophosphate (8-(mB(OH)$_2$PAmdBu)T-cGMP)
Using general procedure H, 8-CBuT-cGMP was reacted with 3-aminobenzeneboronic acid to give the title compound.
Yield (Purity): 50% (>99%).
HPLC: (35% MeOH, 10 mM TEAF buffer, pH 6.8).
UV-VIS: $\lambda_{max}$ = 276 nm (pH 7), $\varepsilon$ = 13700 (est.).
ESI-MS (−): m/z calculated for C$_{21}$H$_{25}$BN$_6$O$_{10}$PS ([M − H]$^-$): 595.12, found: 595.

62

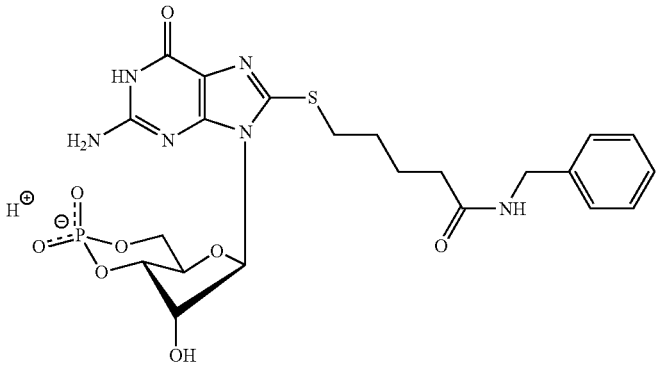

8-Benzylamidobutylthioguanosine-3',5'-cyclic monophosphate (8-BnAmdBuT-cGMP)

TABLE 16-continued

Examples of monomeric precursors and/or monomeric compound of the invention.

| # | Compound/Structure |
|---|---|

Using general procedure H, 8-CBuT-cGMP was reacted with benzylamine to give the title compound.
Yield (Purity): 49% (>99%).
HPLC: (35% MeOH, 10 mM TEAF buffer, pH 6.8).
UV-VIS: $\lambda_{max}$ = 276 nm (pH 7), $\varepsilon$ = 13700 (est.).
ESI-MS (+): m/z calculated for $C_{22}H_{28}N_6O_8PS$ ($[M + H]^+$): 567.14, found: 567.
ESI-MS (−): m/z calculated for $C_{22}H_{26}N_6O_8PS$ ($[M − H]^−$): 565.13, found: 565.

63

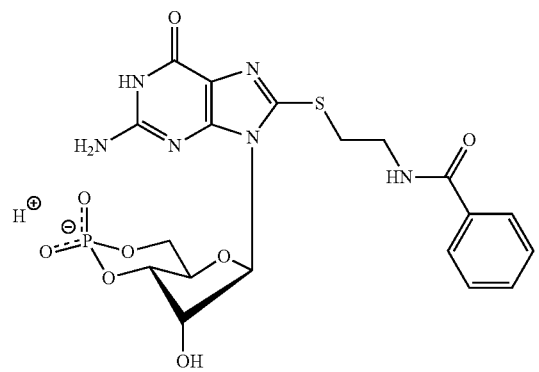

8-Benzamidoethylthioguanosine-3',5'-cyclic monophosphate (8-BAmdET-cGMP)
Using general procedure H, 8-AET-cGMP was reacted with benzoic acid to give the title compound.
Yield (Purity): 12% (>99%).
HPLC: (25% MeOH, 10 mM TEAF buffer, pH 6.8).
UV-VIS: $\lambda_{max}$ = 277 nm (pH 7), $\varepsilon$ = 13700 (est.).
ESI-MS (+): m/z calculated for $C_{19}H_{22}N_6O_8PS$ ($[M + H]^+$): 525.10, found: 525.
ESI-MS (−): m/z calculated for $C_{19}H_{20}N_6O_8PS$ ($[M − H]^−$): 523.08, found: 523.

64

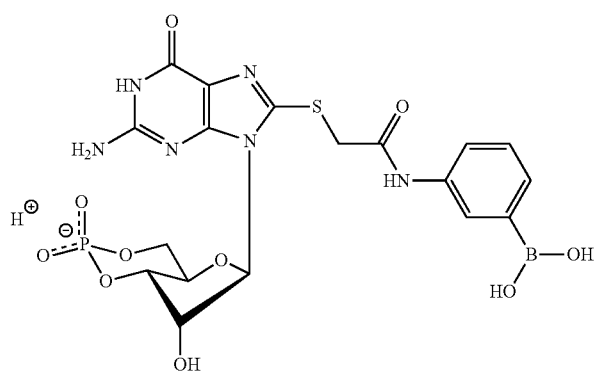

8-(3-Boronatephenyl)amidomethyl-thioguanosine-3',5'-cyclic monophosphate (8-mB(OH)₂PAmdMT-cGMP)
Using general procedure H, 8-CMT-cGMP was reacted with 3-aminophenylboronic acid to give the title compound.
Yield (Purity): 24% (>99%).
HPLC: (15% MeOH, 10 mM TEAF buffer, pH 6.8).
UV-VIS: $\lambda_{max}$ = 272 nm (pH 7), $\varepsilon$ = 13700 (est.).
ESI-MS (−): m/z calculated for $C_{18}H_{19}BN_6O_{10}PS$ ($[M − H]^−$): 553.07, found: 553.

TABLE 16-continued

Examples of monomeric precursors and/or monomeric compound of the invention.

| # | Compound/Structure |
|---|---|
| 65 | 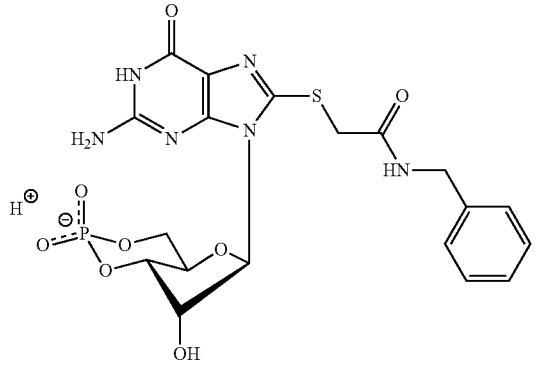 |

8-Benzylamidomethylthio-guanosine-3',5'-cyclic monophosphate (8-BnAmdMT-cGMP)
Using general procedure H, 8-CMT-cGMP was reacted with benzylamine to give the title compound.
Yield (Purity): 53% (>99%).
HPLC: (28% MeOH, 10 mM TEAF buffer, pH 6.8).
UV-VIS: $\lambda_{max}$ = 278 nm (pH 7), $\varepsilon$ = 13700 (est.).
ESI-MS (+): m/z calculated for $C_{19}H_{22}N_6O_8PS$ ([M + H]$^+$): 525.10, found: 525.
ESI-MS (−): m/z calculated for $C_{19}H_{20}N_6O_8PS$ ([M − H]$^-$): 523.08, found: 523.

| 66 | 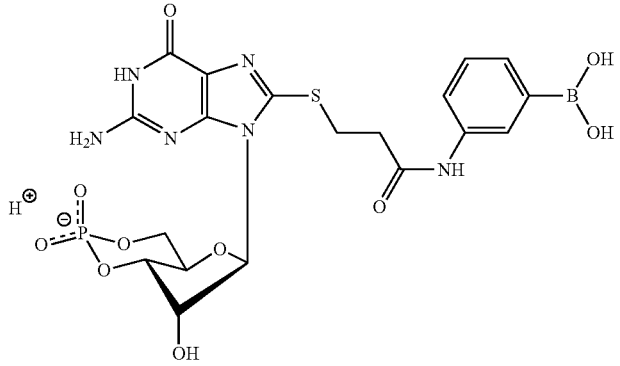 |

8-(3-Boronatephenyl)amidoethylthio-guanosine-3',5'-cyclic monophosphate (8-mB(OH)$_2$PAmdET-cGMP)
Using general procedure H, 8-CET-cGMP was reacted with 3-aminophenylboronic acid to give the title compound.
Yield (Purity): 11% (>99%).
HPLC: (32% MeOH, 10 mM TEAF buffer, pH 6.8).
UV-VIS: $\lambda_{max}$ = 255 (+278) nm (pH 7), $\varepsilon$ = 13700 (est.).
ESI-MS (−): m/z calculated for $C_{19}H_{21}BN_6O_{10}PS$ ([M − H]$^-$): 567.09, found: 567.

| 67 | 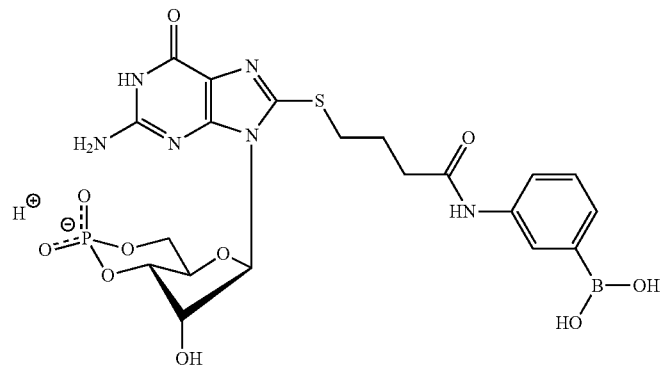 |

TABLE 16-continued

Examples of monomeric precursors and/or monomeric compound of the invention.

| # | Compound/Structure |
|---|---|
| | 8-(3-Boronatephenyl)amidopropylthioguanosine-3',5'-cyclic monophosphate (8-mB(OH)$_2$PAmdPrT-cGMP)<br>Using general procedure H, 8-CPrT-cGMP was reacted with 3-aminophenylboronic acid to give the title compound.<br>Yield (Purity): 65% (>99%).<br>HPLC: (32% MeOH, 10 mM TEAF buffer, pH 6.8).<br>UV-VIS: $\lambda_{max}$ = 276 nm (pH 7), $\varepsilon$ = 13700 (est.).<br>ESI-MS (−): m/z calculated for C$_{20}$H$_{23}$BN$_6$O$_{10}$PS ([M − H]$^-$): 581.10, found: 581. |
| 68 | 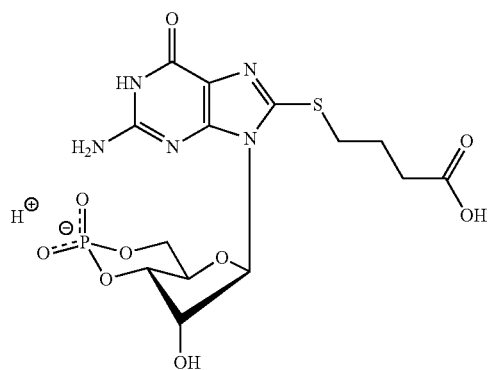<br>8-Carboxypropylthioguanosine-3',5'-cyclic monophosphate (8-CPrT-cGMP)<br>The title compound was synthesized from 8-EButT-cGMP using general procedure F.<br>Yield (Purity): 95% (>99%).<br>HPLC: (5% MeCN, 10 mM TEAF buffer, pH 6.8).<br>UV-VIS: $\lambda_{max}$ = 275 nm (pH 7), $\varepsilon$ = 13700 (est.).<br>ESI-MS (+): m/z calculated for C$_{14}$H$_{19}$N$_5$O$_9$PS ([M + H]$^+$): 464.06, found: 464.<br>ESI-MS (−): m/z calculated for C$_{14}$H$_{17}$N$_5$O$_9$PS ([M − H]$^-$): 462.05, found: 462. |
| 69 | 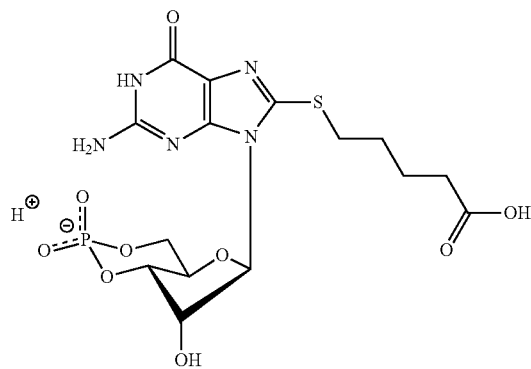<br>8-Carboxybutylthioguanosine-3',5'-cyclic monophosphate (8-CBuT-cGMP)<br>The title compound was synthesized from 8-MVAlT-cGMP using general procedure F.<br>Yield (Purity): 87% (>99%).<br>HPLC: (6% MeCN, 10 mM TEAF buffer, pH 6.8).<br>UV-VIS: $\lambda_{max}$ = 275 nm (pH 7), $\varepsilon$ = 13700 (est.).<br>ESI-MS (+): m/z calculated for C$_{15}$H$_{21}$N$_5$O$_9$PS ([M + H]$^+$): 478.08, found: 478.<br>ESI-MS (−): m/z calculated for C$_{15}$H$_{19}$N$_5$O$_9$PS ([M − H]$^-$): 476.06, found: 476. |

TABLE 16-continued

Examples of monomeric precursors and/or monomeric compound of the invention.

| # | Compound/Structure |
|---|---|
| 70 | 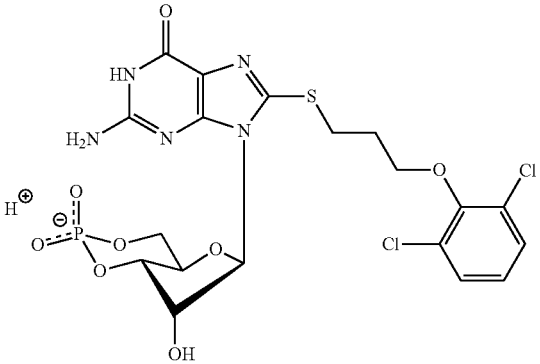 |

8-(2,6-Dichlorophenoxypropyl)thio-guanosine-3',5'-cyclic monophosphase (8-(2,6-DClPheoPr)T-cGMP
Using general procedure D, 8-T-cGMP was reacted with 2-(3-bromopropoxy)-1,3-dichlorobenzene to give the title compound.
Yield (Purity): 21% (>99%).
HPLC: (52% MeOH, 10 mM TEAF buffer, pH 6.8).
US-VIS: $\lambda_{max}$ = 275 nm (pH 7), $\varepsilon$ = 13700 (est.).
ESI-MS (+): m/z calculated for $C_{19}H_{21}Cl_2N_5O_8PS$ ([M + H]$^+$): 580.02, found: 580.
ESI-MS (−): m/z calculated for $C_{19}H_{19}Cl_2N_5O_8PS$ ([M − H]$^-$): 578.01, found: 578.

| 71 | 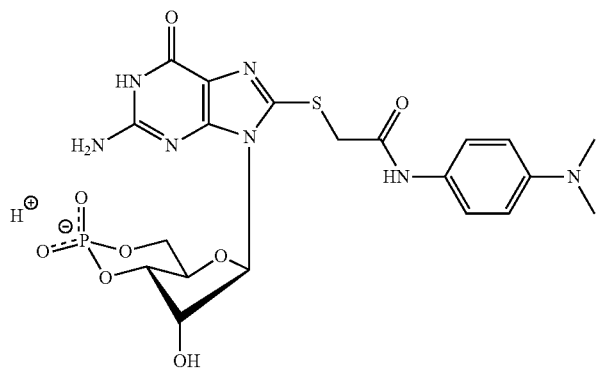 |

8-(4-Dimethylaminophenyl)amido-methylthioguanosine-3',5'-cyclic monophosphate (8-pDMAPAmdMT-cGMP)
Using general procedure H, 8-CMT-cGMP was reacted with N,N-dimethyl-p-phenylenediamine dihydrochloride applying 3.3 eq of N,N-diisopropylethylamie to give the title compound.
Yield (Purity): 73% (>99%).
HPLC: (36% MeOH, 10 mM TEAF buffer, pH 6.8).
UV-VIS: $\lambda_{max}$ = 274 nm (pH 7), $\varepsilon$ = 13700 (est.).
ESI-MS (+): m/z calculated for $C_{20}H_{25}N_7O_8PS$ ([M + H]$^+$): 554.12, found: 554.
ESI-MS (−): m/z calculated for $C_{20}H_{23}N_7O_8PS$ ([M − H]$^-$): 552.11, found: 552.

| 72 | 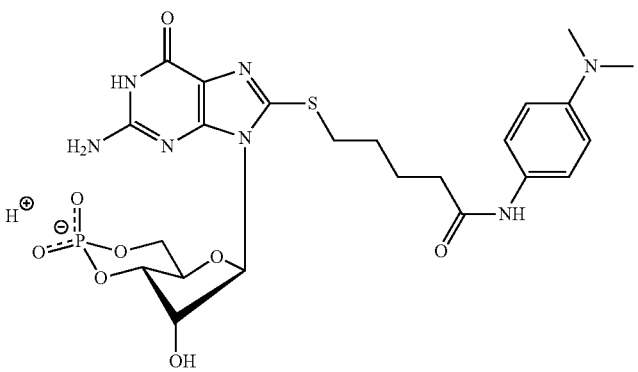 |

TABLE 16-continued

Examples of monomeric precursors and/or monomeric compound of the invention.

| # | Compound/Structure |
|---|---|

8-(4-Dimethylaminophenyl)amido-butylthioguanosine-3',5'-cyclic monophosphate
(8-pDMAPAmdBuT-cGMP)
Using general procedure H, 8-CBuT-cGMP was reacted with N,N-dimethyl-p-
phenylenediamine dihydrochloride applying 3.3 eq of N,N-diisopropylethylamie to give the
title compound.
Yield (Purity): 88% (>99%).
HPLC: (36% MeOH, 10 mM TEAF buffer, pH 6.8).
UV-VIS: $\lambda_{max}$ = 270 nm (pH 7), $\epsilon$ = 13700 (est.).
ESI-MS (+): m/z calculated for $C_{23}H_{31}N_7O_8PS$ ([M + H]$^+$): 596.17, found: 596.
ESI-MS (−): m/z calculated for $C_{23}H_{29}N_7O_8PS$ ([M − H]$^-$): 594.15, found, 594.

73

8-Ethylbutyrylthioguanosine-3',5'-cyclic monophosphate (8-EButT-cGMP)
Using general procedure D, 8-T-cGMP was reacted with ethyl 4-bromobutyrate to give to
title compound.
Yield (Purity): 54% (>99%).
HPLC: (30% MeOH, 10 mM TEAF buffer, pH 6.8).
UV-VIS: $\lambda_{max}$ = 275 nm (pH 7), $\epsilon$ = 13700 (est.).
ESI-MS (+): m/z calculated for $C_{16}H_{23}N_5O_9PS$ ([M + H]$^+$): 492.10, found: 492.
ESI-MS (−): m/z calculated for $C_{16}H_{21}N_5O_9PS$ ([M − H]$^-$): 490.08, found: 490.

74

8-Methylpropionylthioguanosine-3',5'-cyclic monophosphate (8-MPT-cGMP)
Using general procedure D, 8-T-cGMP was reacted with methyl 3-bromopropionate and
equivalents were increased stepwise (methyl 3-bromopropionate up to 9 eq, N,N-
diisopropylethylamine up to 8 eq) to improve the yield of the title compound.
Yield (Purity): 47% (>99%).
HPLC: (15% MeOH, 10 mM TEAF buffer, pH 6.8).
UV-VIS: $\lambda_{max}$ = 275 nm (pH 7), $\epsilon$ = 13700 (est.).
ESI-MS (+): m/z calculated for $C_{14}H_{19}N_5O_9PS$ ([M + H]$^+$): 464.06, found: 464.
ESI-MS (−): m/z calculated for $C_{14}H_{17}N_5O_9PS$ ([M − H]$^-$): 462.05, found: 462.

TABLE 16-continued

Examples of monomeric precursors and/or monomeric compound of the invention.

| # | Compound/Structure |
|---|---|
| 75 | 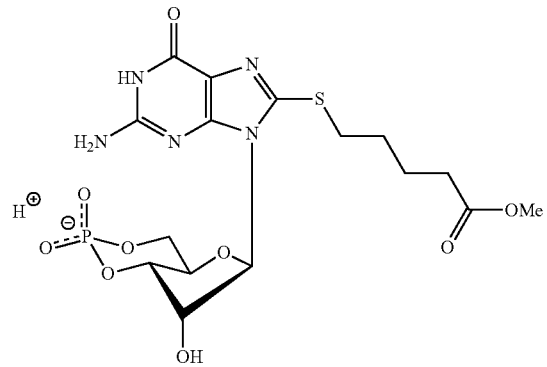 |

8-Methylvalerianylthioguanosine-3',5'-cyclic monophosphate (8-MValT-cGMP)
Using general procedure D, 8-T-cGMP was reacted with methyl 5-bromovalerateto give the title compound.
Yield (Purity): 75% (>99%).
HPLC: (15% MeOH, 10 mM TEAF buffer, pH 6.8).
UV-VIS: $\lambda_{max}$ = 275 nm (pH 7), $\varepsilon$ = 13700 (est.).
ESI-MS (+): m/z calculated for $C_{16}H_{23}N_5O_9PS$ ([M + H]$^+$): 492.10, found: 492.
ESI-MS (−): m/z calculated for $C_{16}H_{21}N_5O_9PS$ ([M − H]$^-$): 490.08, found: 490.

| 76 | 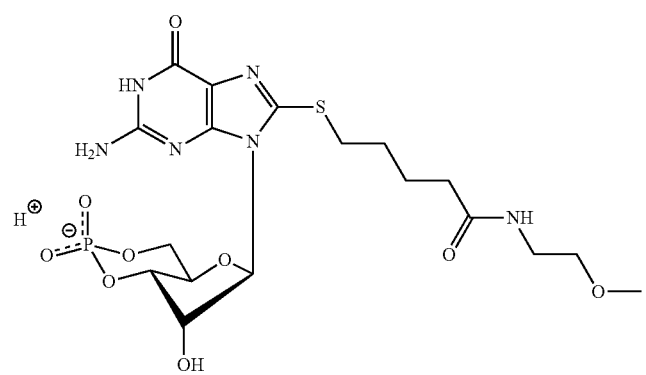 |
|---|---|

8-Methoxyethylamidobutylthio-guanosine-3',5'-cyclic monophosphate (8-MeOEAmdBuT-cGMP)
Using general procedure H, 8-CBuT-cGMP was reacted with 2-methoxyethylamine to give the title compound.
Yield (Purity): 58% (>99%).
HPLC: (30% MeOH, 10 mM TEAF buffer, pH 6.8).
UV-VIS: $\lambda_{max}$ = 276 nm (pH 7), $\varepsilon$ = 13700 (est.).
ESI-MS (+): m/z calculated for $C_{18}H_{28}N_6O_9PS$ ([M + H]$^+$): 535.14, found 535.
ESI-MS (−): m/z calculated for $C_{18}H_{26}N_6O_9PS$ ([M − H]$^-$): 533.12, found 533.

| 77 | 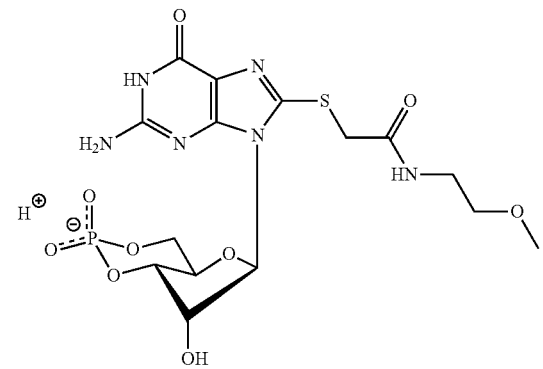 |
|---|---|

TABLE 16-continued

Examples of monomeric precursors and/or monomeric compound of the invention.

| # | Compound/Structure |
|---|---|

8-Methoxyethylamidomethylthio-guanosine-3',5'-cyclic monophosphate (8-MeOEAmdMT-cGMP)
Using general procedure H, 8-CMT-cGMP was reacted with 2-methoxyethylamine to give the title compound.
Yield (Purity): 65% (>99%).
HPLC: (15% MeOH, 10 mM TEAF buffer, pH 6.8).
UV-VIS: $\lambda_{max}$ = 275 nm (pH 7), $\varepsilon$ = 13700 (est.).
ESI-MS (+): m/z calculated for $C_{15}H_{22}N_6O_9PS$ ([M + H]$^+$): 493.09, found: 493.
ESI-MS (−): m/z calculated for $C_{15}H_{20}N_6O_9PS$ ([M − H]$^-$): 491.08, found: 491.

78

8-Methoxyethylamidoethylthio-guanosine-3',5'-cyclic monophosphate (8-MeOEAmdEt-cGMP)
Using general procedure H, 8-CET-cGMP was reacted with 2-methoxyethylamine to give the title compound.
Yield (Purity): 65% (>99%).
HPLC: (21% MeOH, 10 mM TEAF buffer, pH 6.8).
UV-VIS: $\lambda_{max}$ = 275 nm (pH 7), $\varepsilon$ = 13700 (est.).
ESI-MS (+): m/z calculated for $C_{16}H_{24}N_6O_9PS$ ([M + H]$^+$): 507.11, found: 507.
ESI-MS (−): m/z calculated for $C_{16}H_{22}N_6O_9PS$ ([M − H]$^-$): 505.09, found: 505.

79

8-Phenylamidomethylthio-guanosine-3',5'-cyclic monophosphate (8-PAmdMT-cGMP)
Using general procedure H, 8-CMT-cGMP was reacted with aniline to give the title compound.
Yield (Purity): 80% (>99%).
HPLC: (32% MeOH, 10 mM TEAF buffer, pH 6.8).
UV-VIS: $\lambda_{max}$ = 273 nm (pH 7), $\varepsilon$ = 13700 (est.).
ESI-MS (+): m/z calculated for $C_{18}H_{20}N_6O_8PS$ ([M + H]$^+$): 511.08, found: 511.
ESI-MS (−): m/z calculated for $C_{18}H_{18}N_6O_8PS$ ([M − H]$^-$): 509.06, found: 509.

TABLE 16-continued

Examples of monomeric precursors and/or monomeric compound of the invention.

| # | Compound/Structure |
|---|---|
| 80 | 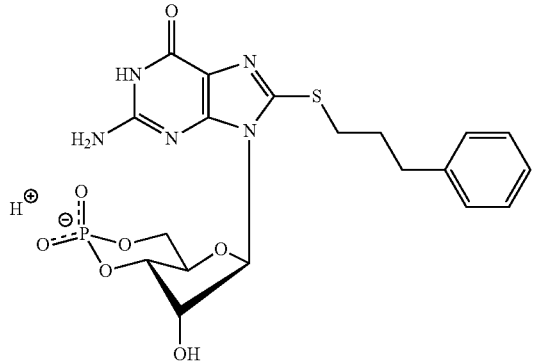 |

8-Phenylpropylthioguanosine-3',5'-cyclic monophosphate (8-PPrT-cGMP)
Using general procedure D, 8-T-cGMP was reacted with 1-Bromo-3-phenylpropane at 90° C.
to give the title compound.
Yield (Purity): 68% (>99%).
HPLC: (49% MeOH, 10 mM TEAF buffer, pH 6.8).
UV-VIS: $\lambda_{max}$ = 276 nm (pH 7), $\varepsilon$ = 13700 (est.).
ESI-MS (+): m/z calculated for $C_{19}H_{23}N_5O_7PS$ ([M + H]$^+$): 496.11, found: 496.
ESI-MS (−): m/z calculated for $C_{19}H_{21}N_5O_7PS$ ([M − H]$^-$): 494.09, found: 494.

81 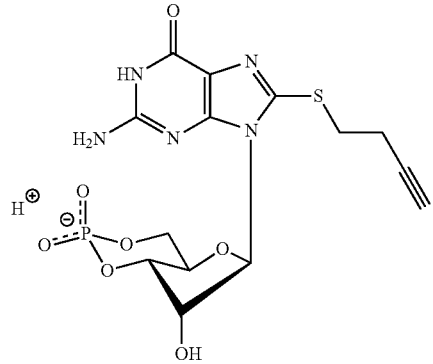

8-(3-Butynylthio)guanosine-3',5'-cyclic monophosphate (8-(Bu(3-yne)T-cGMP)
Using general procedure D, 8-T-cGMP was reacted with 4-bromo-1-butyne to give the title
compound.
Yield (Purity): 51% (>99%).
HPLC: (30% MeOH, 10 mM TEAF buffer, pH 6.8).
US-VIS: $\lambda_{max}$ = 275 nm (pH 7), $\varepsilon$ = 13700 (est.).
ESI-MS (+): m/z calculated for $C_{14}H_{17}N_5O_7PS$ ([M + H]$^+$): 430.06, found: 430.
ESI-MS (−): m/z calculated for $C_{14}H_{15}N_5O_7PS$ ([M − H]$^-$): 428.34, found: 428.

82 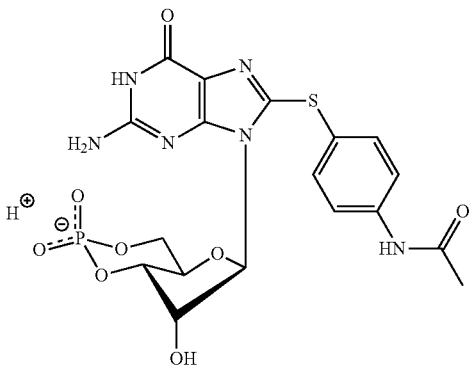

8-(4-Acetamidophenylthio)guanosine-3',5'-cyclic monophosphate
(8-pAcAmdPT-cGMP)
Using general procedure A, 8-Br-cGMP was reacted with 4-acetamidothiophenol
to give the title compound.

| # | Compound/Structure |
|---|---|
| | Yield (Purity): 95% (>99%).<br>HPLC: (35% MeOH, 10 mM TEAF buffer, pH 6.8).<br>UV-VIS: $\lambda_{max}$ = 275 nm (pH 7), $\varepsilon$ = 21500 (est.).<br>ESI-MS (+): m/z calculated for $C_{18}H_{20}N_6O_8PS$ ([M + H]$^+$): 511.08, found: 511.<br>ESI-MS (−): m/z calculated for $C_{18}H_{18}N_6O_8PS$ ([M − H]$^-$): 509.06, found: 509. |
| 83 | 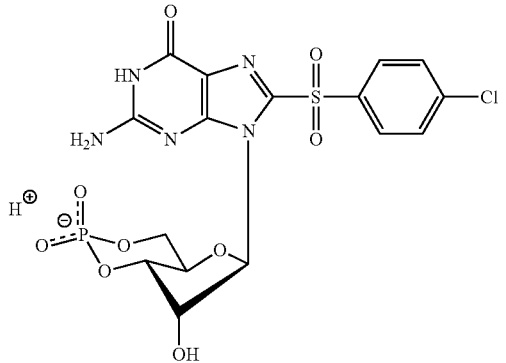<br>8-(4-Chlorophenylsulfonyl)guanosine-3',5'-cyclic monophosphate (8-pCPS-cGMP)<br>The title compound was synthesized from 8-pCPT-cGMP using general procedure O.<br>Yield (Purity): 29% (>99%).<br>HPLC: (19% MeCN, 10 mM TEAF buffer, pH 6.8).<br>UV-VIS: $\lambda_{max}$ = 241 (276, 311) nm (pH 7), $\varepsilon$ = 21500 (est.).<br>ESI-MS (+): m/z calculated for $C_{16}H_{16}ClN_5O_9PS$ ([M + H]$^+$): 520.00, found: 520.<br>ESI-MS (−): m/z calculated for $C_{16}H_{14}ClN_5O_9PS$ ([M − H]$^-$): 517.99, found: 518. |
| 84 | 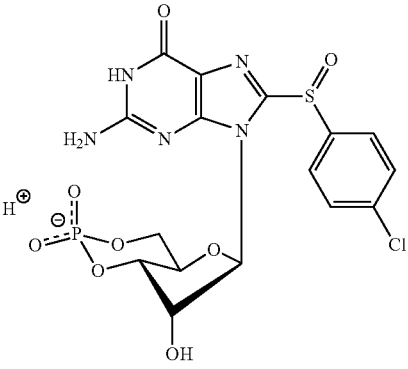<br>8-(4-Chlorophenylsulfoxide)-guanosine-3',5'-cyclic monophosphate (8-(pCPS(O)-cGMP)<br>The title compound was synthesized from 8-pCPT-cGMP using general procedure P.<br>Yield (Purity): 27% (>99%).<br>HPLC: (28% MeOH, 10 mM TEAF buffer, pH 6.8).<br>UV-VIS: $\lambda_{max}$ = 275 nm (pH 7), $\varepsilon$ = 21500 (est.).<br>ESI-MS (+): m/z calculated for $C_{16}H_{16}ClN_5O_8PS$ ([M + H]$^+$): 504.01, found: 504.<br>ESI-MS (−): m/z calculated for $C_{16}H_{14}ClN_5O_8PS$ ([M − H]$^-$): 502.00, found: 502. |
| 85 | 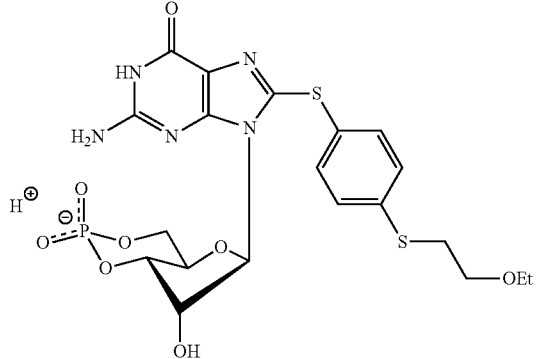 |

TABLE 16-continued

Examples of monomeric precursors and/or monomeric compound of the invention.

| # | Compound/Structure |
|---|---|

8-((2-Ethoxyethyl)-4-thiophenylthio)guanosine-3',5'-cyclic monophosphate (8-(2-EOE)-pTPT-cGMP)
Using general procedure D, 8-pTPT-cGMP was reacted with 2-Bromoethyl ethyl ether to give the title compound.
Yield (Purity): 64% (>99%).
HPLC: (48% MeOH, 10 mM TEAF buffer, pH 6.8).
UV-VIS: $\lambda_{max}$ = 276 nm (pH 7), $\varepsilon$ = 21500 (est.).
ESI-MS (+): m/z calculated for $C_{20}H_{25}N_5O_8PS$ ([M + H]$^+$): 558.09, found: 558.
ESI-MS (−): m/z calculated for $C_{20}H_{23}N_5O_8PS_2$ ([M − H]$^-$): 556.07, found: 556.

86

8-(4-Thiophenyl-4''-thiophenylthio)guanosine-3',5'-cyclic monophosphate (8-pTP-pTPT-cGMP)
Using general procedure B, 8-Br-cGMP was reacted with 4,4'-thiobisbenzenethiol to give the title compound.
Yield (Purity): 13% (>99%).
HPLC: (52% MeOH, 10 mM TEAF buffer, pH 6.8).
UV-VIS: $\lambda_{max}$ = 290 nm (pH 7), $\varepsilon$ = 21500 (est.).
ESI-MS (+): m/z calculated for $C_{22}H_{21}N_5O_7PS_3$ ([M + H]$^+$): 594.03, found: 594.
ESI-MS (−): m/z calculated for $C_{22}H_{19}N_5O_7PS_3$ ([M − H]$^-$): 592.02, found: 592.

87

8-(2-Azidoethylthio)guanosine-3',5'-cyclic monophosphate (8-N$_3$-ET-cGMP)
The title compound was synthesized from 8-T-cGMP and 1,2-dibromoethane using general procedure Q.
Yield (Purity): 54% (>99%).
HPLC: (9% MeCN, 30 mM NaH$_2$PO$_4$ buffer, pH 6.8).
UV-VIS: 275 nm (pH 7), $\varepsilon$ = 13700 (est.).
ESI-MS (+): (+): m/z calculated for $C_{12}H_{16}N_8O_7PS$ ([M + H]$^+$): 447.06, found: 447.
ESI-MS (−): m/z calculated for $C_{12}H_{14}N_8O_7PS$ ([M − H]$^-$): 445.04, found: 445.

TABLE 16-continued

Examples of monomeric precursors and/or monomeric compound of the invention.

| # | Compound/Structure |
|---|---|
| 88 | 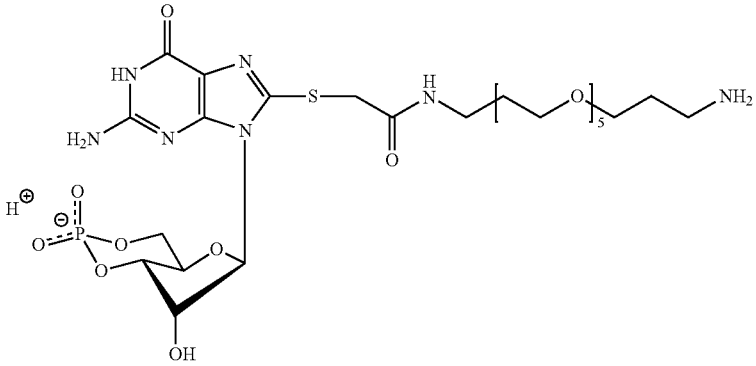 |

8-(3-Aminopropyl)-(pentaethoxy)-methylamidomethylthio-guanosine-3',5'-cyclic
monophosphate (8-APr-(EO)$_5$-MAmdMT-cGMP)
Using general procedure K, 8-CMT-cGMP (1 eq) was reacted with
NH$_2$CH$_2$—PEG$_5$—(CH$_2$)$_3$NH$_2$ (6 eq) to give the title compound.
Yield (Purity): 39% (>95%).
HPLC: (27% MeOH, 20 mM TEAF buffer, pH 6.8).
UV-VIS: $\lambda_{max}$ = 275 nm (pH 7), $\varepsilon$ = 13700 (est.).
ESI-MS (+): m/z calculated for C$_{26}$H$_{45}$N$_7$O$_{13}$PS ([M + H]$^+$): 726.25, found: 726.
ESI-MS (−): m/z calculated for C$_{26}$H$_{43}$N$_7$O$_{13}$PS ([M − H]$^-$): 724.24, found 724.

| 89 | 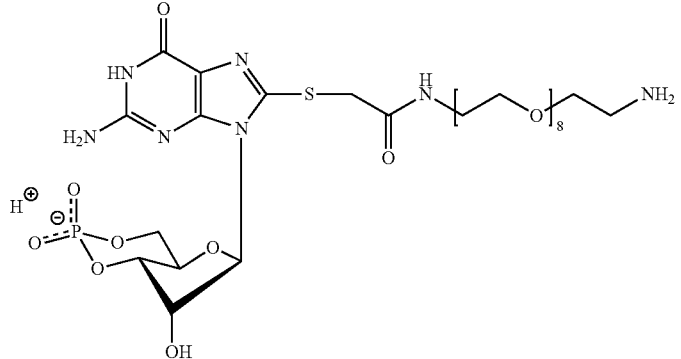 |

8-(2-Aminoethyl)-(octaethoxy)-amidomethylthioguanosine-3',5'-cyclic
monophosphate (8-AE-(EO)$_8$-AmdMT-cGMP)
Using general procedure K, 8-CMT-cGMP (1 eq) was reacted with
NH$_2$—PEG$_8$—(CH$_2$)$_2$NH$_2$ (6 eq) to give the title compound.
Yield (Purity): 53% (>99%).
HPLC: (10% MeCN, 50 mM NaH$_2$PO$_4$ buffer, pH 6.8).
UV-VIS: $\lambda_{max}$ = 275 nm (pH 7), $\varepsilon$ = 13700 (est.).
ESI-MS (+): m/z calculated for C$_{30}$H$_{53}$N$_7$O$_{16}$PS ([M + H]$^+$): 830.30, found: 830.
ESI-MS (−): m/z calculated for C$_{30}$H$_{51}$N$_7$O$_{16}$PS ([M − H]$^-$): 828.29, found: 828.

| 90 | 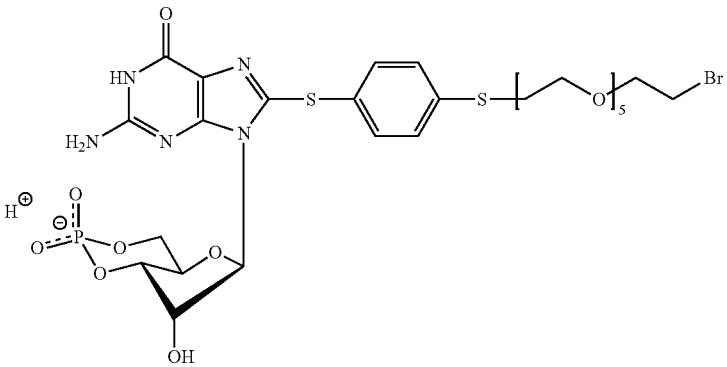 |

8-(2-Bromoethyl)-(pentaethoxy)-(4-thiophenylthio)guanosine-3',5'-cyclic
monophosphate (8-BrE-(EO)$_5$-pTPT-cGMP)

TABLE 16-continued

Examples of monomeric precursors and/or monomeric compound of the invention.

| # | Compound/Structure |
|---|---|

Using general procedure E, 8-pTPT-cGMP was reacted with Br—PEG$_5$—CH$_2$CH$_2$Br.
The title compound was isolated beside the dimeric analogue.
Yield (Purity): 43% (>99%).
HPLC: (52% MeOH, 10 mM TEAF buffer, pH 6.8).
HPLC (analytical): (45% MeOH, 10 mM TEAF buffer, pH 6.8).
UV-VIS: $\lambda_{max}$ = 276 nm (pH 7), $\varepsilon$ = 21500 (est.).
ESI-MS (+): m/z calculated for C$_{28}$H$_{39}$BrN$_5$O$_{12}$PS$_2$Na ([M + Na]$^+$): 834.09, found: 834.
ESI-MS (−): m/z calculated for C$_{28}$H$_{38}$BrN$_5$O$_{12}$PS$_2$ ([M − H]$^−$): 810.09, found: 810.

91

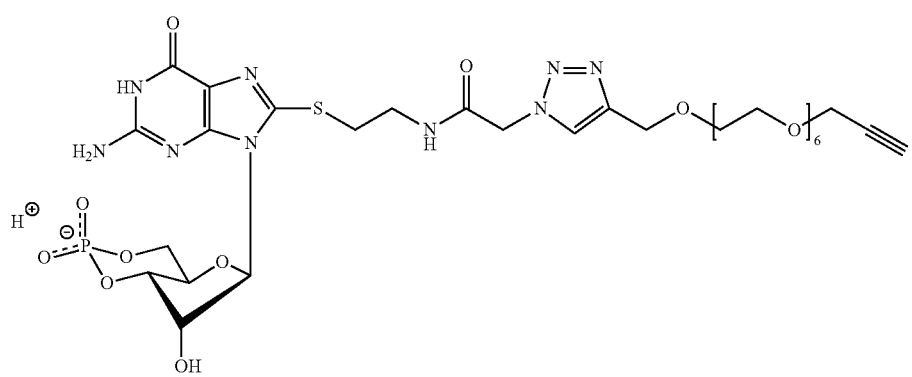

8-(4-(Propargyloxy-(hexaethoxy)-methyl)-[1,2,3]-triazole-1-yl)-methylamidoethylthioguanosine-3',5'-
cyclic monophosphate (8-(4-(PargO-(EO)$_6$-Me)-[1,2,3]-Tz-1)-MAmdET-cGMP)
Using general procedure S, 8-N3-MAmdET-cGMP (1 eq) was reacted with bis-propargyl-PEG$_7$ (2 eq) to give the title
compound. Conditions were chosen to additionally obtain the dimeric analogue (G 045).
Yield (Purity): 38% (>99%).
HPLC: (14% MeCN, 30 mM TEAF buffer, pH 6.8 then (after sepperation of dimer)
15% MeCN, 10 mM TEAF buffer, pH 6.8).
HPLC (analytical): (15% MeCN, 20 mM TEAF buffer, pH 6.8).
UV-VIS: $\lambda_{max}$ = 276 nm (pH 7), $\varepsilon$ = 13700 (est.).
ESI-MS (+): m/z calculated for C$_{32}$H$_{49}$N$_9$O$_{15}$PS ([M + Na]$^+$): 862.28, found: 862.
ESI-MS (−): m/z calculated for C$_{32}$H$_{47}$N$_9$O$_{15}$PS ([M − H]$^−$): 860.27, found: 860.

92

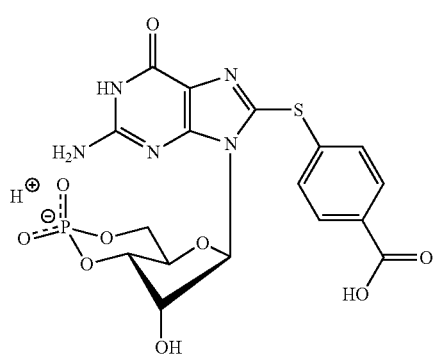

8-(4-Carboxyphenylthio)guanosine-3',5'-cyclic monophosphate (8-pCarbT-cGMP)
Using general procedure C, 8-Br-cGMP (1 eq) was reacted with 4-mercaptobenzoic acid
(2 eq) at 60° C. in the absence of NaOH to give the title compound.
Yield (Purity): 67% (>99%).
HPLC: (9% MeCN, 20 mM TEAF buffer, pH 6.8).
UV-VIS: $\lambda_{max}$ = 277 nm (pH 7), $\varepsilon$ = 21500 (est.).
ESI-MS (−): m/z calculated for C$_{17}$H$_{15}$N$_5$O$_9$PS ([M − H]$^−$): 496.03, found: 496.

TABLE 16-continued

Examples of monomeric precursors and/or monomeric compound of the invention.

| # | Compound/Structure |
|---|---|
| 93 | |

8-(4-Hydroxyphenylsulfonyl)-guanosine-3',5'-cyclic monophosphate
(8-pHPS-cGMP)
The title compound was synthesized from 8-pHPT-cGMP using general procedure O.
Yield (Purity): 38% (>99%).
HPLC: (30% MeOH, 10 mM TEAF buffer, pH 6.8).
UV-VIS: $\lambda_{max}$ = 276 (310) nm (pH 7), $\varepsilon$ = 21500 (est.).
ESI-MS (+): m/z calculated for $C_{16}H_{17}N_5O_{10}PS$ ($[M + H]^+$): 502.04, found: 502.
ESI-MS (−): m/z calculated for $C_{16}H_{15}N_5O_{10}PS$ ($[M − H]^-$): 500.03, found: 500.

94

8-(4-Isopropylphenylsulfonyl)-guanosine-3',5'-cyclic monophosphate (8-pIPrPS-cGMP)
The title compound was synthesized from 8-pIPrPT-cGMP using general procedure O.
Yield (Purity): 30% (>99%).
HPLC: (40% MeOH, 10 mM TEAF buffer, pH 6.8).
UV-VIS: $\lambda_{max}$ = 276 (239, 306) nm (pH 7), $\varepsilon$ = 21500 (est.).
ESI-MS (+): m/z calculated for $C_{19}H_{23}N_5O_9PS$ ($[M + H]^+$): 528.10, found: 528.
ESI-MS (−): m/z calculated for $C_{19}H_{21}N_5O_9PS$ ($[M − H]^-$): 526.08, found: 526.

95

8-(4-Methylcarboxyphenylthio)-guanosine-3',5'-cyclic monophosphate (8-pMeCarbPT-cGMP)
Using general procedure A, 8-Br-cGMP (1 eq) was reacted with methyl 4-mercaptobenzoate (4 eq) at 60° C. replacing NaOH by borate buffer (100 mM, pH 10.4, ex) to give the title compound.
Yield (Purity): 20% (>99%).

TABLE 16-continued

Examples of monomeric precursors and/or monomeric compound of the invention.

| # | Compound/Structure |
|---|---|

HPLC: (22% MeCN, 50 mM NaH$_2$PO$_4$ buffer, pH 6.7).
UV-VIS: $\lambda_{max}$ = 277 nm (pH 7), ε = 21500 (est.).
ESI-MS (+): m/z calculated for C$_{18}$H$_{19}$N$_5$O$_9$PS ([M + H]$^+$): 512.06, found: 512.
ESI-MS (−): m/z calculated for C$_{18}$H$_{17}$N$_5$O$_9$PS ([M − H]$^−$): 510.05, found: 510.

96

8-Methylsulfonylguanosine-3',5'-cyclic monophosphate (8-MSulf-cGMP)
The title compound was synthesized from 8-MeS-cGMP using general procedure O.
Yield (Purity): 35% (>99%).
HPLC: (10% MeOH, 15 mM TEAF buffer, pH 6.8).
UV-VIS: $\lambda_{max}$ = 274 nm (pH 7), ε = 13700 (est.).
ESI-MS (+): m/z calculated for C$_{11}$H$_{15}$N$_5$O$_9$PS ([M + H]$^+$): 424.03, found: 424.
ESI-MS (−): m/z calculated for C$_{11}$H$_{13}$N$_5$O$_9$PS ([M − H]$^−$): 422.02, found: 422.

97

8-(1-Bromo-2-naphthyl)methylthioguanosine-3',5'-cyclic monophosphate (8-(1-Br-2-N)MT-cGMP)
Using general procedure D, 8-T-cGMP was reacted with 1-bromo-2-bromomethylnaphthalene to give the title compound.
Yield (Purity): 40% (>99%).
HPLC: (27% MeCN, 50 mM NaH$_2$PO$_4$ buffer, pH 6.7).
UV-VIS: $\lambda_{max}$ = 280 nm (pH 7), ε = 21500 (est.).
ESI-MS (+): m/z calculated for C$_{21}$H$_{20}$BrN$_5$O$_7$PS ([M + H]$^+$): 596.00, found: 596.
ESI-MS (−): m/z calculated for C$_{21}$H$_{18}$BrN$_5$O$_7$PS ([M − H]$^−$): 593.98, found: 594.

98

TABLE 16-continued

Examples of monomeric precursors and/or monomeric compound of the invention.

| # | Compound/Structure |
|---|---|

8-(2-(1-Benzyl-[1,2,3]-triazole-4-yl)-ethylthio)guanosine-3',5'-cyclic
monophosphate (8-(1-Bn-[1,2,3]-Tz-4)-ET-cGMP)
Using general procedure R, 8-Bu(3-yne)T-cGMP was reacted with benzyl azide to
give the title compound.
Yield (Purity): 30% (>98%).
HPLC: (35% MeOH, 10 mM TEAF buffer, pH 6.8).
UV-VIS: $\lambda_{max}$ = 278 nm (pH 7), $\varepsilon$ = 13700 (est.).
ESI-MS (+): m/z calculated for $C_{21}H_{24}N_8O_7PS$ ([M + H]$^+$): 563.14, found: 563.
ESI-MS (−): m/z calculated for $C_{21}H_{22}N_8O_7PS$ ([M − H]$^-$): 561.11, found: 561.

99

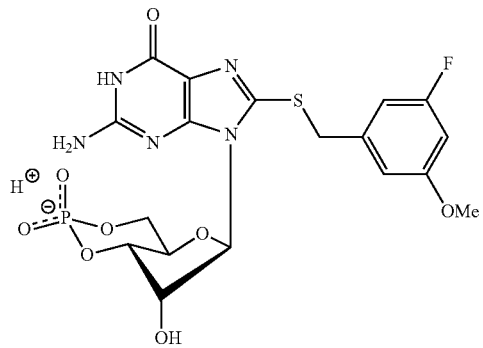

8-(3-Fluoro-5-methoxybenzylthio)guanosine-3',5'-cyclic monophosphate (8-(3-F-5-
MeO)BT-cGMP)
Using general procedure D, 8-T-cGMP was reacted with 3-fluoro-5-methoxybenzyl bromide
to give the title compound.
Yield (Purity): 40% (>99%).
HPLC: (22% MeCN, 50 mM NaH$_2$PO$_4$ buffer, pH 6.7).
UV-VIS: $\lambda_{max}$ = 278 nm (pH 7), $\varepsilon$ = 21500 (est.).
ESI-MS (+): m/z calculated for $C_{18}H_{20}FN_5O_8PS$ ([M + H]$^+$): 516.07, found: 516.
ESI-MS (−): m/z calculated for $C_{18}H_{18}FN_5O_8PS$ ([M − H]$^-$): 514.06, found: 514.

100

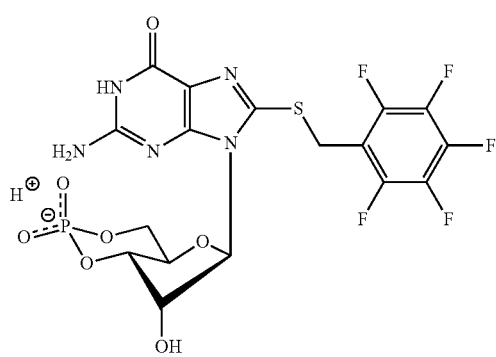

8-Pentafluorobenzylthioguanosine-3',5'-cyclic monophosphate (8-PFBT-cGMP)
Using general procedure D, 8-T-cGMP was reacted with 2,3,4,5,6-pentafluorobenzyl
bromide to give the title compound.
Yield (Purity): 35% (>99%).
HPLC: (27% MeCN, 50 mM NaH$_2$PO$_4$ buffer, pH 6.7).
UV-VIS: $\lambda_{max}$ = 278 nm (pH 7), $\varepsilon$ = 21500 (est.).
ESI-MS (+): m/z calculated for $C_{17}H_{14}F_5N_5O_7PS$ ([M + H]$^+$): 558.03, found: 558.
ESI-MS (−): m/z calculated for $C_{17}H_{12}F_5N_5O_7PS$ ([M − H]$^-$): 556.01, found: 556.

TABLE 16-continued

Examples of monomeric precursors and/or monomeric compound of the invention.

| # | Compound/Structure |
|---|---|
| 101 | 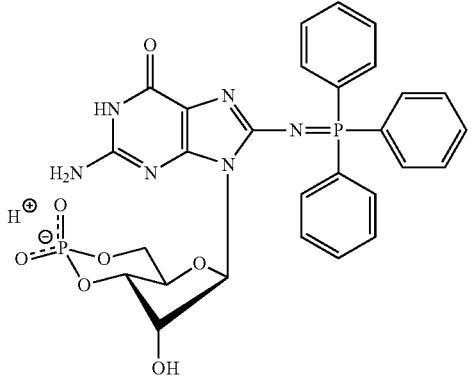<br>8-Triphenyliminophosphoranyl-guanosine-3',5'-cyclic monophosphate (8-Ph₃PN-cGMP)<br>The title compound was synthesized from 8-N₃-cGMP using general procedure W.<br>Yield (Purity): 18% (>99%).<br>HPLC: (26% MeCN, 20 mM NaH₂PO₄ buffer, pH 6.8).<br>UV-VIS: $\lambda_{max}$ = 267 nm (pH 7), ε = 13700 (est.).<br>ESI-MS (+): m/z calculated for $C_{28}H_{27}N_6O_7P_2$ ([M + H]⁺): 621.14, found: 621.<br>ESI-MS (−): m/z calculated for $C_{28}H_{25}N_6O_7P_2$ ([M − H]⁻): 619.13, found: 619. |
| 102 | 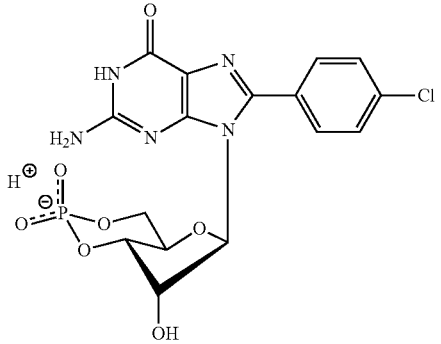<br>8-(4-Chlorophenyl)guanosine-3',5'-cyclic monophosphate (8-pCP-cGMP)<br>Using general procedure X, 8-Br-cGMP was reacted with 4-chlorophenylboronic acid to give the title compound.<br>Yield (Purity): 10% (>99%).<br>HPLC: (17% MeCN, 10 mM TEAF buffer, pH 6.8).<br>US-VIS: $\lambda_{max}$ = 282 nm (pH 7), ε = 21500 (est.).<br>ESI-MS (+): m/z calculated for $C_{16}H_{16}ClN_5O_7P$ ([M + H]⁺): 456.05, found: 456.<br>ESI-MS (−): m/z calculated for $C_{16}H_{14}ClN_5O_7P$ ([M − H]⁻): 454.03, found: 454. |
| 103 | 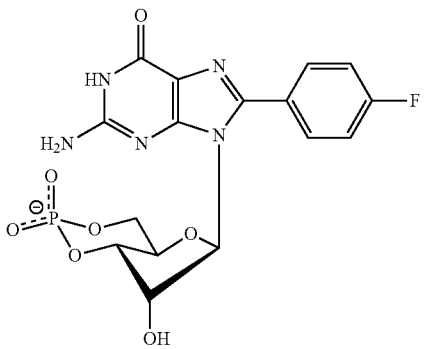<br>8-(4-Fluorophenyl)guanosine-3',5'-cyclic monophosphate (8-pFP-cGMP)<br>Using general procedure X, 8-Br-cGMP was reacted with 4-fluorophenylboronic acid to give the title compound.<br>Yield (Purity): 54% (>99%).<br>HPLC: (31% MeOH, 10 mM TEAF buffer, pH 6.8). |

TABLE 16-continued

Examples of monomeric precursors and/or monomeric compound of the invention.

| # | Compound/Structure |
|---|---|

UV-VIS: $\lambda_{max}$ = 280 nm (pH 7), $\varepsilon$ = 21500 (est.).
ESI-MS (+): m/z calculated for $C_{16}H_{16}FN_5O_7P$ ([M + H]$^+$): 440.08, found: 440.
ESI-MS (−): m/z calculated for $C_{16}H_{14}FN_5O_7P$ ([M − H]$^-$): 438.06, found: 438.

104

8-(2-Furyl)guanosine-3',5'-cyclic monophosphate (8-(2-Fur)-cGMP)
Using general procedure X, 8-Br-cGMP was reacted with 2-furylboronic acid to give the title compound.
Yield (Purity): 40% (>99%).
HPLC: (23% MeOH, 15 mM TEAF buffer, pH 6.8).
UV-VIS: $\lambda_{max}$ = 297 nm (pH 7), $\varepsilon$ = 21500 (est.).
ESI-MS (+): m/z calculated for $C_{14}H_{15}N_5O_8P$ ([M + H]$^+$): 412.07, found: 412.
ESI-MS (−): m/z calculated for $C_{14}H_{13}N_5O_8P$ ([M − H]$^-$): 410.05, found: 410.

105

8-(4-Hydroxyphenyl)guanosine-3',5'-cyclic monophosphate (8-pHP-cGMP)
Using general procedure X, 8-Br-cGMP was reacted with 4-hydroxyphenylboronic acid to give the title compound.
Yield (Purity): 63% (>99%).
HPLC: (21% MeOH, 10 mM TEAF buffer, pH 6.8).
UV-VIS: $\lambda_{max}$ = 282 nm (pH 7), $\varepsilon$ = 21500 (est.).
ESI-MS (+): m/z calculated for $C_{16}H_{17}N_5O_8P$ ([M + H]$^+$): 438.08, found: 438.
ESI-MS (−): m/z calculated for $C_{16}H_{15}N_5O_8P$ ([M − H]$^-$): 436.07, found: 436.

106

| # | Compound/Structure |
|---|---|
| | 8-(4-Isopropylphenyl)guanosine-3',5'-cyclic monophosphate (8-pIPrP-cGMP)<br>Using general procedure X, 8-Br-cGMP was reacted with 4-isopropylphenylboronic acid to give the title compound.<br>Yield (Purity): 33% (>99%).<br>HPLC: (22% MeCN, 50 mM TEAF buffer, pH 6.8).<br>UV-VIS: $\lambda_{max}$ = 281 nm (ph 7), $\varepsilon$ = 21500 (est.).<br>ESI-MS (+): m/z calculated for $C_{19}H_{23}N_5O_7P$ ([M + H]$^+$): 464.13, found: 464.<br>ESI-MS (−): m/z calculated for $C_{19}H_{21}N_5O_7P$ ([M − H]$^-$): 462.12, found: 462. |
| 107 | 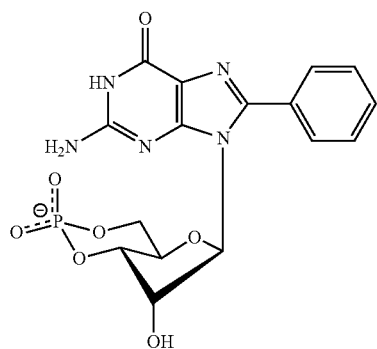<br>8-Phenylguanosine-3',5'-cyclic monophosphate (8-Phe-cGMP)<br>Using general procedure X, 8-Br-cGMP was reacted with phenylboronic acid to give the title compound.<br>2Yield (Purity): 79% (>99%).<br>HPLC: (31% MeOH, 10 mM TEAF buffer, pH 6.8).<br>UV-VIS: $\lambda_{max}$ = 281 nm (pH 7), $\varepsilon$ = 21500 (est.).<br>ESI-MS (+): m/z calculated for $C_{16}H_{17}N_5O_7P$ ([M + H]$^+$): 422.09, found: 422.<br>ESI-MS (−): m/z calculated for $C_{16}H_{15}N_5O_7P$ ([M − H]$^-$): 420.07, found: 420. |
| 108 | 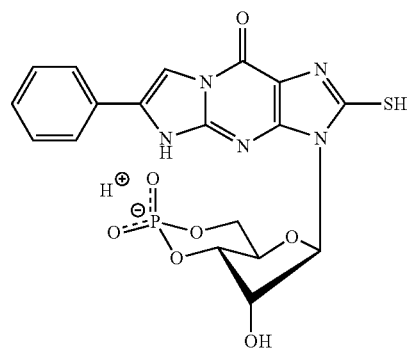<br>β-Phenyl-1,N$^2$-etheno-8-thioguanosine-3',5'-cyclic monophosphate (PET-8-T-cGMP)<br>Using modified general procedure C, NaSH (19 mM, 208 eq) in NaHCO$_3$-Buffer (pH 8.7) was added to 8-Br-PET-cGMP (19 mM, 1 eq) dissolved in NaHCO$_3$-buffer (pH 8.7) and reacted at 75° C. to give the title compound.<br>Yield (Purity): 60% (>99%).<br>HPLC: (21% MeCN, 50 mM NaH$_2$PO$_4$ buffer, pH 6.7).<br>UV-VIS: $\lambda_{max}$ = 288 nm (pH 7), $\varepsilon$ = 40000 (est.).<br>ESI-MS (+): m/z calculated for $C_{18}H_{16}N_5O_7PSNa$ ([M + Na]$^+$): 500.04, found: 500.<br>ESI-MS (−): m/z calculated for $C_{18}H_{15}N_5O_7PS$ ([M − H]$^-$): 476.04, found: 476. |

TABLE 16-continued

Examples of monomeric precursors and/or monomeric compound of the invention.

| # | Compound/Structure |
|---|---|

109

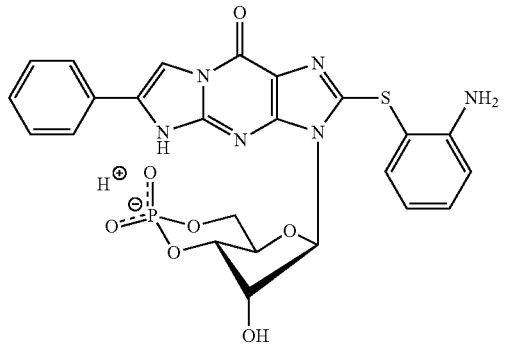

8-(2-Aminophenylthio)-β-phenyl-1,$N^2$-ethenoguanosine-3',5'-cyclic
monophosphate (8-oAPT-PET-cGMP)
Using general procedure A, 8-Br-PET-cGMP (1 eq) was reacted with 2-aminothiophenol
(8 eq) in the presence of NaOH (2 eq) to give the title compound.
Yield (Purity): 57% (>99%).
HPLC: (22% MeCN, 50 mM $NaH_2PO_4$ buffer, pH 6.7).
UV-VIS: $\lambda_{max}$ = 273 nm (pH 7), $\varepsilon$ = 40000 (est.).
ESI-MS (+): m/z calculated for $C_{24}H_{22}N_6O_7PS$ ([M + H]$^+$): 569.10, found: 569.
ESI-MS (−): m/z calculated for $C_{24}H_{20}N_6O_7PS$ ([M − H]$^-$): 567.08, found: 567.

110

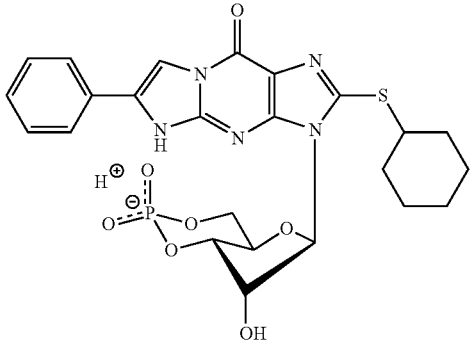

8-Cyclohexylthio-β-phenyl-1,$N^2$-ethenoguanosine-3',5'-cyclic monophosphate (8-
cHeT-PET-cGMP)
Using general procedure A, 8-Br-PET-cGMP (1 eq) was reacted with Cyclohexanethiol
(6.5 eq) in the presence of NaOH (2 eq) to give the title compound.
Yield (Purity): 20% (>99%).
HPLC: (22% MeCN, 50 mM $NaH_2PO_4$ buffer, pH 6.7).
UV-VIS: $\lambda_{max}$ = 275 nm (pH 7), $\varepsilon$ = 40000 (est.).
ESI-MS (+): m/z calculated for $C_{24}H_{27}N_5O_7PS$ ([M + H]$^+$): 560.14, found: 560.
ESI-MS (−): m/z calculated for $C_{24}H_{25}N_5O_7PS$ ([M − H]$^-$): 558.12, found: 558.

111

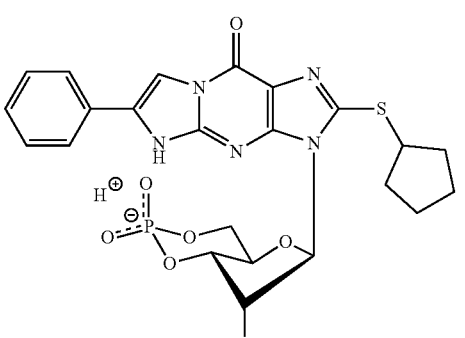

TABLE 16-continued

Examples of monomeric precursors and/or monomeric compound of the invention.

| # | Compound/Structure |
|---|---|

8-Cyclopentylthio-β-phenyl-1,$N^2$-ethenoguanosine-3',5'-cyclic monophosphate
(8-cPeT-PET-cGMP)
Using general procedure A, 8-Br-PET-cGMP (1 eq) was reacted with cyclopentanethiol
(8 eq) in the presence of NaOH (2 eq) to give the title compound.
Yield (Purity): 20% (>99%).
HPLC: (22% MeCN, 50 mM NaH2PO4 buffer, pH 6.7).
UV-VIS: $\lambda_{max}$ = 276 nm (pH 7), ε = 40000 (est.).
ESI-MS (+): m/z calculated for $C_{23}H_{25}O_7PS$ ([M + H]$^+$): 546.12, found: 546.
ESI-MS (−): m/z calculated for $C_{23}H_{23}N_5O_7PS$ ([M − H]$^-$): 544.11, found: 544.

112

8-(4-Methylphenylthio)-β-phenyl-1,$N^2$-ethenoguanosine-3',5'-cyclic
monophosphate (8-pMePT-PET-cGMP)
Using general procedure A, 8-Br-PET-cGMP (1 eq) was reacted with p-toluenethiol
(8 eq) in the presence of NaOH (2 eq) to give the title compound.
Yield (Purity): 70% (>99%).
HPLC: (22% MeCN, 50 mM NaH$_2$PO$_4$, pH 6.7).
UV-VIS: $\lambda_{max}$ = 275 nm (pH 7), ε = 40000 (est.).
ESI-MS (+): m/z calculated for $C_{25}H_{23}N_5O_7PS$ ([M + H]$^+$): 568.11, found: 568.
ESI-MS (−): m/z calculated for $C_{25}H_{21}N_5O_7PS$ ([M − H]$^-$): 566.09, found: 566.

113

8-(4-Methoxyphenylthio)-β-phenyl-1,$N^2$-ethenoguanosine-3',5'-cyclic
monophosphate (8-pMeOPT-PET-cGMP)
Using general procedure A, 8-Br-PET-cGMP (1 eq) was reacted with 4-
methoxybenzenethiol (8 eq) in the presence of NaOH (2 eq) to give the title compound.
Yield (Purity): 82% (>99%).
HPLC: (22% MeCN, 50 mM NaH$_2$PO$_4$ buffer, pH 6.7).
UV-VIS: $\lambda_{max}$ = 274 nm (pH 7), ε = 40000 (est.).
ESI-MS (+): m/z calculated for $C_{25}H_{23}N_5O_8PS$ ([M + H]$^+$): 584.10, found: 584.
ESI-MS (−): m/z calculated for $C_{25}H_{21}N_5O_8PS$ ([M − H]$^-$): 582.08, found: 582.

TABLE 16-continued

Examples of monomeric precursors and/or monomeric compound of the invention.

| # | Compound/Structure |
|---|---|
| 114 | 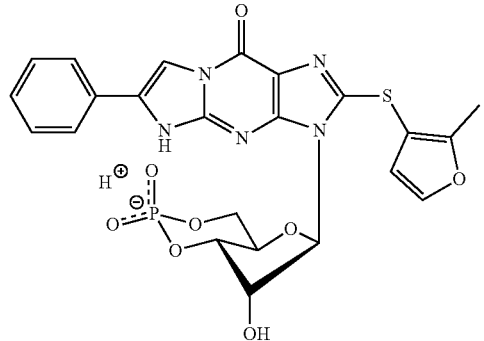<br>8-(3-(2-Methyl)furanyl)thio-β-phenyl-1,$N^2$-ethenoguanosine-3',5'-cyclic monophosphate (8-(3-(2-Me)-FU)T-PET-cGMP)<br>Using general procedure A, 8-Br-PET-cGMP (1 eq) was reacted with 2-methyl-3-furanethiol (6 eq) in the presence of NaOH (2 eq) to give the title compound.<br>Yield (Purity): 70% (>99%).<br>HPLC: (22% MeCN, 50 mM NaH$_2$PO$_4$ buffer, pH 6.7).<br>UV-VIS: $\lambda_{max}$ = 273 nm (pH 7), ε = 40000 (est.).<br>ESI-MS (+): m/z calculated for C$_{23}$H$_{21}$N$_5$O$_8$PS ([M + H]$^+$): 558.08, found: 558.<br>ESI-MS (−): m/z calculated for C$_{23}$H$_{19}$N$_5$O$_8$PS ([M − H]$^-$): 556.07, found: 556. |
| 115 | 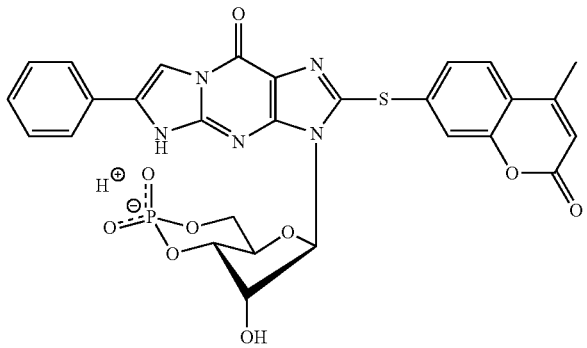<br>8-(7-(4-Methyl)coumarinyl)thio-β-phenyl-1,$N^2$-ethenoguanosine-3',5'-cyclic monophosphate (8-(7-(4-Me)-Cou)T-PET-cGMP)<br>Using general procedure A, 8-Br-PET-cGMP (1 eq) was reacted with 7-mercapto-4-methylcoumarin (6 eq) in the presence of NaOH (2 eq) to give the title compound.<br>Yield (Purity): 80% (>99%).<br>HPLC: (22% MeCN, 50 mM NaH$_2$PO$_4$ buffer, pH 6.7).<br>UV-VIS: $\lambda_{max}$ = 277 nm (pH 7), ε = 40000 (est.).<br>ESI-MS (+): m/z calculated for C$_{28}$H$_{23}$N$_5$O$_9$PS ([M + H]$^+$): 636.09, found: 636.<br>ESI-MS (−): m/z calculated for C$_{28}$H$_{21}$N$_5$O$_9$PS ([M − H]$^-$): 634.08, found: 634. |
| 116 | 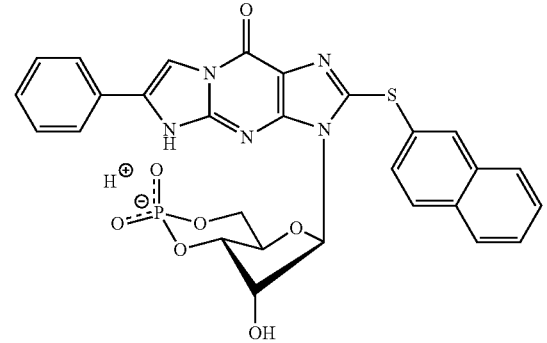<br>8-(2-Naphthyl)thio-β-phenyl-1,$N^2$-ethenoguanosine-3',5'-cyclic monophosphate (8-(2-N)T-PET-cGMP)<br>Using general procedure A, 8-Br-PET-cGMP (1 eq) was reacted with 2-naphthalenethiol (6 eq) in the presence of NaOH (2 eq) to give the title compound.<br>Yield (Purity): 30% (>99%). |

TABLE 16-continued

Examples of monomeric precursors and/or monomeric compound of the invention.

| # | Compound/Structure |
|---|---|

HPLC: (22% MeCN, 50 mM NaH$_2$PO$_4$ buffer, pH 6.7).
UV-VIS: $\lambda_{max}$ = 275 nm (pH 7), $\varepsilon$ = 40000 (est.).
ESI-MS (+): m/z calculated for C$_{28}$H$_{23}$N$_5$O$_7$PS ([M + H]$^+$): 604.11, found: 604.
ESI-MS (−): m/z calculated for C$_{28}$H$_{21}$N$_5$O$_7$PS ([M − H]$^-$): 602.09, found: 602.

117

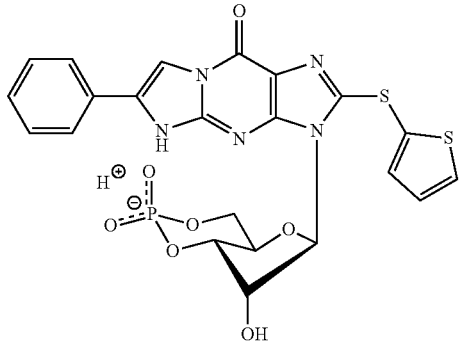

β-Phenyl-1,N$^2$-etheno-8-(2-thiophenyl)thioguanosine-3',5'-cyclic monophosphate
(PET-8-(2-Tp)T-cGMP)
Using general procedure A, 8-Br-PET-cGMP (1 eq) was reacted with 2-thiophenethiol (6 eq)
in the presence of NaOH (2 eq) to give the title compound.
Yield (Purity): 60% (>99%).
HPLC: (22% MeCN, 50 mM NaH$_2$PO$_4$ buffer, pH 6.7).
UV-VIS: $\lambda_{max}$ = 275 nm (pH 7), $\varepsilon$ = 40000 (est.).
ESI-MS (+): m/z calculated for C$_{22}$H$_{19}$N$_5$O$_7$PS$_2$ ([M + H]$^+$): 560.05, found: 560.
ESI-MS (−): m/z calculated for C$_{22}$H$_{17}$N$_5$O$_7$PS$_2$ ([M − H]$^-$): 558.03, found: 558.

118

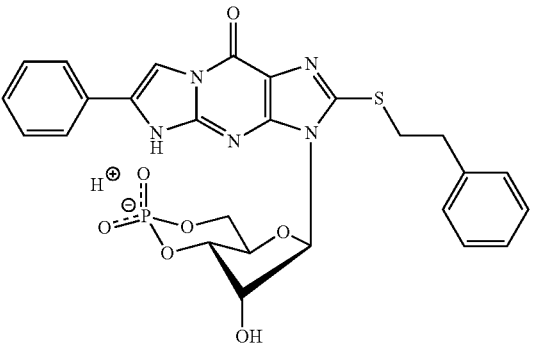

β-Phenyl-1,N$^2$-etheno-8-(2-phenylethyl)thioguanosine-3',5'-cyclic
monophosphate (PET-8-PhEtT-cGMP)
Using general procedure A, 8-Br-PET-cGMP (1 eq) was reacted with 2-phenylethanethiol
(6 eq) in the presence of NaOH (2 eq) to give the title compound.
Yield (Purity): % (>99%).
HPLC: (22% MeCN, 50 mM NaH$_2$PO$_4$ buffer, pH 6.7).
UV-VIS: $\lambda_{max}$ = 276 nm (pH 7), $\varepsilon$ = 40000 (est.).
ESI-MS (+): m/z calculated for C$_{26}$H$_{25}$N$_5$O$_7$PS ([M + H]$^+$): 582.12, found: 582.
ESI-MS (−): m/z calculated for C$_{26}$H$_{23}$N$_5$O$_7$PS ([M − H]$^-$): 580.11, found: 580.

119

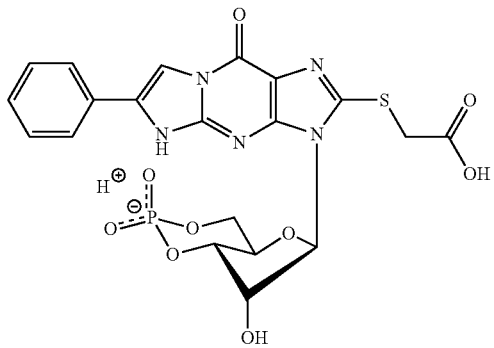

TABLE 16-continued

Examples of monomeric precursors and/or monomeric compound of the invention.

| # | Compound/Structure |
|---|---|

8-Carboxymethylthio-β-phenyl-1,N²-ethenoguanosine-3',5'-cyclic
monophosphate (8-CMT-PET-cGMP)
Using general procedure C, 8-Br-PET-cGMP was reacted with mercaptoacetic acid to give
the title compound.
Yield (Purity): 68% (>99%).
HPLC: (14% MeCN, 50 mM $NaH_2PO_4$ buffer, pH 6.8).
UV-VIS: $\lambda_{max}$ = 273 nm (pH 7), ε = 40000 (est.).
ESI-MS (+): m/z calculated for $C_{20}H_{19}N_5O_9PS$ ([M + H]$^+$): 536.06, found: 536.
ESI-MS (−): m/z calculated for $C_{20}H_{17}N_5O_9PS$ ([M − H]$^-$): 534.05, found: 534.

120

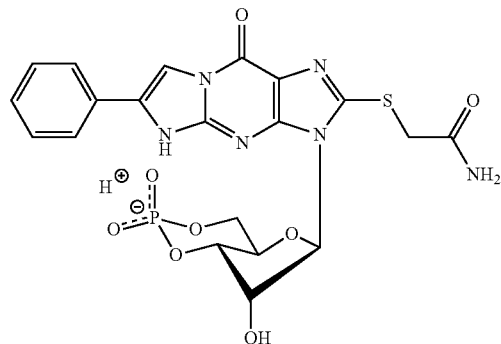

8-Amidomethylthio-β-phenyl-1,N²-ethenoguanosine-3',5'-cyclic monophosphate
(8-AmdMT-PET-cGMP)
In a one pot synthesis 8-T-cGMP was reacted with 2-bromoacetamide following general
procedure D to give 8-AmdMT-cGMP, which was transformed to the title compound by
applying general procedure Y.
Yield (Purity): 19% (>99%).
HPLC: (35% MeOH, 10 mM TEAF buffer, pH 6.8).
UV-VIS: $\lambda_{max}$ = 273 nm (pH 7), ε = 40000 (est.).
ESI-MS (+): m/z calculated for $C_{20}H_{20}N_6O_8PS$ ([M + H]$^+$): 535.08, found: 535.
ESI-MS (−): m/z calculated for $C_{20}H_{18}N_6O_8PS$ ([M − H]$^-$): 533.06, found: 533.

121

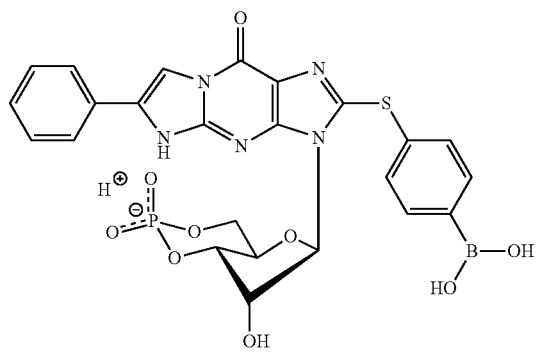

8-(4-Boronatephenylthio)-β-phenyl-1,N²-ethenoguanosine-3',5'-cyclic
monophosphate (8-(pB(OH)$_2$P)T-PET-cGMP)
Using general procedure A, 8-Br-PET-cGMP was reacted with 4-mercaptophenylboronic
acid to give the title compound.
Yield (Purity): 25% (>99%).
HPLC: (52% MeOH, 10 mM TEAF buffer, pH 6.8).
UV-VIS: $\lambda_{max}$ = 276 nm (pH 7), ε = 40000 (est.).
ESI-MS (+): m/z calculated for $C_{24}H_{22}BN_5O_9PS$ ([M + H]$^+$): 598.10, found: 598.
ESI-MS (−): m/z calculated for $C_{24}H_{20}BN_5O_9PS$ ([M − H]$^-$): 596.08, found: 596.

TABLE 16-continued

Examples of monomeric precursors and/or monomeric compound of the invention.

| # | Compound/Structure |
|---|---|
| 122 | 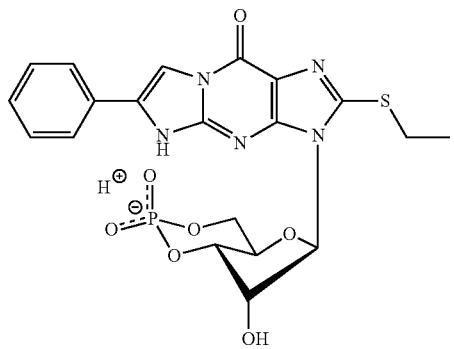 |

8-Ethylthio-β-phenyl-1,N2-ethenoguanosine-3',5'-cyclic monophosphate (8-ET-PET-cGMP)
Using general procedure A, 8-Br-PET-cGMP (1 eq) was reacted with ethanethiol (12 eq) in a tube with screw cap at 70° C. to give the title compound.
Yield (Purity): 46% (>99%).
HPLC: (15% MeCN, 50 mM NaH$_2$PO$_4$ buffer, pH 6.7).
UV-VIS: $\lambda_{max}$ = 274 nm (pH 7), ε = 40000 (est.).
ESI-MS (+): m/z calculated for C$_{20}$H$_{21}$N$_5$O$_7$PS ([M + H]$^+$): 506.09, found: 506.
ESI-MS (−): m/z calculated for C$_{20}$H$_{19}$N$_5$O$_7$PS ([M − H]$^-$): 504.07, found: 504.

| 123 | 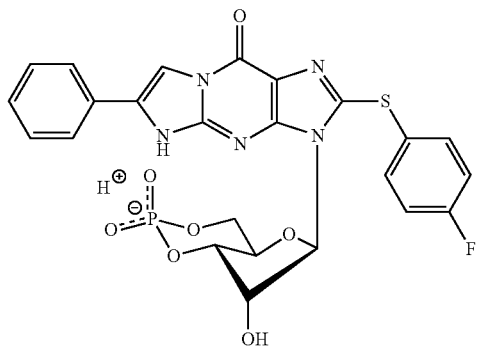 |

8-(4-Fluorophenylthio)-β-phenyl-1,N$^2$-ethenoguanosine-3',5'-cyclic monophosphate (8-pFPT-PET-cGMP)
Using general procedure A, 8-Br-PET-cGMP (1 eq) was reacted with 4-fluorothiophenol (4 eq) in the presence of NaOH (2 eq) to give the title compound.
Yield (Purity): 36% (>99%).
HPLC: (22% MeCN, 50 mM NaH$_2$PO$_4$ buffer, pH 6.7).
UV-VIS: $\lambda_{max}$ = 276 nm (pH 7), ε = 40000 (est.).
ESI-MS (+): m/z calculated for C$_{24}$H$_{20}$FN$_5$O$_7$PS ([M + H]$^+$): 572.08, found: 572.
ESI-MS (−): m/z calculated for C$_{24}$H$_{18}$FN$_5$O$_7$PS ([M − H]$^-$): 570.06, found: 570.

| 124 | 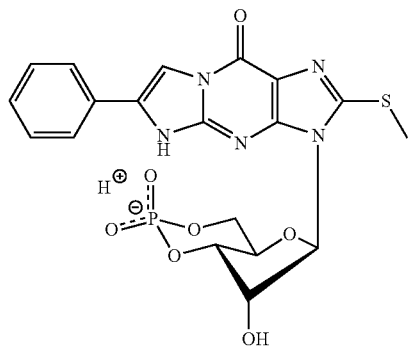 |

8-Methylthio-β-phenyl-1,N$^2$-ethenoguanosine-3',5'-cyclic monophosphate (8-MeS-PET-cGMP)
Using general procedure A, 8-Br-PET-cGMP (1 eq) was reacted with sodium methanethiolate (4 eq) to give the title compound.

TABLE 16-continued

Examples of monomeric precursors and/or monomeric compound of the invention.

| # | Compound/Structure |
|---|---|

Yield (Purity): 75% (>99%).

HPLC: (15% MeCN, 50 mM $NaH_2PO_4$ buffer, pH 6.7).

UV-VIS: $\lambda_{max}$ = 272 nm (pH 7), $\varepsilon$ = 40000 (est.).

ESI-MS (+): m/z calculated for $C_{19}H_{19}N_5O_7PS$ ($[M + H]^+$): 492.07, found: 492.

ESI-MS (−): m/z calculated for $C_{19}H_{17}N_5O_7PS$ ($[M − H]^−$): 490.06, found: 490.

125

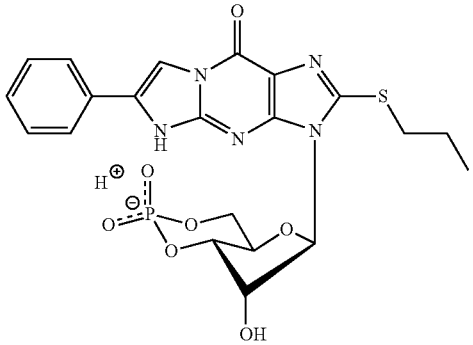

β-Phenyl-1,$N^2$-etheno-8-propylthio-guanosine-3',5'-cyclic monophosphate (PET-8-PrT-cGMP)

Using general procedure A, 8-Br-PET-cGMP (1 eq) was reacted with propanethiol (16 eq) in a tube with screw cap at 70° C. to give the title compound.

Yield (Purity): 46% (>99%).

HPLC: (15% MeCN, 50 mM $NaH_2PO_4$ buffer, pH 6.7).

UV-VIS: $\lambda_{max}$ = 273 nm (pH 7), $\varepsilon$ = 40000 (est.).

ESI-MS (+): m/z calculated for $C_{21}H_{23}N_5O_7PS$ ($[M + H]^+$): 520.11, found: 521.

ESI-MS (−): m/z calculated for $C_{21}H_{21}N_5O_7PS$ ($[M − H]^−$): 518.09, found: 518.

126

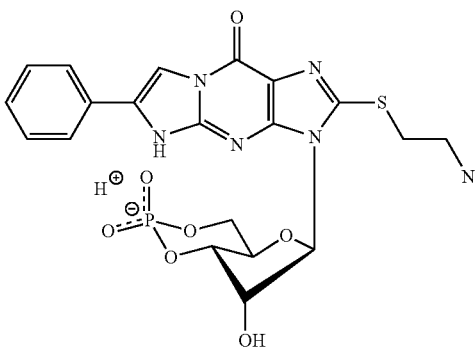

8-Azidoethylthio-β-phenyl-1,$N^2$-ethenoguanosine-3',5'-cyclic monophosphate (8-$N_3$-ET-PET-cGMP)

The title compound was synthesized from PET-8-T-cGMP and 1,2-dibromoethane using general procedure Q.

Yield (Purity): 41% (>99%).

HPLC: (23% MeCN, 40 mM $NaH_2PO_4$ buffer, pH 6.8).

UV-VIS: $\lambda_{max}$ = 273 nm (pH 7), $\varepsilon$ = 40000 (est.).

ESI-MS (+): m/z calculated for $C_{20}H_{20}N_8O_7PS$ ($[M + H]^+$): 547.09, found: 547.

ESI-MS (−): m/z calculated for $C_{20}H_{18}N_8O_7PS$ ($[M − H]^−$): 545.08, found: 545.

TABLE 16-continued

Examples of monomeric precursors and/or monomeric compound of the invention.

| # | Compound/Structure |
|---|---|

127

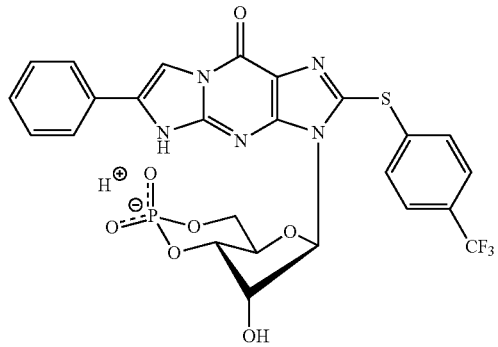

β-Phenyl-1,N²-etheno-8-(4-trifluoromethylphenylthio)guanosine-3',5'-cyclic
monophosphate (PET-8-pTFMePT-cGMP)
Using general procedure A, 8-Br-PET-cGMP (1 eq) was reacted with
4-(trifluoromethyl)thiophenol (4 eq) in the presence of NaOH (2 eq) to give the title
compound.
Yield (Purity): 60% (>99%).
HPLC: (22% MeCN, 50 mM NaH$_2$PO$_4$ buffer, pH 6.7).
UV-VIS: $\lambda_{max}$ = 276 nm (pH 7), $\varepsilon$ = 40000 (est.).
ESI-MS (+): m/z calculated for C$_{25}$H$_{20}$F$_3$N$_5$O$_7$PS ([M + H]$^+$): 622.08, found: 622.
ESI-MS (−): m/z calculated for C$_{25}$H$_{18}$F$_3$N$_5$O$_7$PS ([M − H]$^-$): 620.06, found: 620.

128

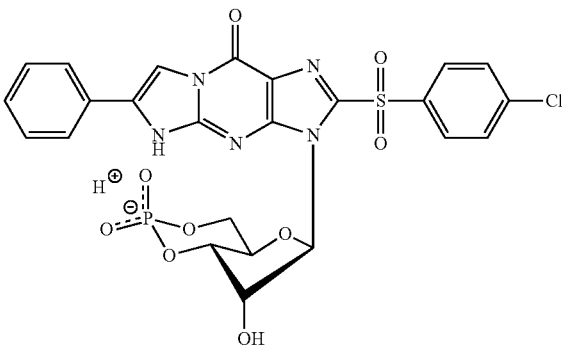

8-(4-Chlorophenylsulfonyl)-β-phenyl-1,N²-ethenoguanosine-3',5'-cyclic
monophosphate (8-pCPS-PET-cGMP)
Using general procedure Y, 8-pCPS-cGMP was reacted with 2-bromoacetophenone to give
the title compound.
Yield (Purity): 45% (>99%).
HPLC: (30% MeCN, 10 mM TEAF buffer, pH 6.8).
UV-VIS: $\lambda_{max}$ = 287 nm (pH 7), $\varepsilon$ = 40000 (est.).
ESI-MS (+): m/z calculated for C$_{24}$H$_{20}$ClN$_5$O$_9$PS ([M + H]$^+$): 620.04, found: 620.
ESI-MS (−): m/z calculated for C$_{24}$H$_{18}$ClN$_5$O$_9$PS ([M − H]$^-$): 618.03, found: 618.

129

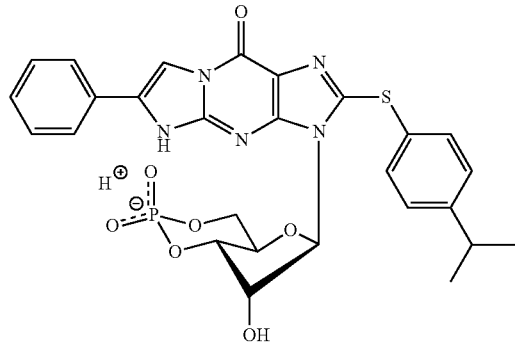

TABLE 16-continued

Examples of monomeric precursors and/or monomeric compound of the invention.

| # | Compound/Structure |
|---|---|

8-(4-Isopropylphenylthio)-β-phenyl-1,N²-ethenoguanosine-3',5'-cyclic
monophosphate (8-pIPrPT-PET-cGMP)
Using general procedure A, 8-Br-PET-cGMP (1 eq) was reacted with 4-isopropylthiophenol
(4 eq) in the presence of NaOH (2 eq) at 60° C. to give the title compound.
Yield (Purity): 20% (>99%).
HPLC: (27% MeCN, 50 mM NaH$_2$PO$_4$ buffer, pH 6.8).
UV-VIS: $\lambda_{max}$ = 274 nm (pH 7), ε = 40000 (est.).
ESI-MS (+): m/z calculated for C$_{27}$H$_{27}$N$_5$O$_7$PS ([M + H]$^+$): 596.14, found: 596.
ESI-MS (−): m/z calculated for C$_{27}$H$_{25}$N$_5$O$_7$PS ([M − H]$^−$): 594.12, found: 594.

130

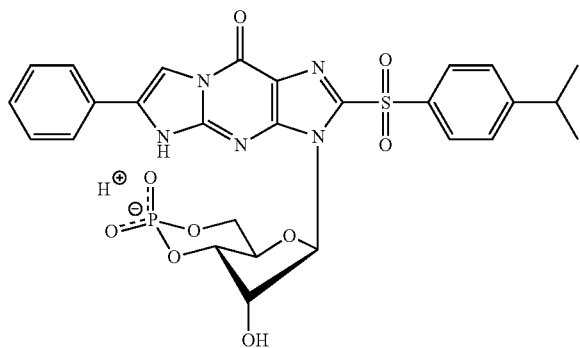

8-(4-Isopropylphenylsulfonyl)-β-phenyl-1,N²-ethenoguanosine-3',5'-cyclic
monophosphate (8-pIPrPS-PET-cGMP)
Using general procedure Y, 8-pIPrPS-cGMP was reacted with 2-bromoacetophenone to
give the title compound.
Yield (Purity): 38% (>99%).
HPLC: (61% MeOH, 10 mM TEAF buffer, pH 6.8).
UV-VIS: $\lambda_{max}$ = 285 nm (pH 7), ε = 40000 (est.).
ESI-MS (+): m/z calculated for C$_{27}$H$_{27}$N$_5$O$_9$PS ([M + H]$^+$): 628.13, found: 628.
ESI-MS (−): m/z calculated for C$_{27}$H$_{25}$N$_5$O$_9$PS ([M − H]$^−$): 626.11, found: 626.

131

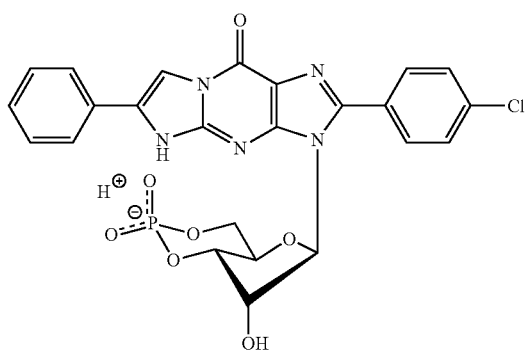

8-(4-Chlorophenyl)-β-phenyl-1,N²-ethenoguanosine-3',5'-cyclic monophosphate
(8-pCP-PET-cGMP)
Using general procedure X, 8-Br-PET-cGMP was reacted with 4-chlorophenylboronic acid to
give the title compound.
Yield (Purity): 29% (>99%).
HPLC: (27% MeCN, 25 mM NaH$_2$PO$_4$ buffer, pH 6.8).
UV-VIS: $\lambda_{max}$ = 279 nm (pH 7), ε = 40000 (est.).
ESI-MS (+): m/z calculated for C$_{24}$H$_{20}$ClN$_5$O$_7$P ([M + H]$^+$): 556.08, found: 556.
ESI-MS (−): m/z calculated for C$_{24}$H$_{18}$ClN$_5$O$_7$P ([M − H]$^−$): 554.06, found: 554.

TABLE 16-continued

Examples of monomeric precursors and/or monomeric compound of the invention.

| # | Compound/Structure |
|---|---|
| 132 | 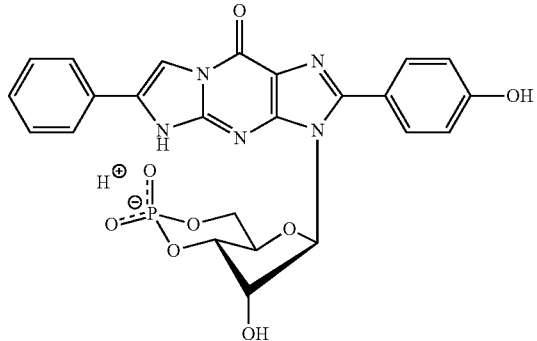 |

8-(4-Hydroxyphenyl)-β-phenyl-1,N²-ethenoguanosine-3',5'-cyclic monophosphate (8-pHP-PET-cGMP)
Using general procedure X, 8-Br-PET-cGMP was reacted with 4-hydroxyphenylboronic acid to give the title compound.
Yield (Purity): 43% (>99%).
HPLC: (20% MeCN, 25 mM NaH$_2$PO$_4$ buffer, pH 6.8).
UV-VIS: $\lambda_{max}$ = 279 nm (pH 7), ε = 40000 (est.).
ESI-MS (+): m/z calculated for C$_{24}$H$_{21}$N$_5$O$_8$P ([M + H]$^+$): 538.11, found: 538.
ESI-MS (−): m/z calculated for C$_{24}$H$_{19}$N$_5$O$_8$P ([M − H]$^-$): 536.10, found: 536.

| 133 | 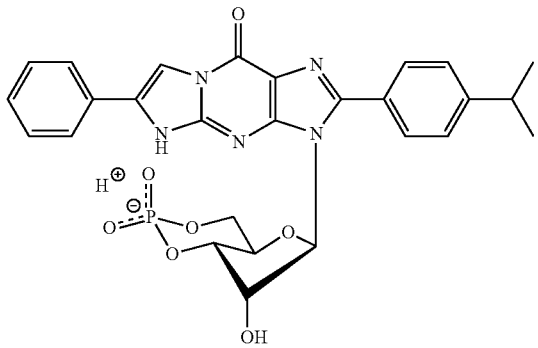 |

8-(4-Isopropylphenyl)-β-phenyl-1,N²-ethenoguanosine-3',5'-cyclic monophosphate (8-pIPrP-PET-cGMP)
Using general procedure X, 8-Br-PET-cGMP was reacted with 4-isopropylphenylboronic acid to give the title compound.
Yield (Purity): 25% (>99%).
HPLC: (31% MeCN, 30 mM NaH$_2$PO$_4$ buffer, pH 6.8).
UV-VIS: $\lambda_{max}$ = 277 nm (pH 7), ε = 40000 (est.).
ESI-MS (+): m/z calculated for C$_{27}$H$_{27}$N$_5$O$_7$P ([M + H]$^+$): 564.16, found: 564.
ESI-MS (−): m/z calculated for C$_{27}$H$_{25}$N$_5$O$_7$P ([M − H]$^-$): 562.15, found: 562.

| 134 | 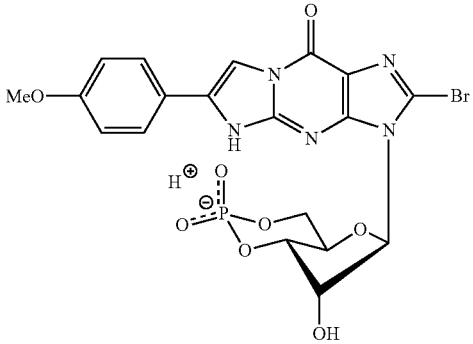 |

8-Bromo-(4-methoxy-β-phenyl-1,N2-etheno)guanosine-3',5'-cyclic monophosphate (8-Br-pMeO-PET-cGMP)
Using general procedure Y, 8-Br-cGMP was reacted with 2-bromo-4'-methoxyacetophenone to give the title compound.

Yield (Purity): 17% (>97%).
HPLC: (50% MeOH, 25 mM TEAF buffer, pH 6.8).
UV-VIS: $\lambda_{max}$ = 267 nm (pH 7), $\varepsilon$ = 40000 (est.).
ESI-MS (+): m/z calculated for $C_{19}H_{17}BrN_5O_8PNa$ ([M + Na]$^+$): 575.99, found: 576.
ESI-MS (−): m/z calculated for $C_{19}H_{16}BrN_5O_8P$ ([M − H]$^-$): 551.99, found: 552.

135

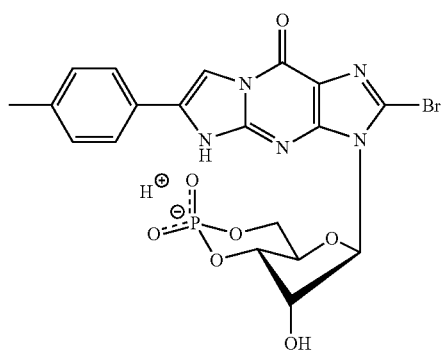

8-Bromo-(4-methyl-β-phenyl-1,N2-etheno)guanosine-3',5'-cyclic
monophosphate (8-Br-pMe-PET-cGMP)
Using general procedure Y, 8-Br-cGMP was reacted with 2-bromo-4'-
methylacetophenone to give the title compound.
Yield (Purity): 11% (>98%).
HPLC: (23% i-PrOH, 50 mM TEAF buffer, pH 6.8).
UV-VIS: $\lambda_{max}$ = 262 nm (pH 7), $\varepsilon$ = 40000 (est.).
ESI-MS (+): m/z calculated for $C_{19}H_{17}BrN_5O_7PNa$ ([M + Na]$^+$): 559.99, found: 560.
ESI-MS (−): m/z calculated for $C_{19}H_{16}BrN_5O_7P$ ([M − H]$^-$): 536.00, found: 536.

136

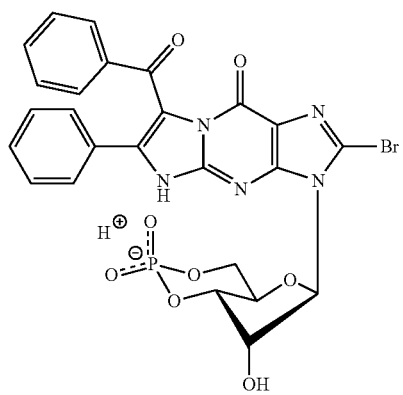

alpha-Benzoyl-beta-phenyl-1,N2-etheno-8-bromoguanosine-3',5'-cyclic
monophosphate (Bnz-PET-8-Br-cGMP)
Using general procedure Y, 8-Br-cGMP was reacted with 2-bromo-1,3-diphenylpropane-
1,3-dione to give the title compound.
Yield (Purity): 12% (>94%).
HPLC: (45% MeOH, 25 mM TEAF buffer, pH 6.8).
UV-VIS: $\lambda_{max}$ = 255 nm (pH 7), $\varepsilon$ = 40000 (est.).
ESI-MS (+): m/z calculated for $C_{25}H_{19}BrN_5O_8PNa$ ([M + Na]$^+$): 650.01, found: 650.
ESI-MS (−): m/z calculated for $C_{25}H_{18}BrN_5O_8P$ ([M − H]$^-$): 626.01, found: 626.

TABLE 16-continued

Examples of monomeric precursors and/or monomeric compound of the invention.

| # | Compound/Structure |
|---|---|
| 137 | 8-Bromo-(4-chloro-β-phenyl-1,N2-etheno)guanosine-3',5'-cyclic monophosphate (8-Br-pCl-PET-cGMP)<br>Using general procedure Y, 8-Br-cGMP was reacted with 2-bromo-4'-chloroacetophenone to give the title compound.<br>Yield (Purity): 28% (>99%).<br>HPLC: (57% MeOH, 20 mM TEAF buffer, pH 6.8).<br>UV-VIS: $\lambda_{max}$ = 263 nm (pH 7), ε = 40000 (est.).<br>ESI-MS (+): m/z calculated for $C_{18}H_{13}BrClN_5O_7PNa_2$ ([M + 2Na − H]$^+$): 601.92, found: 602.<br>ESI-MS (−): m/z calculated for $C_{18}H_{13}BrClN_5O_7P$ ([M − H]$^-$): 555.94, found: 556. |
| 138 | 8-Bromo-(3-nitro-β-phenyl-1,N2-etheno)guanosine-3',5'-cyclic monophosphate (8-Br-mN-PET-cGMP)<br>Using general procedure Y, 8-Br-cGMP was reacted with 2-bromo-3'-nitroacetophenone to give the title compound.<br>Yield (Purity): 14% (>98%).<br>HPLC: (45% MeOH, 25 mM TEAF buffer, pH 6.8).<br>UV-VIS: $\lambda_{max}$ = 261 nm (pH 7), ε = 40000 (est.).<br>ESI-MS (+): m/z calculated for $C_{18}H_{15}BrN_6O_9P$ ([M + H]$^+$): 568.98, found: 569.<br>ESI-MS (−): m/z calculated for $C_{18}H_{13}BrN_6O_9P$ ([M − H]$^-$): 566.97, found: 567. |
| 139 | 8-Bromo-(β-tert.-butyl-1,N2-etheno)guanosine-3',5'-cyclic monophosphate (8-Br-tBuET-cGMP)<br>Using general procedure Y, 8-Br-cGMP was reacted with 1-bromo-3,3-dimethyl-2-butanone to give the title compound. |

TABLE 16-continued

Examples of monomeric precursors and/or monomeric compound of the invention.

| # | Compound/Structure |
|---|---|

Yield (Purity): 38% (>99%).
HPLC: (48% MeOH, 10 mM TEAF buffer, pH 6.8).
UV-VIS: $\lambda_{max}$ = nm (pH 7), $\varepsilon$ = 40000 (est.).
ESI-MS (+): m/z calculated for $C_{16}H_{20}BrN_5O_7P$ ([M + H]$^+$): 504.03, found: 504.
ESI-MS (−): m/z calculated for $C_{16}H_{18}BrN_5O_7P$ ([M − H]$^-$): 502.01, found: 502.

140

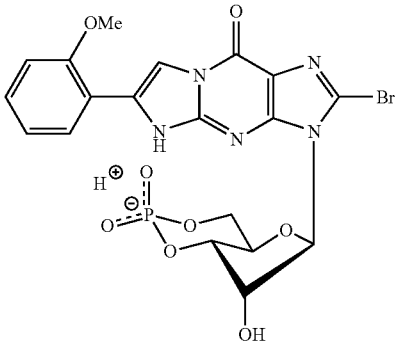

8-Bromo-(2-methoxy-β-phenyl-1,N2-etheno)guanosine-3',5'-cyclic monophosphate (8-Br-oMeO-PET-cGMP)

Using general procedure Y, 8-Br-cGMP was reacted with 2-bromo-2'-methoxyacetophenone to give the title compound.

Yield (Purity): 4% (>99%).
HPLC: (52% MeOH, 10 mM TEAF buffer, pH 6.8).
UV-VIS: $\lambda_{max}$ = 256 nm (pH 7), $\varepsilon$ = 40000 (est.).
ESI-MS (+): m/z calculated for $C_{19}H_{18}BrN_5O8P$ ([M + H]$^+$): 554.01, found: 554.
ESI-MS (−): m/z calculated for $C_{19}H_{16}BrN_5O8P$ ([M − H]$^-$): 551.99, found: 552.

141

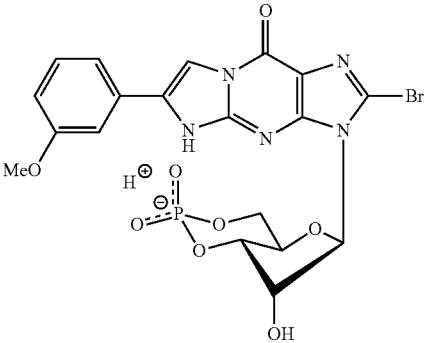

8-Bromo-(3-methoxy-β-phenyl-1,N2-etheno)guanosine-3',5'-cyclic monophosphate (8-Br-mMe-PET-cGMP)

Using general procedure Y, 8-Br-cGMP was reacted with 2-bromo-3'-methoxyacetophenone to give the title compound.

Yield (Purity): 10% (>99%).
HPLC: (23% i-PrOH, 50 mM TEAF buffer, pH 6.8).
UV-VIS: $\lambda_{max}$ = 258 nm (pH 7), $\varepsilon$ = 40000 (est.).
ESI-MS (+): m/z calculated for $C_{19}H_{18}BrN_5O8P$ ([M + H]$^+$): 554.01, found: 554.
ESI-MS (−): m/z calculated for $C_{19}H_{16}BrN_5O8P$ ([M − H]$^-$): 551.99, found: 552.

TABLE 16-continued

Examples of monomeric precursors and/or monomeric compound of the invention.

| # | Compound/Structure |
|---|---|
| 142 | 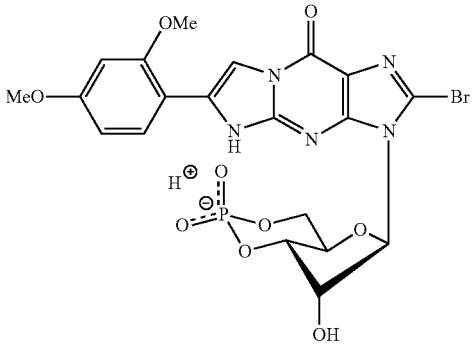 |

8-Bromo-(2,4-dimethoxy-β-phenyl-1,N2-etheno)guanosine-3',5'-cyclic
monophosphate (8-Br-o,pDMeO-PET-cGMP)
Using general procedure Y, 8-Br-cGMP was reacted with 2-bromo-2',4'-
dimethoxyacetophenone to give the title compound.
Yield (Purity): 14% (>98%).
HPLC: (18% MeCN, 50 mM NaH$_2$PO$_4$ buffer, pH 6.7).
UV-VIS: $\lambda_{max}$ = 267 nm (pH 7), ε = 40000 (est.).
ESI-MS (+): m/z calculated for C$_{20}$H$_{20}$BrN$_5$O$_9$P ([M + H]$^+$): 584.02, found: 584.
ESI-MS (−): m/z calculated for C$_{20}$H$_{18}$BrN$_5$O$_9$P ([M − H]$^−$): 582.00, found: 582.

| 143 | 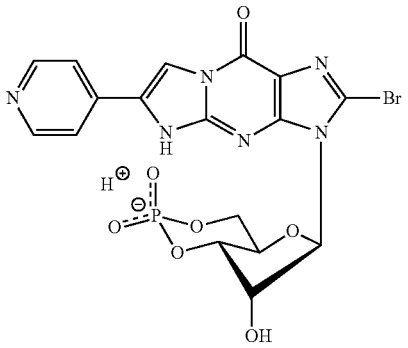 |

8-Bromo-(4-pyridinyl-1,N2-etheno)guanosine-3',5'-cyclic monophosphate (8-Br-
(4-Pyr)ET-cGMP)
Using general procedure Y, 8-Br-cGMP was reacted with 2-bromo-1-(4-pyridinyl)-1-
ethanone hydrochloride to give the title compound.
Yield (Purity): 31% (>98%).
HPLC: (15% MeCN, 50 mM NaH$_2$PO$_4$ buffer, pH 6.7).
UV-VIS: $\lambda_{max}$ = 266 nm (pH 7), ε = 40000 (est.).
ESI-MS (+): m/z calculated for C$_{17}$H$_{15}$BrN$_6$O$_7$P ([M + H]$^+$): 524.99, found: 525.
ESI-MS (−): m/z calculated for C$_{17}$H$_{13}$BrN$_6$O$_7$P ([M − H]$^−$): 522.98, found: 523.

| 144 | 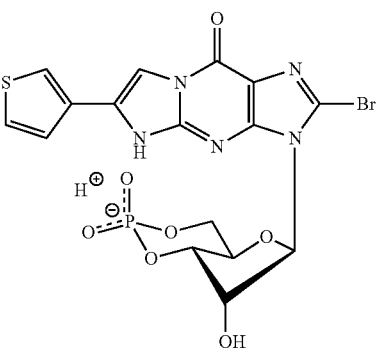 |

8-Bromo-(3-thiophen-yl-1,N2-etheno)guanosine-3',5'-cyclic monophosphate (8-
Br-(3-Tp)ET-cGMP)
Using general procedure Y, 8-Br-cGMP was reacted with 3-(bromoacetyl)-thiophene to give
the title compound.

TABLE 16-continued

Examples of monomeric precursors and/or monomeric compound of the invention.

| # | Compound/Structure |
|---|---|

Yield (Purity): 52% (>99%).
HPLC: (15% MeCN, 50 mM NaH$_2$PO$_4$ buffer, pH 6.7).
UV-VIS: λmax = 261 nm (pH 7), ε = 40000 (est.).
ESI-MS (+): m/z calculated for C$_{16}$H$_{14}$BrN$_5$O$_7$PS ([M + H]$^+$): 529.95, found: 530.
ESI-MS (−): m/z calculated for C$_{16}$H$_{12}$BrN$_5$O$_7$PS ([M − H]$^−$): 527.94, found: 528.

145

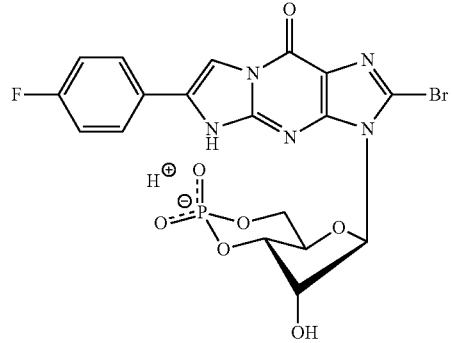

8-Bromo-(4-fluoro-β-phenyl-1,N2-etheno)guanosine-3',5'-cyclic
monophosphate (8-Br-pF-PET-cGMP)
Using general procedure Y, 8-Br-cGMP was reacted with 4-fluorophenacyl bromide to give
the title compound.
Yield (Purity): 25% (>99%).
HPLC: (15% MeCN, 50 mM NaH$_2$PO$_4$ buffer, pH 6.7).
UV-VIS: λmax = 257 nm (pH 7), ε = 40000 (est.).
ESI-MS (+): m/z calculated for C$_{18}$H$_{15}$BrFN$_5$O$_7$P ([M + H]$^+$): 541.99, found: 542.
ESI-MS (−): m/z calculated for C$_{18}$H$_{13}$BrFN$_5$O$_7$P ([M − H]$^−$): 539.97, found: 540.

146

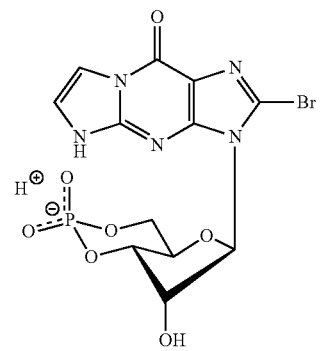

8-Bromo-1,N2-ethenoguanosine-3',5'-cyclic monophosphate (8-Br-ET-cGMP)
Using general procedure Y, 8-Br-cGMP was reacted with chloroacetaldehyde to give the
title compound.
Yield (Purity): 10% (>99%).
HPLC: (9% MeCN, 20 mM TEAF buffer, pH 6.9).
UV-VIS: λmax = 287 nm (pH 7), ε = 14600 (est.).
ESI-MS (+): m/z calculated for C$_{12}$H$_{12}$BrN$_5$O$_7$P ([M + H]$^+$): 447.97, found: 448.
ESI-MS (−): m/z calculated for C$_{12}$H$_{10}$BrN$_5$O$_7$P ([M − H]$^−$): 445.95, found: 446.

147

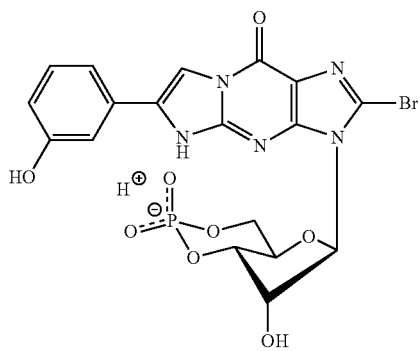

TABLE 16-continued

Examples of monomeric precursors and/or monomeric compound of the invention.

| # | Compound/Structure |
|---|---|
| | 8-Bromo-(3-hydroxy-β-phenyl-1,N2-etheno)guanosine-3',5'-cyclic monophosphate (8-Br-mH-PET-cGMP)<br>Using general procedure Y, 8-Br-cGMP was reacted with 3'-benzoyloxy-2-bromoacetophenone to give the O-benzoyl protected analogue of the title compound. Prior to chromatographic workup the crude product was subjected to NaOH (2M, 10 eq), to effect cleavage of the protecting group, and neutralized with HCl (1M).<br>Yield (Purity): 13% (>99%).<br>HPLC: (43% MeOH, 10 mM TEAF buffer, pH 6.8), second chromatographic workup (20% MeCN, 10 mM TEAF buffer, pH 6.8).<br>UV-VIS: $\lambda_{max}$ = 258 nm (pH 7), ε = 40000 (est.).<br>ESI-MS (+): m/z calculated for $C_{18}H_{16}BrN_5O_8P$ ([M + H]$^+$): 539.99, found: 540.<br>ESI-MS (−): m/z calculated for $C_{18}H_{14}BrN_5O_8P$ ([M − H]$^−$): 537.98, found: 538. |
| 148 | 8-Bromo-(4-hydroxy-β-phenyl-1,N$^2$-etheno)guanosine-3',5'-cyclic monophosphate (8-Br-pHPET-cGMP)<br>Using general Y, 8-Br-cGMP was reacted with 4-(bromoacetyl)-phenyl benzoate to give the O-benzoyl protected analogue of the title compound. Prior to chromatographic workup the crude product was subjected to NaOH (2M, 10 eq), to effect cleavage of the protecting group, and neutralized with HCl (1M).<br>Yield (Purity): 12% (>99%).<br>HPLC: (43% MeOH, 10 mM TEAF buffer, pH 6.8), second chromatographic workup (20% MeCN, 10 mM TEAF buffer, pH 6.8).<br>UV-VIS: $\lambda_{max}$ = 267 nm (pH 7), ε = 40000 (est.).<br>ESI-MS (+): m/z calculated for $C_{18}H_{16}BrN_5O_8P$ ([M + H]$^+$): 539.99, found: 540.<br>ESI-MS (−): m/z calculated for $C_{18}H_{14}BrN_5O_8P$ ([M − H]$^−$): 537.98, found: 538. |
| 149 | 8-Bromo-(β-(2,3-dihydro-1,4-benzodioxin)-1,N2-etheno)guanosine-3',5'-cyclic monophosphate (8-Br-(2,3-DHy-1,4-BnzDiox)-ET-cGMP)<br>Using general procedure Y, 8-Br-cGMP was reacted with 2-bromo-1-(2,3-dihydro-1,4-benzodioxin-6-yl)ethanone to give the title compound.<br>Yield (Purity): 8% (>99%).<br>HPLC: (52% MeOH, 10 mM TEAF buffer, pH 6.8).<br>UV-VIS: $\lambda_{max}$ = 267 nm (pH 7), ε = 40000 (est.).<br>ESI-MS (+): m/z calculated for $C_{20}H_{18}BrN_5O_9P$ ([M + H]$^+$): 582.00, found: 582.<br>ESI-MS (−): m/z calculated for $C_{20}H_{16}BrN_5O_9P$ ([M − H]$^−$): 579.99, found: 580. |

| # | Compound/Structure |
|---|---|
| 150 | 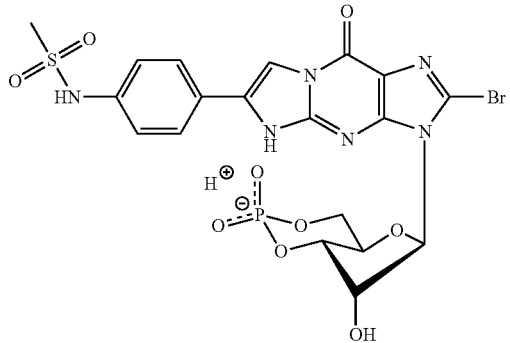 8-Bromo-(4-methylsulfonamido-β-phenyl-1,N2-etheno)guanosine-3',5'-cyclic monophosphate (8-Br-pMSulfAmd-PET-cGMP)<br>Using general procedure Y, 8-Br-cGMP was reacted with N-[4-(2-bromoacetyl)phenyl]-methanesulfonamide to give the title compound.<br>Yield (Purity): 25% (>97%).<br>HPLC: (45% MeOH, 10 mM TEAF buffer, pH 6.8).<br>UV-VIS: $\lambda_{max}$ = 270 nm (pH 7), ε = 40000 (est.).<br>ESI-MS (+): m/z calculated for $C_{19}H_{19}BrN_6O_9PS$ ([M + H]$^+$): 616.99, found: 617.<br>ESI-MS (−): m/z calculated for $C_{19}H_{17}BrN_6O_9PS$ ([M − H]$^-$): 614.97, found: 615. |
| 151 | 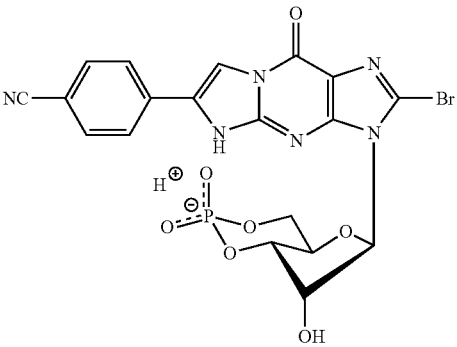 8-Bromo-(4-cyano-β-phenyl-1,N$^2$-etheno)guanosine-3',5'-cyclic monophosphate (8-Br-pCN-PET-cGMP)<br>Using general procedure Y, 8-Br-cGMP was reacted with 2-bromo-4'-cyanoacetophenone to give the title compound.<br>Yield (Purity): 12% (>99%).<br>HPLC: (45% MeOH, 10 mM TEAF buffer, pH 6.8), second chromatographic workup (22% MeCN, 10 mM TEAF buffer, pH 6.8).<br>UV-VIS: $\lambda_{max}$ = 272 nm (pH 7), ε = 40000 (est.).<br>ESI-MS (+): m/z calculated for $C_{19}H_{15}BrN_6O_7P$ ([M + H]$^+$): 548.99, found: 549.<br>ESI-MS (−): m/z calculated for $C_{19}H_{13}BrN_6O_7P$ ([M − H]$^-$): 546.98, found: 547. |
| 152 | 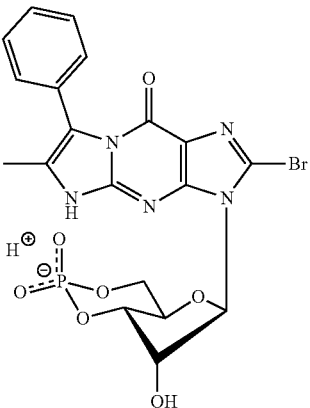 |

TABLE 16-continued

Examples of monomeric precursors and/or monomeric compound of the invention.

| # | Compound/Structure |
|---|---|

8-Bromo-(α-phenyl-β-methyl-1,N$^2$-etheno)guanosine-3',5'-cyclic
monophosphate (8-Br-alpha-Phe-beta-Me-ET-cGMP)
Using general procedure Y, 8-Br-cGMP was reacted with 1-bromo-1-phenylpropan-2-one to
give the title compound.
Yield (Purity): 9% (>99%).
HPLC: (45% MeOH, 10 mM TEAF buffer, pH 6.8).
UV-VIS: $\lambda_{max}$ = 294 nm (pH 7), ε = 40000 (est.).
ESI-MS (+): m/z calculated for $C_{19}H_{18}BrN_5O_7P$ ([M + H]$^+$): 538.01, found: 538.
ESI-MS (−): m/z calculated for $C_{19}H_{16}BrN_5O_7P$ ([M − H]$^−$): 536.00, found: 536.

153

β-(4-Aminophenyl)-1,N$^2$-etheno-8-bromoguanosine-3',5'-cyclic monophosphate
(pNH$_2$-PET-8-Br-cGMP)
The title compound was synthesized from 4-N$_3$-PET-8-Br-cGMP using general procedure V.
Yield (Purity): 10% (>98%).
HPLC: (18% MeCN, 50 mM NaH$_2$PO$_4$ buffer, pH 6.7).
UV-VIS: $\lambda_{max}$ = 274 nm (pH 7), ε = 40000 (est.).
ESI-MS (+): m/z calculated for $C_{18}H_{17}BrN_6O_7P$ ([M + H]$^+$): 539.01, found: 539.
ESI-MS (−): m/z calculated for $C_{18}H_{17}BrN_6O_7P$ ([M − H]$^−$): 536.99, found: 537.

154

8-Bromo-(6-methoxy-2-naphthyl-1,N$^2$-etheno)guanosine-3',5'-cyclic
monophosphate (8-Br-(6-MeO-2-N)ET-cGMP)
Using general procedure Y, 8-Br-cGMP was reacted with 2-bromo-6'-methoxy-2'-
acethonaphtone to give the title compound.
Yield (Purity): 6% (>99%).
HPLC: (27% MeCN, 10 mM NaH$_2$PO$_4$ buffer, pH 7.3).
UV-VIS: $\lambda_{max}$ = 260 nm (pH 7), ε = 40000 (est.).
ESI-MS (+): m/z calculated for $C_{23}H_{20}BrN_5O_8P$ ([M + H]$^+$): 604.02, found: 604.
ESI-MS (−): m/z calculated for $C_1H_1N_5O_9PS$ ([M − H]$^−$): 602.01, found: 602.

TABLE 16-continued

Examples of monomeric precursors and/or monomeric compound of the invention.

| # | Compound/Structure |
|---|---|
| 155 | 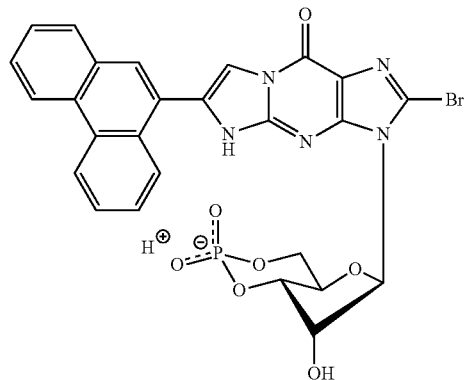<br>8-Bromo-(9-phenanthrenyl-1,$N^2$-etheno)guanosine-3',5'-cyclic monophosphate<br>(8-Br-(9-Phethr)ET-cGMP)<br>Using general procedure Y, 8-Br-cGMP was reacted with 9-(2-bromoacetyl)phenantrene to give the title compound.<br>Yield (Purity): 10% (>99%).<br>HPLC: (28% MeCN, 50 mM NaH$_2$PO$_4$ buffer, pH 6.7).<br>HPLC (analytical): (26% MeCN, 50 mM NaH$_2$PO$_4$ buffer, pH 7.2)<br>UV-VIS: $\lambda_{max}$ = 254 nm (pH 7), $\varepsilon$ = 40000 (est.).<br>ESI-MS (+): m/z calculated for C$_{26}$H$_{20}$BrN$_5$O$_7$P ([M + H]$^+$): 624.03, found: 624.<br>ESI-MS (−): m/z calculated for C$_{26}$H$_{18}$BrN$_5$O$_7$P ([M − H]$^-$): 622.01, found: 622. |
| 156 | 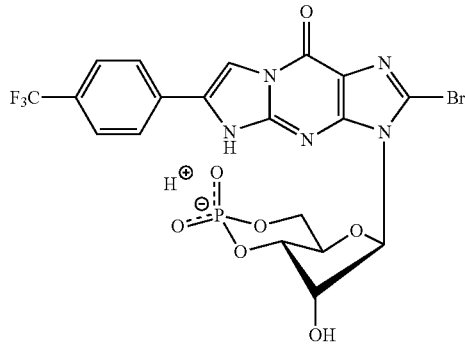<br>8-Bromo-(4-trifluoromethyl-β-phenyl-1,$N^2$-etheno)guanosine-3',5'-cyclic monophosphate (8-Br-pTFMe-PET-cGMP)<br>Using general procedure Y, 8-Br-cGMP was reacted with 2-bromo-4'-(trifluoromethyl)-acetophenon to give the title compound.<br>Yield (Purity): 18% (>99%).<br>HPLC: (27% MeCN, 50 mM NaH$_2$PO$_4$ buffer, pH 6.7).<br>UV-VIS: $\lambda_{max}$ = 258 nm (pH 7), $\varepsilon$ = 40000 (est.).<br>ESI-MS (+): m/z calculated for C$_{19}$H$_{15}$BrF$_3$N$_5$O$_7$P ([M + H]$^+$): 591.98, found: 592.<br>ESI-MS (−): m/z calculated for C$_{19}$H$_{13}$BrF$_3$N$_5$O$_7$P ([M − H]$^-$): 589.97, found: 590. |
| 157 | 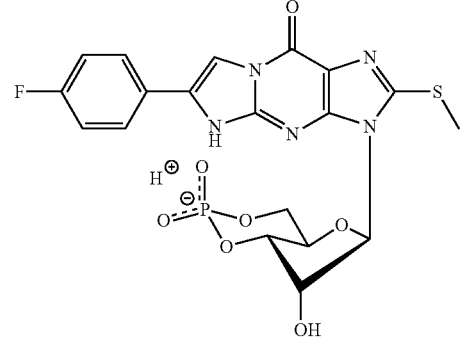<br>(4-Fluoro-β-phenyl-1,N2-etheno)-8-methylthioguanosine-3',5'-cyclic monophosphate (pF-PET-8-MeS-cGMP) |

TABLE 16-continued

Examples of monomeric precursors and/or monomeric compound of the invention.

| # | Compound/Structure |
|---|---|

Using general procedure A, 8-Br-pF-PET-cGMP (1 eq) was reacted with sodium
methanethiolate (4 eq) to give the title compound.
Yield (Purity): 30% (>99%).
HPLC: (18% MeCN, 50 mM NaH$_2$PO$_4$ buffer, pH 6.7).
UV-VIS: $\lambda_{max}$ = 270 nm (pH 7), $\varepsilon$ = 40000 (est.).
ESI-MS (+): m/z calculated for C$_{19}$H$_{18}$FN$_5$O$_7$PS ([M + H]$^+$): 510.06, found: 510.
ESI-MS (−): m/z calculated for C$_{19}$H$_{16}$FN$_5$O$_7$PS ([M − H]$^-$): 508.05, found: 508.

158

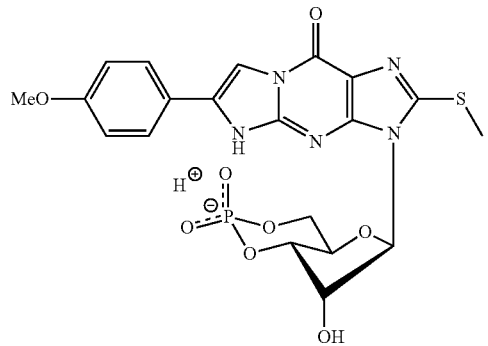

(4-Methoxy-β-phenyl-1,N2-etheno)-8-methylthioguanosine-3',5'-cyclic
monophosphate (pMeO-PET-MeS-cGMP)
Using general procedure A, 8-Br-pMeO-PET-cGMP (1 eq) was reacted with sodium
methanethiolate (4 eq) to give the title compound.
Yield (Purity): 88% (>99%).
HPLC: (18% MeCN, 50 mM NaH$_2$PO$_4$ buffer, pH 6.7).
UV-VIS: $\lambda_{max}$ = 275 nm (pH 7), $\varepsilon$ = 40000 (est.).
ESI-MS (+): m/z calculated for C$_{20}$H$_{21}$N$_5$O$_8$PS ([M + H]$^+$): 522.08, found: 522.
ESI-MS (−): m/z calculated for C$_{20}$H$_{19}$N$_5$O$_8$PS ([M − H]$^-$): 520.07, found: 520.

159

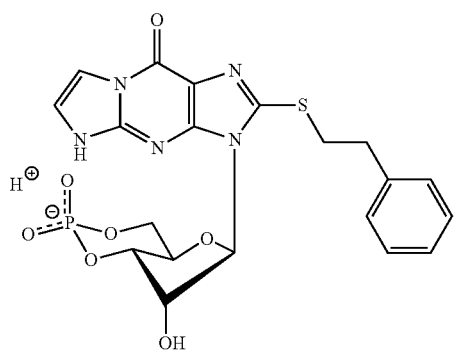

1,N$^2$-Etheno-8-(2-phenylethyl)thioguanosine-3',5'-cyclic monophosphate (ET-8-
PhEtT-cGMP)
Using general procedure A, 8-Br-Et-cGMP (B 177) was reacted with 2-phenyethanethiol to
give the title compound.
Yield (Purity): 18% (>99%).
HPLC: (18% MeCN, 50 mM NaH$_2$PO$_4$ buffer, pH 6.7).
UV-VIS: $\lambda_{max}$ = 288 nm (pH 7), $\varepsilon$ = 19900 (est.).
ESI-MS (+): m/z calculated for C$_{20}$H$_{21}$N$_5$O$_7$PS ([M + H]$^+$): 506.09, found: 506.
ESI-MS (−): m/z calculated for C$_{20}$H$_{19}$N$_5$O$_7$PS ([M − H]$^-$): 504.07, found: 504.

TABLE 16-continued

Examples of monomeric precursors and/or monomeric compound of the invention.

| # | Compound/Structure |
|---|---|
| 160 | 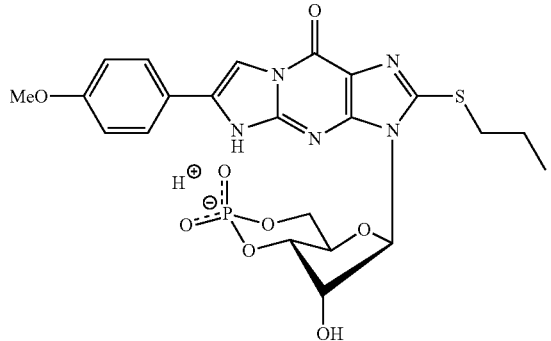 |

(4-Methoxy-β-phenyl-1,N2-etheno)-8-propylthioguanosine-3',5'-cyclic monophosphate (pMeO-PET-8-PrT-cGMP)

Using general procedure A, 8-Br-pMeO-PET-cGMP (1 eq) was reacted with 1-Propanethiol (40 eq) to give the title compound.
Yield (Purity): 40% (>99%).
HPLC: (22% MeCN, 50 mM NaH$_2$PO$_4$ buffer, pH 6.7).
UV-VIS: $\lambda_{max}$ = 276 nm (pH 7), ε = 40000 (est.).
ESI-MS (+): m/z calculated for C$_{22}$H$_{24}$N$_5$O$_8$PS ([M + H]$^+$): 550.12, found: 550.
ESI-MS (−): m/z calculated for C$_{22}$H$_{24}$N$_5$O$_8$PS ([M − H]$^-$): 548.10, found: 548.

| 161 | 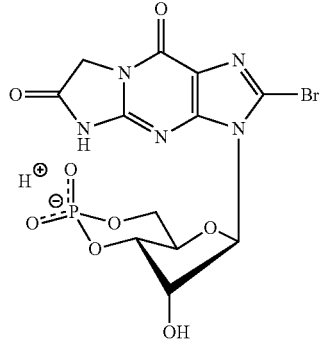 |

β-1,N$^2$-Acetyl-8-bromoguanosine-3',5'-cyclic monophosphate (β-1,N$^2$-Ac-8-Br-cGMP)

Using general procedure Y2, 8-Br-cGMP was reacted with methyl bromoacetate to give the title compound.
Yield (Purity): 34% (>99%).
HPLC: (7% MeCN, 30 mM TEAF buffer, pH 6.7).
UV-VIS: $\lambda_{max}$ = 266 nm (pH 7), ε = 15000 (est.).
ESI-MS (+): m/z calculated for C$_{12}$H$_{12}$N$_5$O$_8$PBr ([M + H]$^+$): 463.96, found: 464.
ESI-MS (−): m/z calculated for C$_{12}$H$_{10}$N$_5$O$_8$PBr ([M − H]$^-$): 461.95, found: 462.

| 162 | 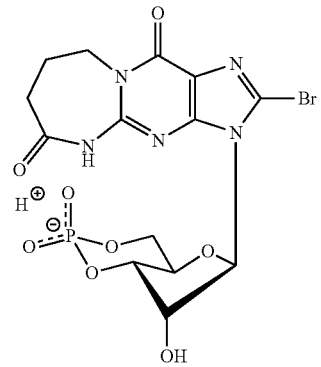 |

8-Bromo-β-1,N$^2$-butyrylguanosine-3',5'-cyclic monophosphate (8-Br-δ-1,N$^2$-But-cGMP)

TABLE 16-continued

Examples of monomeric precursors and/or monomeric compound of the invention.

| # | Compound/Structure |
|---|---|
| | Using general procedure Y3, 8-Br-1-CPr-cGMP was transformed into the title compound.<br>Yield (Purity): 50% (>99%).<br>HPLC: (26% MeOH, 50 mM TEAF buffer, pH 6.7).<br>UV-VIS: $\lambda_{max}$ = 265 nm (pH 7), $\varepsilon$ = 16200 (est.).<br>ESI-MS (+): m/z calculated for $C_{14}H_{16}N_5O_8PBr$ ([M + H]$^+$): 491.99, found: 492.<br>ESI-MS (−): m/z calculated for $C_{14}H_{14}N_5O_8PBr$ ([M − H]$^−$): 489.98, found: 490. |
| 163 | *[Structure of 8-Bromo-1-(3-carboxypropyl)guanosine-3′,5′-cyclic monophosphate]*<br><br>8-Bromo-1-(3-carboxypropyl)guanosine-3′,5′-cyclic monophosphate (8-Br-1-CPr-cGMP)<br>Using general procedure Z, 8-Br-cGMP was reacted with ethyl 4-bromobutyrate to give the corresponding ethylester of the title compound. The crude product was transformed into the titel compound without prior chromatographic workup using general procedure F.<br>Yield (Purity): 62%, 2 steps (>99%).<br>HPLC: (22% MeOH, 200 mM TEAF buffer, pH 6.7).<br>UV-VIS: $\lambda_{max}$ = 266 nm (pH 7), $\varepsilon$ = 16200 (est.).<br>ESI-MS (+): m/z calculated for $C_{14}H_{18}N_5O_9PBr$ ([M + H]$^+$): 510.00, found: 510.<br>ESI-MS (−): m/z calculated for $C_{14}H_{16}N_5O_9PBr$ ([M − H]$^−$): 507.99, found: 508. |
| 164 | *[Structure of 1-[Aminomethyl-(pentaethoxy)-propylamidopropyl]-8-bromoguanosine-3′,5′-cyclic monophosphate]*<br><br>1-[Aminomethyl-(pentaethoxy)-propylamidopropyl]-8-bromoguanosine-3′,5′-cyclic monophosphate (1-AM-(EO)$_5$-PrAmdPr-8-Br-cGMP)<br>Using adapted general procedure L, 8-Br-1-CPr-cGMP was reacted with NH$_2$CH$_2$—PEG$_5$ (CH$_2$)$_3$ NH$_2$ (3 eq) to receive the title compound.<br>Yield (Purity): 53% (>99%).<br>HPLC: (36% MeOH, 100 mM TEAF buffer, pH 6.8).<br>UV-VIS: $\lambda_{max}$ = 267 nm (pH 7), $\varepsilon$ = 16200 (est.).<br>ESI-MS (+): m/z calculated for $C_{28}H_{48}N_7O_{13}PBr$ ([M + H]$^+$): 800.22, found: 800.<br>ESI-MS (−): m/z calculated for $C_{28}H_{46}N_7O_{13}PBr$ ([M − H]$^−$): 798.20, found: 798. |
| 165 | *[Structure of 1-benzyl-8-bromoguanosine cyclic monophosphate]* |

TABLE 16-continued

Examples of monomeric precursors and/or monomeric compound of the invention.

| # | Compound/Structure |
|---|---|
| | 1-Benzyl-8-bromoguanosine-3',5'-cyclic monophosphate (1-Bn-8-Br-cGMP) Using general procedure Z, 8-Br-cGMP was reacted with benzyl bromide to give the title compound. Yield (Purity): 70% (>99%). HPLC: (16% MeCN, 100 mM NaH$_2$PO$_4$ buffer, pH 6.7). UV-VIS: $\lambda_{max}$ = 265 nm (pH 7), $\varepsilon$ = 16200 (est.). ESI-MS (+): m/z calculated for C$_{17}$H$_{18}$N$_5$O$_7$PBr ([M + H]$^+$): 514.01, found: 514. ESI-MS (−): m/z calculated for C$_{17}$H$_{16}$N$_5$O$_7$PBr ([M − H]$^−$): 512.00, found: 512. |
| 166 | 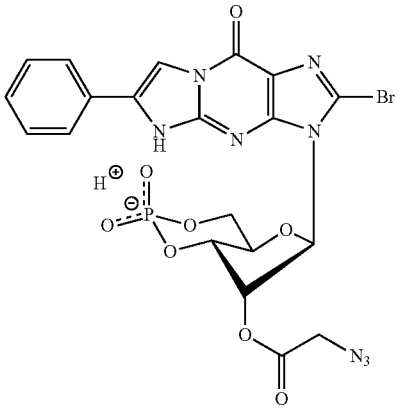 2'-O-(2-Azidoacetyl)-8-bromo-β-phenyl-1,N$^2$-ethenoguanosine-3',5'-cyclic monophosphate (2'-O-(2-N$_3$Ac)-8-Br-PET-cGMP) Using general procedure ZZ, 8-Br-PET-cGMP was transformed into the title compound. Yield (Purity): 60% (>99%). HPLC: (22% MeCN, 50 mM NaH$_2$PO$_4$ buffer, pH 6.8). UV-VIS: $\lambda_{max}$ = 258 nm (pH 7), $\varepsilon$ = 40000 (est.). ESI-MS (+): m/z calculated for C$_{20}$H$_{17}$N$_8$O$_8$PBr ([M + H]$^+$): 607.01, found: 607. ESI-MS (−): m/z calculated for C$_{20}$H$_{15}$N$_8$O$_8$PBr ([M − H]$^−$): 604.99, found: 605. |

2. Activation of PKG Isoforms by cGMP Derivatives

Experimental Part

In vitro activation experiments with PKG isozymes Iα, Iβ and II were performed with the commercially available luminescence assay ADP-Glo™ Kinase Assay (Cat. #V9101) from Promega Corporation (Madison, WI, USA) according to the manufacturer's instruction manual (The ADP-Glo™ Kinase Assay Technical Manual #TM313), standardized and conducted by BIAFFIN GmbH & Co KG (Kassel, Germany). Luminescence detection was accomplished with a LUMIstar Optima microplate luminometer from BMG LABTECH GmbH (Ortenberg, Germany). Bovine PKG type Iα was purified from bovine lung. Human PKGIβ and PKGII were expressed in Sf9 cells and purified by affinity chromatography.[2] Concentrations of enzymes given below refer to the dimeric form. VASPtide (GL Biochem Ltd., Shanghai, China) was used as PKG-selective phosphorylation substrate peptide.[2]

Assay Conditions:

PKG Iα (0.2 nM), 20 mM Tris (pH 7.4), 10 mM Mg$_2$Cl$_2$, 1 mg/mL BSA, 0.15 mM (3-mercaptoethanol, 2.5% DMSO, 130 µM VASPtide, 50 µM ATP, room temperature, 60 min.

PKG Iβ (0.15 nM), 20 mM Tris (pH 7.4), 10 mM Mg$_2$Cl$_2$, 1 mg/mL BSA, 2.5% DMSO, 130 µM VASPtide, 50 µM ATP, room temperature, 60 min.

PKG II (0.5 nM), 20 mM Tris (pH 7.4), 10 mM Mg$_2$Cl$_2$, 1 mg/mL BSA, 5 mM (3-mercaptoethanol, 2.5% DMSO, 130 µM VASPtide, 50 µM ATP, room temperature, 120 min.

Different concentrations (10 pM to 6 µM) of the compounds of the invention and cGMP as reference compound were incubated with the respective PKG isozyme. To increase assay sensitivity in case of PKG II, cGMP and compounds of the invention were preincubated at room temperature for 30 min. The activation values of the compounds are expressed as relative PKG activation compared to cGMP with cGMP set as 1 for each kinase isozyme. The $K_a$-values of cGMP for half-maximal kinase activation were 28 nM for Iα, 425 nM for Iβ and 208 nM for II.

Results

FIGS. 3 to 5 show that all tested PLMs produce significantly higher relative PKG activation for at least 2 of the 3 PKG isozymes compared to the reference compound cGMP. Furthermore, it has to be noted, that the applied standard assay conditions only allowed to determine increased activation potencies of up to 140-fold for PKG Iα, 2832-fold for PKG Iβ and 416-fold for PKG II, which is due to the employed enzyme concentration in the assays and the phenomenon that the isozymes were activity-titrated in some cases by the highly active compounds of the invention. The actual PKG activation potentials of these particular compounds of the invention appear to be significantly higher and are therefore expressed as ≥140-fold for PKG Iα, ≥2832-fold for PKG Iβ and ≥416-fold for PKG II. A careful and more detailed analysis of the results is provided in the detailed description of the invention-section.

3. 661W Cell Line: Assessment of Cell Death Using the Ethidium Homodimer Assay

Background

To test the effect of PKG activators, the 661W cell line was used and increase in cell death after treatment was assessed. The 661W cell line is a photoreceptor precursor cell line, immortalized with the SV40 T antigen. As shown in the FIG. 6, the 661W cells express PKG. This makes them a suitable model for examining PKG activity using cell death as readout since increased PKG activity was previously associated with increased cell death[9]. Because of potentially complex outcomes from the activation of different PKG isoforms this analysis is interpreted as a proof of principle on the use of these compounds in PKG-expressing cells or tissues.

Experimental Part

The 661W cells were cultured in DMEM with 10% FBS (Fetal Bovine Serum), 2 mM Glutamine, 100 U/ml penicillin, and 100 μg/ml streptomycin. For the Ethidium Homodimer Assay, cells were plated in a 24 well plate on slides coated with ECM (extracellular matrix) at 20 000 cells/well and left for 24 hours to attach to the slides. The next day the cells were treated with the compounds. Compounds were dissolved in water and then diluted in the medium at concentrations of 1 nM to 10 μM. 16 hours after treatment cells were washed with PBS and fixed in 4% paraformaldehyde. Afterwards slides were dipped into 2 μM Ethidium Homodimer for 2 minutes and nuclei were stained with DAPI (4',6-diamidino-2-phenylindole). Ethidium Homodimer stains nuclei of dying cells. To assess cell death, microphotographs were taken from three different slides for each compound concentration and the total number of cells, as well as the number of dying Ethidium Homodimer positive cells, were counted in each picture. The value for untreated cells was set to 1. To statistically assess significant differences between untreated and treated cells, the unpaired Student's t-test was used and a P value≤0.05 was considered significant (*≤0.05, ≤0.01, *≤0.001).

Results

FIG. 7 shows percentage of cells undergoing cell death after treatment with non limiting exemplary polymer linked dimeric cGMP analogues of the invention (12 compounds). Six of the tested compounds led to significantly increased cell death at one or more concentrations when compared to untreated cells. The most potent compounds of the invention display a 5-6 fold increase in cell death when compared to untreated cells and 3-4 fold increase in cell death when compared to the reference 8-Br-PET-cGMP.

| Acronyms | |
|---|---|
| BAP | bio-activatable protecting group |
| cAMP | adenosine-3',5'-cyclic monophosphate |
| cGMP | guanosine-3',5'-cyclic monophosphate |
| cGMPS | guanosine-3',5'-cyclic monophosphorothioate |
| CNGC | cyclic nucleotide gated ion channel |
| Cy | cyclohexyl |
| Cyp | cyclopentyl |
| Da | Dalton |
| DAPI | 4',6-diamidino-2-phenylindole |
| DBU | 1,8-diazabicyclo[5.4.0]undec-7-ene |
| DMEM/F12 | Dulbecco's modifiziertes eagle medium in combination with Ham's F-12 medium |
| DMF | N,N-dimethylformamide |
| DMSO | dimethyl sulfoxide |
| dppf | 1,1'-Bis(diphenylphosphino)ferrocene |
| ECM | extracellular matrix |
| EDC | 1-ethyl-3-(3-dimethylaminopropyl)carbodiimide |
| EGTA | ethylene glycol-bis(2-aminoethylether)-N,N,N'N'- tetraacetic acid |
| ESI-MS | electrospray Ionization mass spectrometry |
| est. | estimated |
| $Et_3NH^+$ | triethylammonium |
| FGF | fibroblast growth factor |
| HCN | hyperpolarization-activated cyclic nucleotide-gated |
| HEPES | 4-(2-hydroxyethyl)-1-piperazineethanesulfonic acid |
| HOBt | 1-hydroxybenzotriazole |
| HPLC | high performance liquid chromatography |
| $(i-Pr)_2EtNH^+$ | diisopropylethylammonium |
| i-PrOH | 2-propanol |
| m/z | mass-to-charge ratio |
| MeCN | acetonitrile |
| MTBE | tert-butyl methyl ether |
| $M_w$ | molecular weight |
| N2 | N2-supplement for cell culture |
| NHS | N-hydroxysuccinimid |
| PAP | photo-activatable protecting group |
| PBS | phosphate buffered saline |
| $Pd(dppf)Cl_2$ | 1,1'-bis(diphenylphosphino)ferrocene-palladium(II) dichloride |
| PDE | phosphodiesterase |
| PEG | poly(ethylene glycol) |
| PET | ß- Phenyl-1, $N^2$- etheno |
| PFA | paraformaldehyde |
| PKG | cGMP-dependent protein kinase |
| PLD | polymer linked dimer |
| PLM | polymer linked multimer |
| PN | postnatal |
| PyBOP | benzotriazole-1-yl-oxytripyrrolidinophosphonium hexafluorophosphate |
| Rp | as in Rp-cGMPS refers to configuration of the chiral phosphorus, wherein R/S follows the Cahn-Ingold-Prelog rules while "p" stands for phosphorus. |
| RP-18 | reversed phase octadecyl modified material |
| SD | standard deviation |
| TEA | triethylammonium |

| Acronyms | |
|---|---|
| TEAF | triethylammonium formate |
| UV-VIS | ultraviolet and visible (spectroscopy) |
| VS | vinylsulfone |
| ε | extinction coefficient |
| λ$_{max}$ | wavelength at which absorbance is highest |

LITERATURE 1. (a) Schwede, F.; Maronde, E.; Genieser, H.; Jastorff, B., Cyclic nucleotide analogs as biochemical tools and prospective drugs. *Pharmacol Ther* 2000, 87 (2-3), 199-226; (b) Schmidt, H. H.; Hofmann, F.; Stasch, J., In *cGMP: Generators, Effectors and Therapeutic Implications*, Springer-Verlag Heidelberg: Berlin, 2009; pp 447-506; (c) Schlossmann, J.; Schinner, E., cGMP becomes a drug target. *Naunyn Schmiedebergs Arch Pharmacol* 2012, 385 (3), 243-52.
2. Poppe, H.; Rybalkin, S. D.; Rehmann, H.; Hinds, T. R.; Tang, X. B.; Christensen, A. E.; Schwede, F.; Genieser, H.; Bos, J. L.; Doskeland, S. O.; Beavo, J. A.; Butt, E., Cyclic nucleotide analogs as probes of signaling pathways. *Nat. Methods* 2008, 5, pp 277-278.
3. Schmidt, H. H.; Hofmann, F.; Stasch, J., In *cGMP: Generators, Effectors and Therapeutic Implications*, Springer-Verlag Heidelberg: Berlin, 2009; pp 409-421.
4. Herfindal, L.; Krakstad, C.; Myhren, L.; Hagland, H.; Kopperud, R.; Teigen, K.; Schwede, F.; Kleppe, R.; Doskland, S. O., Introduction of Aromatic Ring-Containing Substituents inCyclic Nucleotides Is Associated with Inhibition of Toxin Uptake by the Hepatocyte Transporters OATP 1B1 and 1B3. *PLoS ONE* 2014, 9 (4), e94926.
5. Kramer, R. H.; Karpen, J. W., Spanning binding sites on allosteric proteins with polymer-linked ligand dimers. *Nature* 1998, 395, 710-713.
6. Sekhar, K. R.; Hatchett, R. J.; Shabb, J. B.; Wolfe, L.; Francis, S. H.; Wells, J. N.; Jastorff, B.; Butt, E.; Chakinala, M. M.; Corbin, J. D., Relaxation of Pig Arteries by New and Potent cGMP Analogs that Selectively Activate Type Iα, Compared with Iβ, cGMP-Dependent Protein Kinase. *Mol. Pharmacol* 1992, pp 103-108.
7. Strassmaier, T.; Karpen, J., Novel N7- and N1-substituted cGMP Derivatives Are Potent Activators of Cyclic Nucleotide-Gated Channels. *J. Med. Chem.* 2007, 50, 4186-4194.
8. Kramer, R. H.; Karpen, J. W. Multimeric Tethered Ligands and Their Use in Receptor-Ligand Interaction. WO 99/25384, 1999.
9. Paquet-Durand, F.; Hauck, S. M.; van Veen, T.; Uefling, M.; Ekstrom, P., PKG activity causes photoreceptor cell death in two retinitis pigmentosa models. *J Neurochem* 2009, 108 (3), 796-810.
10. (a) Wang, Y.; Chen, Y.; Wu, M.; Lan, T.; Wu, Y.; Li, Y.; Qian, H., Type II cyclic guanosine monophosphate-dependent protein kinase inhibits Rac1 activation in gastric cancer cells. *Oncol Lett* 2015, 10 (1), 502-508; (b) Zhu, M.; Yao, X.; Wu, M.; Qian, H.; Wu, Y.; Chen, Y., Type II cGMP-dependent protein kinase directly inhibits HER2 activation of gastric cancer cells. *Mol Med Rep* 2016, 13 (2), 1909-13.
11. (a) Bala, I.; Hariharan, S.; Kumar, M. N., PLGA nanoparticles in drug delivery: the state of the art. *Crit Rev Ther Drug Carrier Syst* 2004, 21 (5), 387-422; (b) Basu, S. C.; Basu, M., *Liposome Methods and Protocols*. Humana Press: 2002; (c) Gregoriadis, G., *Liposome Technology*. Informa Healthcare: 2006; (d) Paquet-Durand, F.; Gaillard, P. J.; Maringo, V.; Ekström, P.; Genieser, H.-G.; Rentsch, A. Targeted liposomal delivery of cGMP analogues.
12. Genieser, H.-G.; Walter, U.; Butt, E. Derivatives of cyclic guanosine-3',5'-monophosphorothioate. U.S. Pat. No. 5,625,056, Apr. 29, 1997.
13. Freudenberg, K.; Eichel, H.; Leutert, F., Synthesen von Abkömmlingen der Amino-säuren. *Berichte der deutschen chemischen Gesellschaft (A and B Series)* 1932, 65 (7), 1183-1191.
14. Genieser, H.-G., New boranophosphate Analogues of cyclic nucleotides. WO/2012/130829, 2012.

We claim:
1. A compound having the structure of formula (I)

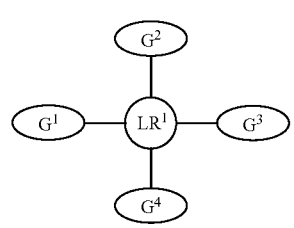

wherein;
$G^3$ and $G^4$ are absent;
each of $G^1$ and $G^2$ is independently a compound having the structure formula (III):

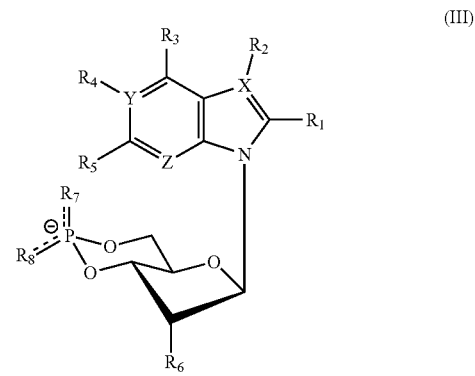

and wherein in formula (III):
X, Y, and Z are N;
$R_1$, $R_4$, $R_5$, $R_7$, and $R_8$ are the same or different for each $G^1$ and $G^2$;
wherein:
$R_2$ is absent;
$R_3$ is OH;
$R_4$ and $R_5$ join together to form an imidazole ring which is substituted with aryl;
$R_6$ is OH;
$R_7$ is OH or SH; and
$R_8$ is OH, O-PAP, or O-BAP;
wherein PAP is a photo-activatable protecting group wherein PAP is o-nitro-benzyl, 1-(o-nitrophenyl)-ethylidene, 4,5-dimethoxy-2-nitro-benzyl, 7-dimethylamino-coumarin-4-yl (DMACM-caged), 7-diethylaminocoumarin-4-yl (DEACM-caged), or 6,7-bis(carboxymethoxy) coumarin-4-yl) methyl (BCMCM-caged);

and wherein BAP is a bio-activatable protecting group wherein BAP is methyl, ethyl, acetoxymethyl, acetoxyethyl, acetoxybutyl, acetoxyisobutyl, pivaloyloxymethyl, methoxymethyl, propionyloxymethyl, butyryloxymethyl, cyanoethyl, phenyl, benzyl, 4-acetoxybenzyl, 4-pivaloyloxybenzyl, 4-isobutyryloxybenzyl, 4-octanoyloxybenzyl, 4-benzoyloxybenzyl, acetyl, propionyl, or benzoyl wherein
linking residue $LR^1$ is covalently bound to the $R_1$ of the $G^1$ or $G^2$ it connects to;
linking residue $LR^1$ is a divalent hydrocarbon moiety optionally comprising incorporated heteroatoms;
wherein the linking residue $LR^1$ is further subdivided as depicted in formula (Ib), (Ib)

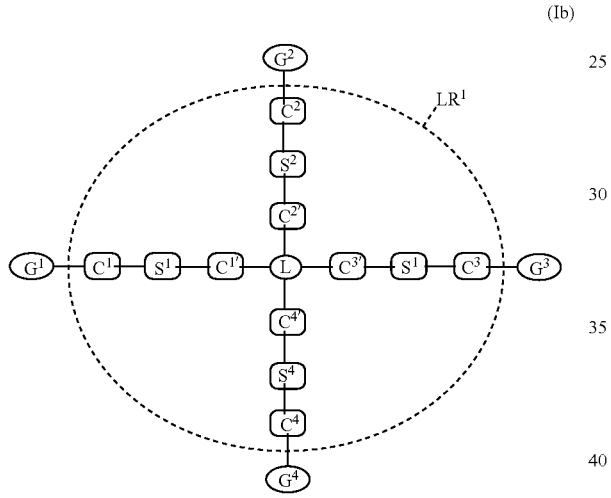

wherein in formula Ib:
coupling functions $C^3$, $C^{3'}$, $C^4$ and $C^{4'}$ and spacers $S^3$ and $S^4$ are absent,
coupling functions $C^1$, $C^{1'}$, $C^2$ and $C^{2'}$ are each independently absent or as defined by structures selected from the group consisting of:

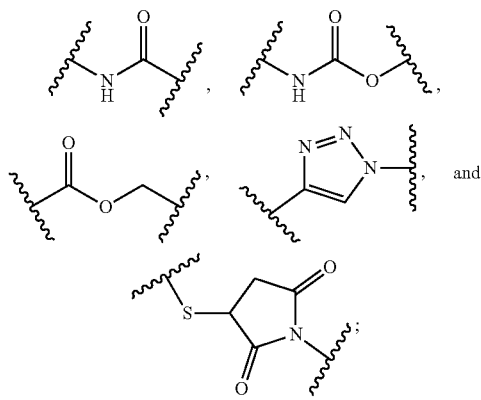

wherein $G^1$, $S^1$, $G^2$, $S^2$, and L bond to any of the squiggly bonds of the $C^1$, $C^{1'}$, $C^2$ and $C^{2'}$ that are present;
wherein the coupling functions $C^1$, $C^{1'}$, $C^2$ and $C^{2'}$ of linking residue $LR^1$ bond to the $R_1$ residue of the respective $G^1$ or $G^2$; wherein $R_1$ has the structure:

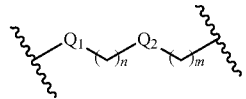

wherein:
n=0-6; m=0-6
$Q_1$=S;
$Q_2$=NH, S, C(O), $CH_2$, OC(O), or NC(O);
wherein the linker L has the structure:

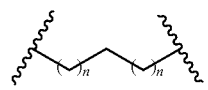

wherein n=0-6;
each index n for L can independently have the same or different value;
each of spacers $S^1$ and $S^2$ are independently present or absent
wherein, if present, each of spacers $S^1$ and $S^2$ independently have the structure $-(CH_2)_{n1}-(CH_2CH_2\beta)_m-(CH_2)_{n2}-$
wherein $\beta$=O; m=1 to 500, n1=0 to 8, n2=0 to 8, wherein each n1 and n2 is independently the same or different from each other; and
$G^1$ and $G^2$ are optionally suitable salts and/or hydrates
wherein optionally suitable salts are lithium, sodium, potassium, calcium, magnesium, zinc, ammonium, or alkylammonium salts.

2. The compound according to claim 1, wherein
each $R_7$ is SH and each $R_8$ is O;
or
each $R_7$ is O and each $R_8$ is OH.

3. The compound according to claim 1, wherein:
$R_4$ and $R_5$ join together to form an imidazole ring which is substituted with aryl having the structure of residue entry 1:

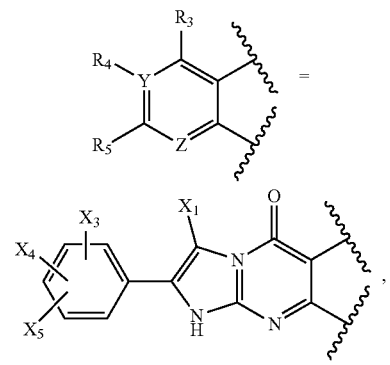

residue entry 1;
wherein:
$X_1$ is H each $X_3$, $X_4$ and $X_5$ is independently H, OH, NH, $CH_3$, Cl, Br, F, CN, $N_3$, $CF_3$, $OCF_3$, $NO_2$, C(O)OH, C(O)$OCH_3$, $OCH_3$, $SCH_3$, t-Bu, N($CH_3$)$_2$, S(O)$_2CH_3$, C(O)$NH_2$, or NHS(O)$_2CH_3$;

and/or $R_8$ is OH, methyloxy, ethyloxy, cyanoethyloxy, acetoxymethyloxy, pivaloyloxymethyloxy, methoxymethyloxy, propionyloxymethyloxy, butyryloxymethyloxy, acetoxyethyloxy, acetoxybutyloxy, acetoxyisobutyloxy, phenyloxy, benzyloxy, 4-acetoxybenzyloxy 4-pivaloyloxybenzyloxy, 4-isobutyryloxybenzyloxy, 4-octanoyloxybenzyloxy, 4-benzoyloxybenzyloxy, acetyloxy, propionyloxy, or benzoyloxy.

4. The compound according to claim 1, wherein:

$R_1$ has the structure

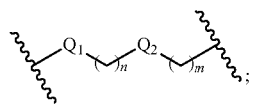

wherein;
n=0-3; m=0-3;
$Q_1$=S;
$Q_2$=NH, S, O, C(O), $CH_2$, or OC(O);
and/or
$R_4$ and $R_5$ join together to form an imidazole ring which is substituted with aryl having the structure of residue entry 1:

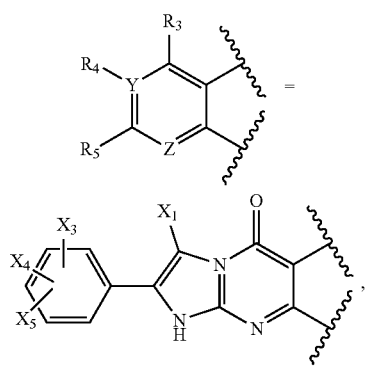

residue entry 1;
wherein:
$X_1$ is H;
$X_3$ is H and each of $X_4$ and $X_5$ is independently H, OH, NH, $CH_3$, Cl, Br, F, CN, $N_3$, $CF_3$, $OCF_3$, $NO_2$, C(O)OH, C(O)$OCH_3$, $OCH_3$, $SCH_3$, t-Bu, N($CH_3$)$_2$, or C(O)$NH_2$;
and/or
coupling functions $C^1$, $C^{1'}$, $C^2$ and $C^{2'}$ are selected from the group consisting of:

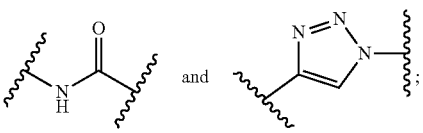

and/or $R_8$ is OH, methyloxy, ethyloxy, cyanoethyloxy, acetoxymethyloxy, pivaloyloxymethyloxy, methoxymethyloxy, propionyloxymethyloxy, butyryloxymethyloxy, acetoxyethyloxy, acetoxybutyloxy, acetoxyisobutyloxy, phenyloxy, benzyloxy, 4-acetoxybenzyloxy, 4-pivaloyloxybenzyloxy, 4-isobutyryloxybenzyloxy, 4-octanoyloxybenzyloxy, 4-benzoyloxybenzyloxy, acetyloxy, propionyloxy, or benzoyloxy.

5. The compound according to claim 1, wherein:
$R_1$ has the structure

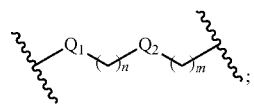

wherein;
n=0-3; m=0-3;
$Q_1$=S;
$Q_2$=NH, S, O, C(O), $CH_2$, or OC(O);
and/or
$R_4$ and $R_5$ join together to form an imidazole ring which is substituted with aryl having the structure of residue entry 1:

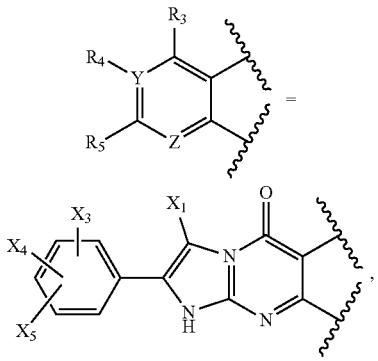

residue entry 1;
wherein:
$X_1$ is H;
each $X_3$ and $X_4$ is H and $X_5$ is H, OH, NH, $CH_3$, Cl, Br, F, CN, $N_3$, $CF_3$, $OCF_3$, $NO_2$, C(O)OH, C(O)$OCH_3$, $OCH_3$, $SCH_3$, t-Bu, N($CH_3$)$_2$, or C(O) $NH_2$;
and/or
coupling functions $C^1$, $C^{1'}$, $C^2$ and $C^{2'}$ are each

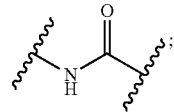

and/or

R₈ is OH.

6. The compound according to claim 1, wherein the compound is selected from the group consisting of:
- (5) β-Phenyl-1, N²-ethenoguanosine-3',5'-cyclic monophosphate-[8-thiomethylamido-(octaethoxy)-ethylamidomethylthio-8]-β-phenyl-1, N²-ethenoguanosine-3',5'-cyclic monophosphate;
- (7) Guanosine-3',5'-cyclic monophosphate-[8-thiomethylamido-(octaethoxy)-ethylamidomethylthio-8]-β-phenyl-1, N²-ethenoguanosine-3',5'-cyclic monophosphate;
- (11) β-Phenyl-1, N²-ethenoguanosine-3',5'-cyclic monophosphate-[8-thiomethylamido-(nonadecaethoxy)-ethylamidomethylthio-8]-guanosine-3',5'-cyclic monophosphate;
- (12) β-Phenyl-1, N²-ethenoguanosine-3',5'-cyclic monophosphate-[8-thiomethylamido-(nonadecaethoxy)-ethylamidomethylthio-8]-β-phenyl-1, N²-ethenoguanosine-3',5'-cyclic monophosphate;
- (13)-Phenyl-1, N²-ethenoguanosine-3',5'-cyclic monophosphate-[8-thiomethylamido-(PEG pd 2000)-amidomethylthio-8]-β-phenyl-1, N²-ethenoguanosine-3',5'-cyclic monophosphate; and
- (23) β-Phenyl-1, N²-ethenoguanosine-3',5'-cyclic monophosphate-[8-thioethyl-(1-[1,2,3]-triazole-4-yl)-methoxy-(hexaethoxy)-methyl-(4-[1,2,3]-triazole-1-yl)-ethylthio-8]-β-phenyl-1, N²-ethenoguanosine-3',5'-cyclic monophosphate.

7. A compound having formula (III):

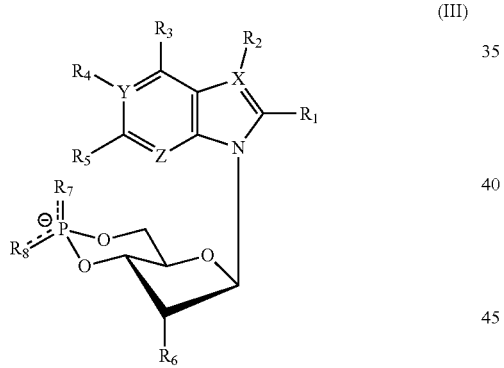

(III)

wherein:
- X, Y, and Z are N;
- R₂ is absent;
- R₃ is OH;
- R₄ and R₅ join together to form an imidazole ring which is substituted with aryl;
- R₆ is OH;
- R₇ is OH; and
- R₈ is OH, O-PAP, or O-BAP;
    - wherein PAP is a photo-activatable protecting group wherein PAP is o-nitro-benzyl, 1-(o-nitrophenyl)-ethylidene, 4,5-dimethoxy-2-nitro-benzyl, 7-dimethylamino-coumarin-4-yl (DMACM-caged), 7-diethylaminocoumarin-4-yl (DEACM-caged), or 6,7-bis(carboxymethoxy) coumarin-4-yl) methyl (BCMCM-caged);
    - and wherein BAP is a bio-activatable protecting group wherein BAP is methyl, acetoxymethyl, pivaloyloxymethyl, methoxymethyl propionyloxymethyl, butyryloxymethyl cyanoethyl, phenyl, benzyl, 4acetoxybenzyl, 4-pivaloyloxybenzyl, 4-isobutyryloxybenzyl, 4octanoyloxybenzyl, or 4-benzoyloxybenzyl;

R₁ is Cl, Br, I, F, N₃, NO₂, SH, NH₂, or CF₃; or

R₁ has the structure:

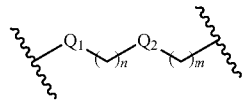

wherein
- n=0-6; m=0;
- Q₁=S;
- Q₂ is NH₂, SH, OH, C(O) OH, or CH₃; and
- R₄ and R₅ join together to form an imidazole ring which is substituted with aryl having the structure of residue entry 1:

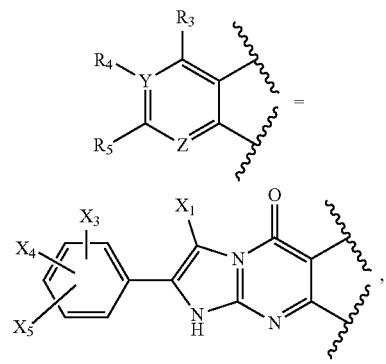

residue entry 1;
wherein
- X₁ is H;
- each X₃ is OH, NH, CH₃, Cl, Br, F, CN, N₃, CF₃, OCF₃, C(O) OH, C(O)OCH₃, OCH₃, SCH₃, t-Bu, N(CH₃)₂, or C(O) NH₂;
- each X₄ and X₅ is independently H, OH, NH, CH₃, Cl, Br, F, CN, N₃, CF₃, OCF₃, C(O) OH, C(O)OCH₃, OCH₃, SCH₃, t-Bu, N(CH₃)₂, or C(O)NH₂;

or the compound of formula (III) is selected from the group consisting of
- (134) 8-Bromo-(4-methoxy-β-phenyl-1, N2-etheno) guanosine-3',5'-cyclic monophosphate;
- (135) 8-Bromo-(4-methyl-β-phenyl-1, N2-etheno) guanosine-3',5'-cyclic monophosphate;
- (137) 8-Bromo-(4-chloro-β-phenyl-1, N2-etheno) guanosine-3',5'-cyclic monophosphate;
- (140) 8-Bromo-(2-methoxy-β-phenyl-1, N2-etheno) guanosine-3',5'-cyclic monophosphate;
- (141) 8-Bromo-(3-methoxy-β-phenyl-1, N2-etheno) guanosine-3',5'-cyclic monophosphate;
- (142) 8-Bromo-(2,4-dimethoxy-β-phenyl-1, N2-etheno) guanosine-3',5'-cyclic monophosphate;
- (147) 8-Bromo-(3-hydroxy-β-phenyl-1, N2-etheno) guanosine-3',5'-cyclic monophosphate;
- (151) 8-Bromo-(4-cyano-β-phenyl-1, N2-etheno) guanosine-3',5'-cyclic monophosphate;

(153) β-(4-Aminophenyl)-1, N2-etheno-8-bromo-guanosine-3',5'-cyclic monophosphate;
(156) 8-Bromo-(4-trifluoromethyl-β-phenyl-1, N2-etheno) guanosine-3',5'-cyclic monophosphate;
(157) (4-Fluoro-β-phenyl-1, N2-etheno)-8-methylthio-guanosine-3',5'-cyclic monophosphate;
(158) (4-Methoxy-β-phenyl-1, N2-etheno)-8-methylthioguanosine-3',5'-cyclic monophosphate; and
(160) (4-Methoxy-β-phenyl-1, N2-etheno)-8-propylthioguanosine-3',5'-cyclic monophosphate.

8. The compound of claim 1, wherein the alkylammonium salts comprise dialkylammonium or trialkylammonium salts.

9. The compound of claim 8, wherein the dialkylammonium or trialkylammonium salts are triethylammonium, trimethylammonium, diethylammonium and octylammonium salts.

10. A method of treating a disease or disorder selected from the group consisting of cancer, cardiovascular disease or disorder, or autoimmune disease or disorder, or neurodegenerative disease or disorder comprising administering an effective amount of a compound of claim 1 to a patient in need thereof.

* * * * *